(12) United States Patent
Ko et al.

(10) Patent No.: US 10,683,518 B2
(45) Date of Patent: Jun. 16, 2020

(54) MUTATED NUCLEOTIDE MOLECULE, AND TRANSFORMED PLANT CELLS AND PLANTS COMPRISING THE SAME

(71) Applicant: Academia Sinica, Taipei (TW)

(72) Inventors: Swee-Suak Ko, Taipei (TW); Min-Jeng Li, Taipei (TW)

(73) Assignee: ACADEMIA SINICA, Taipei (TW)

( * ) Notice: Subject to any disclaimer, the term of this patent is extended or adjusted under 35 U.S.C. 154(b) by 207 days.

(21) Appl. No.: 15/723,312

(22) Filed: Oct. 3, 2017

(65) Prior Publication Data

US 2018/0030473 A1 Feb. 1, 2018

Related U.S. Application Data

(63) Continuation of application No. 14/596,419, filed on Jan. 14, 2015, now abandoned.

(60) Provisional application No. 61/927,592, filed on Jan. 15, 2014.

(51) Int. Cl.
*C12N 15/82* (2006.01)
*C07K 14/415* (2006.01)

(52) U.S. Cl.
CPC ........ *C12N 15/8289* (2013.01); *C07K 14/415* (2013.01)

(58) Field of Classification Search
None
See application file for complete search history.

(56) References Cited

PUBLICATIONS

Emery et al (2003, "Radial Patterning of Arabidopsis Shoots by Class III HD-ZIP and KANADI Genes", Current Biology 13:1768-1774).*
Hsing et al., "A rice gene activation/knockout mutant resource for high throughput functional genomics", 2007, Plant Molecular Biology, vol. 63, pp. 351-364.
Abe et al., "Arabidopsis AtMYC2 (bHLH) and AtMYB2 (MYB) Function as Transcriptional Activators in Abscisic Acid Signaling", the Plant Cell, 2003, vol. 15, pp. 63-78.

* cited by examiner

*Primary Examiner* — Stuart F Baum
(74) *Attorney, Agent, or Firm* — Bacon & Thomas, PLLC

(57) ABSTRACT

The present invention relates to a method for producing male sterile plant, a mutated nucleotide molecule comprising a nucleotide sequence of the transcription factor bHLH142 and an inserted T-DNA segment, and a novel transformed plant cell and a male-sterile mutant plant comprising the mutated nucleotide molecule, in which the transcription factor bHLH142 is not expressed. The present invention also relates to a novel reversible male sterile transgenic plant, wherein the transcription factor bHLH142 is overexpressed, and its preparation method. The bHLH gene is tissue specifically expresses in the anther and it plays a pivotal role in pollen development. Both the male sterile and reversible male sterile transgenic plants showed a completely male sterile phenotype, but the fertility of the reversible male sterile transgenic plant can be restored under low temperature.

11 Claims, 42 Drawing Sheets

Specification includes a Sequence Listing.

C

P35S | eGFP | Tnos

P35S | virD2-NLS | mRFP | Tnos

P35S | bHLH142 | eGFP | Tnos

P35S:eGFP:Tnos
P35S:NLS:mRFP:Tnos
P35S:bHLH142:Tnos

TNG67 (WT)    ms142

B

Hitomebore (WT)    H0530 (eat1)

A

B

C

D

MUTATED NUCLEOTIDE MOLECULE, AND TRANSFORMED PLANT CELLS AND PLANTS COMPRISING THE SAME

CROSS REFERENCE TO RELATED APPLICATIONS

This application is a continuation application of pending U.S. patent application Ser. No. 14/596,419, filed Jan. 14, 2015, which claims benefit to U.S. Provisional Application Ser. No. 61/927,592, filed Jan. 15, 2014, the entire contents which is incorporated herein by reference.

BACKGROUND OF THE INVENTION

Rice (Oryza sativa) is one of the most important staple crops in the world, feeding almost half of the world's population, and it serves as a model for monocots, which include many important agronomic crops (e.g. wheat, maize, sorghum, millet). Food and Agriculture Organization (FAO) predicts that rice yield will have to be increased 50-70% by 2050 to meet the demands. Several approaches are currently adopted to increase rice yields, such as heterosis breeding, population improvement, wide hybridization, genetic engineering, and molecular breeding[1]. Among these, hybrid rice is being considered the most promising one (15-20% increases in yield)[2]. Crops produced from F1 hybrid seeds offer significant benefits in terms of yield improvement, agronomic performance and consistency of end-use quality. This is due to the 'hybrid vigor' generated by combining carefully selected parent lines. Hybrid crops are responsible for a dramatic increase in global crop yields in the past decades, and male sterility (MS) has played a significant role in this advancement. Male sterile traits can be divided into cytoplasmic male sterility (CMS), which is determined by cytoplasmic factors such as mitochondria, and genetic male sterility (GMS), which is determined by nuclear genes. CMS has long been used in hybrid corn production, while both CMS and GMS are currently used for hybrid rice production[3], due to the convenience of controlling sterility expression by manipulating the gene-cytoplasm combinations in any selected genotype. Most importantly, it evades the need for emasculation in cross-pollinated species, thus encouraging cross breeding and producing pure hybrid seeds under natural conditions. However, commercial seed production must be simple and inexpensive, and the requirement for a maintainer line to produce the seed stocks of CMS line increases the production cost for this 3-line hybrid system.

On the other hand, genetic MS (GMS), controlled by nuclear genes, offers an alternative hybrid seed production system. For the two-line hybrid system, it is beneficial to use photoperiod- or temperature-inducible MS (PGMS or TGMS) mutants to maintain seed stocks for hybrid seed production. Currently, in China, PA64S is the most widely used maternal line in two-line hybrid rice breeding, and it is crossed with paternal line 93-11 to generate superhybrid rice, LYP9[4]. PA64S, derived from a spontaneous PGMS japonica mutant NK58S (long day->13.5 h; Shi, 1985), is also a TGMS indica rice, whose MS is promoted by temperatures greater than 23.5° C., but recovers its fertility at temperatures between 21~23° C. Recent mapping analyses demonstrate that the P/TGMS in these MS lines is regulated by a novel small RNA[5]. In the case of another rice genic MS mutant discovered recently, Carbon Starved Anther (CSA), the mutation on the R2R3 MYB transcription regulator defects pollen development[6] and further study shows that csa is a new photoperiod-sensitive mutant, exhibiting MS under short-day conditions but male fertility under long-day conditions[7]. The molecular basis of its MS sensitivity to day length remains to be addressed.

Transgenic male sterility has been generated using a number of transgenes, but its application in commercial production of hybrid seeds is limited due to the lack of an efficient and economical means to maintain the MS lines, or the lack of suitable restorers[8]. Recently, a reversible MS system has been demonstrated in transgenic Arabidopsis plants by manipulating a R2R3 MYB domain protein (AtMYB103)[8]. Blocking the function of AtMYB103 using an insertion mutant or an AtMYB103EAR chimeric repressor construct under the control of the AtMYB103 promoter resulted in complete MS without seed setting[8]. A restorer containing the AtMYB103 gene driven by of a stronger anther-specific promoter was introduced into pollen donor plants and crossed into the MS transgenic plants for the repressor. The male fertility of F1 plants is restored. The chimeric repressor and the restorer constitute a reversible MS system for hybrid seed production. The successful application of this system for large scale hybrid seed production depends on whether the MS female parent lines can be multiplied efficiently and economically. Alternatively, an inducible promoter by chemicals or other factors (e.g. photoperiod or temperature) can be directly used to regulate the expression of a GMS gene (e.g., bHLH142) and control pollen development in transgenic plants, eliminating the costly need to maintain MS lines.

Rice anthers are composed of four lobes attached to a central core by connective and vascular tissue. When anther morphogenesis is completed, microsporocytes form in the middle, surrounded by four anther wall layers: an epidermal outer layer, endothecium, middle layer, and tapetum[9]. The tapetum is located in the innermost cell layer of the anther walls and plays an important role in supplying nutrients such as lipids, polysaccharides, proteins, and other nutrients for pollen development[10]. The tapetum undergoes programmed cell death (PCD) during the late stage of pollen development[11]; this PCD causes tapetal degeneration and is characterized by cellular condensation, mitochondria and cytoskeleton degeneration, nuclear condensation, and internucleosomal cleavage of chromosomal DNA. Tapetal PCD must occur at a specific stage of anther development for normal tapetum function and pollen development, and premature or delayed tapetal PCD and cellular degeneration can cause male sterility[3,12-14].

Genetic and functional genomic studies of MS in Arabidopsis have shown that many transcription factors (TFs) play an essential role in pollen development and the regulation of tapetal PCD, such as mutations in DYSFUNCTIONAL TAPETUM 1 (DYT1), Defective in Tapetal Development and Function 1 (TDF1, AtMYB35), ABORTED MICROSPORES (AMS, homolog of TDR1 in rice), and MALE STERILITY 1 (MS1); and mutations in these factors all result in MS phenotype. The genetic regulatory pathway of pollen development suggests that DYT1, TDF1[15] and AMS[16] function at early tapetum development, while MS188[17] and MS1[15,18,19] play important roles in late tapetum development and pollen wall formation. Whilst, in rice, several TFs, such as Undeveloped Tapetum1 (UDT1, homolog of DYT1), are known to be key regulators of early tapetum development[20]. In addition, mutations in TAPETUM DEGERATION RETARDATION (TDR1)[14], GAMYB[21,22], ETERNAL TAPETUM 1 (EAT1)[23] and DELAYED TAPETUM DEGENERATION (DTD)[24] all cause MS associated with tapetal PCD. TDR1, ortholog of the Arabidopsis AMS gene, plays an essential role in tapetal PCD in rice; and tdr1 shows delayed tapetal degeneration and nuclear DNA fragmentation as well as abortion of microspores after release from the tetrad. Molecular evidences indicate that TDR1 directly binds the promoter of CP1 and C6 for their transcription[14]. C6 encodes a lipid transfer protein that plays a crucial role in the development of lipidic orbicules and pollen exine during anther development[17]. CP1 is involved in intercellular protein degradation in biological system and its mutant shows defected pollen development[25]. EAT1 acts downstream of TDR1 and directly regulates the expression of AP25 and AP37, which encode aspartic proteases involved in tapetal PCD[23].

The basic helix-loop-helix (bHLH) proteins are a superfamily of TFs and one of the largest TF families in plants. There are at least 177 bHLH genes in the rice genome[26,27] and more than 167 bHLH genes in *Arabidopsis* genome[28,29]. Generally, eukaryotic TFs consist of at least two discrete domains, a DNA binding domain and an activation or repression domain that operate together to modulate the rate of transcriptional initiation from the promoter of target genes[30]. The bHLH TFs play many different roles in plant cell and tissue development as well as plant metabolism[3]. The HLH domain promotes protein-protein interaction, allowing the formation of homodimeric or heterodimeric complexes[31]. They bind as dimers to specific DNA target sites and are important regulatory components in diverse biological processes[29]. So far, three of the bHLH TFs have been shown to be involved in rice pollen development— UDT1 (bHLH164), TDR1 (bHLH5), and EAT1/DTD1 (bHLH141).

From a screening of T-DNA tagged rice mutant pool of TNG67[32], we isolated a novel MS-related gene encoding for another member of the bHLH TFs (bHLH142). In this invention, the molecular mechanism of MS in this mutant is elucidated, and it suggests that bHLH142 is specifically expressed in the anther and bHLH142 coordinates with TDR1 in regulating EAT1 promoter activity in transcription of protease genes required for PCD during pollen development. That is to say, bHLH142 plays an essential role in rice pollen development by controlling tapetal PCD. Both null mutant and overexpression transgenic plants showed a completely male sterile phenotype. Most interestingly, the overexpression plants have restored the fertility under low temperature. Homologs of SEQ ID NO: 2 with high similarity are found in other major cereal crops, and its use may increase the productivity of cereal crops by manipulating the bHLH gene for development of male sterility and production of hybrid crops.

SUMMARY OF THE INVENTION

The object of the present invention is developing a mutated nucleotide molecule, and a transformed plant cell and a male sterile mutant plant comprising the mutated nucleotide molecule; in which the male sterile mutant plant can be used as a female parent to produce F1 hybrid seeds, thereby improving yield and quality of crops.

The present invention provides a mutated nucleotide molecule, comprising a nucleotide sequence of the transcription factor bHLH142 and an inserted T-DNA segment. Preferably, the T-DNA segment is inserted in the third intron of the nucleotide sequence of the transcription factor bHLH142; more preferably, the T-DNA segment is inserted at +1257 bp.

In one preferred embodiment of the mutated nucleotide molecule, the T-DNA segment has comprises a single copy of T-DNA.

In one preferred embodiment of the mutated nucleotide molecule, the nucleotide sequence of the transcription factor bHLH142 has a DNA sequence of SEQ ID No: 1 or a DNA sequence having at least 60% similarity to SEQ ID No: 1. Preferably, a DNA sequence having at least 80% similarity to SEQ ID No: 1; more preferably. a DNA sequence having at least 90% similarity to SEQ ID No: 1; even more preferably, a DNA sequence having at least 95% similarity to SEQ ID No: 1; and most preferably, a DNA sequence of SEQ ID No: 1. In addition, the transcription factor bHLH142 has a polypeptide sequence of SEQ ID No: 2 or a polypeptide sequence having at least 60% similarity to SEQ ID No: 2. Preferably, a polypeptide sequence having at least 80% similarity to SEQ ID No: 2; more preferably. a polypeptide sequence having at least 90% similarity to SEQ ID No: 2; even more preferably, a polypeptide sequence having at least 95% similarity to SEQ ID No: 2; and most preferably, a polypeptide sequence of SEQ ID No: 2.

The present invention provides a transformed plant cell, which comprises the above-mentioned mutated nucleotide molecule. Preferably, the T-DNA segment is inserted in the third intron of the nucleotide sequence of the transcription factor bHLH142; more preferably, the T-DNA segment is inserted at +1257 bp.

In one preferred embodiment of the transformed plant cell comprising the mutated nucleotide molecule, the nucleotide sequence of the transcription factor bHLH142 has a DNA sequence of SEQ ID No: 1 or a DNA sequence having at least 60% similarity to SEQ ID No: 1. Preferably, a DNA sequence having at least 80% similarity to SEQ ID No: 1; more preferably. a DNA sequence having at least 90% similarity to SEQ ID No: 1; even more preferably, a DNA sequence having at least 95% similarity to SEQ ID No: 1; and most preferably, a DNA sequence of SEQ ID No: 1. In addition, the transcription factor bHLH142 has a polypeptide sequence of SEQ ID No: 2 or a polypeptide sequence having at least 60% similarity to SEQ ID No: 2. Preferably, a polypeptide sequence having at least 80% similarity to SEQ ID No: 2; more preferably. a polypeptide sequence having at least 90% similarity to SEQ ID No: 2; even more preferably, a polypeptide sequence having at least 95% similarity to SEQ ID No: 2; and most preferably, a polypeptide sequence of SEQ ID No: 2.

The present invention also provides a male sterile mutant plant comprising the above-mentioned mutated nucleotide molecule, and the transcription factor bHLH142 is not expressed; particularly, not expressed in anthers. Preferably, the T-DNA segment is inserted in the third intron of the nucleotide sequence of the transcription factor bHLH142; more preferably, the T-DNA segment is inserted at +1257 bp.

In one preferred embodiment of the male sterile mutant plant, the nucleotide sequence of the transcription factor bHLH142 has a DNA sequence of SEQ ID No: 1 or a DNA sequence having at least 60% similarity to SEQ ID No: 1. Preferably, a DNA sequence having at least 80% similarity to SEQ ID No: 1; more preferably. a DNA sequence having at least 90% similarity to SEQ ID No: 1; even more preferably, a DNA sequence having at least 95% similarity to SEQ ID No: 1; and most preferably, a DNA sequence of SEQ ID No: 1. In addition, the transcription factor bHLH142 has a polypeptide sequence of SEQ ID No: 2 or a polypeptide sequence having at least 60% similarity to SEQ ID No: 2. Preferably, a polypeptide sequence having at least 80% similarity to SEQ ID No: 2; more preferably. a polypeptide sequence having at least 90% similarity to SEQ ID No: 2; even more preferably, a polypeptide sequence having at least 95% similarity to SEQ ID No: 2; and most preferably, a polypeptide sequence of SEQ ID No: 2.

In one preferred embodiment of the male sterile mutant plant, the male sterile mutant plant of the present invention is a homozygous mutant.

In one preferred embodiment of the male sterile mutant plant, the plant is a monocot; preferably, the monocot is rice, maize, wheat, millet, *sorghum* or *Brachypodium distachyon*.

In one preferred embodiment of the male sterile mutant plant, the plant is a dicot; preferably, the dicot is *Arabidopsis* or *Brassica* species.

The present invention also provides a transformed plant cell, which comprises a plasmid comprising the sequence of the transcription factor bHLH142 and a strong promoter.

In one preferred embodiment of the transformed plant cell comprising the sequence of the transcription factor bHLH142, the transcription factor bHLH142 has a DNA sequence of SEQ ID No: 1 or a DNA sequence having at least 60% similarity to SEQ ID No: 1. Preferably, a DNA sequence having at least 80% similarity to SEQ ID No: 1; more preferably. a DNA sequence having at least 90% similarity to SEQ ID No: 1; even more preferably, a DNA sequence having at least 95% similarity to SEQ ID No: 1; and most preferably, a DNA sequence of SEQ ID No: 1.

In one preferred embodiment of the transformed plant cell comprising the sequence of the transcription factor bHLH142, the strong promoter is Ubiquitin promoter, CaMV 35S promoter, Actin promoter, an anther tapetum-specific promoter or a pollen-specific promoter; preferably, the anther tapetum-specific promoter is Osg6B or TA29, and the pollen-specific promoter is LAT52 or LAT59.

The present invention also provides a reversible male sterile transgenic plant, wherein the transcription factor bHLH142 is overexpressed; particularly, overexpressed in anthers.

In one preferred embodiment of the reversible male sterile transgenic plant, the nucleotide sequence of the transcription factor bHLH142 has a DNA sequence of SEQ ID No: 1 or a DNA sequence having at least 60% similarity to SEQ ID No: 1. Preferably, a DNA sequence having at least 80% similarity to SEQ ID No: 1; more preferably. a DNA sequence having at least 90% similarity to SEQ ID No: 1; even more preferably, a DNA sequence having at least 95% similarity to SEQ ID No: 1; and most preferably, a DNA sequence of SEQ ID No: 1. In addition, the transcription factor bHLH142 has a polypeptide sequence of SEQ ID No: 2 or a polypeptide sequence having at least 60% similarity to SEQ ID No: 2. Preferably, a polypeptide sequence having at least 80% similarity to SEQ ID No: 2; more preferably. a polypeptide sequence having at least 90% similarity to SEQ ID No: 2; even more preferably, a polypeptide sequence having at least 95% similarity to SEQ ID No: 2; and most preferably, a polypeptide sequence of SEQ ID No: 2.

In one preferred embodiment of the reversible male sterile transgenic plant, the expression of the transcription factor bHLH142 is controlled by a strong promoter; preferably, by an Ubiquitin promoter, CaMV 35S promoter, Actin promoter, an anther tapetum-specific promoter or a pollen-specific promoter; preferably, the anther tapetum-specific promoter is Osg6B or TA29, and the pollen-specific promoter is LAT52 or LAT59.

In one preferred embodiment of the reversible male sterile transgenic plant, the pollen fertility of the plant is recovered under low temperature. Particularly, the pollen fertility of the plant is recovered at 21-23° C.

In one preferred embodiment of the reversible male sterile transgenic plant, the plant is a monocot; preferably, the monocot is rice, maize, wheat, millet, *sorghum* or *Brachypodium distachyon*.

In one preferred embodiment of the reversible male sterile transgenic plant, the plant is a dicot; preferably, the dicot is *Arabidopsis* or *Brassica* species.

The present invention also provides a method for preparing the above-mentioned reversible male sterile transgenic plant, comprising:
 (a) constructing a plasmid comprising the DNA sequence of bHLH142 and a strong promoter, and
 (b) introducing the plasmid into a target plant.

In one preferred embodiment of the preparation method, the DNA sequence of bHLH142 is SEQ ID No: 1 or a DNA sequence having at least 60% similarity to SEQ ID No: 1. Preferably, a DNA sequence having at least 80% similarity to SEQ ID No: 1; more preferably. a DNA sequence having at least 90% similarity to SEQ ID No: 1; even more preferably, a DNA sequence having at least 95% similarity to SEQ ID No: 1; and most preferably, a DNA sequence of SEQ ID No: 1.

In one preferred embodiment of the preparation method, the strong promoter is Ubiquitin promoter, CaMV 35S promoter, Actin promoter, an anther tapetum-specific promoter or a pollen-specific promoter; preferably, the anther tapetum-specific promoter is Osg6B or TA29, and the pollen-specific promoter is LAT52 or LAT59.

In one preferred embodiment of the preparation method, the plasmid is introduced into calli of the target plant via *Agrobacterium tumefaciens*.

DETAILED DESCRIPTION OF THE INVENTION

Figure 1:
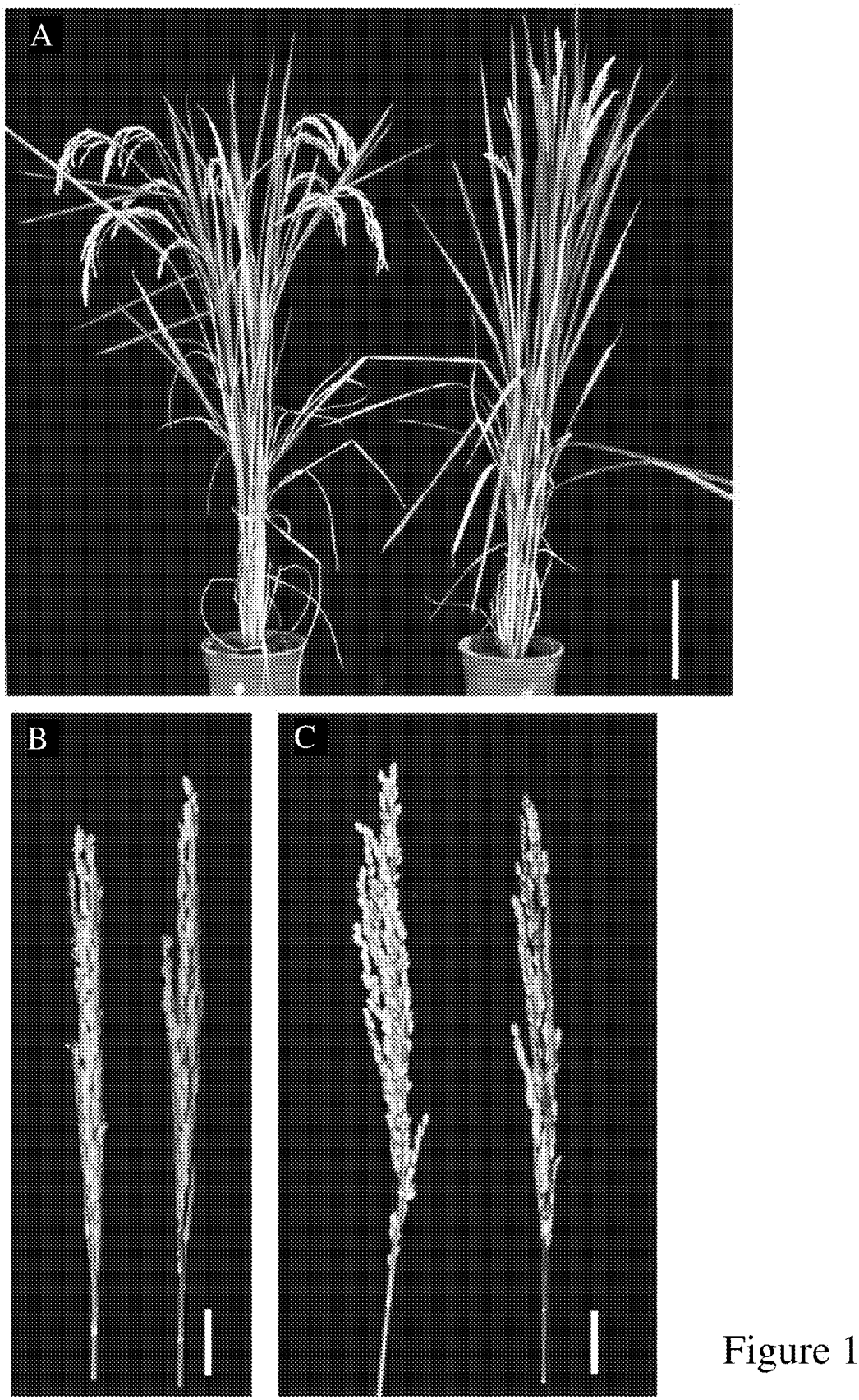
FIG. 1. Phenotypic Analyses of ms142 Mutant. (A) Comparison of the wild-type plant (left) and ms142 mutant (right) after bolting; (B) comparison of the wild-type panicle (left) and ms142 mutant (right) at heading stage; (C) comparison of the wild-type panicle (left) and ms142 mutant (right) at seed maturation stage; (D) phenotype of the wild-type spikelet (left) and ms142 mutant (right) one day before anthesis; (E) phenotype of the wild-type spikelet (left) and ms142 mutant (right) after anthesis; (F) comparison of the wild-type grain (left) and ms142 mutant (right) at harvest stage; (G) phenotype of the wild-type grain (left) and ms142 mutant (right) after removing rice husk; (H) phenotype of the wild-type anther (left) and ms142 mutant (right) one day before anthesis; (I) staining of anther by Sudan black in the wild-type (left) and ms142 mutant (right); (J) staining of wild-type pollen grains by $I_2$/KI solution; and (K) staining of mutant pollen grains by $I_2$/KI solution. Bars=20 cm in (A), 3 cm in (B) and (C), 0.5 cm in (D) to (G), 0.1 cm in (H) and (I), and 20 µm in (J) and (K).
Figure 1:
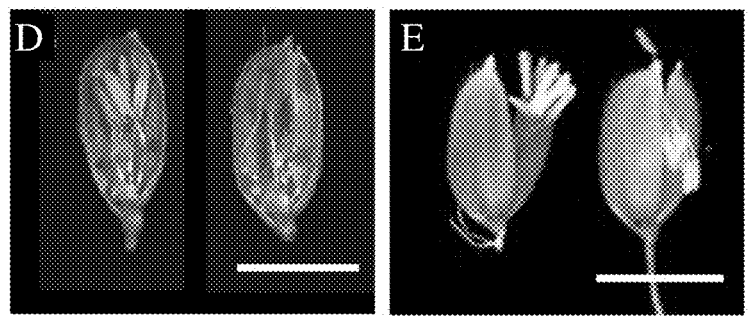
Figure 1:
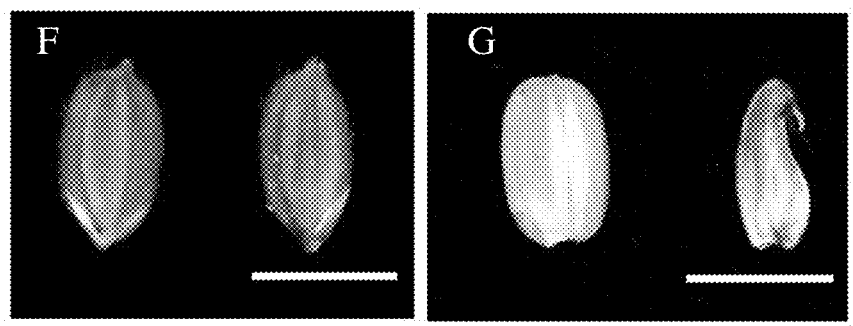
Figure 1:
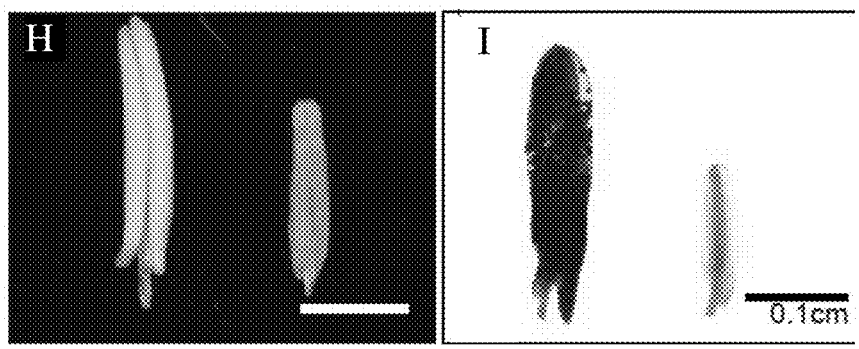
Figure 1:
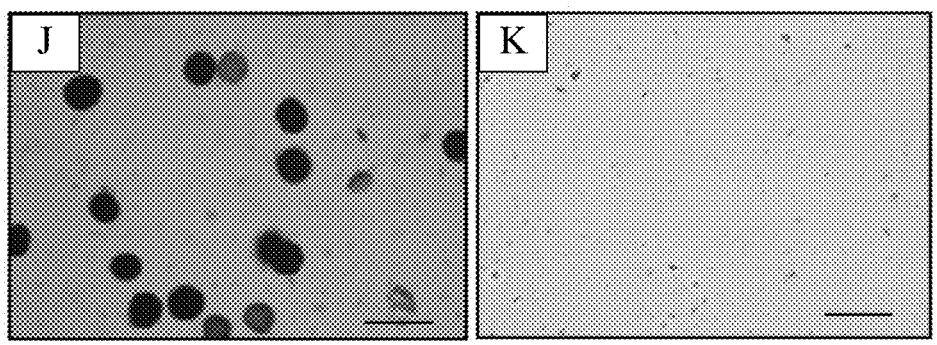

The following examples are presented to demonstrate the present invention. These examples are in no way to be construed as a limitation on the invention. The disclosure would enable those skilled in the art to practice the present invention without engaging in undue experimentation. All recited publications are incorporated herein by reference in their entirety.

Plant Materials and Growth Conditions

The seed of ms142 mutant was obtained from TRIM library. Seedlings of ms142 mutant and its WT (TNG67) were raised in half strength Kimura solution for 3 weeks and then transplanted into soil in AS-BCST GMO screen house located in Tainan, Taiwan.

Anther Anatomy

Spikelets and anthers of the WT and ms142 mutant were sampled at various stages of development and fixed overnight in phosphate buffer, pH 7.0, that contained 4% paraformaldehyde and 2.5% glutaraldehyde. They were then rinsed with the same buffer and post fixed for 30 min in phosphate buffer, pH 7.0, containing 1% osmium tetroxide. After dehydration, the specimens were embedded in Spurr's Resin (EMS). The processor, KOS Rapid Microwave Labstation, was chosen for post fixation, dehydration, resin infiltration, and embedding. For TEM, ultrathin sections (90 to 100 nm thick) collected on coated copper grids were stained with 6% uranyl acetated and 0.4% lead citrate and examine using transmission electron microscope.

Total RNA Isolation and PCR.

Total RNA was isolated from rice tissues using MaestroZol™ RNA PLUS (Invitrogen) as described by the supplier. Various rice organs at different developmental stages were harvested for RNA isolation: root, shoot, flag leaf, internode, panicles of 0.5 cm, 1 cm, 5 cm, 9 cm, and 20 cm length, spikelet at 1 day before anthesis (1 DBA), lemma, palea, anthers, ovary, seed at 5 days after pollination (S1), 15 days after pollination (S3), 25 days after pollination (S5), and callus. The stages of anthers were classified into the following categories according to spikelet length: microspore mother cell (MMC) with spikelet length of approximately 2 mm, meiosis (4 mm), young microspore (YM, 6 mm), vacuolated pollen (VP, 8 mm), mitosis pollen (MP, 8 mm with light green lemma), and mature pollen at one day before anthesis (1 DBA). Total RNA was treated with DNase (Promega), and 1 µg RNA was used to synthesize the oligo(dT) primed first-strand cDNA using the M-MLV reverse transcriptase cDNA synthesis kit (Promega). One µL of the reverse transcription products was used as template in PCR reactions. Ubiquitin-like 5 and 18srRNA were used as normalizer control. Each sample has three biological repeats.

qRT-PCR Analysis.

Fifteen µL of RT-PCR reaction contained 4 µL of 1/4 diluted cDNA, 3 µM of primers, and 7.5 µL of 2×KAPA SYBR FAST master mix (KAPA Biosystems, USA). Quantitative Real-Time PCR (qRT-PCR) was performed using a CFX96 Real-Time PCR detection system (Bio-Rad, USA). Quantification analysis was carried out using CFX Manager Software (Bio-Rad, USA). Primers used for qPCR are listed in Table 1.

TABLE 1

Primers Used in Examples

| Primers Names | RAP Accession No. | Sequence (5'→3') | Sequence ID |
|---|---|---|---|
| Screening of ms142 Mutant T-DNA inserted | | | |
| S80qPCR-F3 | Os01g0293100 | GGAGCACGTACATCCAGCGG | SEQ ID No. 3 |
| S80-GT-R3 | | ACTCATCCACCACTTCAATCAGCC | SEQ ID No. 4 |
| RB-13 | | AACTCATGGCGATCTCTTACC | SEQ ID No. 5 |
| Hyg-F | | GATGTAGGAGGGCGTGGATA | SEQ ID No. 6 |
| Hyg-R | | CGTCT GCTGC TCCAT ACAAG | SEQ ID No. 7 |
| Quantitative Real-time PCR | | | |
| S80qPCR-F3 | Os01g0293100 | GGAGCACGTACATCCAGCGG | SEQ ID No. 8 |
| S80-GT-R3 | | ACTCATCCACCACTTCAATCAGCC | SEQ ID No. 9 |
| OsMS2-qRT-F | Os03g0167600 | TGGAGCAGTTCGCCAGCTACG | SEQ ID No. 10 |
| OsMS2-qRT-R | | CTTCTCCTCCTCCGACATCTCCC | SEQ ID No. 11 |

TABLE 1 -continued

Primers Used in Examples

| Primers Names | RAP Accession No. | Sequence (5'→3') | Sequence ID |
|---|---|---|---|
| OsTDR-F | Os02g0120500 | CGCTCGCTCGTCCCAAACAT | SEQ ID No. 12 |
| OsTDR-R | | CGGTCATTGCTGGGTCCTTGT | SEQ ID No. 13 |
| Os C6-F | Os11g0582500 | TCCTCCTCGTCCTGCTCGTC | SEQ ID No. 14 |
| Os C6-R | | GGTTCACGATGTGGCACAGG | SEQ ID No. 15 |
| 18SrRNA-F2 | | TTAGG CCACG GAAGT TTGAG G | SEQ ID No. 16 |
| 18SrRNA-R2 | | ACACT TCACC GGACC ATTCA A | SEQ ID No. 17 |
| Udt1-F | Os07g0549600 | GATCTTCTGGACCAAGAGGGCAG | SEQ ID No. 18 |
| Udt1-R | | GTCAGGAGTGTCTCAGATGCTTGG | SEQ ID No. 19 |
| OsCP1-F | Os09g0381400 | GGACCACCTGCTGCTGCAACT | SEQ ID No. 20 |
| OsCP1-R | | GAACACTTCGTGCCATCGCC | SEQ ID No. 21 |
| bHLH141-F | Os04g0599300 | TGGTGGAACAGAAGAGGCATGG | SEQ ID No. 22 |
| bHLH141-R | | GCATGAAGCAGAGAGTTGGCCTT | SEQ ID No. 23 |
| OsUBQ5-F | Os01g0328400 | GCGGAAGTAAGGAAGGAGGAGG | SEQ ID No. 24 |
| OsUBQ5-R | | GGCATCACAATCTTCACAGAGGTG | SEQ ID No. 25 |
| MSP1-F | Os01g0917500 | GAGAACTTCGAGCCGAGGGTCT | SEQ ID No. 26 |
| MSP1-R | | CCAGCCGACGAGGTTTCCAC | SEQ ID No. 27 |
| AP37-F | Os04g0448500 | AGGCGGGCAGCGTCTCCAT | SEQ ID No. 28 |
| AP37-R | | CCATAAGCCAGCCACGATGATGA | SEQ ID No. 29 |
| GAMyb-F | Os01g0812000 | CATCCTGGTCCATTCCTCAATGAC | SEQ ID No. 30 |
| GAMyb-R | | TTCAGGATGAGGTGAAGTGTCCC | SEQ ID No. 31 |

Subcellular localization analysis

| | | | |
|---|---|---|---|
| S80cDNA-XbaI-F | | TATCTAGAGTGGTAGAGTGCGAGGAAG | SEQ ID No. 32 |
| KpnI-S80-nonstop-R | | GAGGTACCAGGTACTCATCCACCACTTCAA | SEQ ID No. 33 |

In situ hybridization analysis

| | | | |
|---|---|---|---|
| S80qPCR-F2 | | CATGTTCAACACCAAGATTCATTCG | SEQ ID No. 34 |
| S80FLcds-R2 | | TGCAAACCATGACATACCAAAGATC | SEQ ID No. 35 |

BiFC construction

| | | | |
|---|---|---|---|
| BiFC-TDR-BamHI-F | | AGGGATCCCACCACATGGGAAGAGGAGACC | SEQ ID No. 36 |
| BiFC-TDR-SalI-R | | ATGTCGACTCAAACGCGAGGTAATGCAGG | SEQ ID No. 37 |
| BiFC-UDT-BamHI-F | | GTGGATCCATGCCGCGGCGCGCGAGGGCGA | SEQ ID No. 38 |
| BiFC-UDT-Xho-R | | TGCTCGAGATGCTTGGAACCTCCACAATGCTGG | SEQ ID No. 39 |
| BiFC-bHLH141-Pst-F | | AGCTGCAGTTTGCCAAAATGATTGTTGGG | SEQ ID No. 40 |
| BiFC-bHLH141-Sal-R | | GCGTCGACTTGAATATGTCGAGGGCCTGG | SEQ ID No. 41 |
| S80-Y2H-AD-BamH-F | | GTGGATCCCGAGGAAGATGTATCACC | SEQ ID No. 42 |
| S80-Y2H-AD-Xho-R | | AGCTCGAGCTAGTTAGTACTCATCCACCAC | SEQ ID No. 43 |

Yeast Two Hybrid

| | | | |
|---|---|---|---|
| S80-Y2H-AD-BamH-F | | GTGGATCCCGAGGAAGATGTATCACC | SEQ ID No. 44 |
| S80-Y2H-AD-Xho-R | | AGCTCGAGCTAGTTAGTACTCATCCACCAC | SEQ ID No. 45 |
| S80-Y2H-BD-Pst-R | | CGCTGCAGTTAGTACTCATCCACCACTT | SEQ ID No. 46 |
| 141-Y2H-BD-Eco-F | | AGGAATTCTTTGCCAAAATGATTGTTGGG | SEQ ID No. 47 |
| 141-Y2H-BD-Pst-R | | GCCTGCAGTTAGTTGAATATGTCGAGGGCCTG | SEQ ID No. 48 |
| TDR-Y2H-EcoR-F | | AAGAATTCATGGGAAGAGGAGACCACCTGC | SEQ ID No. 49 |
| TDR-Y2H-BamH-R | | CTGGATCCTCAATCAAACGCGAGGTAATGCA | SEQ ID No. 50 |
| Y2H-Deletion141-N-BD | | TAGAATTCATGAAGGGTGAGTTCGGAAAGGGC | SEQ ID No. 51 |
| Y2H-Deletion141-C-BD | | AGGTCGACTTACCCTCTCCTGCATTCAAGTACA | SEQ ID No. 52 |
| Y2H-DeletionTDR-N-BD | | ACGAATTCATGCATGTCCACCATAAGCCGC | SEQ ID No. 53 |

Co-Immunoprecipitation

| | | | |
|---|---|---|---|
| CO-IP-HA-SacII-F | | AACCGCGGAAATGAGTTACCCATACGATGTTCCTG | SEQ ID No. 54 |
| CO-IP-HA-Not-R | | CAGCGGCCGCAGCGTAATCTGGAACGTCATAT | SEQ ID No. 55 |
| CO-IP-TDR-HA-Xba-F | | AATCTAGACATGGGAAGAGGAGACCACCTGC | SEQ ID No. 56 |
| TDR-cDNA-SalI-R | | CAGTCGACTCAATCAAACGCGAGGTAATGCA | SEQ ID No. 57 |
| CO-IP-S80-Flag-Xba-F | | CGTCTAGAGATGTATCACCCGCAGTG | SEQ ID No. 58 |
| S80-Y2H-AD-Xho-R | | AGCTCGAGCTAGTTAGTACTCATCCACCAC | SEQ ID No. 59 |

Promoter transience assay

| | | | |
|---|---|---|---|
| BiFC-TDR-BamHI-F | | AGGGATCCCACCACATGGGAAGAGGAGACC | SEQ ID No. 60 |
| TDR-cDNA-SalI-R | | CAGTCGACTCAATCAAACGCGAGGTAATGCA | SEQ ID No. 61 |
| BiFC-bHLH141-Pst-F | | AGCTGCAGTTTGCCAAAATGATTGTTGGG | SEQ ID No. 62 |
| bHLH141-cDNA-Sal-R | | GCGTCGACTTAGTTGAATATGTCGAGGGCCT | SEQ ID No. 63 |
| 141-2kb-P-Spe-F | | CCACTAGTTGCTTTGGTTTGATTCCTGGAAG | SEQ ID No. 64 |
| 141-2kb-P-Sal-R | | AAGTCGACAACAGTGCTAGGCACCTTCGC | SEQ ID No. 65 |
| S80-Y2H-AD-BamH-F | | GTGGATCCCGAGGAAGATGTATCACC | SEQ ID No. 66 |
| S80-Y2H-AD-Xho-R | | AGCTCGAGCTAGTTAGTACTCATCCACCAC | SEQ ID No. 67 |

TABLE 1 -continued

Primers Used in Examples

| Primers Names | RAP Accession No. | Sequence (5'→3') | Sequence ID |
|---|---|---|---|
| *RNAi transgenic line* | | | |
| PANDA-GUS-F-Spe | | acactagtATCTACCCGCTTCGCGTCGG | SEQ ID No. 68 |
| PANDA-GUS-R-Pst | | atctgcagCGAGTGAAGATCCCTTTCTTGTTACC | SEQ ID No. 69 |
| 142RNAi-5'-F-Pst | | gcctgcagCAACAAACCTAGTTAATTTAGCTCTAGTTGG | SEQ ID No. 70 |
| 142RNAi-5'-R-Sal | | gcgtcgacAGGCTCTCAAGCGGCATCAG | SEQ ID No. 71 |
| 142RNAi-5'-F-Spe | | gcactagtCAACAAACCTAGTTAATTTAGCTCTAGTTGG | SEQ ID No. 72 |
| 142RNAi-5'-R-Not | | tagcggccgcAGGCTCTCAAGCGGCATCAG | SEQ ID No. 73 |
| *Overexpression bHLH142 in transgenic rice* | | | |
| Hyg-F | | GATGTAGGAGGGCGTGGATA | SEQ ID No. 74 |
| Hyg-R | | CGTCT GCTGC TCCAT ACAAG | SEQ ID No. 75 |
| S80qPCR-GT-F | | GGAGCACGTACATCCAGCGG | SEQ ID No. 76 |
| Pzp200-NOS-R | | ATCGCAAGACCGGCAACAGGA | SEQ ID No. 77 |
| *Overexpression bHLH142 in transgenic maize* | | | |
| Zm142-F | | TGACCTCGTCCACCTCTCCG | SEQ ID No. 117 |
| Zm142-R | | CAGTCTGTAACGAGCAAGCGGA | SEQ ID No. 118 |

In-Situ Hybridization

Spikelets of TNG67 and ms142 at various developmental stages were fixed in PFA [4% paraformaldehyde, 4% dimethylsulfoxide 0.25% glutaraldehyde, 0.1% Tween 20, 0.1% Triton X-100 in diethyl pyrocarbonate (DEPC)-treated H2O] at 4° C. overnight immediately after collection, and the tissue processor, KOS Rapid Microwave Lab station, was used for dehydration and wax infiltration. After embedding, sections of 10 μm thickness were prepared by a rotary microtome (MICROM, 315R) and mounted on APS adhesive microscope slides (FINE FROST). Tissue sections were deparaffinized with xylene, rehydrated through an ethanol series, and pre-treated with proteinase K (2 mg/mL) in 1-phosphate buffered saline (PBS) at 37° C. for 30 min. Pre-hybridization (additionally including 25% RNAmate, BioChain) and hybridization were performed according to the previous protocols[39]. Hybridization was performed at 59° C. in hybridization solution: 50% formamide, 4×SSPE, lx Denhardt's (Fluka), 250 μg/mL fish sperm DNA (Genemarker), 250 μg/mL yeast tRNA (Sigma), 10% dextran sulfate, 40 U/mL RNasin (Promega) and 40 ng of DIG-labeled RNA probe/per slide. RNA probes were synthesized by in vitro transcription of the RT-PCR fragment in pGEM-T easy vector using the DIG RNA labeling kit (SP6/T7, Roche). Antisense RNA probes were synthesized by SP6 RNA polymerase, while sense RNA probes were synthesized by T7 RNA polymerase and used as control. Sequence of fragment to synthesize RNA probe (SEQ ID No. 119):

5'-catgttcaacaccaagattcattcgggatctccagtgtttgcaagtg cagtggccagcaggctgattgaagtggtggatgagtactaactagctcga gctagctaattagccgaccgaccgatcgatatgatgaaagtttctatgtt gctagctagctagggttcttggatgcatgagtactgagtagctctttaat taatttccttttaattttagactgtttaatttggattggtaaagactcgt gttagcttttgggagatctttggtatgtcatggtttgca-3'

Gene Hierarchy Analysis Using Knockout Mutants

We have some T-DNA/Tos17 knock out mutant lines in hands such as: in udt1 (TRIM), bHLH142 (ms142, TRIM), and eat1 (bHLH141) Tos17 mutant line H0530 (background of Hitomebore) was obtained from Rice Tos17 Insertion Mutant Database (http://tos.nias.affrc.go.jp/). Ranking sequences were confirmed by genotyping PCR amplification with specific primers (Table 1). We will verify their gene hierarchy using these mutants. Spikelet samples at various developmental stages were collected, isolated RNA, and performed qRT-PCR analysis.

TUNEL Assay

PCD is characterized by cellular condensation, mitochondria and cytoskeleton degeneration, nuclear condensation, and internucleosomal cleavage of chromosomal DNA[33]. To investigate the nature of the tapetal breakdown in ms142, the terminal deoxynucleotidyl transferase-mediated dUTP nick-end labeling (TUNEL) assay was performed using DeadEnd Fluorometric TUNEL system (Promega). This assay detects in situ DNA cleavage, a hallmark feature of apoptosis-like PCD, by enzymatically incorporating fluorescein-12-dUTP into the 3'-OH ends of fragmented DNA. Stage of anther development was based primarily on spikelet size and developmental stages.

Subcellular Localization of bHLH142

For subcellular localization of bHLH142, the coding sequences of the gene were subcloned into p2FGW7 (Invitrogen) to generate bHLH142-GFP fusion genes driven by the CaMV 35S promoter. Rice protoplasts were isolated and transformed using the polyethylene glycol (PEG) method following procedures described previously[34]. After incubation at room temperature for 16 h in light, protoplasts were observed with a Zeiss LSM 780 laser scanning confocal microscope.

Phylogenetic Analysis of the bHLH142 Subfamily

The bHLH142 protein sequence was used to search for the closest homologues from their plant species using BLASTP programs. Multiple sequence alignment of full-length protein sequences was performed using ClustalW online (http://www.ch.embnet.org/software/ClustalW.html), and the alignment was used to perform neighbor-joining analysis using Mega 5.05[35]. The numbers at the nodes represent percentage bootstrap values based on 1000 replications. The length of the branches is proportional to the expected numbers of amino acid substitutions per site. Gene identification numbers used to generate the phylogenetic trees and the alignment are listed in Table 2.

TABLE 2

Peptide Sequences Used for Phylogenetic Analysis

| Peptide ID. | Peptide sequence (N'→C') | Sequence ID |
|---|---|---|
| BradXP_003567568 | myhpqcellmpheslqmdavvggshlaaqsyvsaipaelnfhllhsfvdtaaspqptvdyffpgtdpppaavfeql aatnhhamsmlrdyyggqypaetylrggprttgsssslvfgvandesaaynmvgpfvesspttraagggrknrgsra aggpahggvekkekqrrlrltekytalmlliipnrtkedratvisdaieyiqelgrtveeltllvglthrrngagehhlhggdv vdaapavgaagelvlaaesseegevqaplaalqpirstyiqrsketfvdvrivedevniktkrrdgclaaasralddlhldlv vhlsggkigdchiymfntkihgspvfasavasklievvdey | SEQ ID No. 78 |
| TriuEMS50437 | myhqqcellmpheglqmdagggehhlaagsavpaelnfhllsyvdtayspqqptveyffggadphaqfeqlaanhqa mtvirdyyggqyhpatadayipggprtgssslvfgaaeeesaaymvggfgcspkprasgsrkrgragssfhgfpangg vekkekgrrqrlsekftalmlliipnrtkedratviydaieyiqelgrtveeltllvekkrgrrehggdvvdpapivaggec sagevaaavmpampappgpirstyiqrrsketfvdvrivedevniktkrrdgclaaasralddlhldlvhlsggkigdc hiymfntkihgspvfasavasklievvdey | SEQ ID No. 79 |
| SbXP_002457706 | myhpqcellmaheaqdldaaggphhllaysgvagsipaelsfhllhslcataavnmsvtpqstidyflgvggadphqpaa lqyeplpppgghhqhtmmlrdycsnggggghyptaepylrgtrtgalvfgatdddesaaaympggpfvetspppra tggrkrgralgggfhaglangvekkekgrrqrlitekytalmhliipnvtkpdratvisdaieyiqelgrtveeltllveldurrr elqgdvvdaaptavvvaaaatgeaeesseegevappppaavgrqpirstyiqrrsketfvdvrivedevniktlarrd gclaaasralddlhldlvhlsggkigdchiymfntkihgssvfasavagrlmevvdey | SEQ ID No. 80 |
| ZmLOC100283549 | Myhpqcelltmahetpldaggphltvsgvasipaelsfhllhsldaaaavnpvtappqstidyflggadphqqamqye plpppaagghhgytmdmfrdycdghyptaepyirgtmtgalvfgatdddsaaaympgghfetsppppratcgrkrg ralgggfhavlangvekkekgrrqrlitekytalmhliipnvtkdratvisdaieyiqelgrtveeltllveklarrrelggdvvd aapaavvaaageaeesseegevappppavprqpirstyiqrrsketfvdvrivedevniktkmdgclaaasralddlrldlv hlsggkigdcqiymfntkihgssvfasavagrlmevvdey | SEQ ID No. 81 |
| AegtEMT16792 | myhqqcellmphedlqmdagggshhlaaasavpaelnfhllsyvddaaysppqptveyffggadphahsfhgfpang gvekkekgrrqrlsekftalmlliipnrtkedratvlydaieyiqelgrtveeltllvekkrgrrehggdvvdpaplivagege csagelrappppgpgpirrsketfrvdvrivedevniktkmdgclaaasralddlhldlvhlsggkigdchiymf ntkihgspvfasavasklievvdey | SEQ ID No. 82 |
| ZmEU974003 | mvfskiqykvvsskiqtptivrvetthetmekllarrrelggdvvdaaapaavvaageaeesssgevapppavprqpir styiqrrskdtsvdvrivedevniktlarridgclaaasralddlrldlvhlsggkigdcqiymfntkihgssvfasavagrl mevvdey | SEQ ID No. 83 |
| VitvCBI38213 | mcrkitrprrmyvyeenacfdgtksvaegdegfsgsvappptmsfedstnmrvsmedasatmeielhqqlafdmd qqcynsnndgnsnqvfsyemqemqfinhhqqqedplllqqhqaemqahqnfsaaypppptpdllnlfihlprctpssl lpnssiftnpdssataasgillydplfhlnlppqppvgggygggddhrqfdngvlkftrdmacigkgregktksfatekq rrehlndkynalrslvpnptksdrasvvgdaieyirelltrvnelkllvekkrcgrerskhhktedestgdvksssikpepd qsyneslrsswlqrksketevdvrriddevtiklvqrkkincllfvskildelqlldlhhvagghvgdyysflfntkiyegssv yasaianklievvdrqyaalpipptssf | SEQ ID No. 84 |
| VitvCAN77001 | Mymyeenacfdgtksvaegdegfsgsvappptmsfedstnmrvsmedasatmeielhqqlafdmdqqcynsnn dgndsnqvfsyemqemgfithhhqqqddplllqqhqaemqnaqqnfsaayppptpdllnlfihlprctpsslpnssisftn pdssataasgilydpllfhhlnlpppqppvfrelfgslphgynlpasrvgslfggmdereaasggyggdhhrqfdngvlkf trdmacigrgregkgtksfatekqrrehlndkynalrslvpnptksdrasvvgdaieyirellrtvnelkllvekkrcgrers krhktedestgdvkssssikpedqsyneslrsswlqrksdtevdvrriddevtiklvqrkkincllfvskildelqlqldlhh vagghvgdyysflfntkiyegssvyasaianklievvdrqyaaipipipptssf | SEQ ID No. 85 |

TABLE 2 -continued

Peptide Sequences Used for Phylogenetic Analysis

| Peptide ID. | Peptide sequence (N'→C') | Sequence ID |
|---|---|---|
| VitvXP_002265098.2 | mgrgfshllgfcksenpindlsrlkrysgpnlrlvhsesnrnniemvdafpvqidlnfsdsmdkatqtishprvkhsh qgarrrimrstnhaeqcqnkrgyrkitrprrmyvyeenacfdgtksvaegddegfsqsvappptnnsfedstnmrvsm edasatmeielhqqlafdmdqcynsndgndsnqvfsyemqemgfnhhqqqedpllqqhqaemqnahqnfs aayptpdlinlfhlprctpsllpnssisftnpdssataasgilydplfhlnlppqpvfrelfqslphgynlpasrvgslfgg gmdereasgygdgdhrqfdngvlkftrdmacigkgregkgtksfatekgrrehlndynalrslvpnptksdrasv vgdaieyirellrtvnelkllveldücgrersktrhtedestgdyksssslkpepdqsyneslrsswlqrksdktevdvrliid devtiklvqrkincllfvsklvldelqldlhhvagghvgdydysflfntkiyegssvyasalanklievvdrqyaaipipipip ptssf | SEQ ID No. 86 |
| RiccXP_002534354.1 | myeetgcfdpnsmvegaddglcqvlqippdqpqplmagsttnshsyeenlklsadqelsyhhsnmphhhgeddas asaaametqlqnhqmfdthlmqdssnqvmafnsstslqdatfaqtpdlinlfhlprgstssllpnssisftnpshtaplg fvgdlpmadtaasasslilydplfhlnlppqpplfrdlfqslpphgyslpgsmvnslfgagvggddhvegsgdggiyqdg dgeqgfdngvldftwdmpcmgkgradagkktkpfatergrrqhlndkykalqnlvpnptkadrtsvvgdaidyikellrt vnelkllveldcrcarersekrqkteedsignghdsscitkplgdpdqsfmngslrsswierkskdtevdvriidedvtiklvqr kkincllfvskvldelqldlhhvagghigdyysflfntkifegssvyasalanklievvdrhyastpstn | SEQ ID No. 87 |
| PoptXP_002323376 | myvetacfepnmvedvtddgfchaiplmagnsttnsfeehlklsmeefsshypqeesaaaasmeeiqlqhhmafs nnntnhhlmqqyrptqllsydhssnwdpniiqfqemhqvldqnssfdatantqsssippdlinlfniprctstsllpnssisft npahkaplgfmgvdntsarfdpytlapqphlfrelvgslpphgytlptplfgsggddhvdqgsgglsyqdgdhgdg vfeftdemacigkgiktgkvtkhfatergrrehlngkytalmlvpnpskndrasvvgeaidyikellrtvgelkllveldu cgrerskwrtteddggvevldnsdikvepdqsaynegslrsswlqrksdktevdvrliedevtiklvqrkrvncllyvsk vldelqldlhhaaggligdyysflfntkinegscvyasalanrlievvdrqyassttvpaagscy | SEQ ID No. 88 |
| Zm_HLH_containing_protein | miagggyfdgshdhilmegsmihdssqssiydntdveqqnfrfapfiiedhsnpanitseaarvidqihqlgidieqdh sdhmmqevppaetenlvpavygvqdhilshqiegphnitveqqrvlqydpasyrngtyaaandllnslhiqrcslipefp stehifsdpaqmvnrldiitndlpgvanhesgmmfdstvplgyhatqshmlkdlyhslpqnygiftsdderdgmvg vpgvsgnifqeidgrqfdsppilgsrkgkqfgkgtkqkanfatererrxqfnvkygalrslfpnptkndrasivgdaieyin elnrtvkelkilleldunsadrrkilldeeaaddqesssmqpvsdqxnqmgtirsswvqrrskecdvdrivddein ikftekkranslicaakvleefhlelihvvggiigdhhifmfntkipkgssvyacavakkllleaveikkqaynifn | SEQ ID No. 89 |
| PoptXP_002308327 | myeetacfetnnsiveggndgfcqvspfmtgssttssfeesfklsmeeisnhyhgeesaaaasmeeiqlqhhmafnn nchhlmeqyptnhhylsydhsnwdpntiqfqemhqvldqngnfnatantcpsllpdlinlfnlprctstsllpnssis ftnpahktpsgfmgvdatsvlfdsmplapqfirelvhslpphgylpaplfgqgqgdhvdglsgqglsyqdgdhgdgv feftaemacigkgirsksgkvitkhfatergrrehingkytalrnlvpnpskndrasvvgdainyikellrtveelklllvekkr ngrerilarkpeedggvdvlensntlveqdgstynmgslrsswlqrkshtevdvrliedevtiklvqrkkvncllsyskv ldelqldlhhaaggligdyyysflfntkinegscvyasglanklievvdrqyasstvpaac | SEQ ID No. 90 |
| SbXP_002452697 | miagggyfdgshdhilmegsmihdseqssiydntdveqqnfrlapfiiedhsnpanitsepavidqihqlgidmeqd hsdnhlmqgvppaetanlvpvvygvqdrilshqiegphnitveqqvldydpasygnqtyaaandlinslqiqrcslipefp stehifgdpaqmvmplditndlgvathesqmmfdstlplgyhatqshmlkdlyhslpqmygiftsdderdgmvqv agvsgnifqeidgrqfdspvlgtrrqfgkgkanfaterereqlnykygalrsswvqrrskecdvdrasivgdaidyinel nrtykelkilleldunstdrrkillddeaaddqessmqpvsddqnnqmgairsswvqrrskecdvdrivddeinik ftekkranslicaakvleefrlelihvvggiigdhhifmfntkipkgssvyacavakkllleaveikkqalnifn | SEQ ID No. 91 |

TABLE 2 -continued

Peptide Sequences Used for Phylogenetic Analysis

| Peptide ID. | Peptide sequence (N'→C') | Sequence ID |
|---|---|---|
| MedtXP_003638306 | mssgsgdkqnmheqngcfdpntkdegvenspndntnmnsleenfkpsveelpyhnhqnsqhldvstytngftpssvdieqlqnlglnigntynnmchthlvqeevyqnstwdpsvqdmdyvnhqehrqlseqqvqfieaqnhqsynpstildphyspdvinlhlprcssslltnssticmtmptqnppnfhnsmtflgdlpigssdntsgssvlydplypinlppqppalrelfqslprgysymptnsrngslfgggdemegdgmgvlefnrvtasvgkgrggkatkhfatekqrreqlngkykilrdlipsptkdrasvvgdaieyirelirtvnelkllveld(rhqremckrlkteddaaescnikpfgdpdgsirtswlqrkskdsevdvriiddadvtiklfqrkkvncllfvskvldelqlelnhvagghvgeycsflfnskvnegssvyasaianrvidvmdtqyaaglphisrl | SEQ ID No. 92 |
| MedtXP_003638303 | mssgsgdnqnmheqtgcfdpdtmaegvenspednnspqtmpnqvvagnsmnsieenfrpsveefsyhnhspqhledvstytngftpsseniaqqnlglnignyyynnmdnlleqevyqnsswdpsaqdmdyanhqeyhqlnnhkqsympsttqaphypspdvinlhlprsassllntnpsticitnptqkppnfhysmsflgdlpigsdnsgssvlydplfpinlpaqspalrelpqslprvysymptnsrngpfgggdemegdgmgvsqfnkvtafvgkgkatehlttekqrreqlkgrykilrslipnstkdadrsvvgdaieylrelirtvnelkllvekkrheieickrkhtedyaaeschmkpfgdpdgsirtswlqrkskdsevdvriiddadvtiklfqrkkvncllfvskvldelqlelnhvagghvgeycsflfnskviegssvhasaianrvidvidtqyaavvphnrm | SEQ ID No. 93 |
| CucsXP_004173553 | meldfqqaaaaptpgfdqeltsdsnpmlcldqsnwvgtqiqemgfithnhvqsfsdsaipptpytqppdllnflnmpptarcsnnssisfsnlhtpamgaflgdlppgdapnssstslsilydplflhlnlppqpplfrelfhslphgygmpaassrgrggslfpegseivereegtagvyedqdgsgvlefsrdmadcigkrdqkmtkhfaterqrvqlndkykalrslvrpiptkndrasivgdainyiqellrevkelklllvekkrssrersrkrvrtaeeieqggsessnakggegvvedqrynlrsswlqrktkdtevdvrivddevtvklvqrklncllvsklllediqldlhhvagghigdyysflfntkiyegssvyasaiankvmeavdrqynntsispltnty | SEQ ID No. 94 |
| BradXP_003580474 | Miiggdvfegsndhslmagslihdassgapkcngntdielqkfkvpsfsseilltnstnlsseaarainhlqhlgidleqdmqpvetatwdasicsiqdhiinnqiesedpqnilveqgiqqydaaiypnssytpapdllnllhctvapafpttsvfgdtslsstnyldlngeftgvaatpesglmftsdsalqlgyhatqshplkdichslpqmyglfpgederevmigvgsvggdifqdiddrqfdtvlecrrgksgefgtkgkganfatererreqlnykyktlkdlfpnptksdrasvvgdaieyidelnrtykelklivqkwhgnkrtkiikldeevaadgesssmkpmrddqdnqfdgtirsswvqrrskechidvrivenevnikteleddcvmslhaarvldefqlelihavggiigdhhifmfntkvsegssvyacavaktilqavdaqhqainifh | SEQ ID No. 95 |
| CucsXP_004139000 | myeetecsdpnsispetmphisafpnsfpppliaqgthpnfhhmnnlnlsidhisyhhhstalqpadameldfqqaaaaptpgfdqeltsdsnpmlcldqsnwvgtqiqemgfithhnvqsfsdsaipptpytqppdllnflnmpptarcsnnssisfsnlhtpamgaflgdlppgdapnssstslsilydplflhlnlppqpplfrelfhslphgygmpaassrgrggslfpegseiveregtagvyedqdgsgvlefsrdmadcigkrdqkmtkhfaterqrvqlndkykalrslvrpiptkndrasivgdainytqellrevkelklllveldcrssrerskrvrtaeeieqggs essnakggegvvedqrynlrsswlqrktkdtevdvrivddevtvklvqrklncllvsklllediqldlhhvagghigdyysflfntkiyegssvyasaiankvmeavdrqynntsispltnty | SEQ ID No. 96 |
| AegtEMT05766 | miaeggyfdgsrdailmagslihdsisicdnteiegqnfhgpsffiedicnptnitseesartinhiqhraefdmdqdllnghmiqegtqvetsnwvpamfgtqnhliisqqsieqmddydaasypdgahtaapdllnllqipyrsymtafpstehifgdpgqnagnqldinmdvlgraihdsgmmlqdstlqyndngshlfkdlyhslpgsfglfssddedramgvvgaagnlqeidgrqfgspklgrkkggfgkakanfatekerreqinvvkygalrsllpsptkndrasivgdaeyinelnrtikeltslvegdtkhrmkrlkldaaacdngesslqqvkddqdsqlngairsswiqrrskechvdvrivgneinikfteleddansllcaakvidefrlelihvvggvigdariffmfntkisegssvyasalaskliramemehlavdifs | SEQ ID No. 97 |

TABLE 2 -continued

Peptide Sequences Used for Phylogenetic Analysis

| Peptide ID. | Peptide sequence (N'→C') | Sequence ID |
|---|---|---|
| FravXP_004308623 | myvdsstaaagacnfdpntdtnpmesapevvlhhqmpttfasthdenlrslsmeeelsnyhhhnaameieqqlqt emgfgtmdqntnntnphlimpfdthqatnwdndnemqgqgqlppaptpdllslfhlpnssylphssitftnpktpggc fpgsfgyetlpetpsgavasnsvmydpmfhlinqlppqpqpplfrellqsiphgykrngslifsnggdevdgsrqlfen gvlefskemkpfgrgrggnkgtkhfaterqrrvqlndkfsalrelvpnptkpdrasvvgdaidyiqelkrtvselklvekk rcgrerskrhteqdigarddescnmkpigdpdhsyrmgslrsswlqrkskdtevdvriiddevtiklvqrrkinlll syskilldelqlelhhaagghignsyslfntkmyegsslyas aiankildtvdrqyaaaipptnsy | SEQ ID No. 98 |
| AegtEMT07628 | miwiegarhcfvkmivggdyfegsdhnlmtgslthdasslapkcndntnielqrfkvqsfs adilsdstnlsseaarainh lqhqlgiqleqdmppvetatwdtsictiqdqiinhqlsedpgnilvqgqiqqydaalypnsgytpapdlnlhctvapyf patasvfgdtalsggtnyldlngeftgvaaipdsglmytsdpalqlqyhaapshalkdichslpqnyglfpsedrdvmlg vgsvgdlfgqmdrqfetvlegrrgkgefgkgkanfaterereqlnykyktrlrmlfpnptkndrasvvgdaleyid elnrtvelkilveqkwhgtnrrrirkldeeaadgessmrpmrdeqdnqldgairsswvqrrsrechvdrrivenelni kltelddcansslhvakvldefhleihhvvggiqdhyifmfntkvtegssvyacavakrilqavdaqhqaldifn | SEQ ID No. 99 |
| AralXP_002879311 | Myeesscfdpnpmvdnngfcaaettfpvshqfqppvgstnsfnddlkiptmeefsafpsvislpnsetcnqnismnn hlinqiepnwgvsedntgffmntshpntttpipdllsllhlprcsmalpssnlsdimagscftydplchlnlppqppli psndysgyllgidtnttgqdesnvgdennaqfdsgiiefskeirrkgrgkrknkpfttererchlneryealkllipnpsk gdrasilqdgivinelmvselkylverkrcgrhkmeldnminmnsndhdnededidenmekkpesdvvdqc ssnnslrcswlqrkskvtevdvriddaevtikvvqkkincllvskvldqlqldlyhvaggqigehysflfntkiyegsti yasaianrvievvdkhymaalpiny | SEQ ID No. 100 |
| AralXP_002892324 | meggmfeeigcfdpnapaemtaessfspaeppptitvigsnsnscsledlseflhspqdsslpasasavyhqlhvnat pncdhgfqssmhqdqpsypqgsmwdngyqdfvnlvpithttpdllsllqlprslppfanpslqdiimttssvaayd plfhlnfplqppngtfigvdqqtelenqgvnlmqdeennmldnginrkgrsrkrkvfpterervhfkdrfgdlknlip nptkndrasivgeaidyikellrtidefkllvekkrtkqmregddvidenfkaqsevveqclinkknnalrcswlikrkskft evdvrriddadvrrikivqkkinclvfskvvdqlqldlhhvagaqigehhsflfnakicegsvyas aiadrvmelekq ymealstnngyhcyssd | SEQ ID No. 101 |
| AtbNP_180679 | myeesscfdpnsmvdnngfcaaettftvshqfgplgstnsfddlkiptmdefsvfpsvislpnsetcnqnismnnh linqmiqesnwgvsednsnfmntshpntttpipdllsllhlprcsmslpssdimagschydplfhlnlppqpplipsnd ysgyllgidtnttgrdesnvgdennmaqfdsgiiefskeirrkgrknkpfttererchlneryealkllipspskgdras ilqdgivinelmvselkylverkrcgrhknnevdnnmnknlddhgneddddenmekkpesdvidqcssnn slrcswlqrkskvtevdvriddavtikvvqkkincllvskvldqlqldlhhvaggqigehysflfntkiyegstiyasai anrvievvdkhytaslpnsny | SEQ ID No. 102 |
| AtbCAD58593 | myeesscfdpnsmvdnngfcaaettftvshqfgplgstnsfddlkiptmdefsvfpsvislpnsetcnqnismnnh linqmiqesnwgvsednsnfmntshpntttpipdllsllhlprcsmslpssdimagschydplfhlnlppqpplipsnd ysgyllgidtnttgrdesnvgdennaqfdsgiiefskeirrkargknkpfttererchlneryealkllipspskgdras ilqdgivinelmvselkylverkrcgrhknnevdnnmnkladhgneddddenmekkpesdvidqcssnn slrcswlqrkskvtevdvriddavtikvvqkkincllvskvldqlqldlhhvaggqigehysflfntkiyegstiyasai anrvievvdkhytaslpnsny | SEQ ID No. 103 |
| AtbNP_172107 | mgggmfeeigcfdpnapaemtaessfspseppptitvigsnsnscsledlsaflhspqdsslpasasayahqlhinat pncdhgfqssmhqdqpsyaqgsmwdngyqdfvnlgpithttpdllsllqlprslppfanpsiqdiimttssvaayd plfhlnfplqppngsfmgvdqqtetnqgvnlmydeennmlddglmrkgrskrkrifpterervhfkdrfgdlknlip nptkndrasivgeaidyikellrtidefkllvekkrvkqmregddvdenfkaqsevveqclinkknnalrcswlikrksk ftdvdvrriddevtikivqkkinclllfskvvdqlelldlhhvagaqigehhsflfnakisegssvyasaladrvmevlkk qymealsanngyhcyssd | SEQ ID No. 104 |

TABLE 2 -continued

Peptide Sequences Used for Phylogenetic Analysis

| Peptide ID. | Peptide sequence (N'→C') | Sequence ID |
|---|---|---|
| GlymXP_003548659 | myeesscydpdammaegaedcfpqmvseseavmsatptqththntfaysyscgedaanangpiamehpqqnpyn ysntqfveelysnqqftyhtpdlldllhlpnpigdnrtnvsysydpylhlnlqqqqpdrellphmpalmdfpgg aaggdqiqdfgngqlvdftqqevglarggkrtkqftsttergrvvdlsskfdalkelipnpsksdrasvvgdainyirelkrtv eelkllveldulekqrvmmrhkvetegessnldpaeyseslrsswigrktkdtevdrvivdnevtiklvqrkkidclvhvs hlldqlnldlqhvagghigdfcsylntkicegsslyastlqvmdtslaaasla | SEQ ID No. 105 |
| GlymXP_003524131 | Mheqtgcfdpntmgesvplfkdnfpqapspivvgntnsnmmdithlvqevidaypyqlstwdpatvqelqdiay anhteqgqgqgneqfqgietqncsqsynnpssildppyspsdllnllhmprcsasslltnpsicltnptqntpnfqnp maflgdltigsentsassvlydplfhnlppgpalrelfqslprgyslptnsrngslfaggdemegdgsqldmqvlefnrv tpsvgkgrggkatkhfatekqrreqingkykilrnlipsptkligwvfwfntddrasvvgdaidyirelirtvnelkllvekkr yakerykrpkteedaaecnikpfgqdpdggirtswlkrkskdsevdvriiddvtiklfqrkkincllfvskvldelqlelh hvagghvegycsflnskglvslrxiimegssvyasaianrvidvldsqytaavphtnsy | SEQ ID No. 106 |
| GlymXP_003532668 | mstgdrpkmhdqtgcfdpnttgesvplkdnfpqtlppsspmvvgnttnsnmmdnhlvqevidafpyqqstwd ptivqelqdmayanhteqtqgqqneqqfqfetqncsqsynnpssildppyspsdllnllhmprcsasslltnpsicltn ptqntpnfqnpmaflgdlpigentsassvlydplfhnlppqpalrelfqslprgyslptnsmgslfgggdemegdgs qldmqvlefnrvtlpsvgkgrrgkatkhfatekqrreqingkykilrnlipsptklvgfvltqdrasvvgdaidyirehrtv nelklivelthvagghvegycsflnskdrckrpkteedaaescnikpfgdpdggirtswlqrkskdsevdvriiddvtiklfqrkkincllfvs kvldelqlelhhvagghvgeycsflnskglvslrxiimegssvyasaianrvidvldsqyaaavphtnsy | SEQ ID No. 107 |
| LotjACN21644 | maegvsssqkdsfpqdldpqpqslmvtenttnsnnimdnhlvqevidaplyqqstwdpnvqevqdmsyanhpeqqf qhidaqnycqsytpsildpsypspdllnflhlptcsassltnppnicisnptqrtpnfqnsmtflgdlpmqpdntsassvly dplfhlnlpppalrelfqslprgyrlptssrddalfgggdemegdgsqldmqvldfnrdtasyvgkegregkgakpfate kdrreqingkykilrslipmptkiylvlfkpdrasvvgdaleyirelirtvmelkllvekkrhererckrpkneedaeescn ikpfgdpgyirtswlqrksdsevdvriiddvtikffqrkkincllfvskvldelqlelhhlagghvgeywsflnfnskrp vsltqviegssvyasaianrvidvldsqyaaavpqtssy | SEQ ID No. 108 |
| AtbAAL55717 | mgcfdpntpaevtvessfsqaeqtvesssfqaevpppppqvlvagstsnscsveveelsefhlspdcpqasstplqfhinppppppp cdqlhnnlihqmashqqqhsnwdngyqdfvnlgpnsattpdllsllhlprcslppnhhpssmlptsfsdimsssaaav mydplfhlnfpmqprdqnqlingscllgvedqiqmdangqmnvlyfegannmngfeneilefnngvtrkgrsrks rtspterrrvhfndrfidalknlipnptkidrasivgeaidyikellrtieefkmlvekkrcgrfrskkrarvgegggedgee eedtvnykpqsevdqscfnknmnnslrcswlkrksktevdvriiddevtiklvqkkkincllfftkvldqlqldlhhvag gqigehysflntkicegscvyasgiaddmevevekqymeavpsngy | SEQ ID No. 109 |
| AtbNP_180680 | meeereslyeemgcfdpntpaevtvessfsqaepppppqvlvagstsnsncsveveelsefhlspdcpqasstplqf hinppppppcdqlhnnlihqmashqqghsnwdngyqdfvnlgpmsattpdllsllhlpreslppnhhpssmlptsf sdimsssaaavmydplfhlnfpmqprdqnqlingscllgvedqiqmdanggnanvlyfegannmngfeneilefn ngvtrkgrgsrksrtspterrrvhfndrfidalknlipnptkidrasivgeaidyikellrtieefkmlvekkrcgrfrskkrar vgegggedgeeeedtvrnykpqsevdqscfnknmnnslrcswlkrksktevdvriiddevtiklvqkkkincllfftkv ldqlqldlhhvagggqigehysflntkicegscvyasgiadtlmevvekqymeavpsngy | SEQ ID No. 110 |
| OsBAD67851 | Mdeqrgrggfdelvlhqqeqrrreqqeeeeevrqmfgavvgglaafpaaaalggqqvdcggelggfcdse aggssepeaagarprggsgskrsraaevhnlselarrsknekmkalqsllipnsktdkasmldealeyllkqlqlqvq mlsmrngvylnpsylsgalepaqasqmfaalggnnvtvvhpgtvmppvnqssgahhlfdplnsppqnpqslilpsv pstaipeppfhlessqshlrqfqlpqssefhkillfyllsvkdgyswrdnhakappiitsrksarkrdelhqerilhvehq | SEQ ID No. 111 |

TABLE 2 -continued

Peptide Sequences Used for Phylogenetic Analysis

| Peptide ID. | Peptide sequence (N'→C') | Sequence ID |
|---|---|---|
| OsbHLH141_LOC_Os04g51070 | mivgagyfedshdqslmagslihdsnqapassentsidlqkfkvhpystealsntanlaeaarainhlqhqleidleqevp pvetanwdpaictipdhiinhqfsedpqnilveqqiqqydsalypngvytpapdllnlmqctmapafpattsvfgdttln gtnyldlingeltgvaavpdsgsglmfasdsalqlgyhgtqshlikdichslipqnylfpsederdvilgvsgdlifqeiddr qfdsvleccrgkgefgkgkanfaterereqlnvkfrtlrmlfpnptkndrasivgdaieyidelnrtvkelkilveqkrh gnnrrkylkldqeaaadgesssmrpvrddqnqlhgairsswvqrrskechvdvrlvddevnikteklckansllhaak vldefqlelihvvggiigdhhifmfntkvsegsavyacavakkllqavdvqhqaldifn | SEQ ID No. 112 |
| OsbHLH142_LOC_Os01g18870 | myhpqcellmpleslemdvqgshlaaavaaampgelnfhllhsldaaaaaasstaasasassqptvdyffggadqpppp aamqydqlaaphhhqtvamlrdyygghyppaaaaaateayfrggprtagsslvfgpaddesafmvgpfesssptprs gggrkrsratagfhggpangvekkekqrrirlitekynalmllipnrtkedratvisdaieyiqelgrtveeldliveldurre mqgdvvdaatssvvagmdqaaessegevmaaaamgavapppqrqapirstyiqrrsketfvdvriveddvniktlarr dgclaaasraldlridlvhlsggkigdchiymfntkihsgspvfasavasrlievvdey | SEQ ID No. 113 |
| OsUDT_LOC_Os07g36460 | mprrararggggggggeevkveddfidsvinfggggggeedgdgeeeqqqgaaaaamgkefksknleaerrrrgrl ngnifalravvpkitkmskeadsdaiehikniqnevlelqrqlgdspgeawekqcsascsesfvptenahyggqvelisl gsckynlkifwtkraglftkvlealcsykvqvlsintisfyygyaesfftievkgeqdvvmvelrsllssivevpsi | SEQ ID No. 114 |
| OsTDR_LOC_Os02g02820 | mgrgdhllmknsnaaaaaavnggtvsldaalrplvgsdgwdyciywrlspdqrflemtgfccsseleaqvsalidlps sipldsssigmhaqallsnqpiwqssseeeaadggggaktrllvpvagglvelfasrymaeeqmaelvmaqcgggga gddgggqawppetpsfqwdggadaqrlmyggsslnlifdaaaaddpflgggggdavgdeaaaagawPyagma vsepsevavaqeqmqhaaggvaessegrlhggdpeddgdgegrsggakrqgcknleaerkrrklnghlykirsl vpnitkmdrasilgdaidyivglqkvkelqdeledhvhhkppdvlidhppaslvglndaspppnshqqqpplav sgsssrrsnkdpamtddkvgggggghrmepqlevrqvqnelfvqvlwehkpgfvrlmdamnalglevinvnv ttyktiviny frvmvrdsevavqadrvrdsllevtretypgvwpspqeedakfdggdgggaaaaagehyhdev gggyhqhlhylafd | SEQ ID No. 115 |

Yeast Two Hybrid (Y2H) Assay

The MATCHMAKER GAL4 Two-Hybrid System (Clontech, USA) was used for Y2H assays. Since both full-length EAT1 and TDR1 proteins were reported having self-activation (Ji et al., 2013), we made a truncated EAT1 (EAT1$^\Delta$, amino acids 1-254) and a truncated TDR1 (TDR$^\Delta$, amino acids 1-344) to reduce self activation. The full length cDNA of bHLH142 was cloned into pGAD-T7 (Clontech, USA), and full length bHLH142, EAT1, TDR, EAT1$^\Delta$, and TDR$^\Delta$ were cloned into pGBK-T7 (Clontech, USA), respectively. The pairs of constructs to be tested were co-transformed into AH109 yeast cells and selected on plates containing Leu (for pGADT7 plasmid) and Trp (for pGBKT7 plasmid) dropout medium for 3~4 days at 30° C. Transformants were tested for specific protein interactions by growing on SD/-Leu/-Trp/-His plates with 30 mM 3-amino-1,2,4 triazole (3AT), and tested after X-α-Gal induction to confirm positive interaction. This system provides a transcriptional assay for detecting and confirming protein interactions in vivo in yeast.

Bimolecular Fluorescence Complementation (BiFC) Assay

BiFC assay allows visualization of protein-protein interactions in living cells and the direct detection of the protein complexes in subcellular compartments, providing insights into their functions. Full-length cDNAs of bHLH142, UDT1, TDR1, and EAT1 were independently introduced into pJET1.2 (Thermo Scientific). The sequence for the N-terminal amino acid residues 1-174 of YFP was then in-frame fused to the sequence of the C-terminal region of the tested proteins, while the sequence of the C-terminal amino acid residues 175-239 of YFP was in-frame fused to the sequence of the N-terminal end of the proteins. Next, the tested genes were introduced into pSAT5-DEST_CYN1 and pSAT4(A)-DEST_NYN1. Ballistic bombardment-mediated transient transformation in rice protoplasts was carried out following a previously published protocol[36]. Florescence images were photographed on a LSM 780 Plus ELYRA S.1 confocal microscope with Plan-Apochromat 40x/1.4 oil objective lens (Zeiss, Germany).

Co-Immunoprecipitation Assay

Recombinant proteins of bHLH142 and TDR1 fused with hemagglutinin (HA) tag were expressed in bacteria harboring pET-53-DEST (HIS-tag), and cell extracts after lysis were cleared by centrifugation at 12,000 rpm for 15 min, suspended in binding buffer (20 mM Tris-HCl, pH 7.9, 500 mM NaCl), and sonicated on ice for 30 s using an ultrasonic homogenizer (Misonix XL Sonicator Ultrasonic Cell Processor). The supernatants were purified using Ni$^{2+}$ resin. For immunoprecipitation, extracts were pre-cleared by 30 min incubation with 20 µl of Pure Proteome Protein G Magnetic Beads (Millipore Co., Billerica, Mass.) at 4° C. with rotation. The antibodies (anti-bHLH142 or anti-HA) were then added to the pre-cleared extracts. After incubation for 4 h at 4° C., 40 µL of PureProteome Protein G Magnetic Beads was added, and the extracts were further incubated for 10 min at room temperature with rotation. After extensive washing, bound proteins were analyzed by western blotting. Rabbit antiserum against rice bHLH142 was produced using a synthetic peptide (CSPTPRSGGGRKRSR, SEQ ID No. 116) as antigen (GenScript Co).

RNAi-Mediated Gene Silencing of bHLH142

To generate an RNA intereference (RNAi) construct for suppressing the expression of bHLH142, a 149 bp fragment from 5' UTR region of bHLH142 was amplified by PCR with specific primers (Table 1) and cloned into pENTR (Invitrogen) to yield an entry vector pPZP200 hph-Ubi-bHLH142 RNAi-NOS (12,483 bp). The RNAi construct was transformed into WT (TNG67) rice calli via *Agrobacterium tumefaciens*-mediated transformation system[37]. Transgenic plants were regenerated from transformed calli by selection on hygromycin-containing medium.

Examples

Identification of a New Male Sterility Rice Mutant

From the T2 population of Taiwan Rice Insertional Mutants (TRIM) (http://trim.sinica.edu.tw) lines we identified a T-DNA-tagged rice mutant (denoted ms142) with a completely MS phenotype. In the field, this mutant produced no viable seeds but maintained a normal vegetative growth (FIG. 1A), with panicles and spikelet developing similarly to those of the wild-type (WT) (FIGS. 1B to 1E). The ms142 mutant exhibits normal opening of spikelets and elongation of anther filaments, and its anthers are exerted completely in the husk (FIG. 1E). However, the anthers of ms142 were significantly smaller in size and appeared yellowish white (FIG. 1H), and there were no pollen dehiscence (FIGS. 1B and 1E) and pollen grain filling (FIGS. 1F and 1G). The anthers of the ms142 mutant could not be stained by Sudan black due to the lack of lipid accumulation (FIG. 1I) and showed no pollen grain development (FIG. 1K). As revealed later, ms142 with a full MS is a null mutant.

Sequence Analysis of the T-DNA-Tagged Gene in ms142 Mutant

Figure 2:
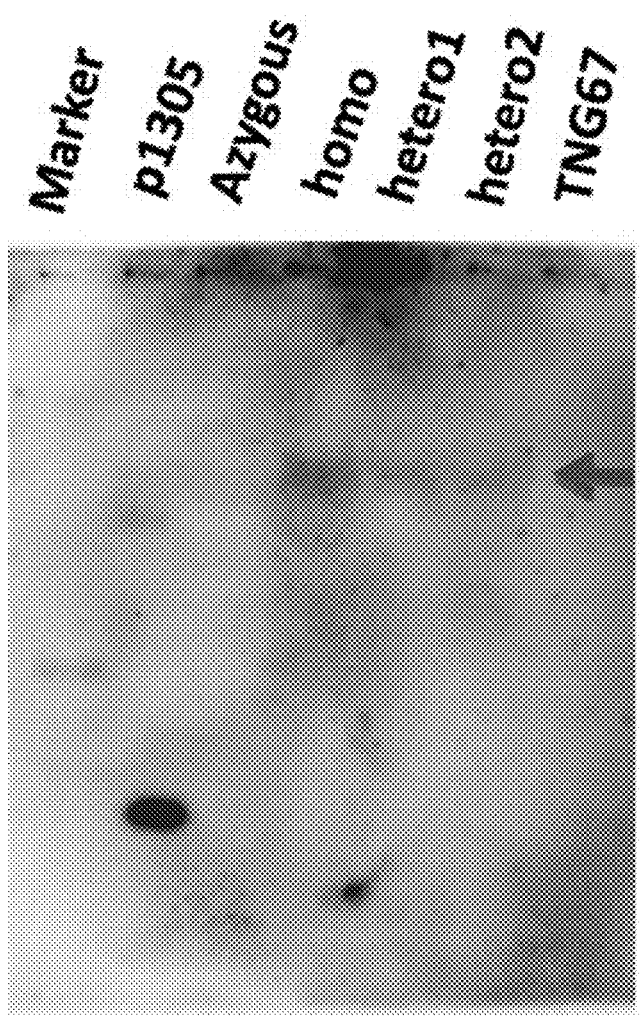
FIG. 2. Evidences of T-DNA insertion in ms142 mutant. (A) Southern blotting to hptII probe confirmed single T-DNA insertion (marked with arrow) in ms142 mutant. (B) T-DNA tagged construction map of pTag4 vector. (C) Gene structure and T-DNA insertion site in the mutant at 3rd intron (+1257 bp from ATG). (D) Genotyping heterozygous T4 mutant progeny. Genotype: WT, wild-type like; He, heterozygous; and Ho, homozygous. Grain fertility: F, fertile; and S, sterile.
Figure 2:
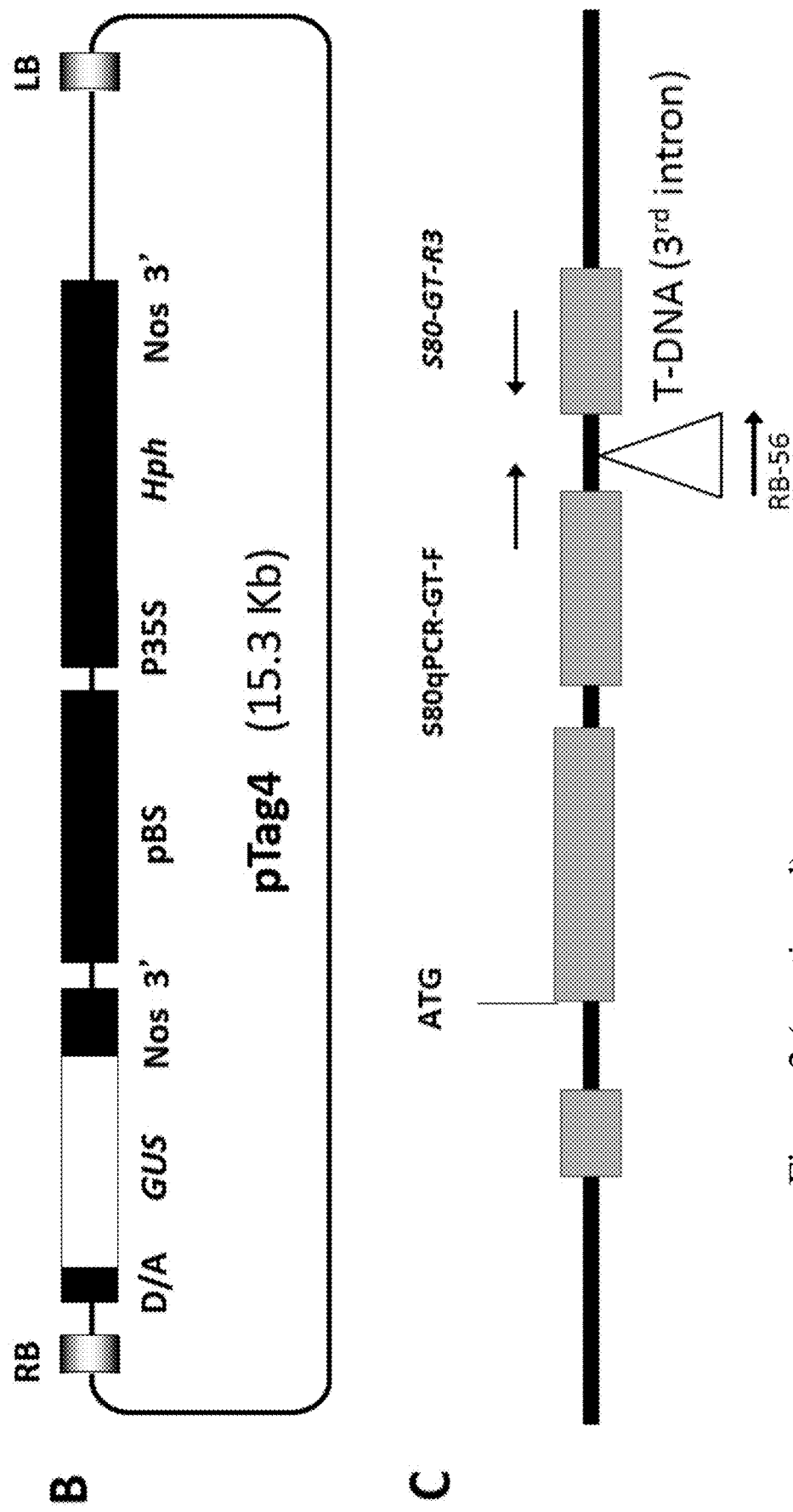
Figure 2:
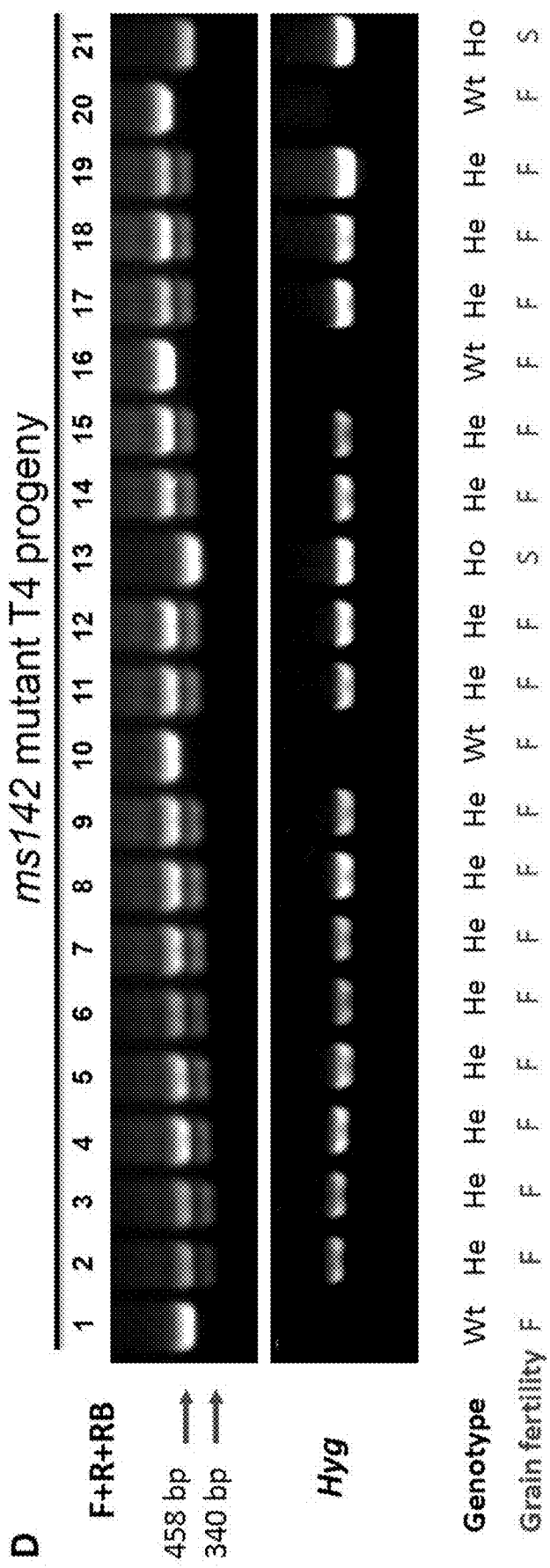

To determine T-DNA insertion copy number, Southern blot analysis of T2 mutant lines using hptII as a probe was conducted, and only a single band was detected in the mutant lines (FIG. 2A). Thus, the mutation in ms142 is due to a single T-DNA insertion. Analysis of flanking sequence tag (FST) in the TRIM database suggests that ms142 is a putative mutant with T-DNA inserted at 1257 bp from the ATG start codon in the 3$^{rd}$ intron of bHLH142 (RAP Locus Os01g0293100, MSU Locus Os01g18870). The protein encoded by the gene is annotated as a basic helix-loop-helix dimerization region bHLH domain containing protein (RiceXPro Version 3.0). The bHLH142 gene comprises of four exons and three introns. Furthermore, genotyping by PCR using specific primers a crossing the T-DNA insertion site verified its FST (FIG. 2). The primers are designed for the mutant allele (R+RB, amplicon=340 bp) and wild-type allele (F+R, amplicon=458 bp). Three primers sets were incorporated in one PCR reaction for genotyping.

Agronomic Traits of ms142 Mutant and Genetic Study

The agronomic traits of the mutant were examined in the selfed progenies of heterozygous mutant grown in the outdoor GMO net house. Heterozygous plants behaved similarly to WT in terms of vegetative and reproductive growth and produced fertile seeds. However, homozygous ms142 mutant plants exhibited similar plant height, panicle number, and panicle length to the WT, but produced no viable seeds.

To understand whether the sterility in ms142 is due to male sterility or female sterility, homozygous mutant was backcrossed with WT pollen; and all F1 plants displayed WT-like phenotype in growth and fertility (data not shown). These results imply that the female organs of ms142 develop normally. When the ms142 BCF1 was selfed, the BCF2 progenies segregated into fertile and sterile plants in a ratio of 3:1 (Table 3), suggesting the MS trait is controlled by a recessive gene. Consistent with mutant phenotype, backcross segregants showed MS only in the homozygous plants, indicating that the MS phenotype co-segregated with the genotype. Moreover, when the selfed seeds derived from heterozygous plants of T2, T3, T4, and BCF2 generations were planted in different years and different cropping seasons, the scoring of phenotype indicated that MS in ms142 is stable and not affected by cropping season or year. Again, the fertile and sterile plants segregated approximately in a 3:1 ratio, supported by Chi-square analysis (data for T4 and BCF2 shown in Table 4). Taken together, these genetic analyses validate that the MS in ms142 is controlled by a single recessive locus.

TABLE 3

| Trait | Genotype | | |
|---|---|---|---|
| | WT like | Heterozygote | Homozygote |
| Plant height (cm) | 118.4 ± 7.9 | 116.7 ± 8 | 118.4 ± 7 |
| Tiller number | 8 ± 2.7 | 9 ± 2.4 | 13.8 ± 3.8 |
| Panicle number | 7.8 ± 2.7 | 8.7 ± 2.5 | 8.7 ± 2.1 |
| Ave. panicle length (cm) | 20.1 ± 1.4 | 20.1 ± 1.5 | 20.2 ± 1.6 |
| Panicle Fwt (g) | 30.8 ± 12.6 | 34 ± 12.5 | 8.8 ± 3 |
| Grain No./panicle | 168.3 ± 28.1 | 164.3 ± 30.2 | 180 ± 31.2 |
| Fertile grain number | 1137 ± 466 | 1248 ± 464 | 6 ± 4.2 |
| Grain fertility (%) | 84.9 ± 7.5 | 86.6 ± 6 | 0.4 ± 0.2 |
| Grain yield/plant (g) | 28.3 ± 11.3 | 31.3 ± 11.3 | 0.2 ± 0.1 |
| 1000 grain wt. (g) | 25 ± 0.8 | 25.2 ± 1 | 6.8 ± 1.2 |
| n = | 27 | 62 | 22 |

TABLE 4

| Cropping season | Wild type | Heterozygous | Homozygous | $X^2$ |
|---|---|---|---|---|
| BCF$_2$ (n = 111) | | | | |
| 1$^{st}$ Crop | | | | |
| No. of plant | 28 | 61 | 22 | 1.59 |
| Grain fertility | Fertile | Fertile | Sterile | |
| ms142 T$_4$ (n = 119)$^a$ | | | | |
| 1$^{st}$ Crop | | | | |
| No. of plant | 30 | 58 | 31 | 0.07 |
| Grain fertility | Fertile | Fertile | Sterile | |
| ms142 T$_4$ (n = 120)$^a$ | | | | |
| 2$^{nd}$ Crop | | | | |
| No. of plant | 29 | 57 | 34 | 0.71 |
| Grain fertility | Fertile | Fertile | Sterile | |

Defects in Anther Wall and Pollen Development in the ms142 Mutant

To determine the defects in the anthers of ms142, we examined the anatomy of anther in WT and homozygous mutant. At the microspore mother cell (MMC) stage, the WT anther walls contained epidermal cell layer, endothecial cell layer, middle layer and tapetal cell layer (FIG. 3A). During the early meiosis stage, the microspore mother cells underwent meiosis to form tetrads of haploid microspores; the tapetal cells differentiated to form large vacuole; and the middle layer cells began to degenerate (FIG. 3B). At tetrad stage, the meiocytes formed tetrads (FIG. 3C). During the young microspore stage, free microspores were released into the anther locule, and the microspores developed and exine was deposited on pollen grain wall. The middle layers shrinked and the tapetal cell layers became very dense (FIG. 3D). At the mature pollen stage, the uninucleate pollen developed to trinucleate pollen with starch, protein, lipid, and other nutrients enriched in the pollen cytoplasm. At maturity, the tapetal cells were completely degenerated and the endothecial cell layers were thickening, ready for anther dehiscence (FIG. 3E).

At the MMC stage, there were no visible differences in the anthers between WT and ms142. The ms142 anther consisted of normal epidermis, endothecium, middle layer and tapetum (FIG. 3F). During early meiosis stage, however, ms142 microspore mother cells did not enter meiosis and formed abnormal organelles (FIG. 3G, indicated by arrows). Abnormal endoplasmic reticulum structure and apoptosis was also observed by transmission electron microscopy. The ms142 tapetal cells continuously became vacuolated and elongated, with some cells divided into two tapetum layers (FIG. 3G). The mid-layers of the mutant tapetum maintained their initial shapes, but failed to divide into four cells at tetrad stage (FIG. 3H). The ms142 mutant's microspores finally degenerated during the vacuolated pollen stage. The tapetal and middle layer cells contained a large vacuole, and the middle layer cells did not degenerate (FIG. 3I). Consequently, there were no mature pollen grains formed in the locules at the mature stage. The mutant anther wall still retained four to five layers of cells, i.e. epidermis, endothecium, middle layer, and one or two layers of tapetum cells. By contrast, the endothecial cell layer did not become thickened in the mutant even at the latter stage of anther development (FIG. 3J).

Mutated bHLH142 Causes Defects in Tapetal PCD

Figure 3:
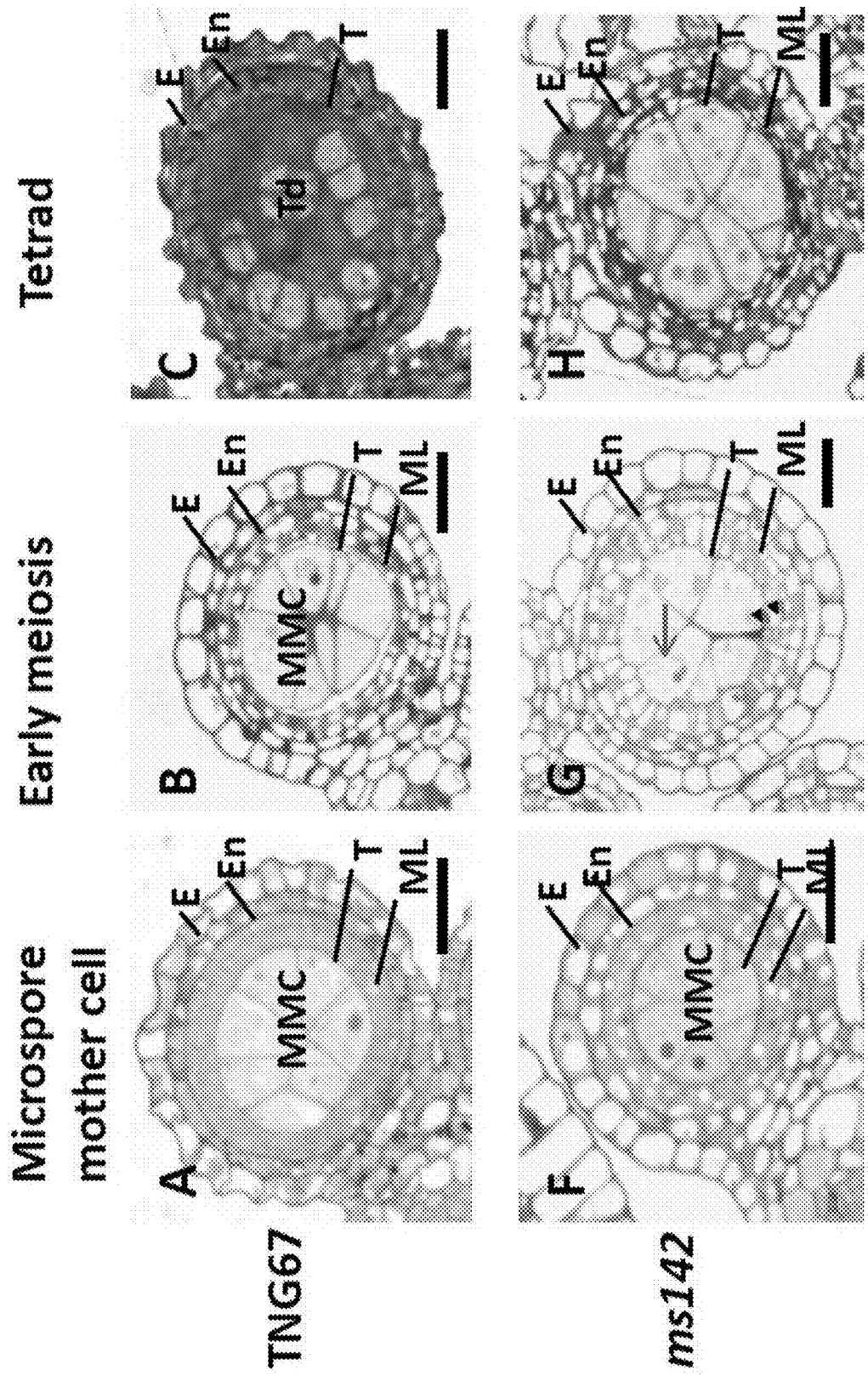
FIG. 3. Transverse anatomical comparison of the anther development in the wild type (TNG67) and ms142 mutant. E, epidermis; En, endothecium; ML, middle layer; T, tapetum; Ms, microsporocyte; Td, tetrads; Msp, microspore; MP, mature pollen; Arrow, degenerated microspore; and arrowhead, two tapetum layers. Bars=20 μm.
Figure 3:
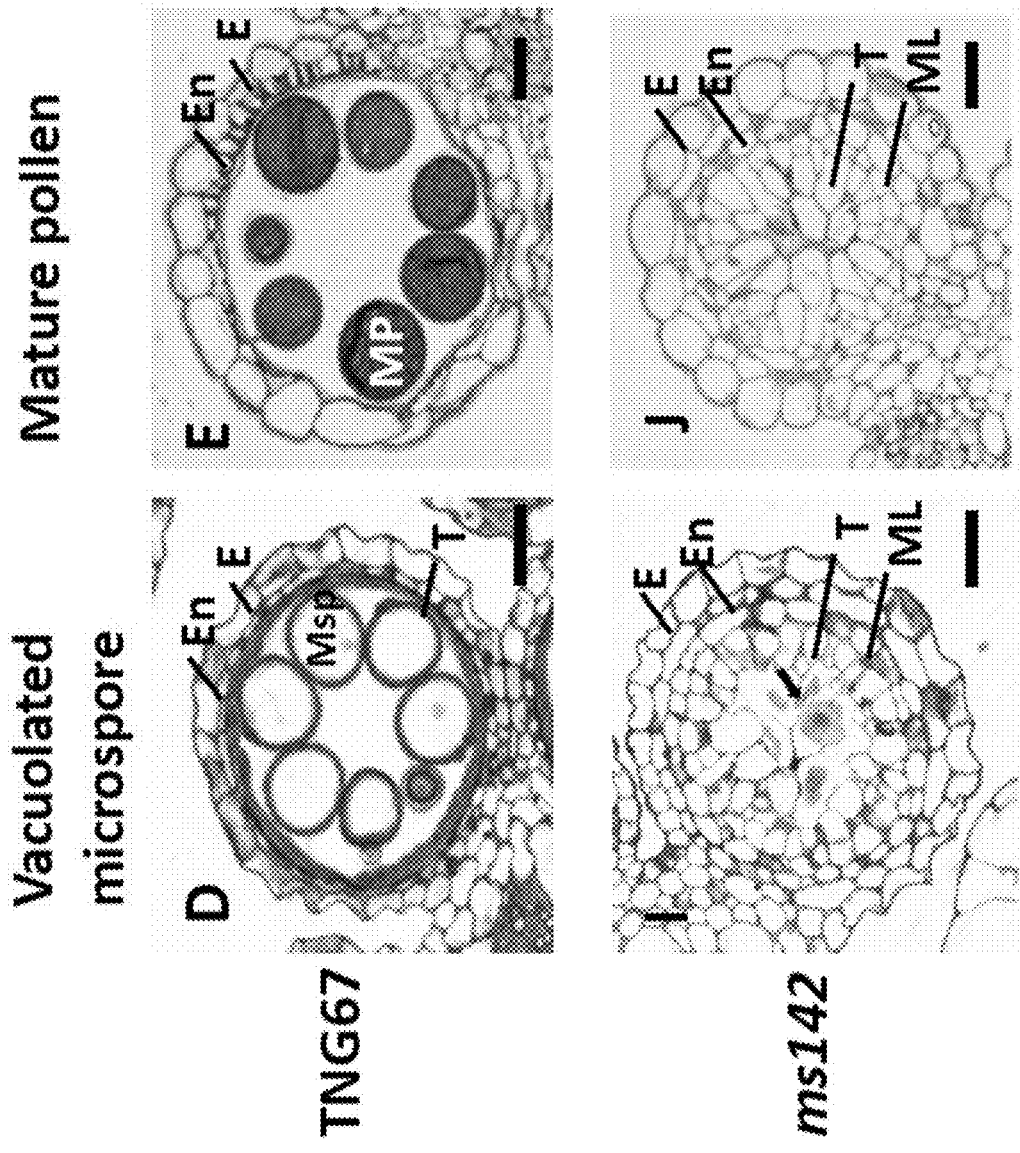
Figure 4:
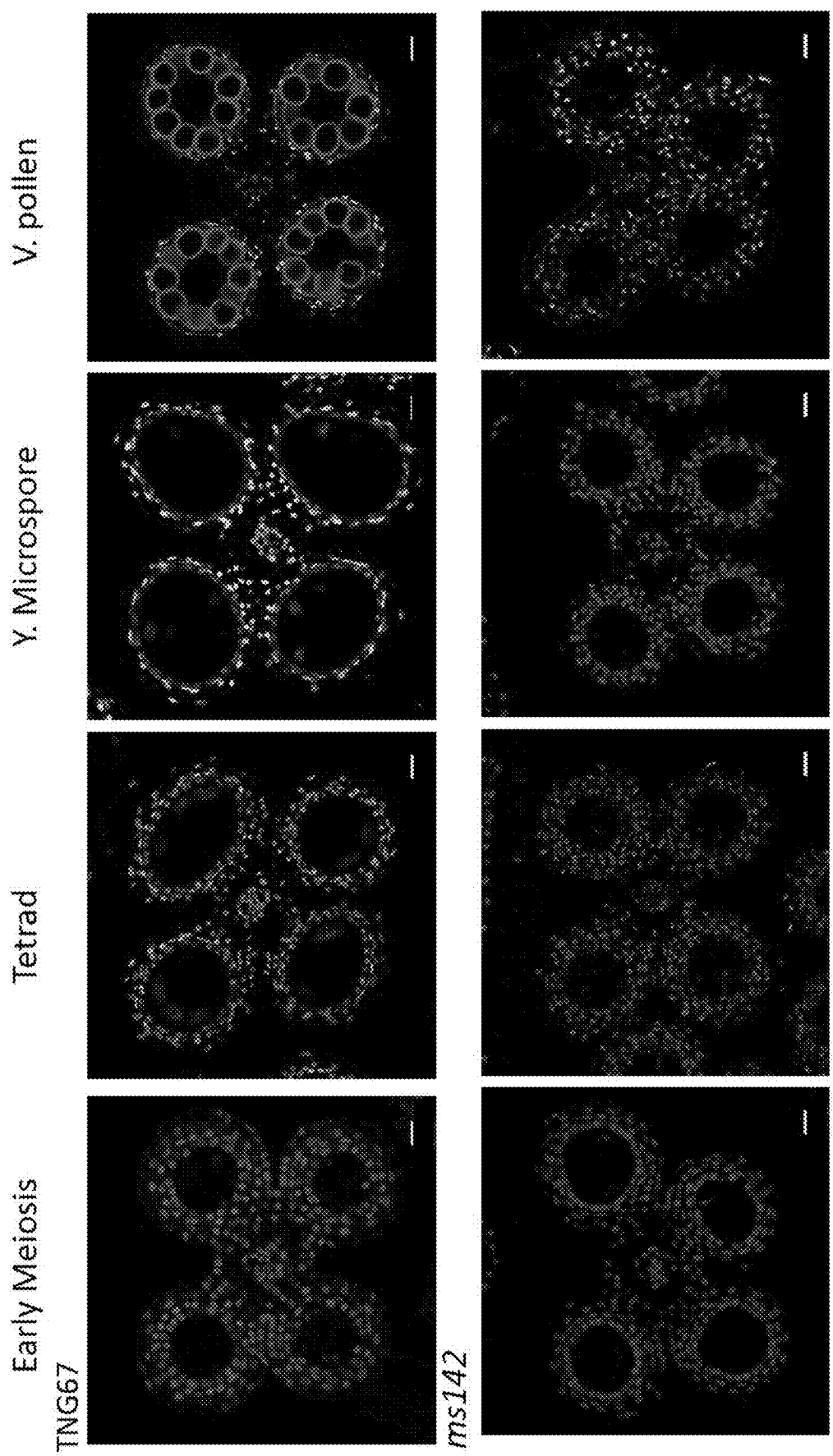
FIG. 4. TUNEL assay showed defect tapetal program cell death in ms142 mutant. DNA fragmentation signals (yellow fluorescence) started at tetrad stage and exhibited obvious positive signal at young microspore stage in wild type (TNG67). No DNA fragmentation signal was observed in ms142 anther. Red signal shows the propidium iodide (PI) staining, and yellow fluorescence is the merged signal from TUNEL (green) and PI. Scale bar=50 μm.

Histological analysis indicated that ms142 has abnormal anther morphology and aborted degradation of tapetal cells (FIG. 3). Thus, we suspect that mutation of bHLH142 might have altered tapetal PCD, which is responsible for tapetal degeneration[3,12-14]. Tapetal PCD is characterized by cellular condensation, mitochondria and cytoskeleton degeneration, nuclear condensation, and internucleosomal cleavage of chromosomal DNA[33]. Therefore, we performed the TUNEL assay to detect DNA fragmentation in the anthers of WT and ms142. A TUNEL positive signal began to appear in the tapetal cells of WT during meiosis and a strong TUNEL signal was detected during the young microspore stages (FIG. 4). In contrast, no DNA fragmentation was observed in the tapetal layer in ms142 throughout anther development (FIG. 4).

bHLH142 is a Nuclear Protein

Figure 5:
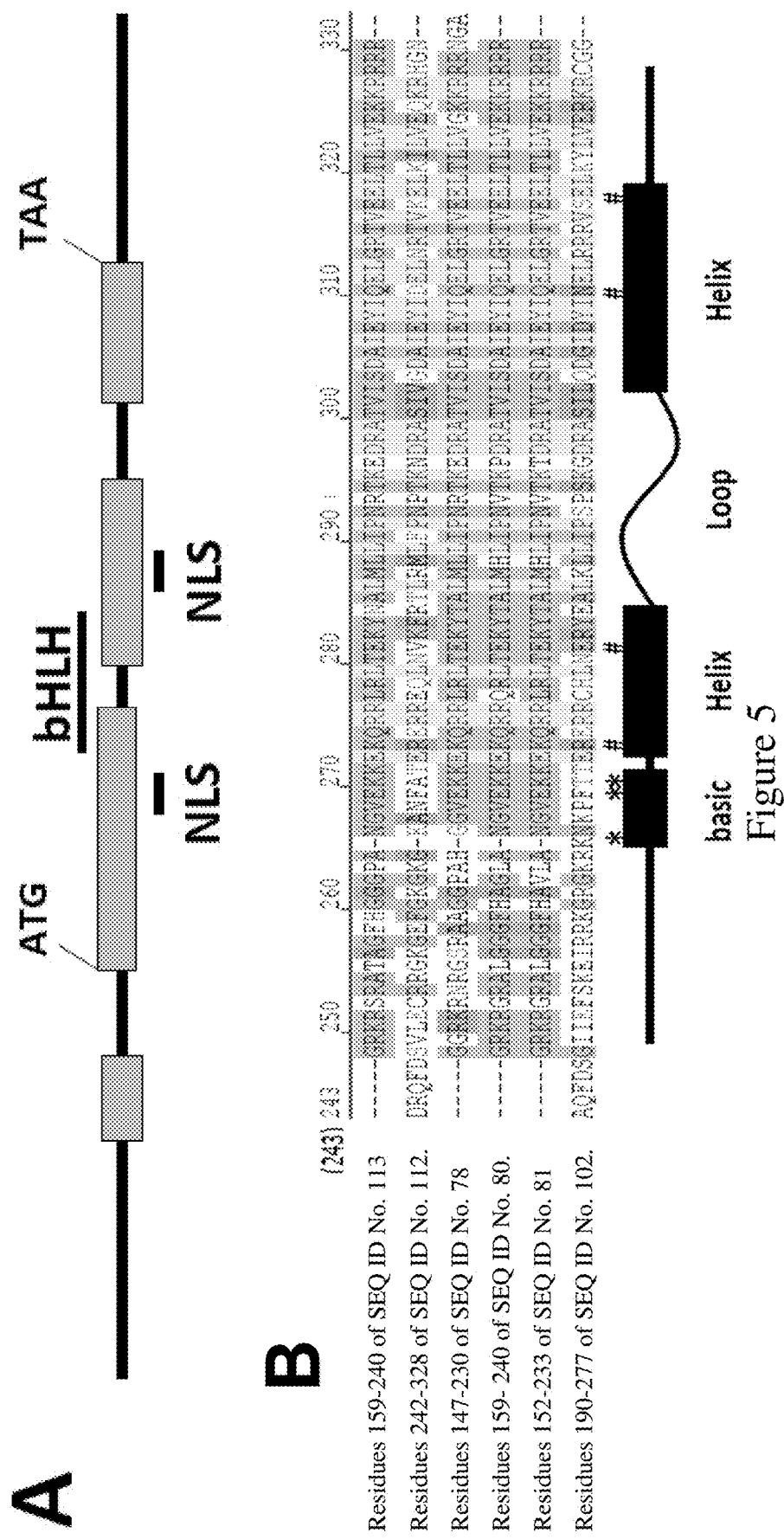
FIG. 5. Scheme of bHLH142 gene, multiple alignment, and subcellular localization of bHLH142 fused with GFP. (A) Scheme of the bHLH142 gene and T-DNA insertion position. Gray boxes represent exons and interventing lines represent introns. The ATG start codon and TGA stop codon are indicated. bHLH, basic helix-loop-helix domain (amino acids 182 to 228); NLS, two nuclear localization signals (amino acids 159 to 165 and 235 to 240, respectively). (B) Alignment of bHLH domains. The bHLH142 protein was aligned with the bHLH domains of the analogous proteins from other species. Asterisks indicate the conserved basic amino acid Arg that is important for binding DNA. Pound signs indicate conserved Leu residues important for forming the α-helix. bHLH142 (159): residues 159-240 of SEQ ID No. 113. bHLH141 (242): residues 242-328 of SEQ ID No. 112. *Brachypodium distachyon* (147): residues 147-230 of SEQ ID No. 78. *Sorghum bicolor* (159): residues 159-240 of SEQ ID No. 80. *Zea mays* (152): residues 152-233 of SEQ ID No. 81. *Arabidopsis thaliana* (190): residues 190-277 of SEQ ID No. 102. (C) Schemes of fusion constructs. P35S, cauliflower mosaic virus 35S promoter; Tnos, nopaline synthase gene terminator. The NLS domain of VirD2 fused with mRFP was used as the nuclear marker. (D) In vivo targeting of fusion protein. DIC (bright field, left column) and overlays (Merge, right column) are shown. Scale bar=20 μm.
Figure 5:
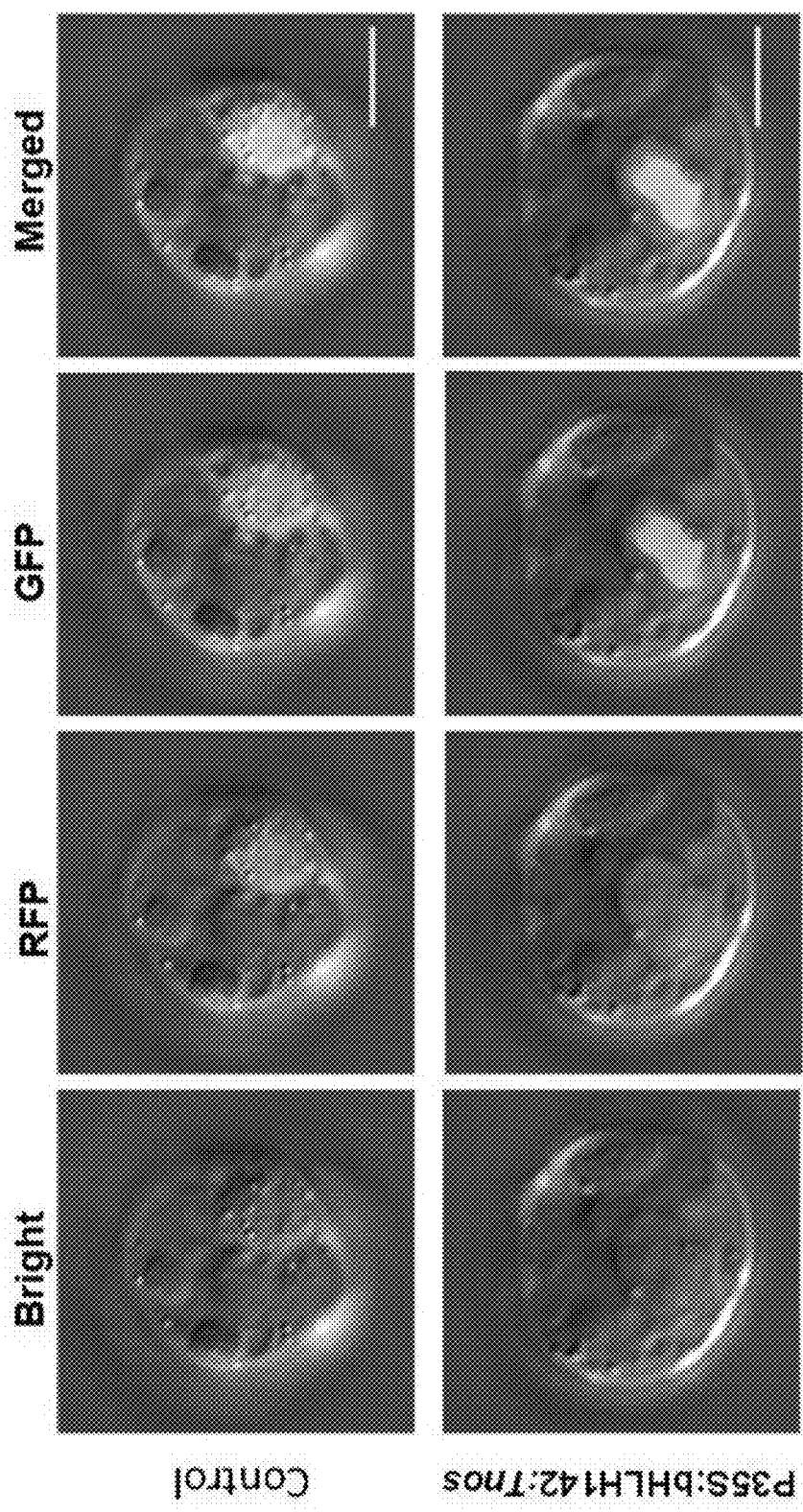

The gene structure of bHLH142, shown in FIG. 5A, indicates that bHLH domain contains bipartite nuclear localization signal (NLS), and the gene is predicted to encode a protein of 379 amino acids with a theoretical molecular mass of 40.7 kDa and pI of 6.2.

The nucleotide sequence of bHLH142 is shown below:

SEQ ID No: 1
AAGAAACCAACTGCTTTCTCCTACCCAATATCACCCTTGCCCCTTTTATATACTCTTCCTCTCATCACCT

TCTCGATCGGCCTCTCTCCTCTCCTCTCATCAGCTCACACCCCCAACCAACAAACCTAGTTAATTTAGCT

CTAGTTGGTTCATCCCTGCTGCACTGCGAGCTCAAGTAATCGATCTGAGCTCTGAAGAAAAAGGTGGTAG

AGTGCGAGGAAGATGTATCACCCGCAGTGCGAGCTCCTGATGCCGCTTGAGAGCCTGGAGATGGACGTCG

GCCAGTCGCACCTCGCCGCCGCCGTCGCAGCAGCCATGCCGGGGGAGCTCAACTTCCACCTCCTCCACTC

```
-continued
GCTCGACGCCGCCGCGGCGGCTGCCTCCTCCACCGCCGCCTCGGCCTCCTCCCAGCCCACCGTCGACTAC

TTCTTCGGCGGCGCCGACCAGCAGCCGCCGCCGCCGGCGGCGATGCAGTACGACCAGCTGGCGGCGCCGC

ACCACCACCAGACGGTGGCCATGCTGCGCGACTACTACGGCGGCCACTACCCGCCGGCGGCGGCGGCGGC

GGCGGCCACCGAGGCGTACTTCCGCGGCGGGCCAAGGACGGCCGGGTCGTCGTCGCTCGTGTTCGGCCCG

GCCGACGACGAGTCGGCCTTCATGGTCGGACCCTTCGAGAGCTCCCCGACGCCGCGGTCCGGCGGCGGCA

GGAAGCGTAGCCGCGCCACCGCCGGCTTCCACGGCGGCGGGCCGGCCAACGCGTCGAGAAGAAGGAGAA

GCAGCGCCGCCTGCGGCTCACCGAGAAGTACAACGCCCTCATGCTCCTCATCCCCAACCGCACCAAGGAG

GATAGAGCGACGGTGATCTCAGACGCGATCGAGTACATCCAGGAGCTAGGGAGGACGGTGGAGGAGCTGA

CGCTGCTGGTGGAGAAGAAGCGGCGGCGGAGGGAGATGCAGGGGGACGTGGTGGACGCGGCGACGTCGTC

GGTGGTGGCGGGGATGGATCAGGCGGCGGAGAGCTCGGAGGGCGAGGTGATGGCGGCGGCGGCGATGGGC

GCGGTGGCACCGCCGCCGCGGCAGGCGCCGATCCGGAGCACGTACATCCAGCGGCGGAGCAAGGAGACGT

TCGTGGACGTGCGGATCGTGGAGGACGACGTGAACATCAAGCTCACCAAGCGCCGCCGCGACGGCTGTCT

CGCCGCCGCGTCGCGCGCGCTGGACGACCTCCGCCTCGACCTCGTCCACCTCTCCGGCGGCAAGATCGGC

GACTGCCACATCTACATGTTCAACACCAAGATTCATTCGGGATCTCCAGTGTTTGCAAGTGCAGTGGCCA

GCAGGCTGATTGAAGTGGTGGATGAGTACTAACTAGCTCGAGCTAGCTAATTAGCCGACCGACCGATCGA

TATGATGAAAGTTTCTATGTTGCTAGCTAGCTAGGGTTCTTGGATGCATGAGTACTGAGTAGCTCTTTAA

TTAATTTCCTTTTAATTTTAGACTGTTTAATTTGGATTGGTAAAGACTCGTGTTAGCTTTTGGGAGATCT

TTGGTATGTCATGGTTTGCATGTATTATTTTGGTCTACTTGGATAAATAATTGATGCTCTTTGAGACGTT

AATTAAT.
```

The amino acid sequence of bHLH142 is shown below:

```
                                               SEQ ID No: 2
MYHPQCELLMPLESLEMDVGQSHLAAAVAAAMPGELNFHLLHSLDAAAAA

ASSTAASASSQPTVDYFFGGADQQPPPPAAMQYDQLAAPHHHQTVAMLRD

YYGGHYPPAAAAAAATEAYFRGGPRTAGSSSLVFGPADDESAFMVGPFES

SPTPRSGGGRKRSRATAGFHGGGPANGVEKKEKQRRLRLTEKYNALMLLI

PNRTKEDRATVISDAIEYIQELGRTVEELTLLVEKKRRRREMQGDVVDAA

TSSVVAGMDQAAESSEGEVMAAAAMGAVAPPPRQAPIRSTYIQRRSKETF

VDVRIVEDDVNIKLTKRRRDGCLAAASRALDDLRLDLVHLSGGKIGDCHI

YMFNTKIHSGSPVFASAVASRLIEVVDEY
```

Since the bHLH proteins are characterized as TFs, we assumed that bHLH142 is localized in the nucleus. To verify its subcellular localization, we constructed a fusion gene of the green fluorescent protein gene (GFP) and bHLH142 under the control of the 35S promoter and the nos terminator for transient expression in rice leaf mesophyll protoplasts (FIG. 5C). As a positive control, NLS sequence was also fused to red fluorescent protein (RFP) gene using the same regulatory elements. These constructs were introduced into rice protoplasts by particle bombardment. As expected, with the GFP construct alone, free GFP was found in the nucleoplasm as well as in the cytoplasm. However, bHLH142:GFP fusion protein and the positive control of NLS:RFP were exclusively located in the nucleus (FIG. 5D). These results confirm that, as a TF, bHLH142 protein is localized in the nucleus.

Phylogenetic Analysis

Figure 6:
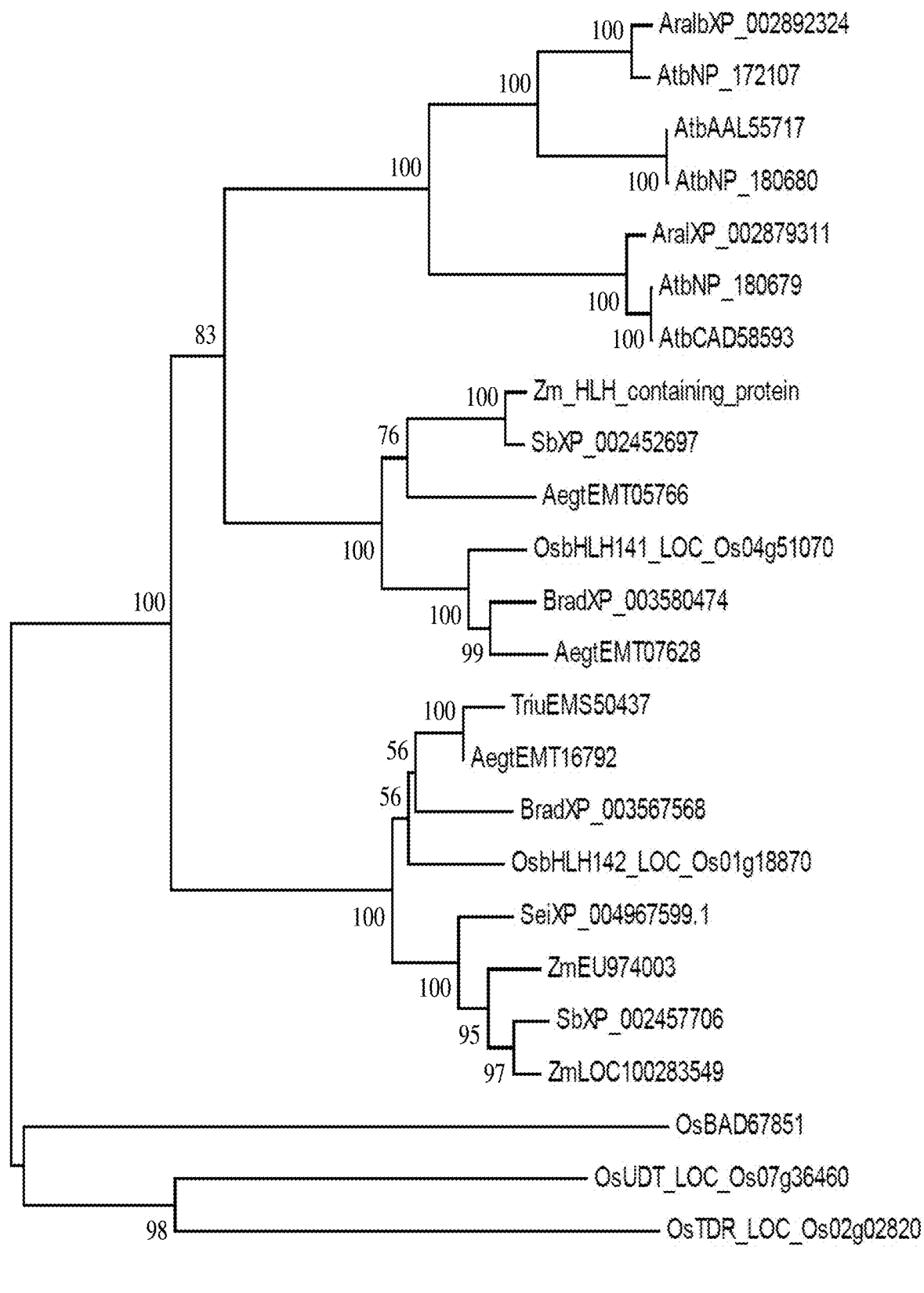
FIG. 6. Phylogenetic analysis of bHLH142 related proteins. Aral, *Arabidopsis lyrata*; Aegt, *Aegilops tauschii*; At, *Arabidopsis thaliana*; Brad, *Brachypodium distachyon*; Os, *Oryza sativa*; Sei, *Setaria italica*; Sb, *Sorghum bicolor*; Selm, *Selaginella moellendorffii*; Triu, *Triticum urartu*; and Zm, *Zea may*.
Figure 14:
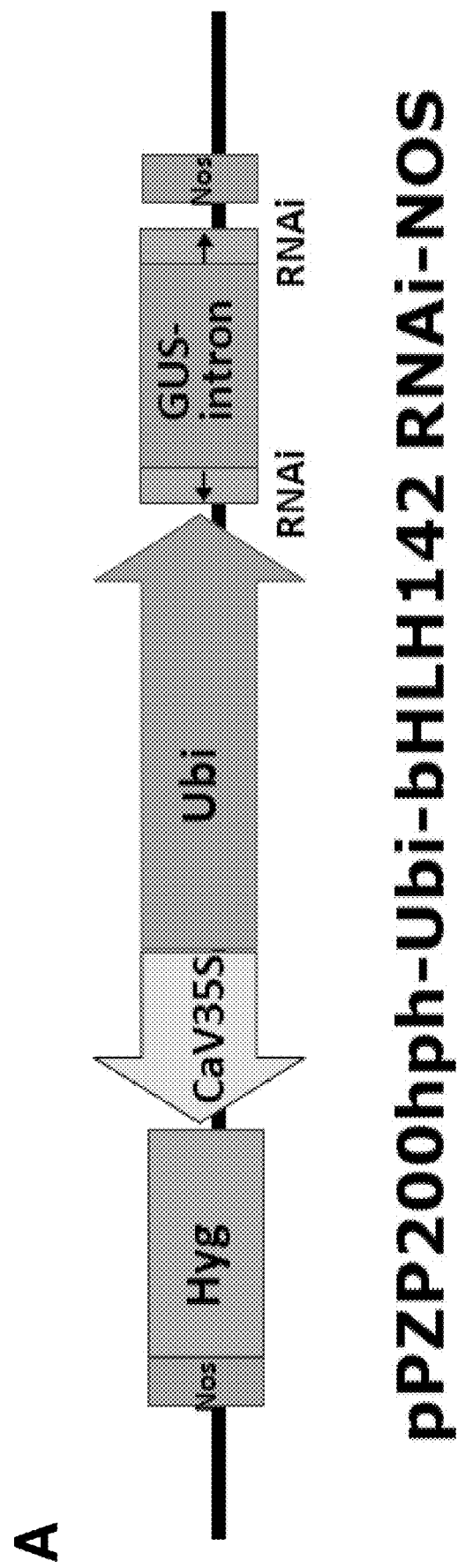
FIG. 14. RNAi Knockdown (KD) of bHLH142 Inhibited Pollen Development. (A) Construct of RNAi vector. (B) RT-PCR showed down regulation of bHLH142 in the anthers of four RNAi knock down lines. (C) Phenotype of WT and KD line #3. Scale bars=20 cm in (C), 0.5 mm (D), 1 mm (E) and 20 μm (F).
Figure 14:
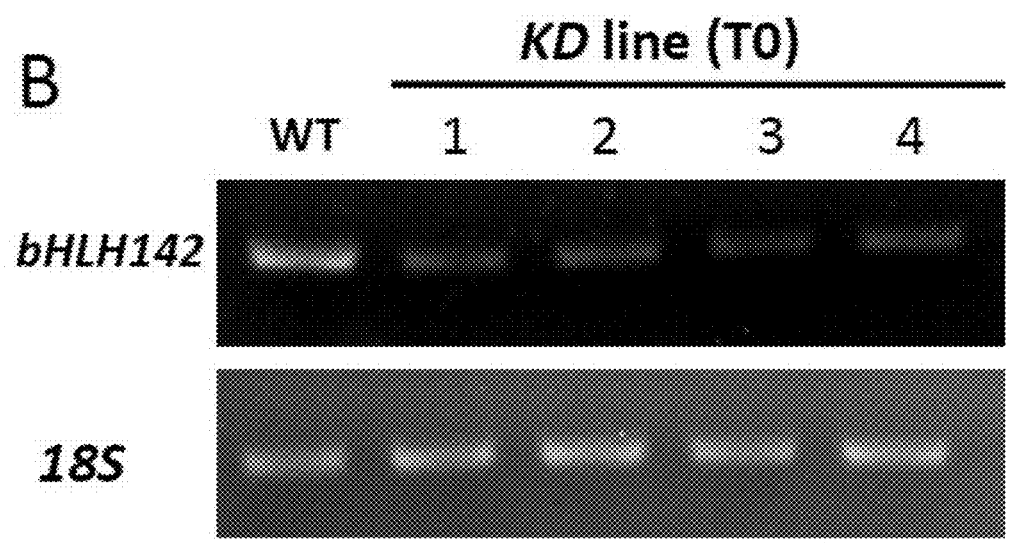
Figure 14:
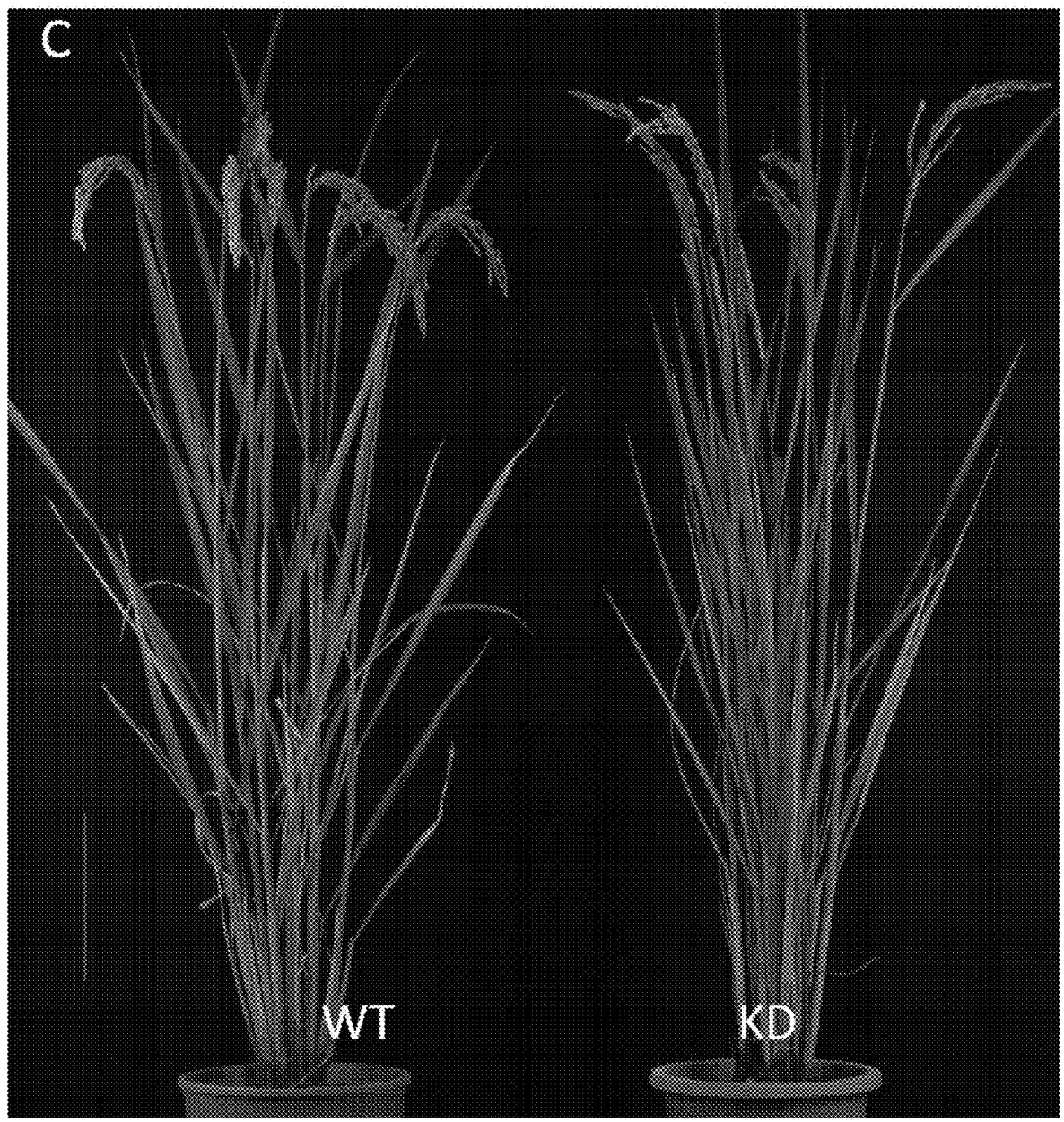
Figure 14:
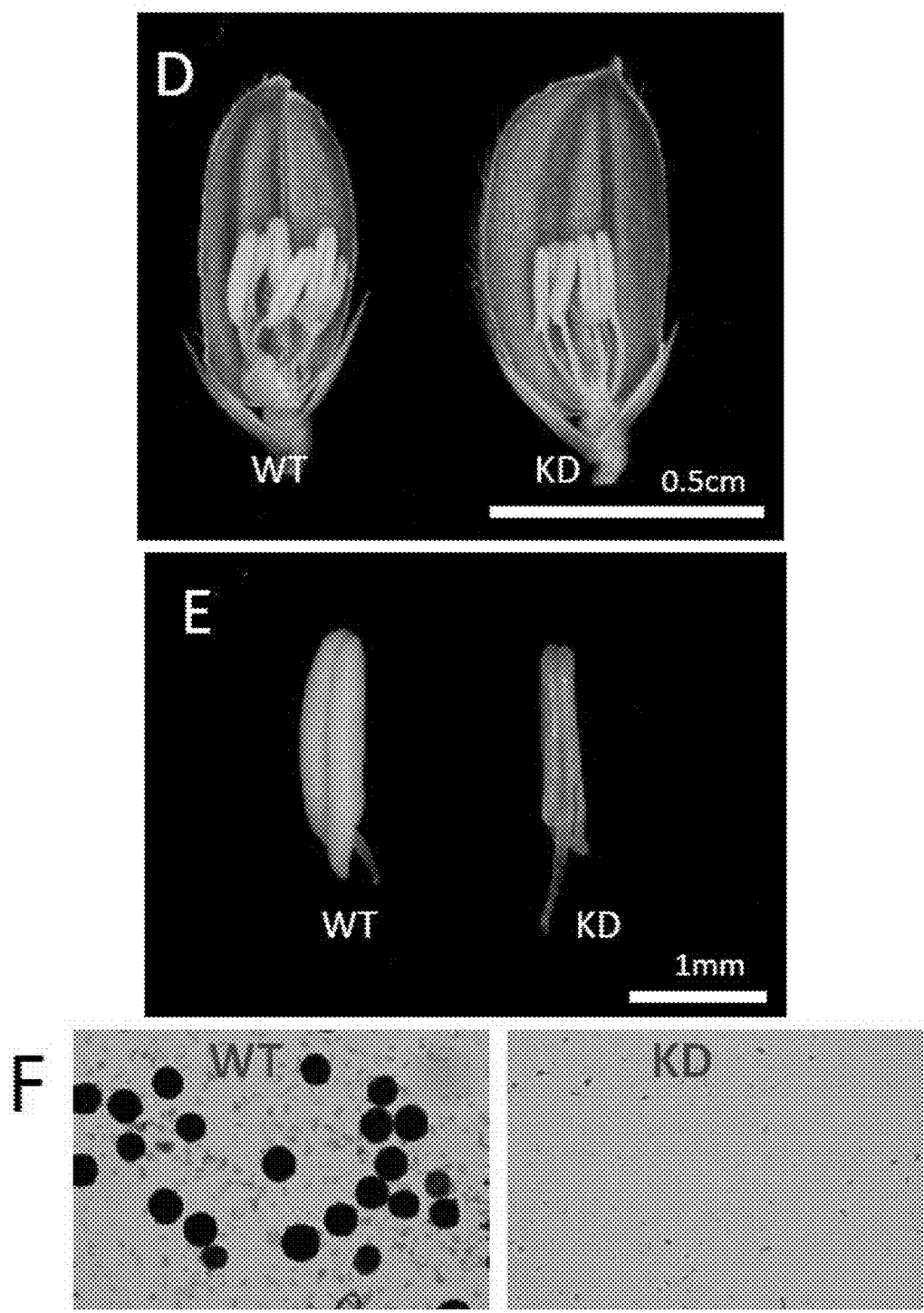

To understand the evolutionary relationship of bHLH142 among various organisms, we used full-length bHLH142 protein sequence to NCBI BLAST database and retrieved 21 homologs containing bHLH domain from 10 diverse terrestrial plants. The phylogenetic tree shows that UDT1 (bHLH164) and TDR1 (bHLH5) are in the same cluster, while bHLH142 and EAT1 (bHLH141) evolved and diversified into two separate clades. Phylogenetic analysis also suggests that bHLH142 is descended from a common ancestor of monocots. Rice bHLH142 shares a high similarity with the related proteins from Brachypodium distachyon, millet (Setaria italica), Triticum urartu, maize (Zea may), Sorghum (Sorghum bicolor) and Aegilops tauschii (FIG. 6). The conserved homologs of bHLH142 from the important cereal crops, such as maize, millet, sorghum and wheat, share 84.1%, 79.2%, 72.2%, and 78% similarity in amino acid sequence to the rice counterpart (Table 5). The maize homolog, GRMZM2G021276, is highly expressed in immature tassel and meiotic tassel and anther. In accordance, our RT-PCR data also verified that maize homolog is tissue specifically expressed in meiotic anther (FIG. 14). This result implies that the maize bHLH142 homolog may also play a similar role in anther and pollen development.

TABLE 5

| Crop | Accession No. | Amino acid similarity |
|---|---|---|
| Sorghum | XP 002457706 | 72.2% |
| Maize | ZmLOC100283549 | 84.1% |
| Wheat | EMS50437 | 78.0% |
| Millet | XP_004967599 | 79.2% |
| Brachypodium | XP_003567568 | 80.7% |

Expression Pattern of bHLH142

Figure 7:
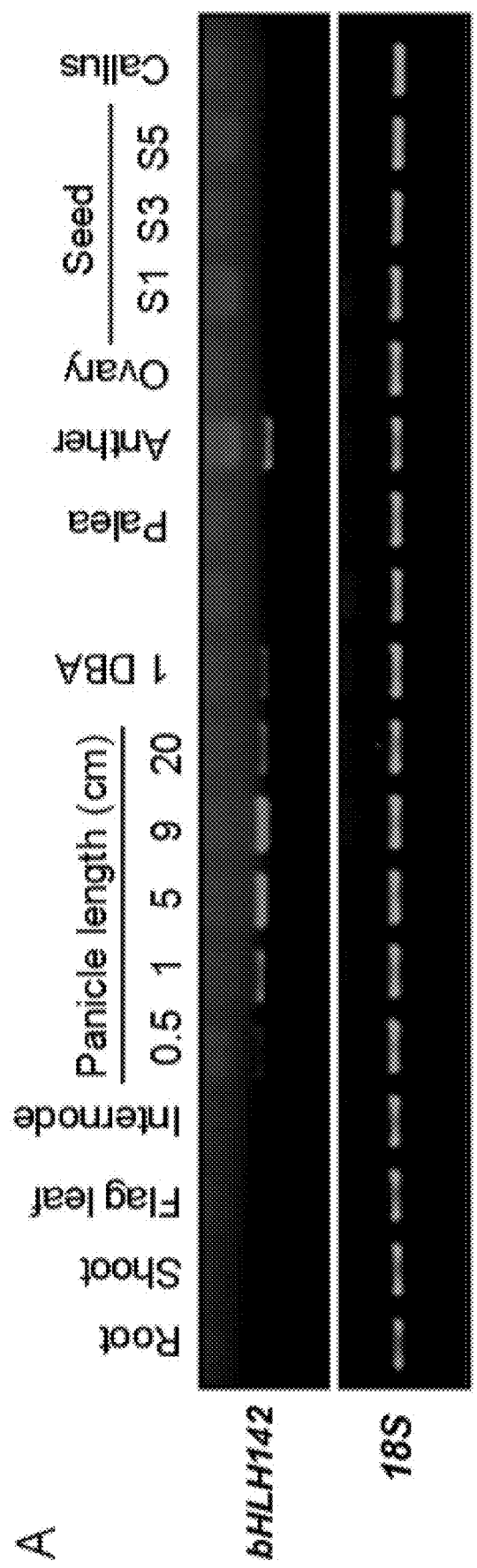
FIG. 7. Spatial and temporal gene expression of bHLH142 in various tissues of TNG67 (WT) by (A) RT-PCR and (B) qRT-PCR, and (C) in TNG67 spikelet at various developmental stages; and (D) ISH of bHLH142 antisense (left panel) and sense (right panel) probes in spikelet of TNG67 at meiosis stage. Error bars indicate SD (n=3). SC, sporogenous cell; MMC, meiocyte mother cell; Mei, meiosis; YM, young microspore; VP, vacuolated pollen; PM, pollen mitosis; and MP, mature pollen. Scale bar=1 mm in (C), 50 μm in (D).
Figure 7:
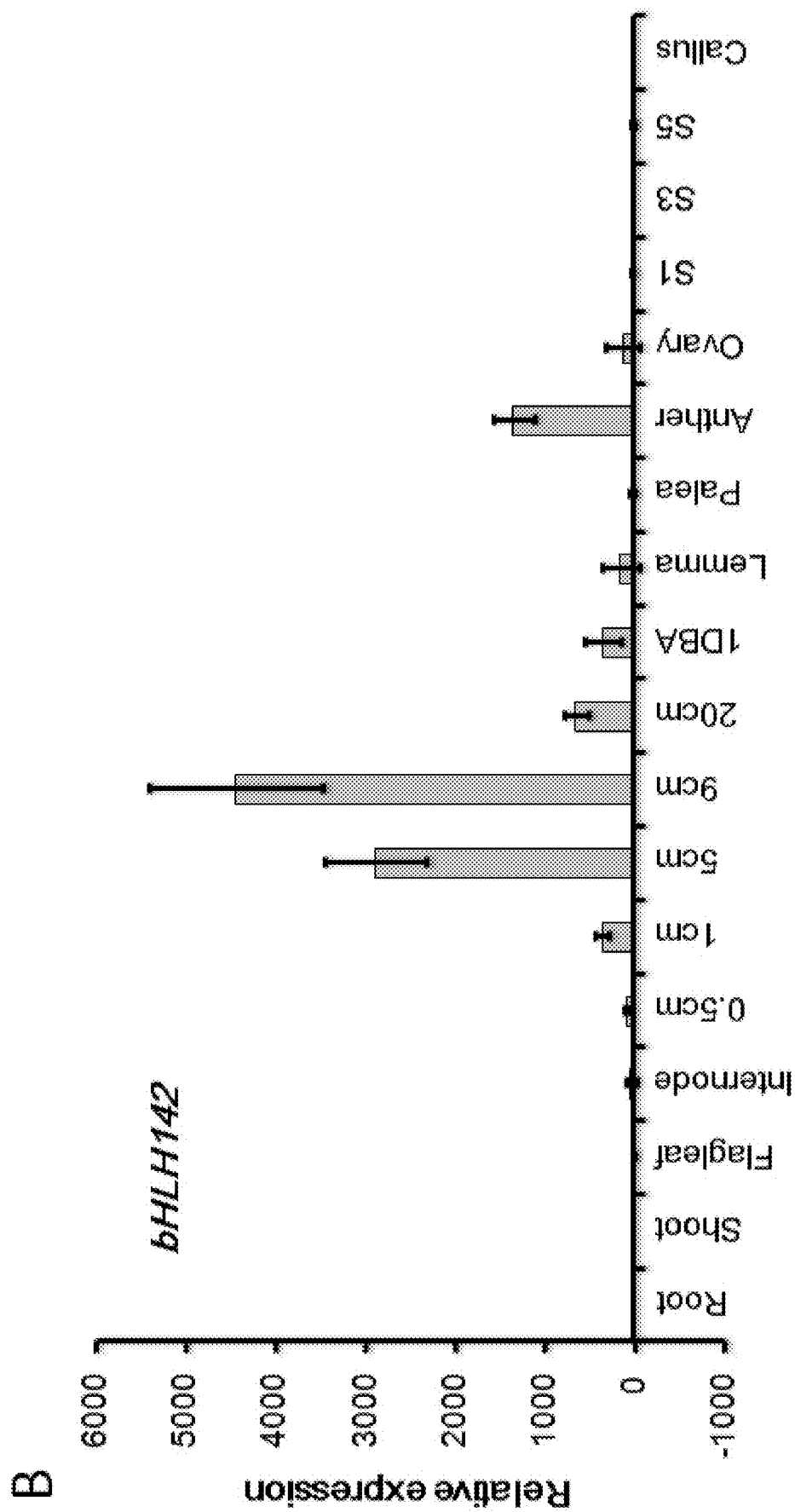
Figure 7:
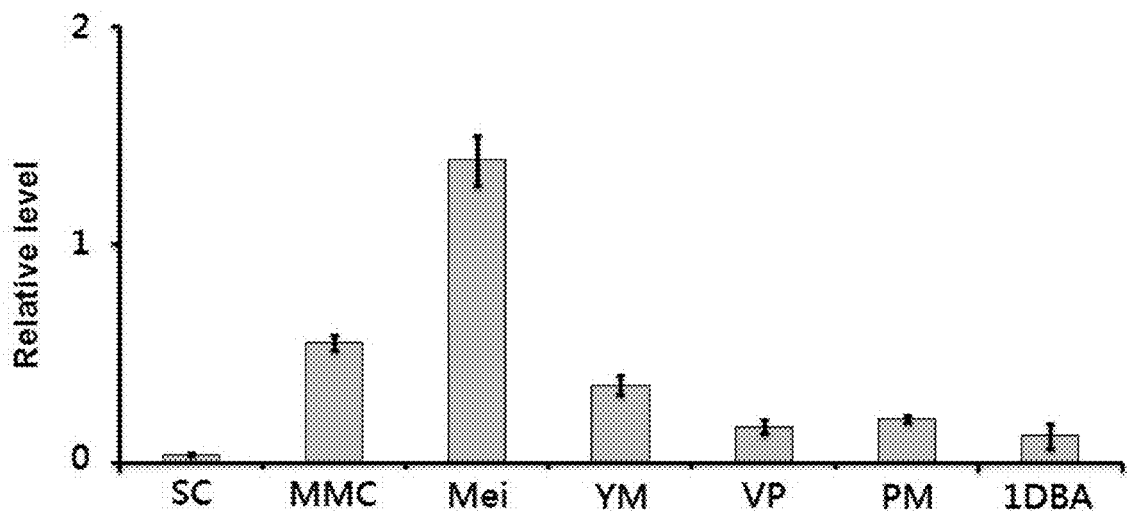
Figure 7:
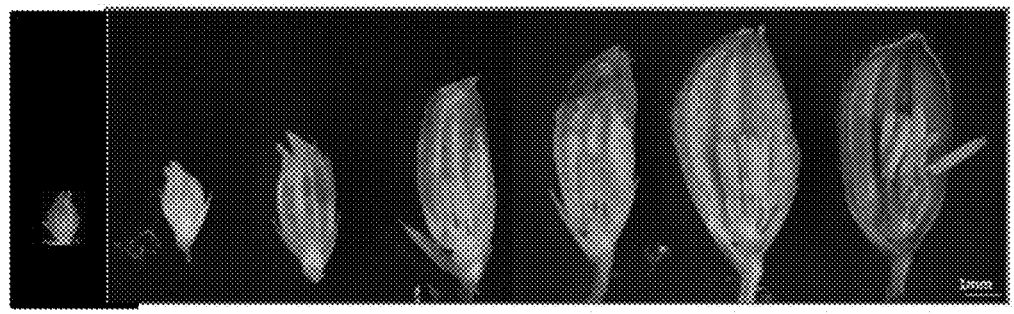
Figure 7:
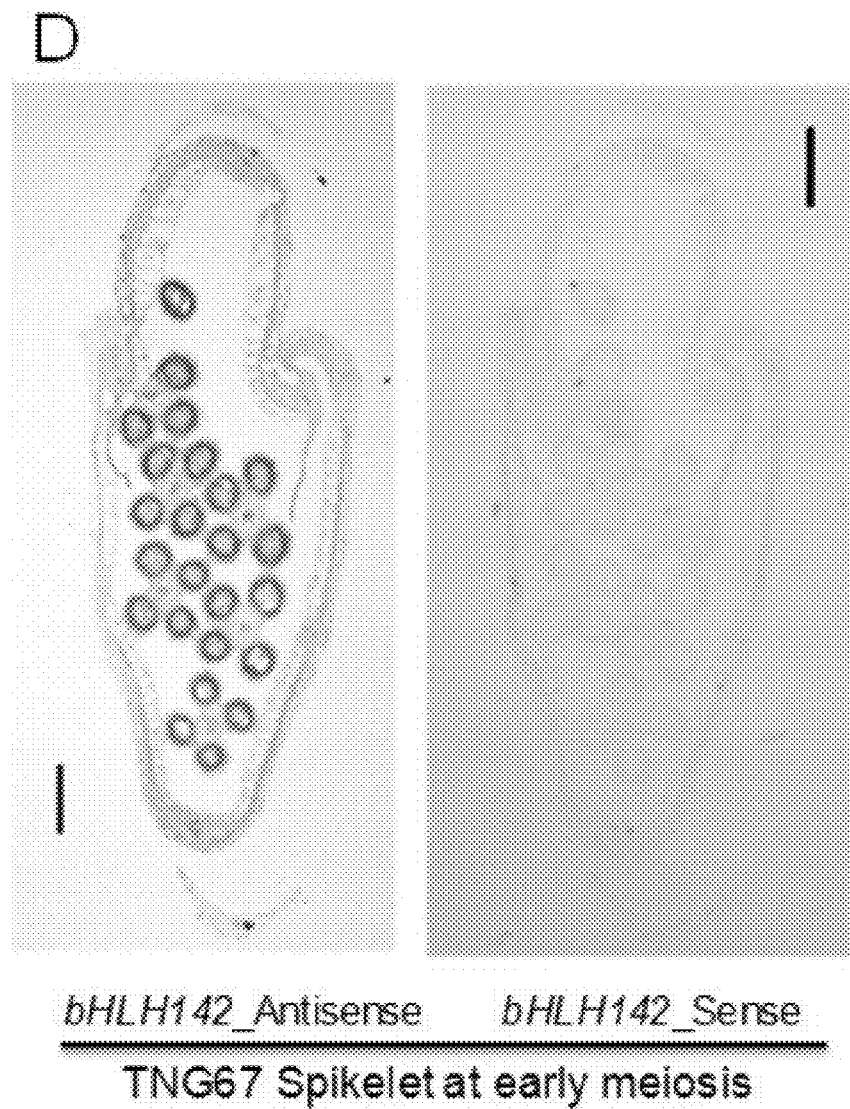
Figure 8:
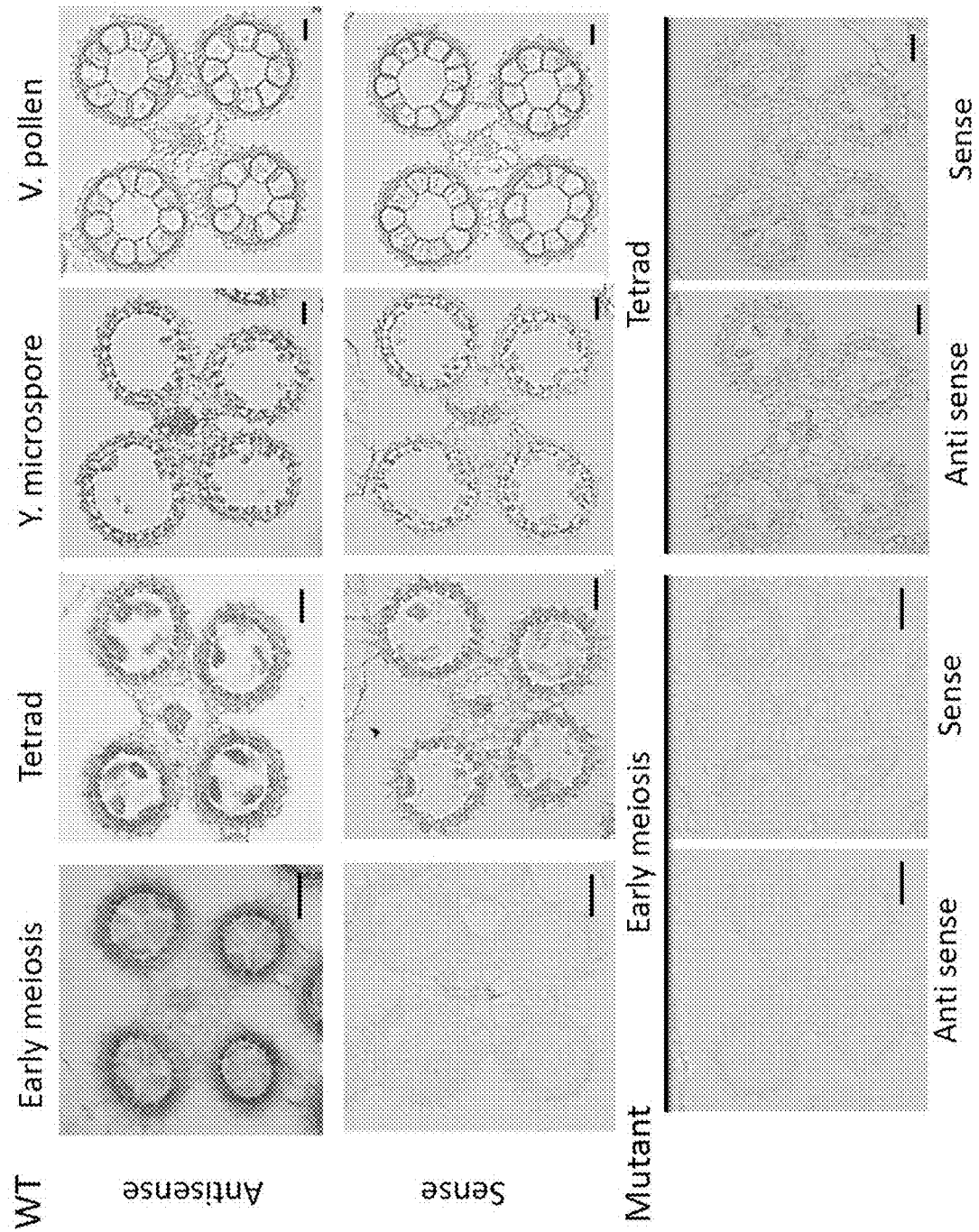
FIG. 8. In situ hybridization analysis of bHLH142 expression in the anther of WT and ms142 mutant at various developmental stages. Transverse sections of anther were hybridized with antisense or sense dig-labeled probe of bHLH142. Scale bar=20 μm.

Both RT-PCR and qRT-PCR analyses with WT showed that the bHLH142 mRNA is accumulated in young rice panicle and anther only, but not in other tissues (e.g. root, shoot, leaf, lemma, palea, ovary, and seed). In particular, high levels of transcripts were found in developing panicles (FIGS. 7A and 7B). Specifically, bHLH142 transcripts were highly expressed in meiocyte mother cells (MMC) and extremely highly expressed in the anther at meiosis stage (FIG. 7C). Also, in-situ hybridization (ISH) clearly demonstrated the specific expression of bHLH142 in the anther but not in lemma and palea of WT spikelet at early meiosis stage (FIG. 7D). ISH with the cross sections of WT anther at various developmental stages showed positive signals in the tapetal layers at early meiosis stage and in the tapetal layers and meiocytes during meiosis stage, with decreasing signals at young microspore stage and negligible signals after vacuolated pollen stage. Interestingly, ISH signal was also detected in the vascular cells (FIG. 8), suggesting that the target genes of bHLH142 might also be associated with nutrient acquisition in the anther. On the contrary, there was no ISH signal detected in the anthers of the null mutant of ms142 (FIG. 8).

In addition, the expression patterns of various known pollen regulatory genes in the anther of WT versus ms142, as examined by qRT-PCR, confirmed the knockout of bHLH142 transcript in the ms142 null mutant (FIG. 9A). Also, expression of TDR1, bHLH141 (EAT1), AP37, AP25, CP1, CYP703A3, CYP704B2, MS2 and C6 was significantly down-regulated in the ms142 anther, relative to the WT anthers (FIG. 9E, 9G-9M). However, MSP1 and UDT1 transcripts were up-regulated in the mutant at MMC and meiosis stages (FIG. 9B-9C). There was no significant change in the GAMYB transcripts in ms142 (FIG. 9D). Interestingly, the suppression of TDR1 expression in ms142 was less, compared to other downstream genes (FIG. 9E-9M). In WT anther, bHLH142 transcript was more abundant during meiosis stage, but it was negligible in the ms142 null mutant. Interestingly, EAT1 mutant also showed a lower amount of bHLH142 mRNA during meiosis stage (FIG. 10). We also compared EAT1 mRNA expression in these mutants to gain more insights into the regulatory interplay of these TFs in pollen development. In WT, EAT1 was expressed slightly later (at young microspore stage) than bHLH142 (at meiosis stage) (FIG. 10). Interestingly, ms142 anther exhibited a similar amount of EAT1 mRNA to WT anthers at MMC, but tended to decline after young microspore stage (FIG. 10). Taken together, these data suggest that bHLH142 plays a role in the downstream of UDT1, but upstream of EAT1.

bHLH142 and TDR1 Coordinately Regulate EAT1 Promoter Activity

Figure 10:
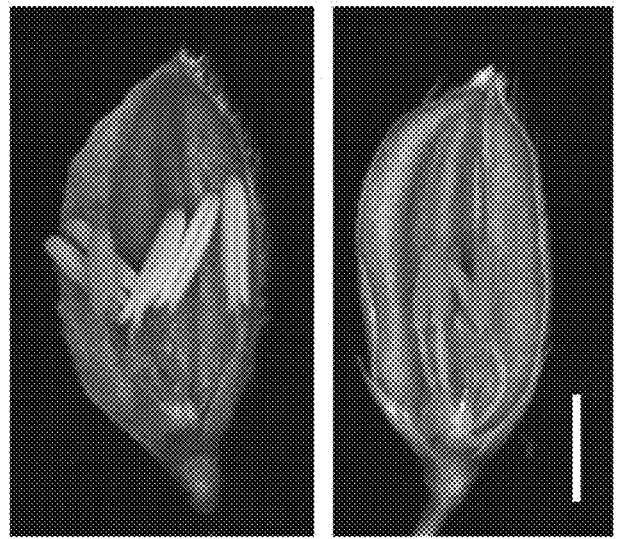
FIG. 10. Gene hierarchy of bHLH142, as determined by the expression profiles of the key regulatory genes involved in pollen development in ms142 and eat1 mutants. (A) Phenotype of spikelet in TNG67 (WT) and ms142. (B) Phenotype of spikelet in Hitomebore and H0530 (eat1 mutant). (C) Real-time RT-PCR of bHLH142 in ms142 and eat1 mutants and their respective wild-types. (D) Real-time RT-PCR of EAT1 (bHLH141) in ms142 and eat1 mutants and their respective wild types. qRT-PCR value presented are means±SE (n=3). MMC, meiocyte mother cell; Mei, meiosis; YM, young microspore; and VP, vacuolated pollen.
Figure 10:
Figure 10:
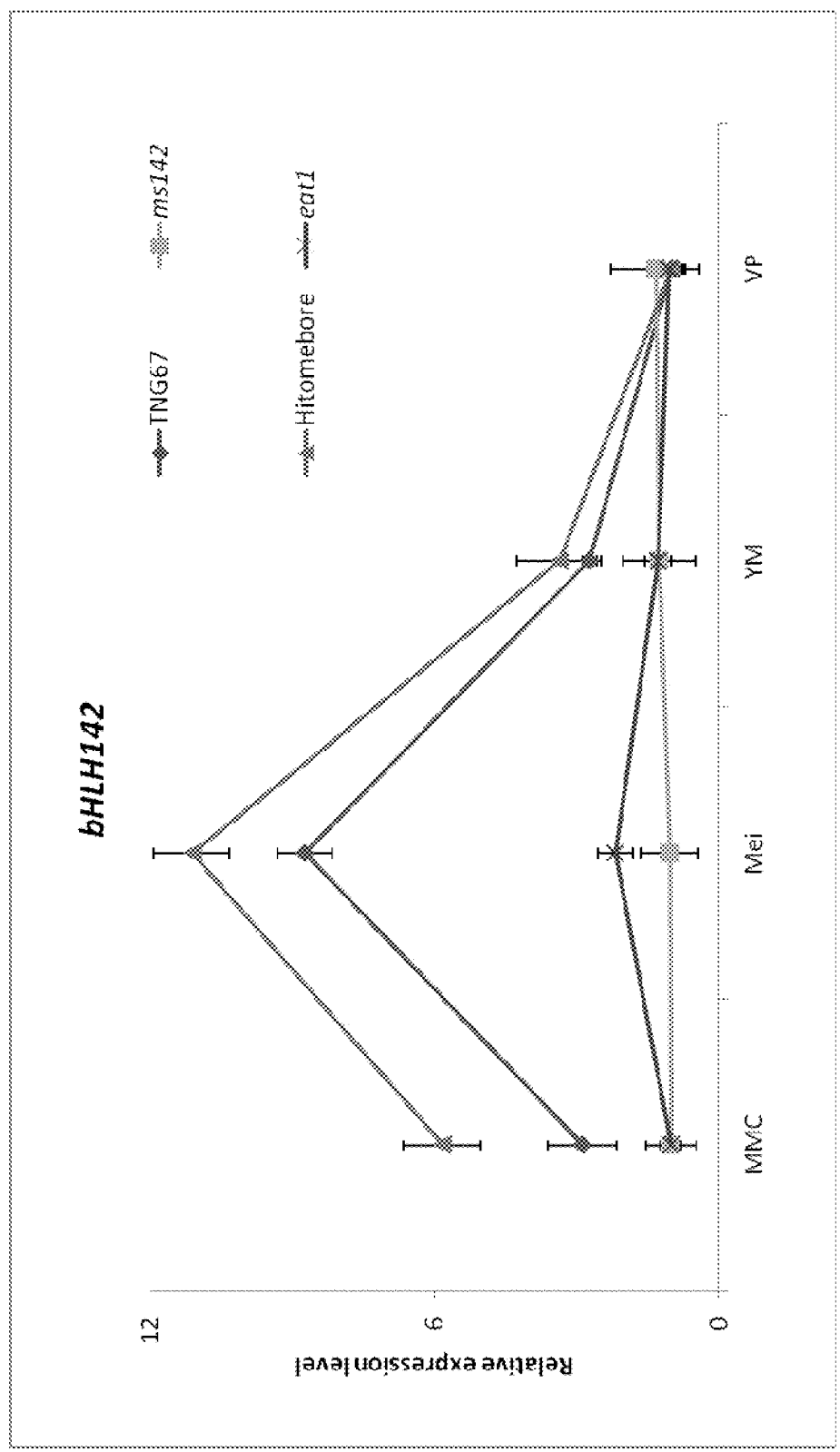
Figure 10:
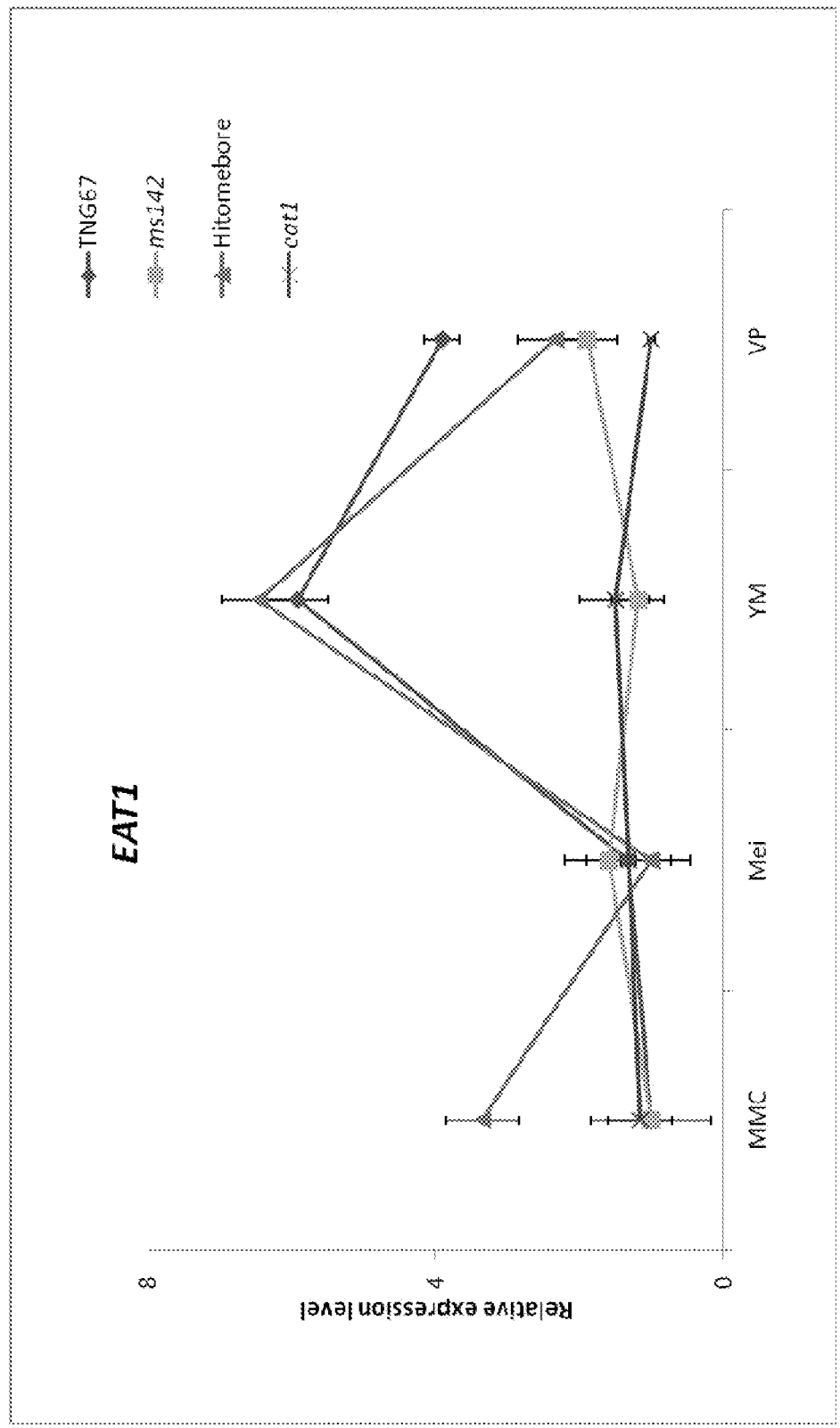
Figure 11:
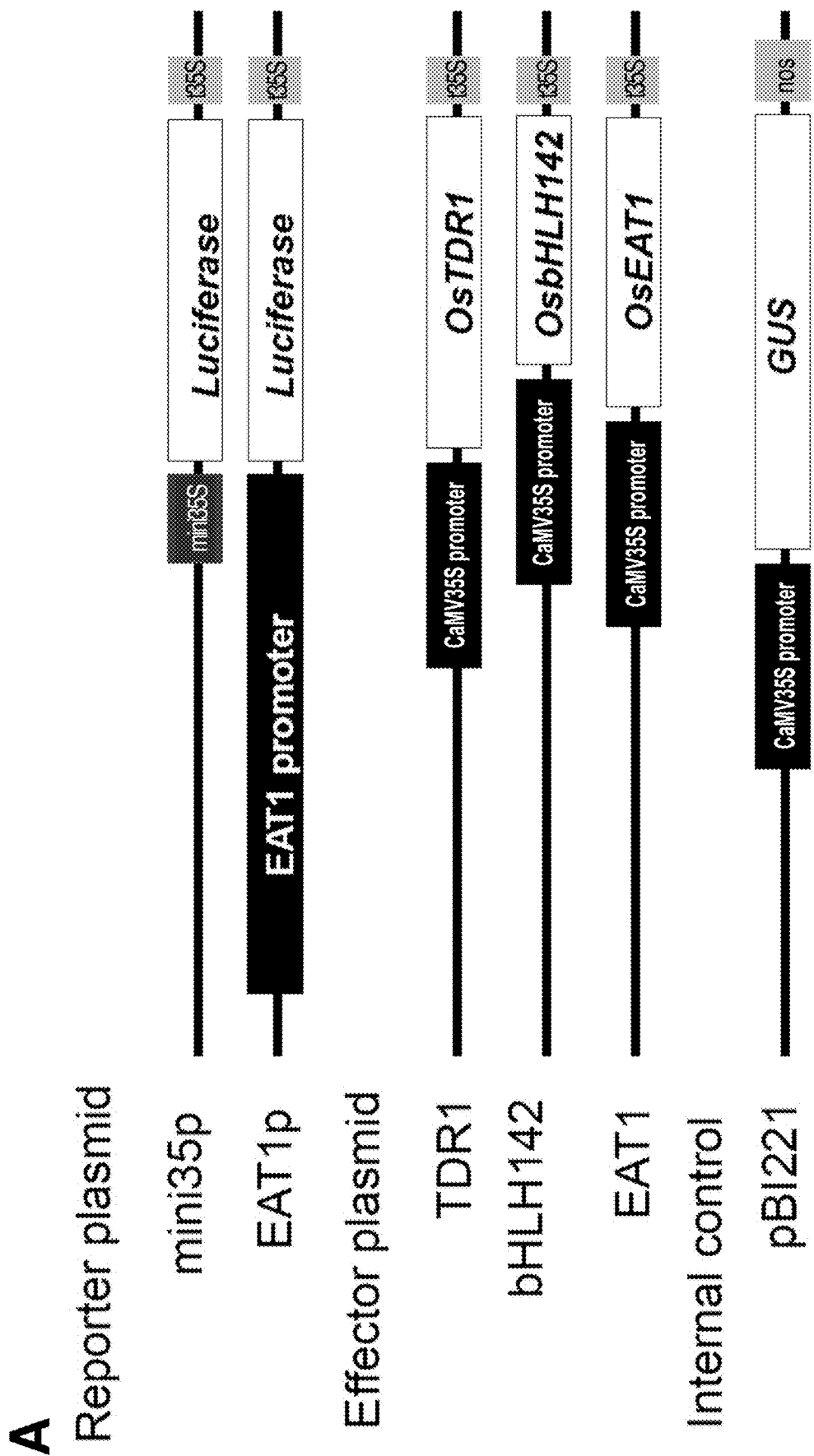
FIG. 11. Coordinated Regulation of EAT1 Promoter by bHLH142 and TDR1. (A) Schematic diagrams of the reporter, effector, and internal control plasmids used in the transient transactivation assay in rice leaf protoplasts. The reporter plasmid contains the CaMV35S minimal promoter and the EAT1 promoter sequence (2 Kb) fused to the firefly luciferase gene (Luc). In the effector plasmids, bHLH142, TDR1, and EAT1 genes were driven under the control of the CaMV35S promoter. Nos and t35s denote the terminators of nopaline synthase and CaMV35S, respectively. The pBI221 vector contains a CaMV35S promoter driving the expression of GUS as the internal control. (B) Transactivation of the Luc reporter gene by bHLH142 and TDR in rice protoplasts. Different effectors were co-transfected with the reporter and internal control plasmid (pBI221). The data represent means of three independent transient transformations. Error bars indicate SD. Transient transformation without the effector plasmid (mini35p) was used as a negative control.
Figure 11:
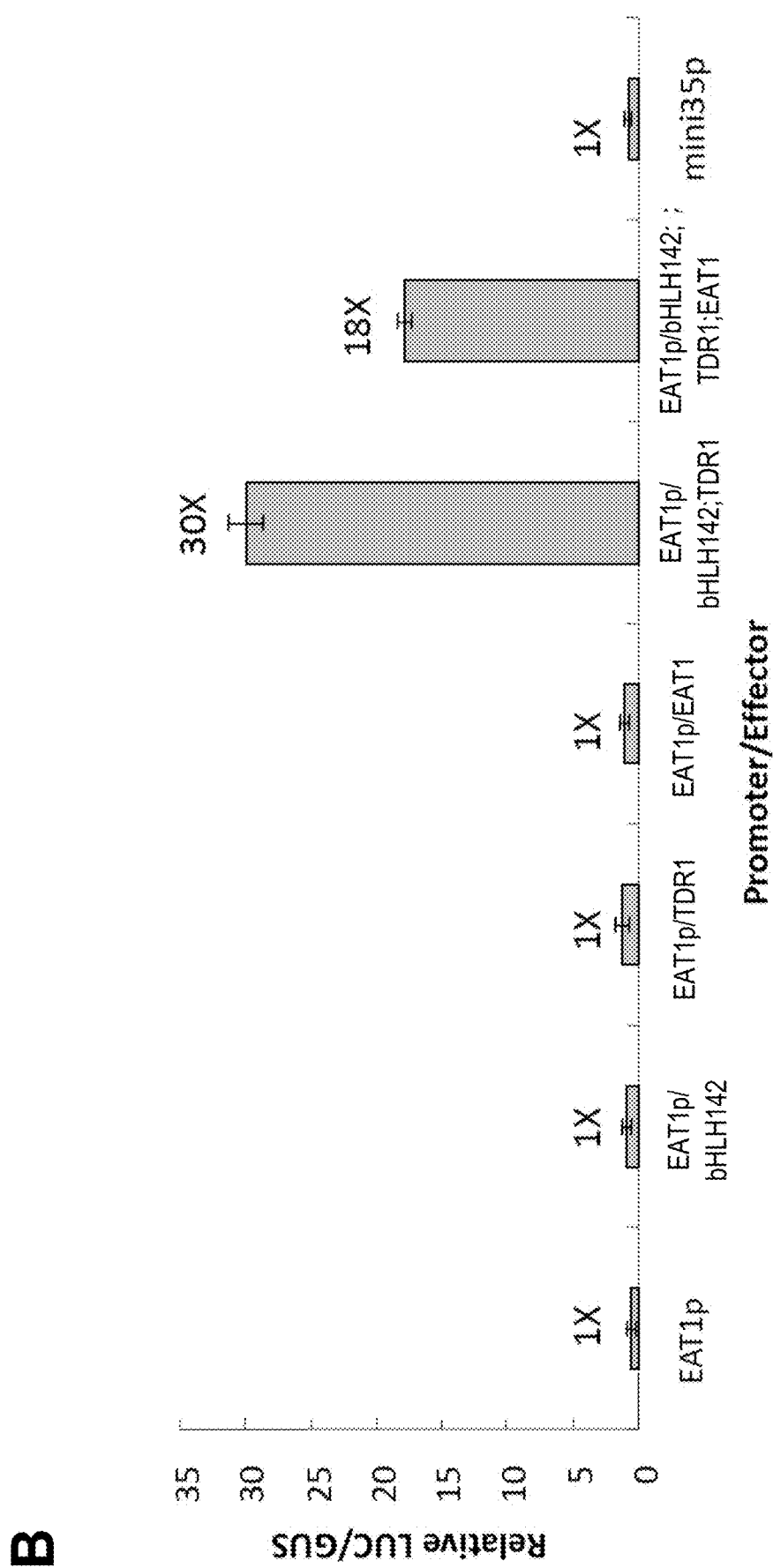

Based on the alternations in expression of known pollen regulatory genes in the different mutants (FIG. 9 and FIG. 10), we assumed that bHLH142 might regulate EAT1 promoter activity and carried out transient promoter assays with EAT1$_{pro}$-Luc construct. Our results demonstrated that bHLH142 or TDR1 protein alone cannot drive the expression of EAT1$_{pro}$-Luc independently. However, when combined, these two TF proteins together significantly increased Luc expression from the EAT1 promoter by up to 30 fold. However, additional expression of EAT1 in the same cells reduced Luc expression from a 30-fold down to an 18-fold increase, presumably due to the competition between EAT1 and bHLH142 in binding to TDR1 (FIG. 11). Apparently, TDR1 and bHLH142 co-regulate the activity of EAT1 promoter.

Protein Interactions Among bHLH142, TDR1 (bHLH5) and EAT1 (bHLH141)

We performed yeast two-hybrid analysis to determine whether bHLH142, as bait, interacts with the prey, TDR1 or EAT1. As previously reported that full-length EAT1 and TDR1 proteins possess self-activation activity in nature[23,24], our Y2H study also confirmed this phenomenon (FIG. 12A). Therefore, we also constructed a truncated EAT1$^{\Delta aa(1-254)}$ (truncated EAT1 at amino acids 1-254) and TDR$^{\Delta aa(1-344)}$ (truncated TDR amino acids at 1-344) to eliminate self activation (FIG. 12A). Our results showed bHLH142 is not self-activated (FIG. 12A); only the yeast strains co-expressing both bHLH142 and TDR$^{\Delta aa(1-344)}$ grew normally on stringent selection media (FIG. 13A) and there was no direct interaction between bHLH142 and EAT1$^{\Delta aa(1-254)}$. Thus, bHLH142 was not directly interacting with EAT1 as demonstrated in the yeast cells (FIG. 10A), and the retention of the C-terminal sequences of TDR1 is sufficient to confer the interaction of the two proteins. Clearly, the amino acid sequences in TDR$^{\Delta aa(1-344)}$ and EAT1$^{\Delta aa(1-254)}$ contain the interacting sites, consistent with the previous study[24]. These results are further supported by our results of EAT1 promoter assays in that both bHLH142 and TDR1 are required for the transcription of EAT1 (FIG. 11). Moreover, bimolecular fluorescent complementation (BiFC) assay showed that yellow fluorescent protein (YFP) signals are detected only in the nucleus of the rice cells co-expressing both NYN1-bHLH142 and CYN1-TDR1 and in the cells co-expressing both NYN1-TDR1 and CYN1-EAT1, but not in the cells co-expressing both NYN1-bHLH142 and CYN1-EAT1 (FIG. 13B). In vitro interaction of bHLH142 and TDR1 proteins was further validated by co-immunoprecipitation (Co-IP) experiment, where interaction between HA fused TDR1 and bHLH142 was confirmed (FIGS. 13C and 13D). Taken together, all of these molecular data provide solid evidences of the physical interaction between TDR1 and bHLH142.

RNAi Transgenic Rice Lines Validate the Role of bHLH142 in Pollen Development

Figure 15:
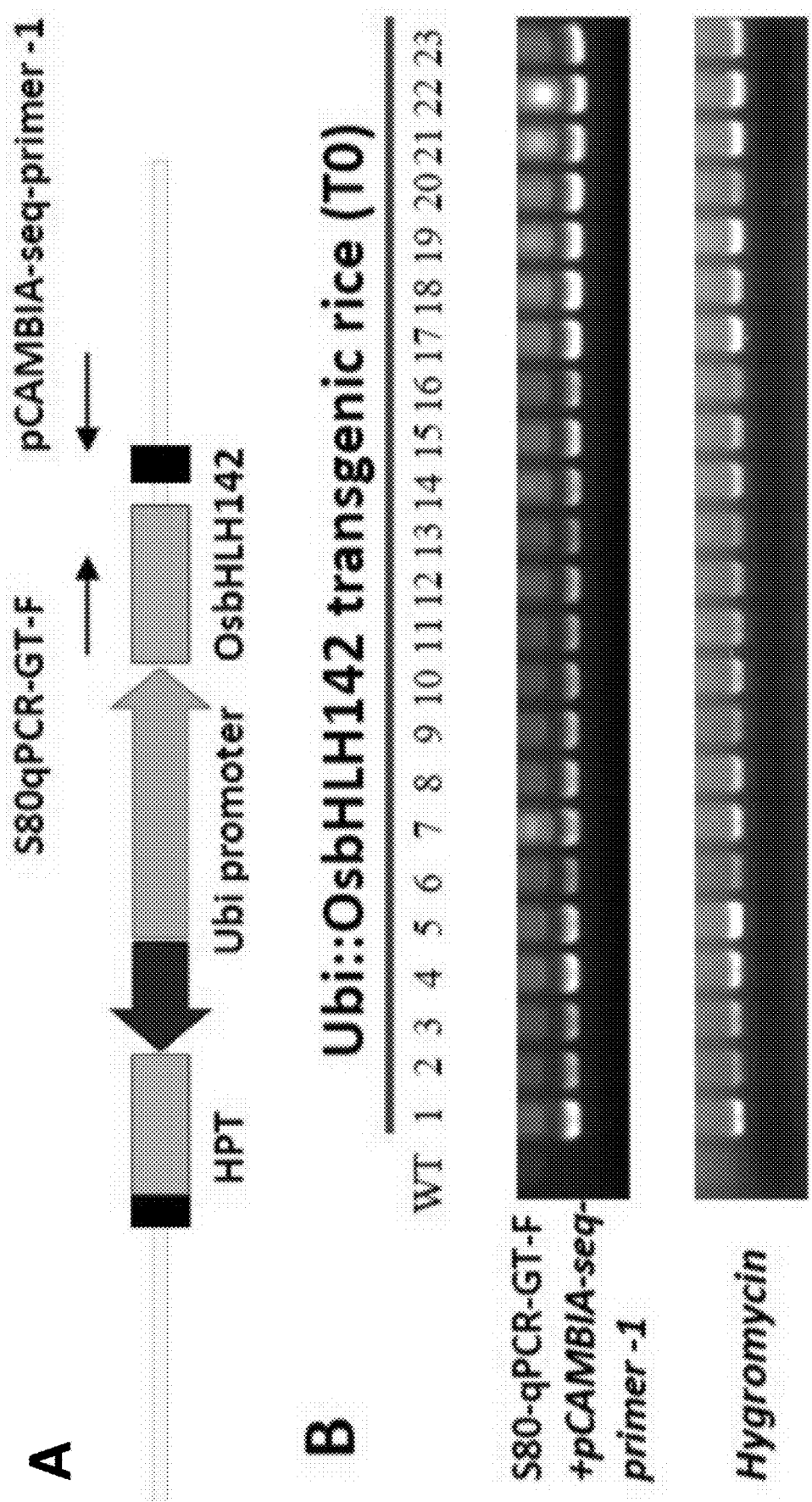
FIG. 15. Overexpression rice bHLH142 driven by Ubiquitin promoter in transgenic rice. (A) Construction of bHLH142 (LOC_Os01g18870) driven by Ubiquitin promoter in pCAMBIA1301 vector. (B) Genomic PCR confirmed T-DNA insertion of target gene (upper panel) and selection marker hygromycin (lower panel) in the transgenic rice.

To further validate the biological function of bHLH142, we generated an RNA interference (RNAi) construct to suppress the expression of bHLH142 in rice. The gene specific region from the 5' UTR of bHLH142 was amplified, fused with β-glucuronidase (GUS) intron and introduced into WT calli via *Agrobacterium tumefaciens*. All 16 T0 RNAi transgenic lines obtained had a MS phenotype similar to the T-DNA mutant ms142. These RNAi lines showed reduced expression of bHLH142, as examined by RT-PCR, and produced poorly developed anthers without pollen grains (FIG. 14). This result further supports the notion that bHLH142 plays a key role in rice anther and pollen development. The RNAi fragment (SEQ ID No. 120):

caacaaacctagttaatttagctctagttggttcatccctgctgcactg cgagctcaagtaatcgatctgagctctgaagaaaaaggtggtagagtgc gaggaagatgtatcacccgcagtgcgagctcctgatgccgcttgagagc ct Overexpression bHLH142 Caused Male Sterility For functional genomic study, we constructed overexpressing bHLH142 driven by constitutively express Ubiquitin promoter (FIG. 15A) and introduced into wild-type (TNG67 background) calli via *Agrobacterium tumefaciens*[38]. Genomic PCR confirmed T-DNA insertion of target gene and selection marker hygromycin (lower panel) PCR has band in the 23 tested T0 transgenic lines (FIG. 15B).

Figure 16:
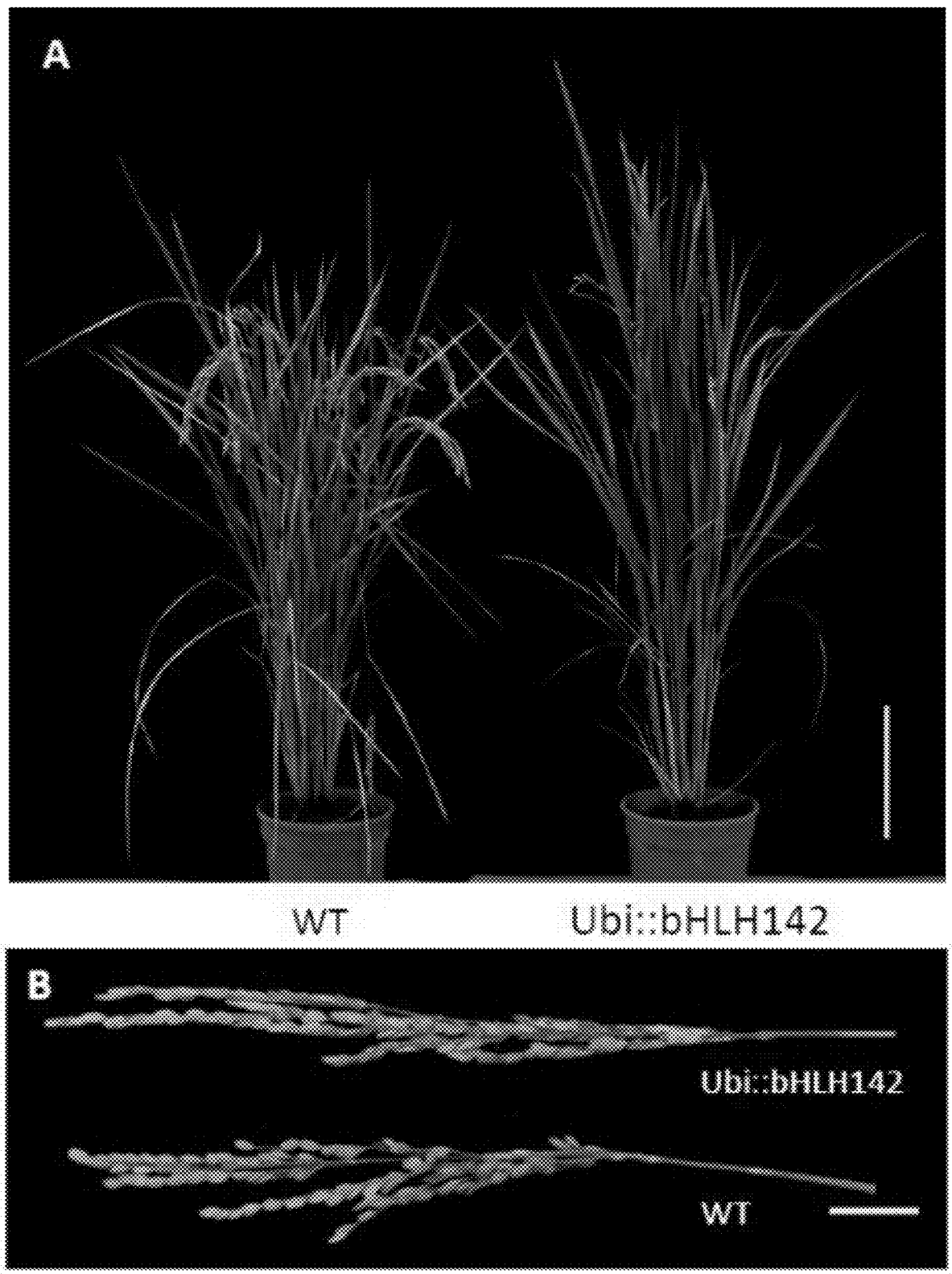
FIG. 16. Phenotype of TNG67 (WT) and Ubi::bHLH142 transgenic lines. (A) Plant type of WT (left) and transgenic line (right), (B) panicles of WT (bottom) and transgenic line (top panel), (C) panicles of WT (left) and different transgenic lines, (D) spikelet of WT (left) and different transgenic lines at one day before anthesis, (E) mature seed of WT (left) and different transgenic lines, and (F) removed husk rice seed of WT (left) and different transgenic lines. Scale bars=20 cm in (A), 3 cm in (B), 7 cm in (C) and 1 cm in (F).
Figure 16:
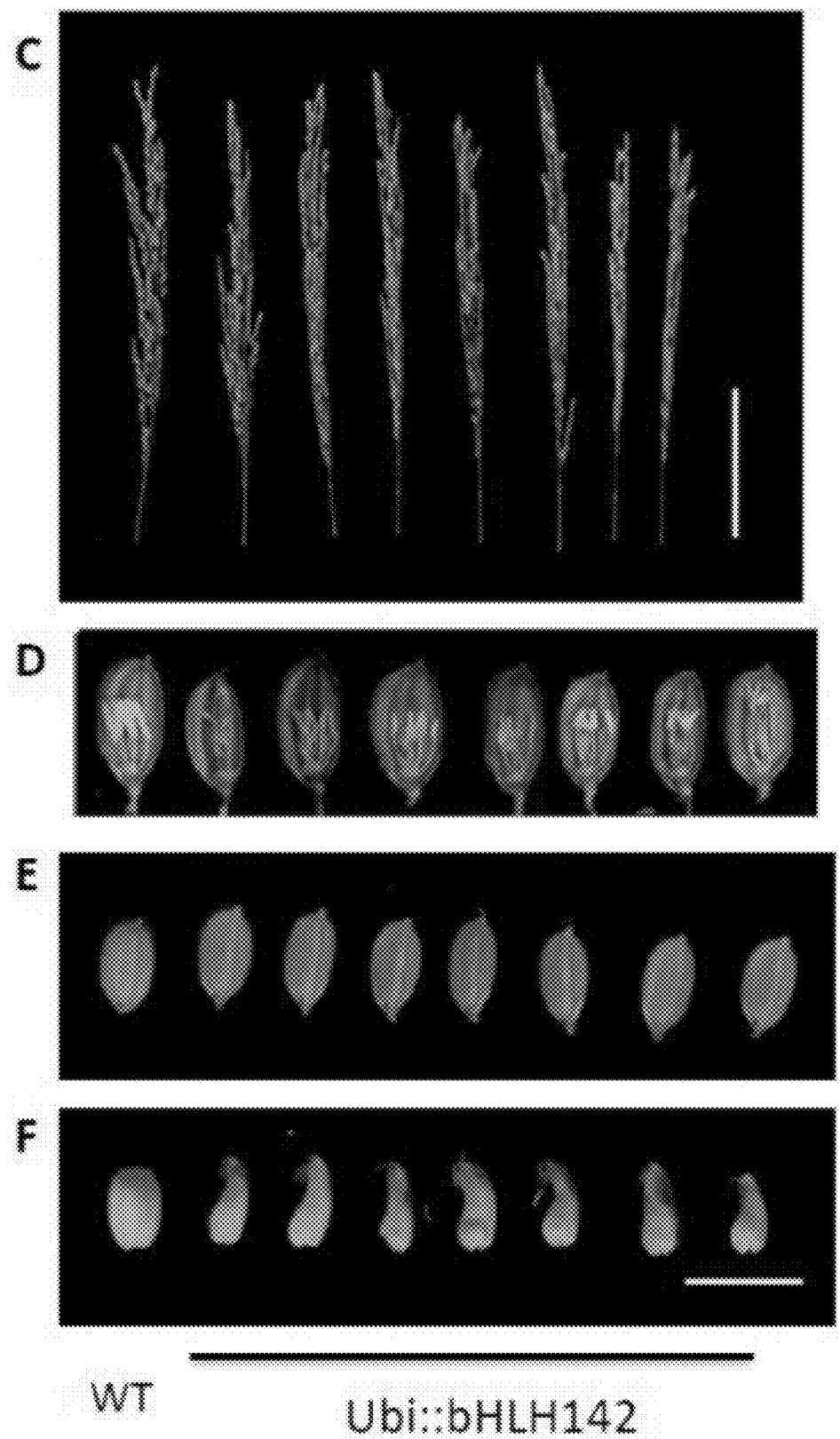

Interesting to observe that overexpressing bHLH142 T0 transgenic plants all showed grain sterility (FIG. 16). Ubi::

bHLH142 transgenic lines have similar plant type and panicle length (FIGS. 16B and 16C) with the WT except no grain filling after anthesis stage (FIG. 16A). It was observed anthers of overexpression transgenic lines were shorter and showed light yellow color than the WT (FIG. 16D). After seed maturation stage, grain of WT was filled with starch but there was no viable seed in those overexpressing lines (FIGS. 16E and 16F).

Figure 17:
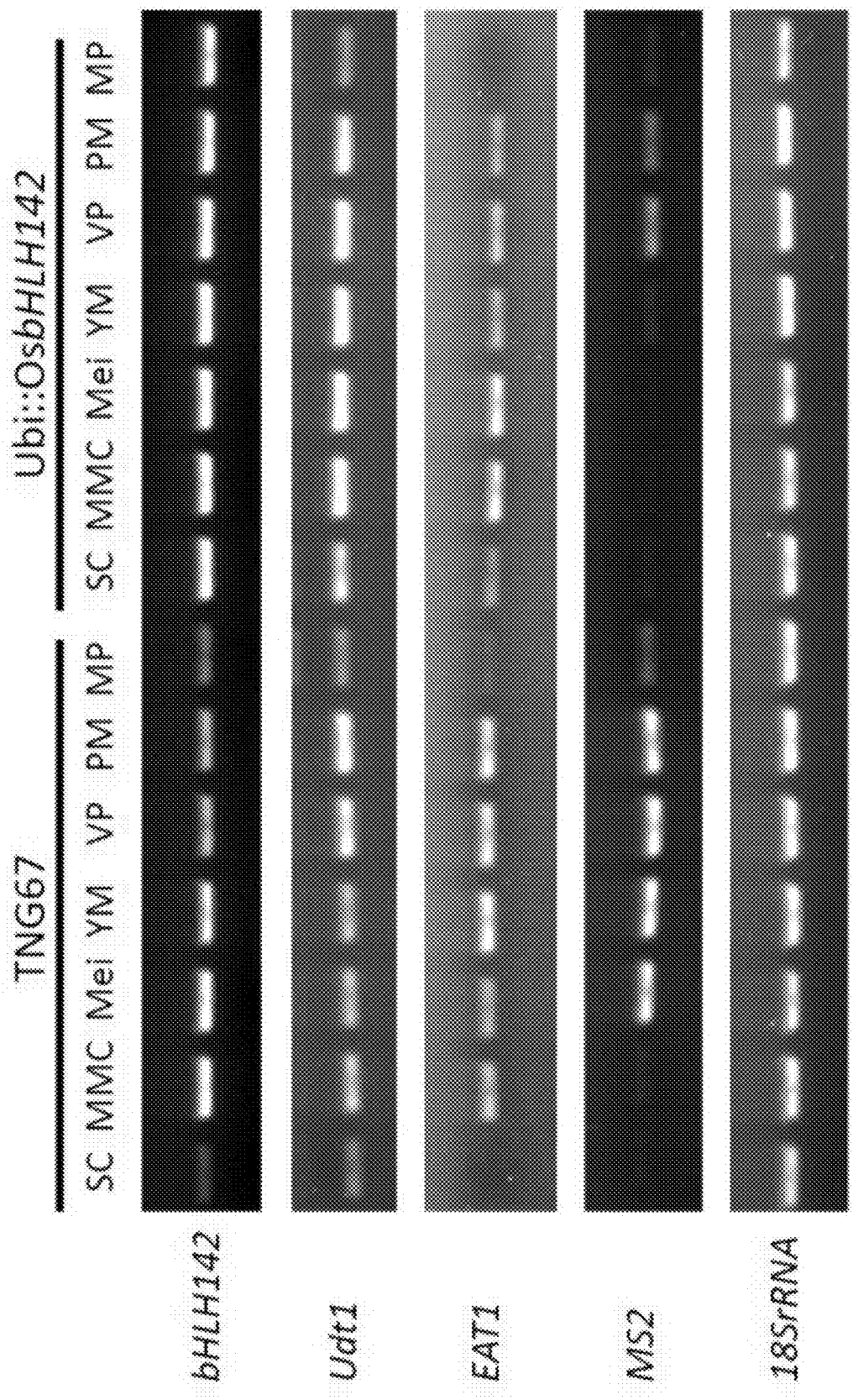
FIG. 17. Overexpression bHLH142 prematurely up-regulated Udt1 and EAT1 before meiosis stage but significantly down-regulated MS2 that associated in pollen exine development. SC=sporogenous cell, MMC=meiocyte mother cell, Mei=meiosis, YM=young microspore, PM=pollen mitosis, MP=mature pollen.

By using RT-PCR, we detected some regulatory genes associated with pollen development in rice. As expected, overexpression line constitutively express abundant of bHLH142 transcripts during various stages of anther development. Interestingly, Udt1 was simultaneously upregulated in the overexpression line. EAT1 mRNA also prematurely upregulated before meiosis stage but decrease its expression at latter stage of anther development. However, MS2 was significantly downregulated in the overexpressing line (FIG. 17). Defect of grain fertility in overexpressing line presumably due to prematurely upregulation of tapetal program cell death genes such as UDT1[20] and EAT1[23]. Moreover, down-regulation of MS2 that reported contribution to pollen exine development might associate with the defect of pollen development in the overexpression line.

Heterologuos Overexpression bHLH142 Confers Male Sterility in Maize

Figure 18:
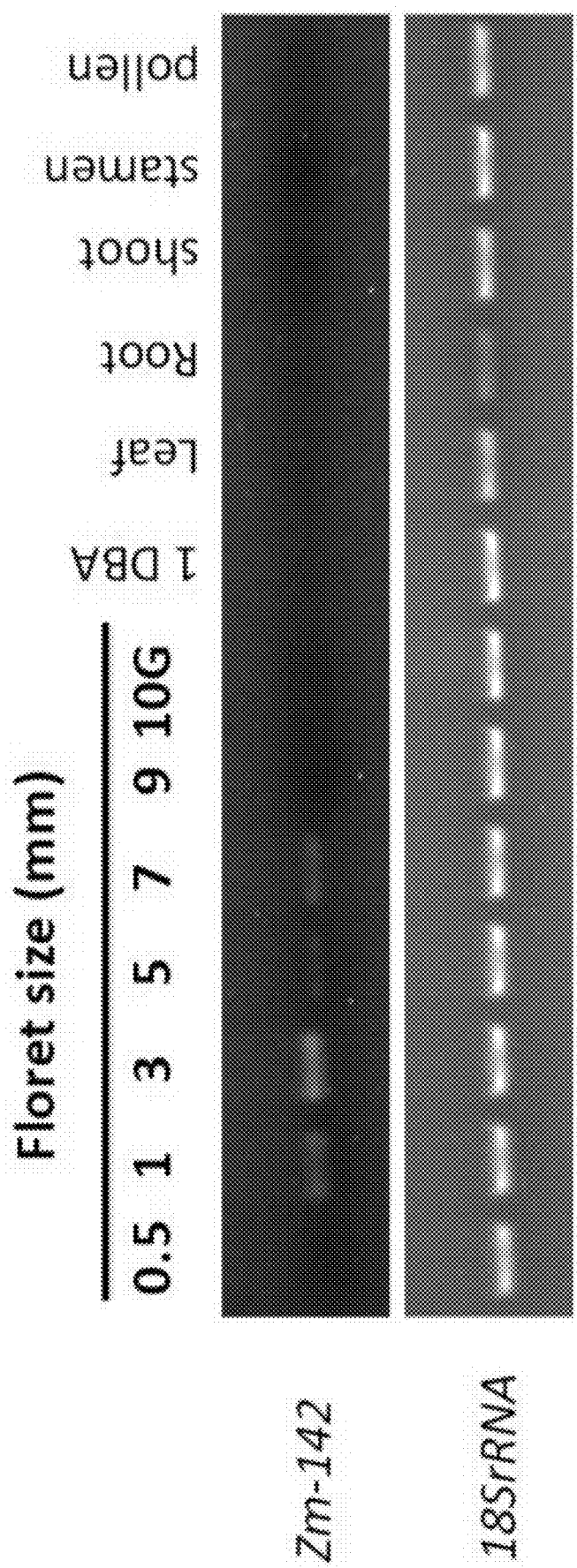
FIG. 18. Gene expression pattern of bHLH142 homolog in various organs of maize by using RT-PCR. Floret size by measuring the length of floret. 10G, floret length at 10 mm with green color. 1DBA, one day before anthesis.

Since bHLH142 shares high identity with maize[38], and gene specific primer sets were designed from homolog of maize ZmLOC100283549 (denoted Zm-142). RT-PCR indicated that Zm-142 was not expressed in vegetative organs of maize such as leaf, root, shoot, and stamen. Interestingly, Zm-142 specifically expressed in floret of 1 mm to 7 mm length but not detectable at later stage and in the mature pollen (FIG. 18). The expression pattern of Zm-142 was similar to bHLH142[38].

Figure 19:
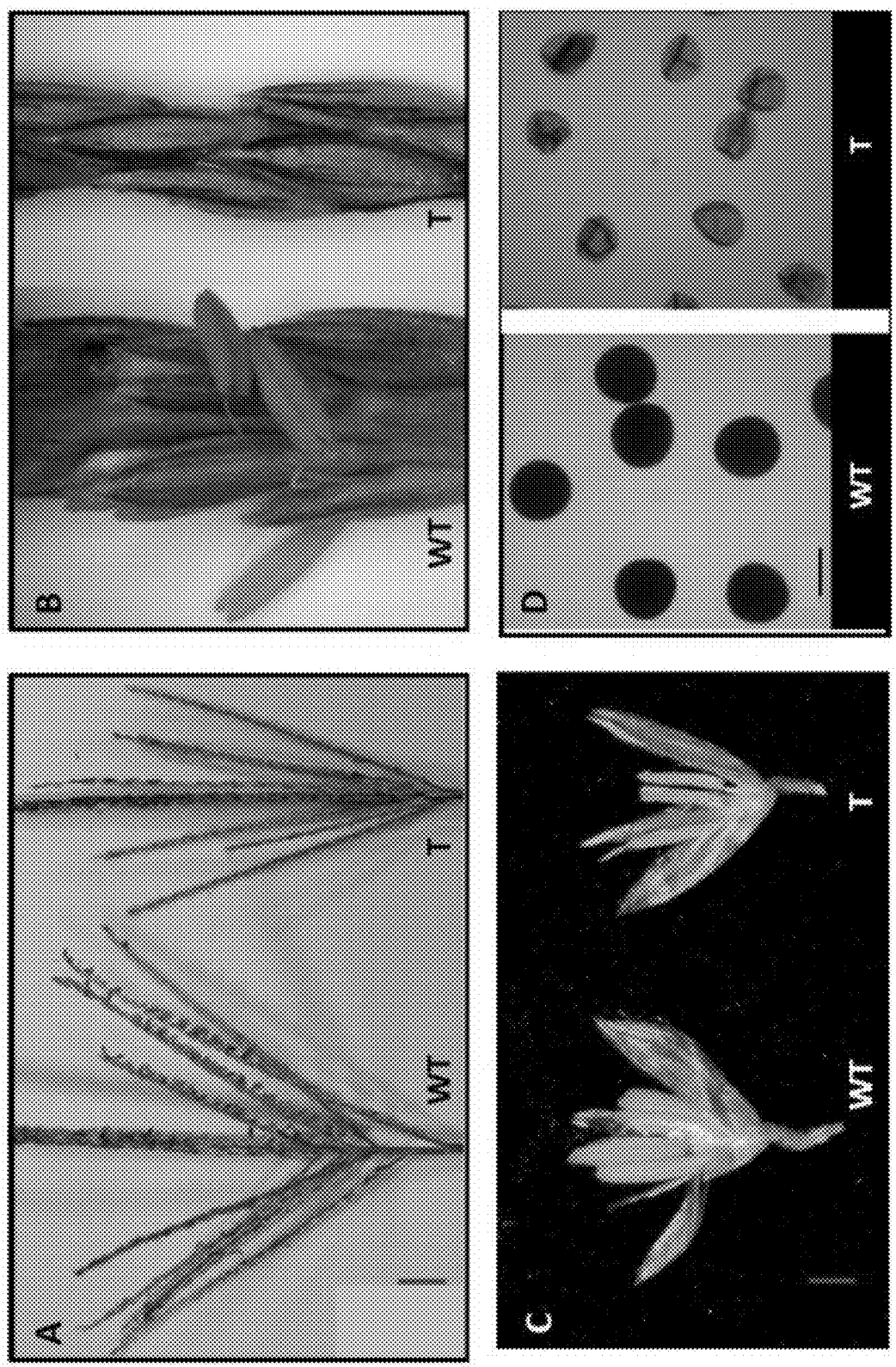
FIG. 19. Heterologus overexpressing Ubi::bHLH142 caused male sterility in transgenic maize. (A) The transgenic line has smaller angle of tassel branch (right panel) than the WT (left panel). (B) Closed up tassel during anthesis stage, WT has large and anther opened during anthesis stage (left panel), while anther of transgenic maize were significantly smaller in size and anther no dehiscence (right panel). (C) Morphology of spikelet of WT (left panel) and transgenic line (right panel). (D) Stained of pollen grains by $I_2$/KI solution in the fertile WT, but not stainable in the transgenic line and pollen was not viable showing transparent pollen. Scale bars=3 cm in (A), 2 mm in (C) and 50 um in (D).

Therefore, we use the similar construct of overexpression bHLH142 in FIG. 15A was transformed into maize (in cultivar Crystal White background) using *agrobacterium*-mediated pollen transformation method. One transgenic maize showed obvious male sterility phenotype with smaller angle of tassel branch (FIG. 19A, right panel) than the WT (FIG. 19A, left panel). Closed up tassel during anthesis stage, WT has larger anther than transgenic line and it has normal opening of spikelets and elongation of anther filaments during anthesis stage (FIG. 19B, left panel). Whilst, anther of transgenic maize were significantly smaller in size and anther was completely no elongation of anther filaments (FIG. 19B, right panel). Morphology of spikelet of WT at one day before anthesis was shown in FIG. 19C (left panel) with long and fat anther, but anther of transgenic line was short and shrinkage (FIG. 19C, right panel). Stained of maize mature pollen grains with $I_2$/KI solution, and the fertile WT pollen grains stained with dark red color. However, pollens of transgenic line could not be stained and transparent due to no starch accumulation. That implied transgenic line was male sterile (FIG. 19D).

Figure 20:
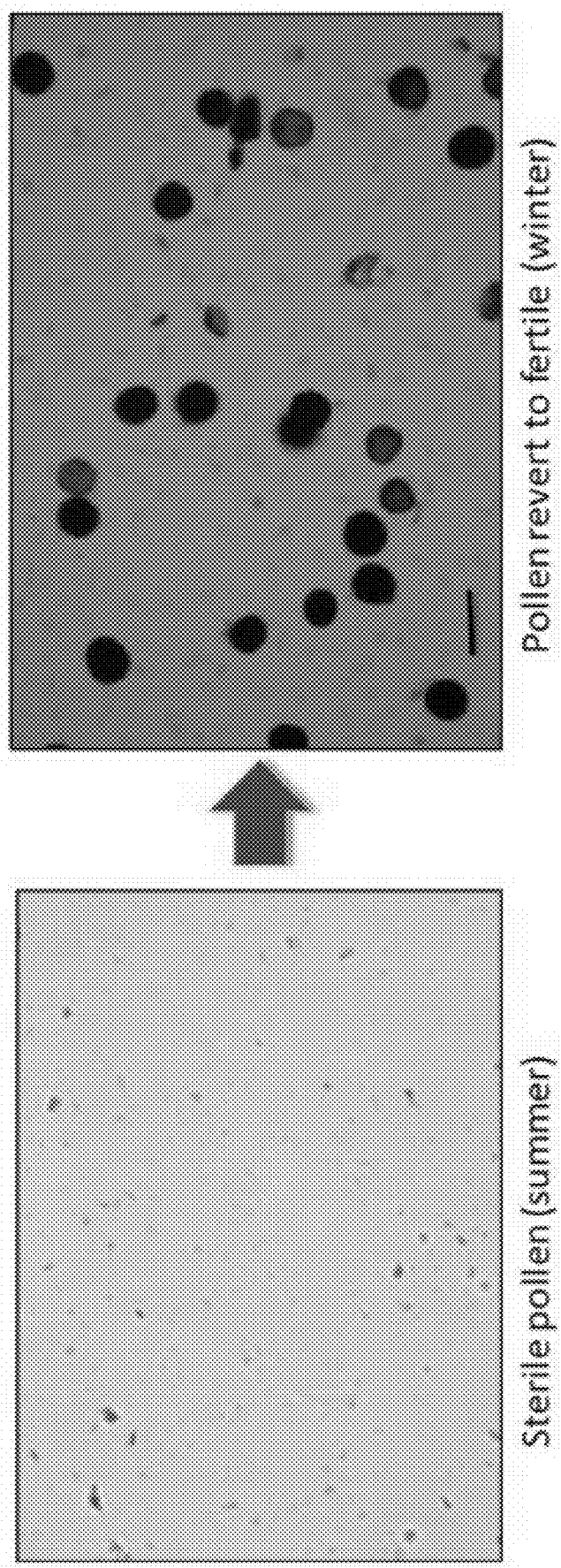
FIG. 20. The male sterility of Overexpression Ubi::bHLH142 transgenic line is sensitive to environment. The bHLH142 overexpressed lines produced no pollen grains during summer season (Left panel) but had fertile pollens during winter seasons. Pollen grains were stained by $I_2$/KI solution.

Overexpression bHLH142 Induces Reversible Male Sterility in Low Temperature bHLH142-overexpressed plants also showed a completely male sterile phenotype during summer season (FIG. 20, left panel). By contrast, during winter low temperature conditions, anthers of overexpression transgenic line produce many pollen grains inside the locules and their pollen grains can be stained by $I_2$/KI solution, indicating that the plants have restored the fertility (FIG. 20, right panel). Therefore, this novel functionality nature of our target bHLH142 has a big advantage over other genetic MS (GMS) genes for hybrid crop production. This reversible pollen fertility trait makes it more desirable in producing hybrid crop seeds just in one cross without the need to maintain the seed stocks of the MS lines as with cytoplasmic MS (CMS). In addition, biotech companies are known to prefer adopting overexpression over suppression approach in generating transgenic lines because overexpression lines are more stable than RNAi or antisense knock-down lines.

Rice bHLH142 have homologous in maize, *sorghum* and wheat, and they share more than 70% similarity in amino acid sequence to the rice counterpart (Table 3). This will benefit to genetic engineering male sterile for F1 hybrid seed production and generating hybrid vigor (heterosis) in terms of growth and grain yield in cereal crops.

bHLH142 is a New Major Regulator of Rice Anther Development

Figure 21:
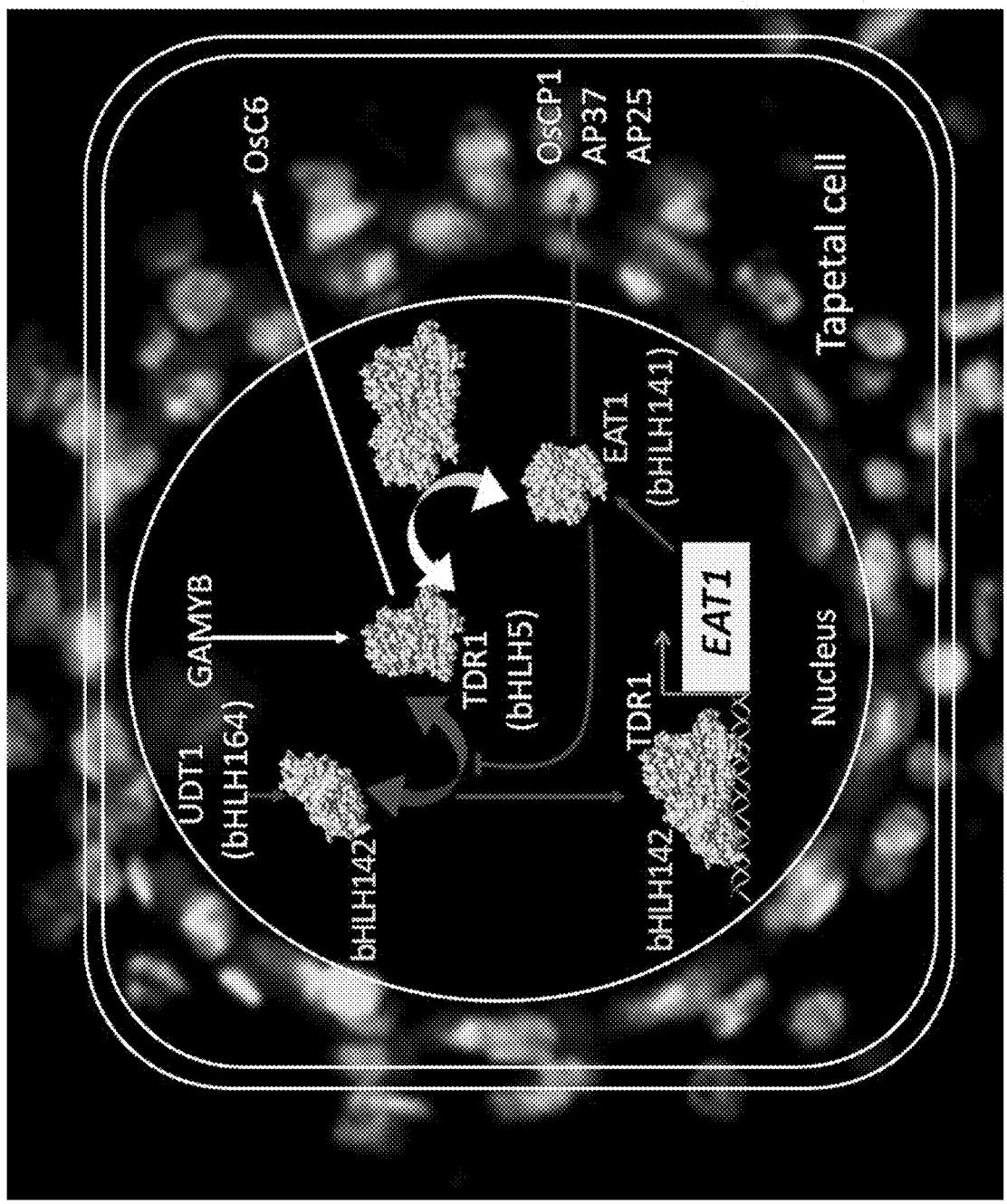
FIG. 21. A proposed model for the molecular function of bHLH142 in rice anther development, relative to other key regulators. bHLH142 is in the downstream of UDT1 but upstream of TDR1, and bHLH142 interacts with TDR1 protein and coordinately regulate the promoter of EAT1. In turn, EAT1 regulates AP37 and CP1 and promotes tapetal PCD. Evidences from previous works were indicated by black arrows, while data demonstrated in the present study were indicated by red arrows.

So far, three of the bHLH TFs have been shown to be involved in pollen development in rice and mutations of these TF genes all lead to complete MS, including UDT1 (bHLH164)[20], TDR1 (bHLH5)[14], and EAT1/DTD1 (bHLH141)[23,24]. They all play an important role in pollen development by regulating tapetal PCD. In this invention, we identified a novel rice MS mutant, ms142 (FIG. 1), with T-DNA inserted in the intron of bHLH142, which encodes another basic helix-loop-helix dimerization region bHLH domain containing TF protein. The phenotype is characterized by having small anthers without pollen grain development (FIG. 1). Genetic analyses suggest that the mutation is due to a single T-DNA insertion event. We further show that this TF is located in the nuclei (FIG. 5) and plays an essential role in regulating rice pollen development. Close anatomical examination of anther development, in parallel with TUNEL assay of DNA degradation and ISH of key gene transcripts, in the null mutant demonstrate that defects in microspore development is associated with defects in tapetal PCD. Timely degradation of tapetum cells is essential for viable pollen development. Furthermore, suppressed expression of bHLH142 in WT rice by RNAi confers the MS phenotype (FIG. 21). Thus, this invention identifies the involvement of another bHLH TF in the dynamic regulation of pollen development in rice and likely in other plants as well.

Figure 9:
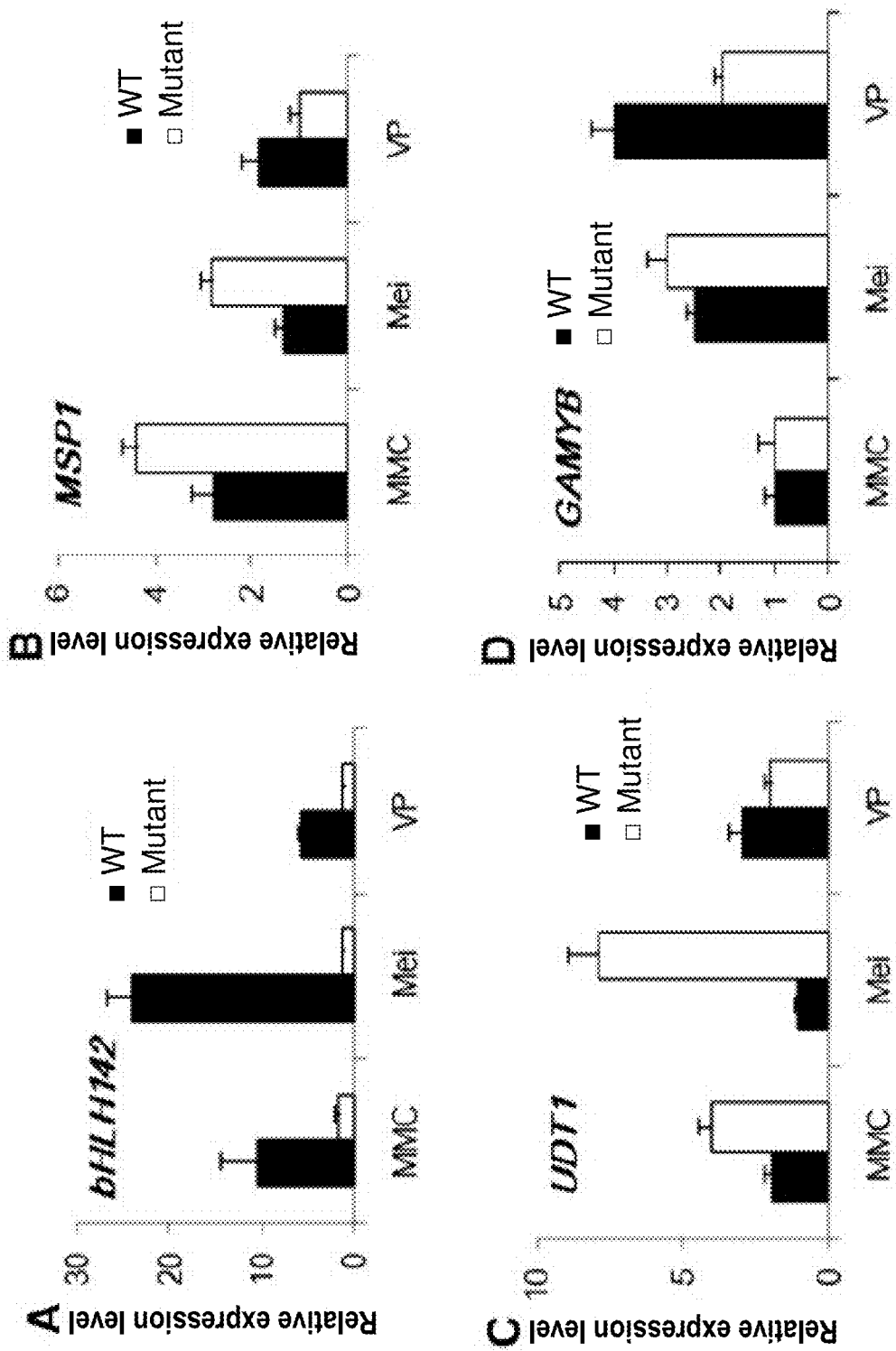
FIG. 9. Analysis of alternation in expression of key regulatory genes involved in pollen development in ms142 by qRT-PCR. Error bars indicate SD (n=3). MMC, meiocyte mother cell; Mei, meiosis; and VP, vacuolated pollen.
Figure 9:
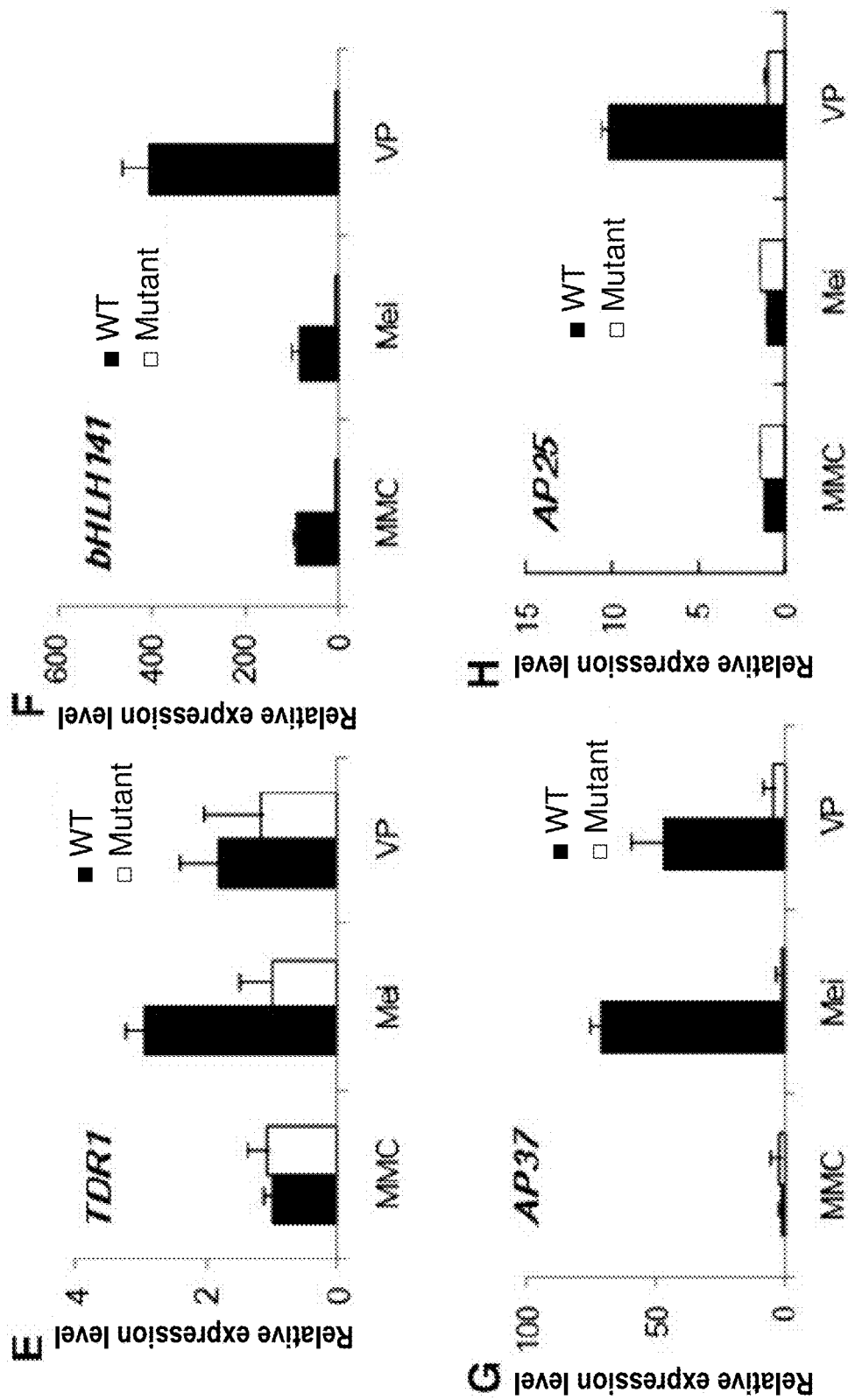
Figure 9:
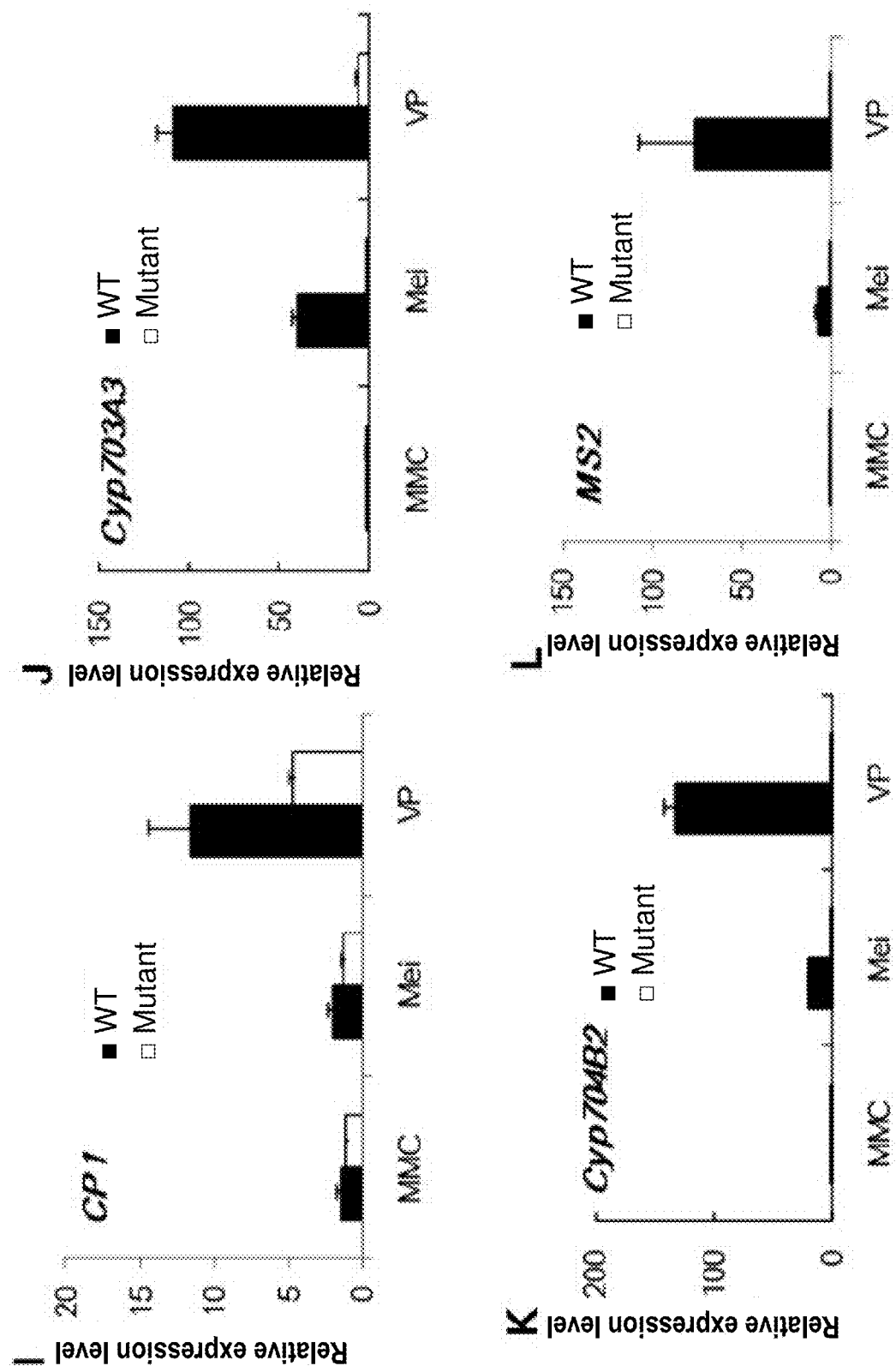
Figure 9:
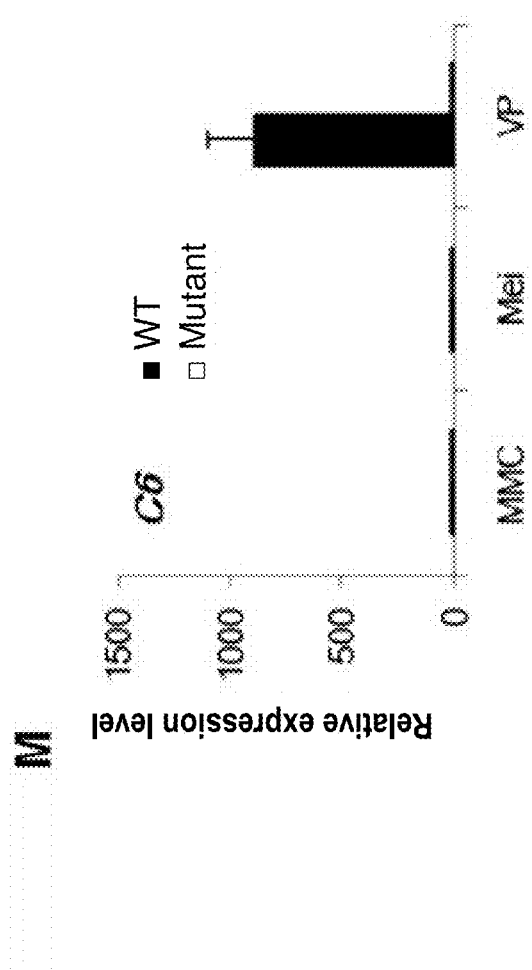

Our analysis of expression profile of known regulatory genes involved in pollen development demonstrates the down-regulation of several genes, such as TDR1, EAT1, AP37, CP1, C6, MS2, etc. in ms142 during pollen development (FIG. 9). Therefore, we suggest that bHLH142 participates in the same regulatory pathway of anther development, with a higher gene hierarchy (FIG. 10). An earlier study reports that TDR1 positively regulates CP1 and C6[14], while a recent study suggests that EAT1 interacts with TDR1 in regulating the expression of two aspartic protease genes, AP25 and AP37[23]. Another study also reported that mutation in DTD (same as EAT1, bHLH141) in rice results in severe MS[24]. In consistent with this report, we also find that the NIAS Tos17 mutant H0530, a knockout of EAT1 (bHLH141) gene, also fails to produce pollens (FIG. 10B). However, the eat1/dtd mutant exhibits normal meiosis process, but ms142 cannot exceed beyond meiosis cell division, which may be due to the extra role played by bHLH142. Consistent with this notion, our ISH analysis revealed that, besides tapetal layer, bHLH142 is also expressed in meiocytes as well as in the vascular bundle (FIG. 8). This result suggests that bHLH142 might also play an additional role in nutrient acquisition for cell plate formation during microspore development.

This invention uncovers bHLH142 as another critical factor in the bHLH TF family for pollen development, besides UDT1 (bLHL164), TDR1 (bLHL5) and EAT1

(bHLH141). Our mutagenesis analysis suggests that the gene hierarchy of bHLH142 is in the downstream of UDT1 (bHLH164) but upstream of TDR1 (bHLH5) and EAT1 (bHLH141) (FIG. 10 and FIG. 9). Interestingly, all these 4 bHLH TFs are tissue specifically expressed in the anther and participate in the important process of sequential pollen development events, particularly in tapetal PCD. Thus, it is rather unique in that several of the bHLH TFs coordinate in regulating the anther development; and it is likely that more TFs might be involved in controlling the regulatory network to ensure normal pollen development.

Also, we noticed a lower suppression in expression of TDR1 in ms142, compared to other downstream genes in the regulatory network, which may be attributed to the fact that TDR1 is also known to be regulated by another TF GAMYB[22]. In agreement, we also found that the expression of GAMYB is not altered in ms142 (FIG. 9). Taken together, these results suggest that two parallel pathways may exist in the regulatory circuit leading to TDR1 during pollen development.

bHLH142 Functions Coordinately with TDR1 to Regulate EAT1 Promoter

Figure 13:
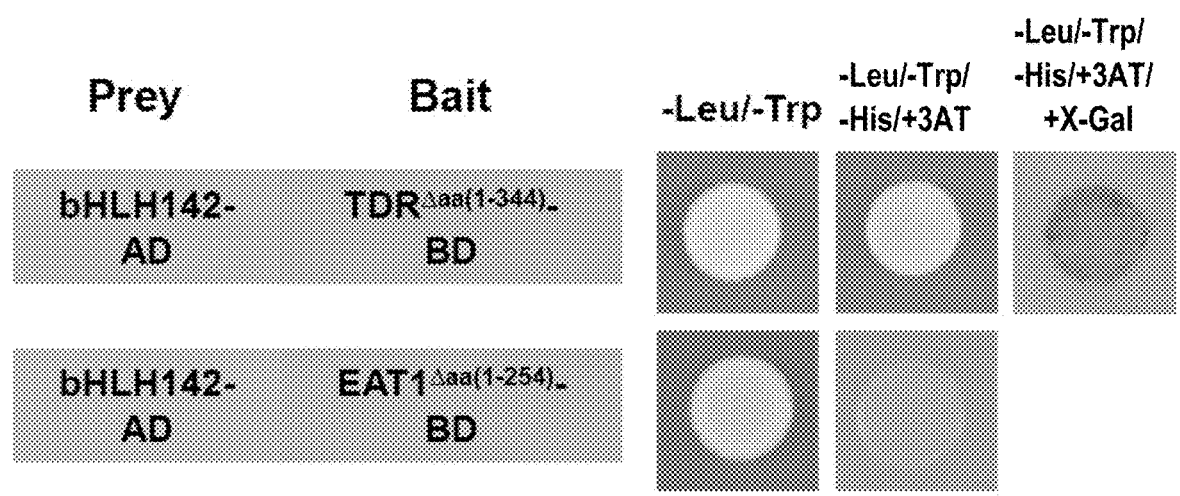
FIG. 13. The Interactions between bHLH142 Protein and TDR1, and between TDR1 and EAT1. (A) Yeast two-hybrid (Y2H) assays. Constructs expressing the full length bHLH142 were cloned into the prey vector pGADT7 (AD), and truncated forms of TDR and EAT1 were prepared in the bait vector pGBKT7 (BD). (B) BiFC in rice protoplasts expressing the indicated constructs. Bars represent 10 (C) Co-IP assay of HA fused TDR and bHLH142 recombinant proteins expressed in *E. coli* using anti-HA antibody. (D) Co-IP assay of HA fused TDR and bHLH142 recombinant proteins expressed in *E. coli* using bHLH142 antibody.
Figure 13:
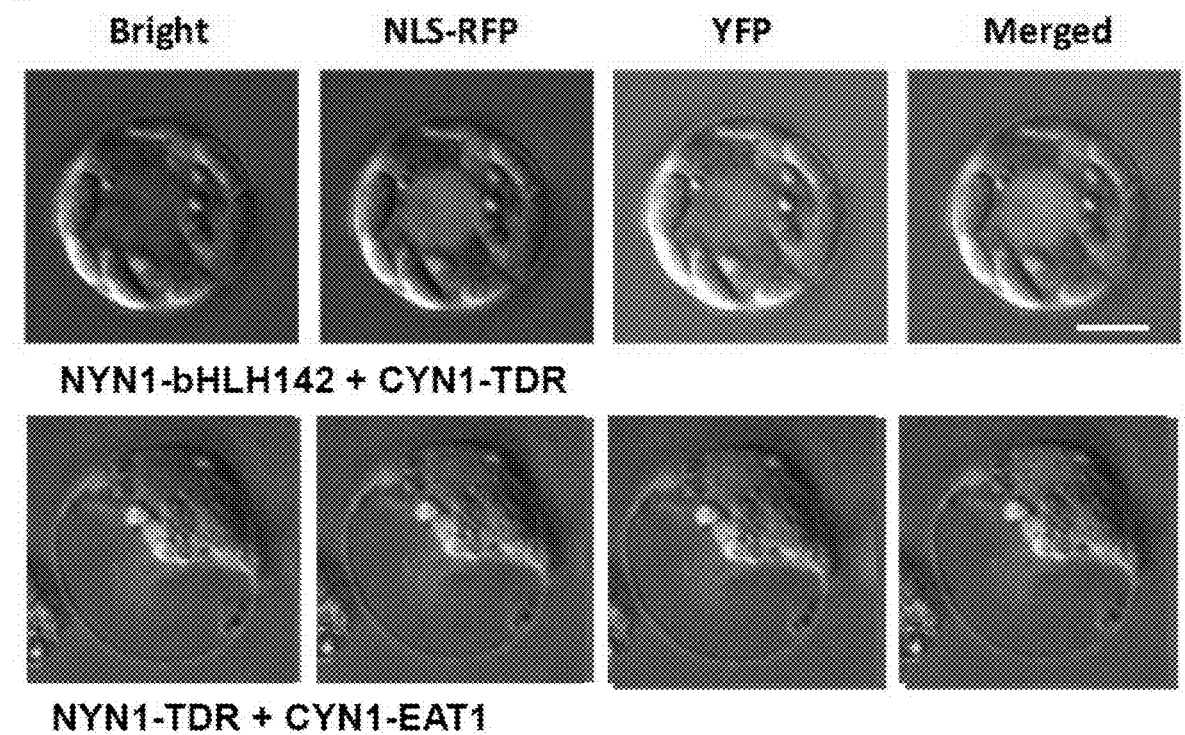
Figure 13:
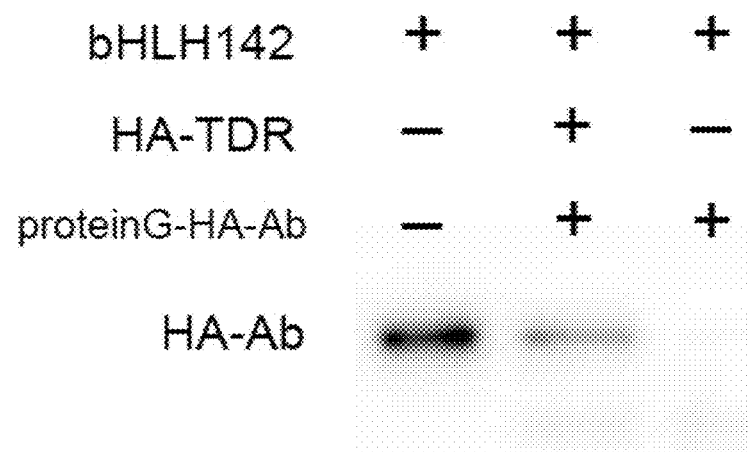
Figure 13:
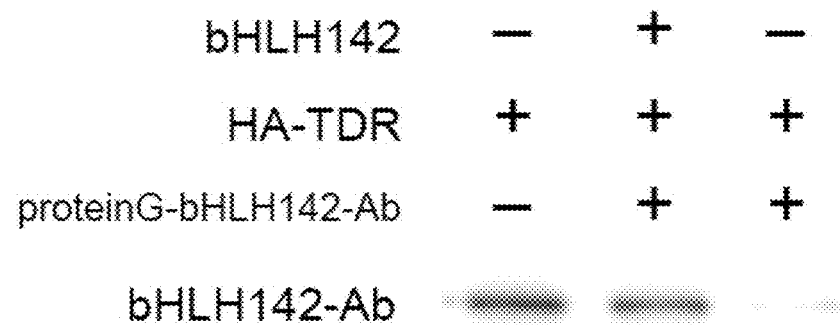

Since TDR1 and EAT1 mRNA are both down-regulated in ms142, we hypothesize that TDR1 interacts with bHLH142 and positively regulate EAT1 promoter for transcriptional activities of AP25 and AP37, encoding aspartate proteases for tapetal PCD. Our promoter transient assay provides solid evidence that bHLH142 and TDR1 work coordinately in regulating EAT1 promoter (FIG. 11). We also demonstrates that additional expression of EAT1 protein significantly reduced EAT1-Luc promoter strength from a 30 fold down to 18 fold increase (FIG. 11), which may be attributed to the competition between bHLH142 and EAT to interact with TDR1. Presumably, more EAT1 favors TDR1-EAT1 interaction and might consequently reduce the interaction between bHLH142 and TDR1, therefore reducing EAT1 transcriptional activation (FIG. 11). It is likely that bHLH142 interacts with TDR1 and TDR1 in turn interacts with EAT1 and bHLH142 does not directly interact with EAT1 (FIG. 13). Whether some other TFs may be required to regulate the transcription of bHLH142 is worth further investigation to unravel the entire regulatory gene hierarchy.

Figure 12:
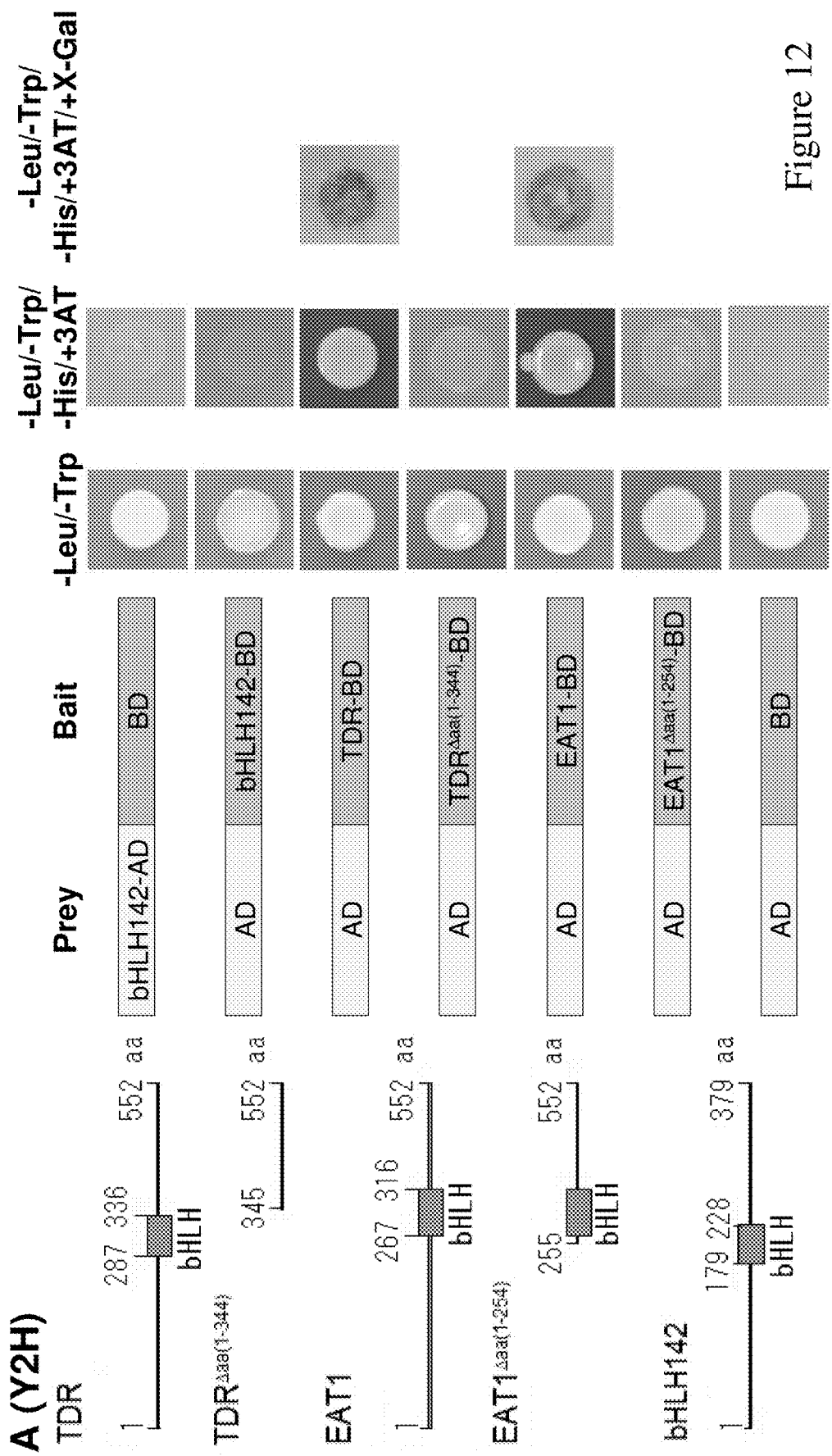
FIG. 12. Analysis of protein interaction between bHLH142, TDR1, and EAT1 by (A) Yeast two-hybrid assay and (B) BiFC in rice leaf protoplasts expressing the indicated constructs. Scale bars=20 μm.
Figure 12:
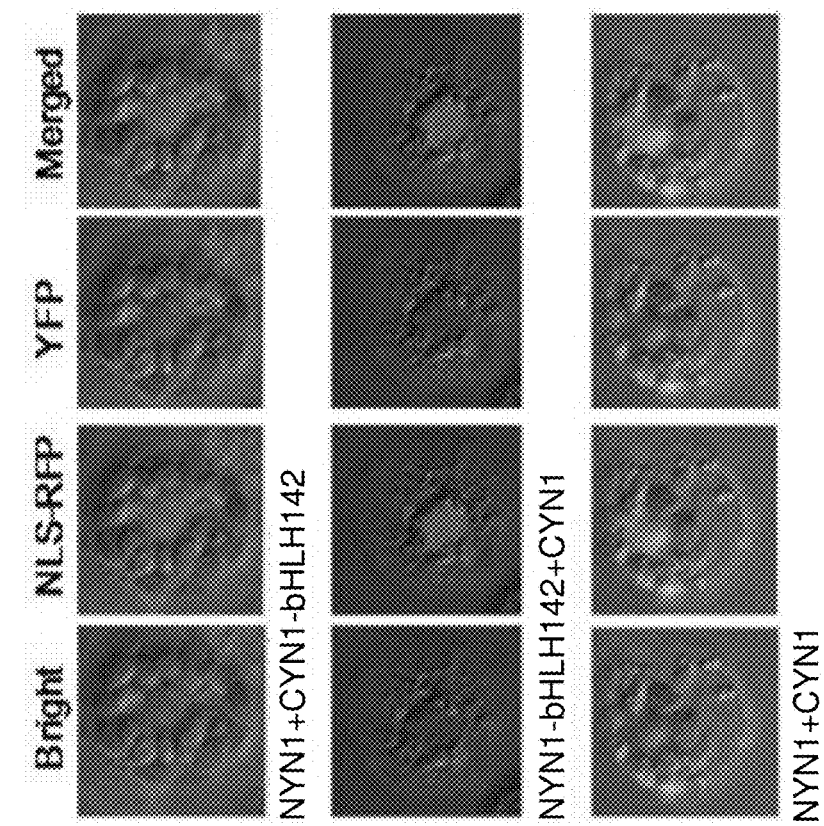
Figure 12:
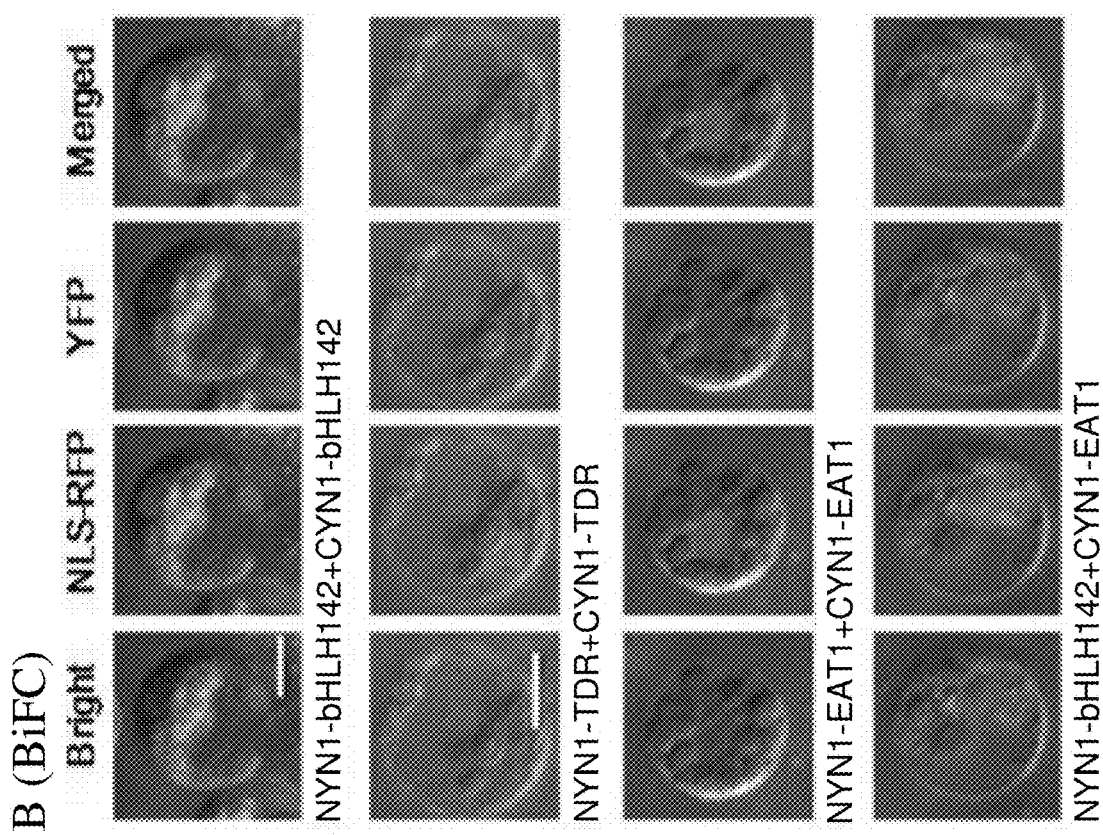

Our molecular studies provide solid in vivo (Y2H, BiFC) and in vitro (co-IP) evidences that both bHLH142 and TDR1 can form protein interaction (FIG. 13). The co-IP provides the most convincing evidence that the two proteins physically interact in vitro. Subcellular localization also demonstrates that bHLH142 protein is localized in the nucleus (FIGS. 5D and 13B) and its protein is not self activated (FIG. 13 and FIG. 12). Since we also found self activation of full length TDR1 and EAT1 in our Y2H experiment (FIG. 12), N-terminal truncated forms of $TDR^{\Delta aa(1-344)}$ and $EAT1^{\Delta aa(1-254)}$, were used in our experiment to reduce self activation. These two N-terminal truncated protein forms did not exhibit self activation in yeast cells (FIG. 12A). Therefore, we are confident that bHLH142 interacts with TDR1 by using these truncated proteins to eliminate the bias (FIG. 13). Our data indicate that bHLH142 interacts with TDR1 in the C-terminal (FIG. 13), and support the conclusion of the previous study in that DTD/EAT1 (bHLH141) interacts with TDR1 in the C-terminal region. In other words, both bHLH142 and EAT1 (bHLH141) can interact with TDR1 in the C' terminal of TDR1. This finding also supports the result of our EAT1 promoter assay, where additional EAT1 protein reduces EAT1 promoter activity, presumably due to the competition between bHLH142 and EAT1 proteins in the C' terminal of TDR1. Based on this and previous works, the current regulatory network for rice pollen development is presented in FIG. 21. Previous works with various rice MS mutants suggest that UDT1 and GAMYB may positively regulate the transcription of TDR1[22] and TDR1 in turn controls the transcription of C6 and CP1[14]. A recent study presents evidence that TDR1 interacts with EAT1 for its direct regulation of the expression of two aspartate proteinase genes for initiation of tapetal PCD[23]. In this invention, we demonstrate that bHLH142 acts downstream of UDT1 but upstream of TDR1 and EAT1, and then bHLH142 interact with TDR1 in activating EAT1 transcription (indicated by red arrows in FIG. 21). Furthermore, we showed that EAT1 also positively regulate the transcription of AP37 and CP1 directly, two proteins involved in tapetal PCD at late pollen development stage.

REFERENCES

1. Khush, (2000), Rice Germplasm enhancement at IRRI. Phillipp. J. Crop Sci. 25, 45-51.
2. Gao et al., (2013), Dissecting yield-associated loci in super hybrid rice by resequencing recombinant inbred lines and improving parental genome sequences. Proc Natl Acad Sci USA 110, 14492-14497.
3. Luo et al., (2013), A detrimental mitochondrial-nuclear interaction causes cytoplasmic male sterility in rice. Nat Genet 45, 573-577.
4. Luo, et al., (1992), Pei'ai 64S, a dual purpose sterile line whose sterility is induced by low critical temperature. Hybrid Rice 1:27-29.
5. Zhou et al., (2012), Photoperiod- and thermo-sensitive genic male sterility in rice are caused by a point mutation in a novel noncoding RNA that produces a small RNA. Cell Res 22, 649-660.
6. Zhang et al., (2010), Carbon starved anther encodes a MYB domain protein that regulates sugar partitioning required for rice pollen development. Plant Cell 22, 672-689.
7. Zhang et al., (2013), Mutation in CSA creates a new photoperiod-sensitive genic male sterile line applicable for hybrid rice seed production. Proc Natl Acad Sci USA 110, 76-81.
8. Li et al., (2007), Suppression and restoration of male fertility using a transcription factor. Plant Biotechnol J 5, 297-312.
9. Goldberg et al., (1993). Anther development: basic principles and practical applications. Plant Cell 5: 1217-1229.
10. Zhu et al., (2008). Defective in Tapetal development and function 1 is essential for anther development and tapetal function for microspore maturation in *Arabidopsis*. Plant J. 55: 266-277.
11. Wu and Cheun, (2000). Programmed cell death in plant reproduction. Plant Mol. Biol. 44: 267-281.
12. Papini et al., (1999). Programmed-cell-death events during tapetum development of angiosperms. Protoplasma 207: 213-221.
13. Kawanabe et al., (2006). Abolition of the tapetum suicide program ruins microsporogenesis. Plant Cell Physiol. 47: 784-787.
14. Li et al., (2006a), The rice tapetum degeneration retardation gene is required for tapetum degradation and anther development. Plant Cell 18, 2999-3014.
15. Ito and Shinozaki, (2002), The male sterility1 gene of *Arabidopsis*, encoding a nuclear protein with a PHD-finger motif, is expressed in tapetal cells and is required for pollen maturation. Plant Cell Physiol 43, 1285-1292.

16. Sorensen et al., (2003), The *Arabidopsis* ABORTED MICROSPORES (AMS) gene encodes a MYC class transcription factor. Plant J 33, 413-423.
17. Zhang et al., (2007), Transcription factor AtMYB103 is required for anther development by regulating tapetum development, callose dissolution and exine formation in *Arabidopsis*. Plant J 52, 528-538.
18. Wilson et al., (2001), The *Arabidopsis* MALE STERILITY1 (MS1) gene is a transcriptional regulator of male gametogenesis, with homology to the PHD-finger family of transcription factors. Plant J 28, 27-39.
19. Ito et al., (2007), *Arabidopsis* MALE STERILITY1 encodes a PHD-type transcription factor and regulates pollen and tapetum development. Plant Cell 19, 3549-3562.
20. Jung et al., (2005), Rice Undeveloped Tapetum1 is a major regulator of early tapetum development. Plant Cell 17, 2705-2722.
21. Aya et al., (2009), Gibberellin modulates anther development in rice via the transcriptional regulation of GAMYB. Plant Cell 21, 1453-1472.
22. Liu et al., (2010), Identification of gamyb-4 and analysis of the regulatory role of GAMYB in rice anther development. J Integr Plant Biol 52, 670-678.
23. Niu et al., (2013), EAT1 promotes tapetal cell death by regulating aspartic proteases during male reproductive development in rice. Nat Commun 4, 1445.
24. Ji et al., (2013), A Novel Rice bHLH Transcription Factor, DTD, Acts Coordinately with TDR in Controlling Tapetum Function and Pollen Development. Mol Plant.
25. Lee et al., (2004), Isolation and characterization of a rice cysteine protease gene, OsCP1, using T-DNA gene-trap system. Plant Mol Biol 54, 755-765.
26. Li et al., (2006b), Genome-wide analysis of basic/helix-loop-helix transcription factor family in rice and *Arabidopsis*. Plant Physiol 141, 1167-1184.
27. Carretero-Paulet et al., (2010), Genome-wide classification and evolutionary analysis of the bHLH family of transcription factors in *Arabidopsis*, poplar, rice, moss, and algae. Plant Physiol 153, 1398-1412.
28. Bailey et al., (2003), Update on the basic helix-loop-helix transcription factor gene family in *Arabidopsis thaliana*. Plant Cell 15, 2497-2502.
29. Toledo-Ortiz et al., (2003), The *Arabidopsis* basic/helix-loop-helix transcription factor family. Plant Cell 15, 1749-1770.
30. Ptashne, (1988), How eukaryotic transcriptional activators work. Nature 335, 683-689.
31. Massari and Murre, (2000), Helix-loop-helix proteins: regulators of transcription in eucaryotic organisms. Mol Cell Biol 20, 429-440.
32. Hsing et al., (2007), A rice gene activation/knockout mutant resource for high throughput functional genomics. Plant Mol Biol 63, 351-364.
33. Phan et al., (2011). The MYB80 transcription factor is required for pollen development and the regulation of tapetal programmed cell death in *Arabidopsis thaliana*. Plant Cell 23: 2209-2224.
34. Bart et al., (2006), A novel system for gene silencing using siRNAs in rice leaf and stem-derived protoplasts. Plant Methods 2, 13.
35. Tamura et al., (2011), MEGA5: molecular evolutionary genetics analysis using maximum likelihood, evolutionary distance, and maximum parsimony methods. Mol Biol Evol 28, 2731-2739.
36. Hsu et al., (2011), Integration of molecular biology tools for identifying promoters and genes abundantly expressed in flowers of Oncidium Gower Ramsey. BMC Plant Biol 11, 60.
37. Chan et al., (1993), *Agrobacterium*-mediated production of transgenic rice plants expressing a chimeric alpha-amylase promoter/beta-glucuronidase gene. Plant Mol Biol 22, 491-506.
38. Ko et al., (2014). The bHLH142 Transcription Factor Coordinates with TDR1 to Modulate the Expression of EAT1 and Regulate Pollen Development in Rice. Plant Cell 26, 2486-2504.
39. Bi et al. (2005). The rice nucellin gene ortholog OsAsp1 encodes an active aspartic protease without a plant-specific insert and is strongly expressed in early embryo. Plant Cell Physiol 46, 87-98.

What is claimed is:

1. A RNAi vector comprising SEQ ID No: 120 operably linked to a plant ubiquitin promoter, wherein a rice plant comprising said RNAi vector has reduced expression of the bHLH142 gene, wherein said gene exhibits at least 95% identity to SEQ ID NO:1.

2. The RNAi vector according to claim 1, further comprising a reporter gene.

3. The RNAi vector according to claim 1, wherein the reporter gene is a β-glucuronidase (GUS) intron.

4. A rice cell, comprising the RNAi vector according to claim 1.

5. The rice cell according to claim 4, wherein the RNAi vector further comprises a reporter gene.

6. The rice cell according to claim 4, wherein the reporter gene is β-glucuronidase (GUS) intron.

7. A rice plant comprising the rice cell of claim 4, wherein expression of bHLH142 is down regulated in said plant.

8. A rice seed comprising the RNAi vector according to claim 1.

9. The rice seed according to claim 8, wherein the RNAi vector further comprises a reporter gene.

10. The rice seed according to claim 8, wherein the reporter gene is β-glucuronidase (GUS) intron.

11. The rice seed according to claim 8, wherein a plant grown from said seed is a male sterile plant.

* * * * *

SEQUENCE LISTING

```
<160> NUMBER OF SEQ ID NOS: 120

<210> SEQ ID NO 1
<211> LENGTH: 1617
<212> TYPE: DNA
<213> ORGANISM: Oryza sativa

<400> SEQUENCE: 1
aagaaaccaa ctgctttctc ctacccaata tcacccttgc cccttttata tactcttcct     60
ctcatcacct tctcgatcgg cctctctcct ctcctctcat cagctcacac ccccaaccaa    120
caaacctagt taatttagct ctagttggtt catccctgct gcactgcgag ctcaagtaat    180
cgatctgagc tctgaagaaa aaggtggtag agtgcgagga agatgtatca cccgcagtgc    240
gagctcctga tgccgcttga gagcctggag atggacgtcg gccagtcgca cctcgccgcc    300
gccgtcgcag cagccatgcc gggggagctc aacttccacc tcctccactc gctcgacgcc    360
gccgcggcgg ctgcctcctc caccgccgcc tcggcctcct cccagcccac cgtcgactac    420
ttcttcggcg gcgccgacca gcagccgccg ccgccgcgcg cgatgcagta cgaccagctg    480
gcggcgccgc accaccacca gacggtggcc atgctgcgcg actactacgg cggccactac    540
```

-continued

| | |
|---|---|
| ccgccggcgg cggcggcggc ggcggccacc gaggcgtact tccgcggcgg gccaaggacg | 600 |
| gccgggtcgt cgtcgctcgt gttcggcccg gccgacgacg agtcggcctt catggtcgga | 660 |
| cccttcgaga gctccccgac gccgcggtcc ggcggcggca ggaagcgtag ccgcgccacc | 720 |
| gccggcttcc acggcggcgg gccggccaac ggcgtcgaga agaaggagaa gcagcgccgc | 780 |
| ctgcggctca ccgagaagta caacgccctc atgctcctca tccccaaccg caccaaggag | 840 |
| gatagagcga cggtgatctc agacgcgatc gagtacatcc aggagctagg gaggacggtg | 900 |
| gaggagctga cgctgctggt ggagaagaag cggcggcgga gggagatgca gggggacgtg | 960 |
| gtggacgcgg cgacgtcgtc ggtggtggcg gggatggatc aggcggcgga gagctcggag | 1020 |
| ggcgaggtga tggcggcggc ggcgatgggc gcggtggcac cgccgccgcg gcaggcgccg | 1080 |
| atccggagca cgtacatcca gcggcggagc aaggagacgt tcgtggacgt gcggatcgtg | 1140 |
| gaggacgacg tgaacatcaa gctcaccaag cgccgccgcg acggctgtct cgccgccgcg | 1200 |
| tcgcgcgcgc tggacgacct ccgcctcgac ctcgtccacc tctccggcgg caagatcggc | 1260 |
| gactgccaca tctacatgtt caacaccaag attcattcgg gatctccagt gtttgcaagt | 1320 |
| gcagtggcca gcaggctgat tgaagtggtg gatgagtact aactagctcg agctagctaa | 1380 |
| ttagccgacc gaccgatcga tatgatgaaa gtttctatgt tgctagctag ctagggttct | 1440 |
| tggatgcatg agtactgagt agctctttaa ttaatttcct tttaattta gactgtttaa | 1500 |
| tttggattgg taaagactcg tgttagcttt tgggagatct ttggtatgtc atggtttgca | 1560 |
| tgtattattt tggtctactt ggataaataa ttgatgctct ttgagacgtt aattaat | 1617 |

<210> SEQ ID NO 2
<211> LENGTH: 379
<212> TYPE: PRT
<213> ORGANISM: Oryza sativa

<400> SEQUENCE: 2

Met Tyr His Pro Gln Cys Glu Leu Leu Met Pro Leu Glu Ser Leu Glu
1               5                   10                  15

Met Asp Val Gly Gln Ser His Leu Ala Ala Val Ala Ala Ala Ala Met
            20                  25                  30

Pro Gly Glu Leu Asn Phe His Leu Leu His Ser Leu Asp Ala Ala Ala
        35                  40                  45

Ala Ala Ala Ser Ser Thr Ala Ala Ser Ala Ser Ser Gln Pro Thr Val
    50                  55                  60

Asp Tyr Phe Phe Gly Gly Ala Asp Gln Gln Pro Pro Pro Ala Ala
65                  70                  75                  80

Met Gln Tyr Asp Gln Leu Ala Ala Pro His His Gln Thr Val Ala
            85                  90                  95

Met Leu Arg Asp Tyr Tyr Gly Gly His Tyr Pro Pro Ala Ala Ala Ala
            100                 105                 110

Ala Ala Ala Thr Glu Ala Tyr Phe Arg Gly Gly Pro Arg Thr Ala Gly
        115                 120                 125

Ser Ser Ser Leu Val Phe Gly Pro Ala Asp Asp Glu Ser Ala Phe Met
    130                 135                 140

Val Gly Pro Phe Glu Ser Ser Pro Thr Pro Arg Ser Gly Gly Gly Arg
145                 150                 155                 160

Lys Arg Ser Arg Ala Thr Ala Gly Phe His Gly Gly Pro Ala Asn
            165                 170                 175

Gly Val Glu Lys Lys Glu Lys Gln Arg Arg Leu Arg Leu Thr Glu Lys
            180                 185                 190

Tyr Asn Ala Leu Met Leu Leu Ile Pro Asn Arg Thr Lys Glu Asp Arg
195                 200                 205

Ala Thr Val Ile Ser Asp Ala Ile Glu Tyr Ile Gln Glu Leu Gly Arg
210                 215                 220

Thr Val Glu Glu Leu Thr Leu Leu Val Glu Lys Lys Arg Arg Arg Arg
225                 230                 235                 240

Glu Met Gln Gly Asp Val Val Asp Ala Ala Thr Ser Ser Val Val Ala
            245                 250                 255

Gly Met Asp Gln Ala Ala Glu Ser Ser Glu Gly Val Met Ala Ala
            260                 265                 270

Ala Ala Met Gly Ala Val Ala Pro Pro Arg Gln Ala Pro Ile Arg
        275                 280                 285

Ser Thr Tyr Ile Gln Arg Arg Ser Lys Glu Thr Phe Val Asp Val Arg
290                 295                 300

Ile Val Glu Asp Asp Val Asn Ile Lys Leu Thr Lys Arg Arg Arg Asp
305                 310                 315                 320

Gly Cys Leu Ala Ala Ala Ser Arg Ala Leu Asp Asp Leu Arg Leu Asp
            325                 330                 335

Leu Val His Leu Ser Gly Gly Lys Ile Gly Asp Cys His Ile Tyr Met
            340                 345                 350

Phe Asn Thr Lys Ile His Ser Gly Ser Pro Val Phe Ala Ser Ala Val
        355                 360                 365

Ala Ser Arg Leu Ile Glu Val Val Asp Glu Tyr
        370                 375

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggagcacgta catccagcgg                                            20

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
actcatccac cacttcaatc agcc                                       24

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
aactcatggc gatctcttac c                                          21

<210> SEQ ID NO 6
<211> LENGTH: 20
<212> TYPE: DNA
<213> ORGANISM: Artificial Sequence
<220> FEATURE:

```
<223> OTHER INFORMATION: primer

<400> SEQUENCE: 6
gatgtaggag ggcgtggata                                            20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cgtctgctgc tccatacaag                                            20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggagcacgta catccagcgg                                            20

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
actcatccac cacttcaatc agcc                                       24

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tggagcagtt cgccagctac g                                          21

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
cttctcctcc tccgacatct ccc                                        23

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cgctcgctcg tcccaaacat                                            20
```

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
cggtcattgc tgggtccttg t                                    21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tcctcctcgt cctgctcgtc                                      20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ggttcacgat gtggcacagg                                      20

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
ttaggccacg gaagtttgag g                                    21

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
acacttcacc ggaccattca a                                    21

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
gatcttctgg accaagaggg cag                                  23

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
gtcaggagtg tctcagatgc ttgg                                    24

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
ggaccacctg ctgctgcaac t                                       21

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gaacacttcg tgccatcgcc                                         20

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
tggtggaaca gaagaggcat gg                                      22

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
gcatgaagca gagagttggc ctt                                     23

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
gcggaagtaa ggaaggagga gg                                      22

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
ggcatcacaa tcttcacaga ggtg                                    24

<210> SEQ ID NO 26
<211> LENGTH: 22

```
<212> TYPE: DNA
<213> ORGANISM: Artificial Sequence
<220> FEATURE:
<223> OTHER INFORMATION: primer

<400> SEQUENCE: 26
gagaacttcg agccgagggt ct                                        22

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ccagccgacg aggtttccac                                           20

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
aggcgggcag cgtctccat                                            19

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
ccataagcca gccacgatga tga                                       23

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30
catcctggtc cattcctcaa tgac                                      24

<210> SEQ ID NO 31
<211> LENGTH: 23
<212> TYPE: DNA
<213> ORGANISM: Artificial Sequence
<220> FEATURE:
<223> OTHER INFORMATION: primer

<400> SEQUENCE: 31
ttcaggatga ggtgaagtgt ccc                                       23

<210> SEQ ID NO 32
<211> LENGTH: 27
<212> TYPE: DNA
<213> ORGANISM: Artificial Sequence
<220> FEATURE:
<223> OTHER INFORMATION: primer

<400> SEQUENCE: 32
```
tatctagagt ggtagagtgc gaggaag                                        27

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
gaggtaccag gtactcatcc accacttcaa                                     30

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
catgttcaac accaagattc attcg                                          25

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
tgcaaaccat gacataccaa agatc                                          25

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
agggatccca ccacatggga agaggagacc                                     30

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
atgtcgactc aaacgcgagg taatgcagg                                      29

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
gtggatccat gccgcggcgc gcgagggcga                                     30

<210> SEQ ID NO 39
<211> LENGTH: 33
<212> TYPE: DNA
<213> ORGANISM: Artificial Sequence

```
<220> FEATURE:
<223> OTHER INFORMATION: primer

<400> SEQUENCE: 39
tgctcgagat gcttggaacc tccacaatgc tgg                              33

<210> SEQ ID NO 40
<211> LENGTH: 29
<212> TYPE: DNA
<213> ORGANISM: Artificial Sequence
<220> FEATURE:
<223> OTHER INFORMATION: primer

<400> SEQUENCE: 40
agctgcagtt tgccaaaatg attgttggg                                   29

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
gcgtcgactt gaatatgtcg agggcctgg                                   29

<210> SEQ ID NO 42
<211> LENGTH: 26
<212> TYPE: DNA
<213> ORGANISM: Artificial Sequence
<220> FEATURE:
<223> OTHER INFORMATION: primer

<400> SEQUENCE: 42
gtggatcccg aggaagatgt atcacc                                      26

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
agctcgagct agttagtact catccaccac                                  30

<210> SEQ ID NO 44
<211> LENGTH: 26
<212> TYPE: DNA
<213> ORGANISM: Artificial Sequence
<220> FEATURE:
<223> OTHER INFORMATION: primer

<400> SEQUENCE: 44
gtggatcccg aggaagatgt atcacc                                      26

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
agctcgagct agttagtact catccaccac                                  30
```

<210> SEQ ID NO 46
<211> LENGTH: 28
<212> TYPE: DNA
<213> ORGANISM: Artificial Sequence
<220> FEATURE:
<223> OTHER INFORMATION: primer

<400> SEQUENCE: 46
cgctgcagtt agtactcatc caccactt                28

<210> SEQ ID NO 47
<211> LENGTH: 29
<212> TYPE: DNA
<213> ORGANISM: Artificial Sequence
<220> FEATURE:
<223> OTHER INFORMATION: primer

<400> SEQUENCE: 47
aggaattctt tgccaaaatg attgttggg               29

<210> SEQ ID NO 48
<211> LENGTH: 32
<212> TYPE: DNA
<213> ORGANISM: Artificial Sequence
<220> FEATURE:
<223> OTHER INFORMATION: primer

<400> SEQUENCE: 48
gcctgcagtt agttgaatat gtcgagggcc tg           32

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
aagaattcat gggaagagga gaccacctgc              30

<210> SEQ ID NO 50
<211> LENGTH: 31
<212> TYPE: DNA
<213> ORGANISM: Artificial Sequence
<220> FEATURE:
<223> OTHER INFORMATION: primer

<400> SEQUENCE: 50
ctggatcctc aatcaaacgc gaggtaatgc a            31

<210> SEQ ID NO 51
<211> LENGTH: 32
<212> TYPE: DNA
<213> ORGANISM: Artificial Sequence
<220> FEATURE:
<223> OTHER INFORMATION: primer

<400> SEQUENCE: 51
tagaattcat gaagggtgag ttcggaaagg gc           32

<210> SEQ ID NO 52
<211> LENGTH: 33
<212> TYPE: DNA
<213> ORGANISM: Artificial Sequence
<220> FEATURE:
<223> OTHER INFORMATION: primer

<400> SEQUENCE: 52
aggtcgactt accctctcct gcattcaagt aca         33

<210> SEQ ID NO 53
<211> LENGTH: 30
<212> TYPE: DNA
<213> ORGANISM: Artificial Sequence
<220> FEATURE:
<223> OTHER INFORMATION: primer

<400> SEQUENCE: 53
acgaattcat gcatgtccac cataagccgc             30

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
aaccgcggaa atgagttacc catacgatgt tcctg       35

<210> SEQ ID NO 55
<211> LENGTH: 32
<212> TYPE: DNA
<213> ORGANISM: Artificial Sequence
<220> FEATURE:
<223> OTHER INFORMATION: primer

<400> SEQUENCE: 55
cagcggccgc agcgtaatct ggaacgtcat at          32

<210> SEQ ID NO 56
<211> LENGTH: 31
<212> TYPE: DNA
<213> ORGANISM: Artificial Sequence
<220> FEATURE:
<223> OTHER INFORMATION: primer

<400> SEQUENCE: 56
aatctagaca tgggaagagg agaccacctg c           31

<210> SEQ ID NO 57
<211> LENGTH: 31
<212> TYPE: DNA
<213> ORGANISM: Artificial Sequence
<220> FEATURE:
<223> OTHER INFORMATION: primer

<400> SEQUENCE: 57
cagtcgactc aatcaaacgc gaggtaatgc a           31

<210> SEQ ID NO 58
<211> LENGTH: 26
<212> TYPE: DNA
<213> ORGANISM: Artificial Sequence
<220> FEATURE:
<223> OTHER INFORMATION: primer

<400> SEQUENCE: 58
cgtctagaga tgtatcaccc gcagtg                 26

<210> SEQ ID NO 59

```
<211> LENGTH: 30
<212> TYPE: DNA
<213> ORGANISM: Artificial Sequence
<220> FEATURE:
<223> OTHER INFORMATION: primer

<400> SEQUENCE: 59
agctcgagct agttagtact catccaccac                                          30

<210> SEQ ID NO 60
<211> LENGTH: 30
<212> TYPE: DNA
<213> ORGANISM: Artificial Sequence
<220> FEATURE:
<223> OTHER INFORMATION: primer

<400> SEQUENCE: 60
agggatccca ccacatggga agaggagacc                                          30

<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61
cagtcgactc aatcaaacgc gaggtaatgc a                                        31

<210> SEQ ID NO 62
<211> LENGTH: 29
<212> TYPE: DNA
<213> ORGANISM: Artificial Sequence
<220> FEATURE:
<223> OTHER INFORMATION: primer

<400> SEQUENCE: 62
agctgcagtt tgccaaaatg attgttggg                                           29

<210> SEQ ID NO 63
<211> LENGTH: 31
<212> TYPE: DNA
<213> ORGANISM: Artificial Sequence
<220> FEATURE:
<223> OTHER INFORMATION: primer

<400> SEQUENCE: 63
gcgtcgactt agttgaatat gtcgagggcc t                                        31

<210> SEQ ID NO 64
<211> LENGTH: 31
<212> TYPE: DNA
<213> ORGANISM: Artificial Sequence
<220> FEATURE:
<223> OTHER INFORMATION: primer

<400> SEQUENCE: 64
ccactagttg ctttggtttg attcctggaa g                                        31

<210> SEQ ID NO 65
<211> LENGTH: 29
<212> TYPE: DNA
<213> ORGANISM: Artificial Sequence
<220> FEATURE:
<223> OTHER INFORMATION: primer

<400> SEQUENCE: 65
```
aagtcgacaa cagtgctagg caccttcgc                                    29

<210> SEQ ID NO 66
<211> LENGTH: 26
<212> TYPE: DNA
<213> ORGANISM: Artificial Sequence
<220> FEATURE:
<223> OTHER INFORMATION: primer

<400> SEQUENCE: 66
gtggatcccg aggaagatgt atcacc                                       26

<210> SEQ ID NO 67
<211> LENGTH: 30
<212> TYPE: DNA
<213> ORGANISM: Artificial Sequence
<220> FEATURE:
<223> OTHER INFORMATION: primer

<400> SEQUENCE: 67
agctcgagct agttagtact catccaccac                                   30

<210> SEQ ID NO 68
<211> LENGTH: 28
<212> TYPE: DNA
<213> ORGANISM: Artificial Sequence
<220> FEATURE:
<223> OTHER INFORMATION: primer

<400> SEQUENCE: 68
acactagtat ctacccgctt cgcgtcgg                                     28

<210> SEQ ID NO 69
<211> LENGTH: 34
<212> TYPE: DNA
<213> ORGANISM: Artificial Sequence
<220> FEATURE:
<223> OTHER INFORMATION: primer

<400> SEQUENCE: 69
atctgcagcg agtgaagatc cctttcttgt tacc                              34

<210> SEQ ID NO 70
<211> LENGTH: 39
<212> TYPE: DNA
<213> ORGANISM: Artificial Sequence
<220> FEATURE:
<223> OTHER INFORMATION: primer

<400> SEQUENCE: 70
gcctgcagca acaaacctag ttaatttagc tctagttgg                         39

<210> SEQ ID NO 71
<211> LENGTH: 28
<212> TYPE: DNA
<213> ORGANISM: Artificial Sequence
<220> FEATURE:
<223> OTHER INFORMATION: primer

<400> SEQUENCE: 71
gcgtcgacag gctctcaagc ggcatcag                                     28

<210> SEQ ID NO 72
<211> LENGTH: 39
<212> TYPE: DNA

<213> ORGANISM: Artificial Sequence
<220> FEATURE:
<223> OTHER INFORMATION: primer

<400> SEQUENCE: 72
gcactagtca acaaacctag ttaatttagc tctagttgg         39

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
tagcggccgc aggctctcaa gcggcatcag         30

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
gatgtaggag ggcgtggata         20

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
cgtctgctgc tccatacaag         20

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
ggagcacgta catccagcgg         20

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
atcgcaagac cggcaacagg a         21

<210> SEQ ID NO 78
<211> LENGTH: 366
<212> TYPE: PRT
<213> ORGANISM: Brachypodium distachyon

<400> SEQUENCE: 78

Met Tyr His Pro Gln Cys Glu Leu Leu Met Pro His Glu Ser Leu Asp
1               5                   10                  15

```
Met Asp Ala Val Val Gly Gln Ser His Leu Ala Ala Ser Gly Val Ser
             20                  25                  30

Ala Ile Pro Ala Glu Leu Asn Phe His Leu Leu His His Ser Phe Val
         35                  40                  45

Asp Thr Ala Ala Ser Pro Gln Pro Thr Val Asp Tyr Phe Phe Pro
 50                  55                  60

Gly Thr Asp Pro Pro Ala Ala Val Gln Phe Glu Gln Leu Ala Ala
 65                  70                  75                  80

Thr Asn His His Ala Met Ser Met Leu Arg Asp Tyr Tyr Gly Gln Gln
                 85                  90                  95

Tyr Pro Ala Glu Thr Tyr Leu Arg Gly Gly Pro Arg Thr Thr Thr Gly
            100                 105                 110

Ser Ser Ser Leu Val Phe Gly Val Ala His Asp Asp Glu Ser Ala Ala
            115                 120                 125

Tyr Asn Met Val Gly Pro Phe Val Glu Ser Ser Pro Thr Thr Arg Ala
            130                 135                 140

Ala Gly Gly Gly Arg Lys Arg Asn Arg Gly Ser Arg Ala Ala Gly Gly
145                 150                 155                 160

Pro Ala His Gly Gly Val Glu Lys Lys Glu Lys Gln Arg Arg Leu Arg
            165                 170                 175

Leu Thr Glu Lys Tyr Thr Ala Leu Met Leu Leu Ile Pro Asn Arg Thr
            180                 185                 190

Lys Glu Asp Arg Ala Thr Val Ile Ser Asp Ala Ile Glu Tyr Ile Gln
            195                 200                 205

Glu Leu Gly Arg Thr Val Glu Glu Leu Thr Leu Leu Val Gly Lys Lys
            210                 215                 220

Arg Arg Arg Asn Gly Ala Gly Glu His His Leu His Gln Gly Asp Val
225                 230                 235                 240

Val Asp Ala Ala Pro Ala Val Gly Ala Ala Gly Glu Leu Val Leu Ala
                245                 250                 255

Ala Glu Ser Ser Glu Gly Glu Val Gln Ala Pro Leu Ala Ala Leu Gln
            260                 265                 270

Pro Ile Arg Ser Thr Tyr Ile Gln Arg Lys Ser Lys Glu Thr Phe Val
            275                 280                 285

Asp Val Arg Ile Val Glu Asp Glu Val Asn Ile Lys Leu Thr Lys Arg
            290                 295                 300

Arg Arg Asp Gly Cys Leu Ala Ala Ala Ser Arg Ala Leu Asp Asp Leu
305                 310                 315                 320

Arg Leu Asp Leu Val His Leu Ser Gly Gly Lys Ile Gly Asp Cys His
                325                 330                 335

Ile Tyr Met Phe Asn Thr Lys Ile His Gln Gly Ser Pro Val Phe Ala
            340                 345                 350

Ser Ala Val Ala Ser Lys Leu Ile Glu Val Val Asp Glu Tyr
            355                 360                 365

<210> SEQ ID NO 79
<211> LENGTH: 350
<212> TYPE: PRT
<213> ORGANISM: Triticum urartu

<400> SEQUENCE: 79

Met Tyr His Gln Gln Cys Glu Leu Leu Met Pro His Glu Gly Leu Asp
 1               5                  10                  15

Met Asp Ala Gly Gln Ser His His Leu Ala Ala Gly Ser Ala Val Pro
             20                  25                  30
```

Ala Glu Leu Asn Phe His Leu Leu Ser Tyr Val Asp Thr Ala Val Ser
            35                  40                  45

Pro Gln Gln Pro Thr Val Glu Tyr Phe Gly Gly Ala Asp Gln Pro
    50                  55                  60

His Ala Gln Phe Glu Gln Leu Ala Ala Asn His Gln Ala Met Thr Val
 65                  70                  75                  80

Leu Arg Asp Tyr Tyr Gly Gln Tyr His Pro Ala Thr Ala Asp Ala Tyr
                85                  90                  95

Leu Pro Gly Gly Gly Pro Arg Thr Gly Ser Ser Ser Leu Val Phe Gly
            100                 105                 110

Ala Ala Glu Glu Glu Ser Ala Tyr Met Val Gly Gly Phe Gln Cys Ser
            115                 120                 125

Pro Lys Pro Arg Ala Ser Gly Ser Arg Lys Arg Gly Arg Gly Ala Gly
    130                 135                 140

Ser Ser Phe His Gly Phe Pro Ala Asn Gly Gly Val Glu Lys Lys Glu
145                 150                 155                 160

Lys Gln Arg Arg Gln Arg Leu Ser Glu Lys Phe Thr Ala Leu Met Leu
                165                 170                 175

Leu Ile Pro Asn Arg Thr Lys Glu Asp Arg Ala Thr Val Ile Tyr Asp
            180                 185                 190

Ala Ile Glu Tyr Ile Gln Glu Leu Gly Arg Thr Val Glu Glu Leu Thr
            195                 200                 205

Leu Leu Val Glu Lys Lys Arg Gly Arg Arg Glu His Gln Gly Asp Val
    210                 215                 220

Val Asp Pro Ala Pro Thr Leu Val Ala Gly Asp Gly Glu Cys Ser Ala
225                 230                 235                 240

Gly Glu Val Ala Ala Ala Val Met Pro Ala Met Pro Ala Pro Pro Gln
                245                 250                 255

Pro Ile Arg Ser Thr Tyr Ile Gln Arg Arg Ser Lys Glu Thr Phe Val
            260                 265                 270

Asp Val Arg Ile Val Glu Asp Glu Val Asn Ile Lys Leu Thr Lys Arg
            275                 280                 285

Arg Arg Asp Gly Cys Leu Ala Ala Ala Ser Arg Ala Leu Asp Asp Leu
    290                 295                 300

His Leu Asp Leu Val His Leu Ser Gly Gly Lys Ile Gly Asp Cys His
305                 310                 315                 320

Ile Tyr Met Phe Asn Thr Lys Ile His Pro Gly Ser Pro Val Phe Ala
                325                 330                 335

Ser Ala Val Ala Ser Lys Leu Ile Glu Val Val Asp Glu Tyr
            340                 345                 350

<210> SEQ ID NO 80
<211> LENGTH: 379
<212> TYPE: PRT
<213> ORGANISM: Sorghum bicolor

<400> SEQUENCE: 80

Met Tyr His Pro Gln Cys Glu Leu Leu Met Ala His Glu Ala Gln Asp
 1               5                  10                  15

Leu Asp Ala Ala Gly Gln Pro His His Leu Ala Val Ser Gly Val Ala
            20                  25                  30

Gly Ser Ile Pro Ala Glu Leu Ser Phe His Leu Leu His Ser Leu Asp
            35                  40                  45

Ala Thr Ala Ala Val Asn Asn Ser Val Thr Pro Gln Ser Thr Ile Asp

```
            50                  55                  60
Tyr Phe Leu Gly Val Gly Gly Ala Asp Pro His Gln Pro Ala Ala Leu
 65                  70                  75                  80

Gln Tyr Glu Pro Leu Pro Pro Gly Gly His His Gln His Thr Met
                 85                  90                  95

Asn Met Leu Arg Asp Tyr Cys Ser Asn Gly Gly Gly Gly His Tyr
                100                 105                 110

Pro Thr Ala Glu Pro Tyr Leu Arg Gly Thr Arg Thr Gly Ala Leu Val
                115                 120                 125

Phe Gly Ala Thr Asp Asp Glu Ser Ala Ala Ala Tyr Met Pro Gly
130                 135                 140

Gly Pro Phe Val Glu Thr Ser Pro Pro Arg Ala Thr Gly Gly Arg
145                 150                 155                 160

Lys Arg Gly Arg Ala Leu Gly Gly Gly Phe His Ala Gly Leu Ala Asn
                165                 170                 175

Gly Val Glu Lys Lys Glu Lys Gln Arg Arg Gln Arg Leu Thr Glu Lys
                180                 185                 190

Tyr Thr Ala Leu Met His Leu Ile Pro Asn Val Thr Lys Pro Asp Arg
                195                 200                 205

Ala Thr Val Ile Ser Asp Ala Ile Glu Tyr Ile Gln Glu Leu Gly Arg
210                 215                 220

Thr Val Glu Glu Leu Thr Leu Leu Val Glu Lys Lys Arg Arg Arg Arg
225                 230                 235                 240

Glu Leu Gln Gly Asp Val Val Asp Ala Ala Pro Thr Ala Val Val Val
                245                 250                 255

Ala Ala Ala Ala Thr Gly Gly Glu Ala Glu Ser Ser Glu Gly Glu Val
                260                 265                 270

Ala Pro Pro Pro Pro Pro Ala Ala Val Gln Arg Gln Pro Ile Arg
                275                 280                 285

Ser Thr Tyr Ile Gln Arg Arg Ser Lys Asp Thr Ser Val Asp Val Arg
                290                 295                 300

Ile Val Glu Glu Asp Val Asn Ile Lys Leu Thr Lys Arg Arg Arg Asp
305                 310                 315                 320

Gly Cys Leu Ala Ala Ala Ser Arg Ala Leu Asp Asp Leu Arg Leu Asp
                325                 330                 335

Leu Val His Leu Ser Gly Gly Lys Ile Gly Asp Cys His Ile Tyr Met
                340                 345                 350

Phe Asn Thr Lys Ile His Lys Gly Ser Ser Val Phe Ala Ser Ala Val
                355                 360                 365

Ala Ser Arg Leu Met Glu Val Val Asp Glu Tyr
370                 375

<210> SEQ ID NO 81
<211> LENGTH: 365
<212> TYPE: PRT
<213> ORGANISM: Zea mays

<400> SEQUENCE: 81

Met Tyr His Pro Gln Cys Glu Leu Leu Thr Met Ala His Glu Thr Pro
  1               5                  10                  15

Asp Leu Asp Ala Gly Gln Pro His Leu Thr Val Ser Gly Val Ala Ser
                 20                  25                  30

Ile Pro Ala Glu Leu Ser Phe His Leu Leu His Ser Leu Asp Ala Ala
                 35                  40                  45
```

-continued

```
Ala Ala Val Asn Pro Val Thr Ala Pro Pro Gln Ser Thr Ile Asp Tyr
         50                  55                  60

Phe Leu Gly Gly Ala Asp Pro His Gln Gln Ala Met Gln Tyr Glu Pro
 65                  70                  75                  80

Leu Pro Pro Ala Ala Gly Gly His His Gln Tyr Thr Met Asp Met Phe
                 85                  90                  95

Arg Asp Tyr Cys Asp Gly His Tyr Pro Thr Ala Glu Pro Tyr Ile Arg
                100                 105                 110

Gly Thr Met Thr Gly Ala Leu Val Phe Gly Ala Thr Asp Asp Asp
                115                 120                 125

Ser Ala Ala Ala Tyr Met Pro Gly Gly His Phe Glu Thr Ser Pro Pro
        130                 135                 140

Pro Pro Arg Ala Thr Gly Arg Gly Arg Lys Arg Gly Arg Ala Leu Gly
145                 150                 155                 160

Gly Gly Phe His Ala Val Leu Ala Asn Gly Val Glu Lys Lys Glu Lys
                165                 170                 175

Gln Arg Arg Leu Arg Leu Thr Glu Lys Tyr Thr Ala Leu Met His Leu
                180                 185                 190

Ile Pro Asn Val Thr Lys Thr Asp Arg Ala Thr Val Ile Ser Asp Ala
                195                 200                 205

Ile Glu Tyr Ile Gln Glu Leu Gly Arg Thr Val Glu Glu Leu Thr Leu
210                 215                 220

Leu Val Glu Lys Lys Arg Arg Arg Glu Leu Gln Gly Asp Val Val
225                 230                 235                 240

Asp Ala Ala Pro Ala Ala Val Ala Ala Gly Glu Ala Glu Ser
                245                 250                 255

Ser Glu Gly Glu Val Ala Pro Pro Pro Ala Val Pro Arg Gln Pro
        260                 265                 270

Ile Arg Ser Thr Tyr Ile Gln Arg Arg Ser Lys Asp Thr Ser Val Asp
        275                 280                 285

Val Arg Ile Val Glu Glu Asp Val Asn Ile Lys Leu Thr Lys Arg Arg
        290                 295                 300

Arg Asp Gly Cys Leu Ala Ala Ala Ser Arg Ala Leu Asp Asp Leu Arg
305                 310                 315                 320

Leu Asp Leu Val His Leu Ser Gly Gly Lys Ile Gly Asp Cys Gln Ile
                325                 330                 335

Tyr Met Phe Asn Thr Lys Ile His Lys Gly Ser Ser Val Phe Ala Ser
                340                 345                 350

Ala Val Ala Gly Arg Leu Met Glu Val Val Asp Glu Tyr
        355                 360                 365

<210> SEQ ID NO 82
<211> LENGTH: 268
<212> TYPE: PRT
<213> ORGANISM: Aegilops tauschii

<400> SEQUENCE: 82

Met Tyr His Gln Gln Cys Glu Leu Leu Met Pro His Glu Asp Leu Asp
 1               5                  10                  15

Met Asp Ala Gly Gln Ser His His Leu Ala Ala Ser Ala Val Pro
                20                  25                  30

Ala Glu Leu Asn Phe His Leu Leu Ser Tyr Val Asp Ala Ala Val Ser
            35                  40                  45

Pro Gln Gln Pro Thr Val Glu Tyr Phe Phe Gly Gly Ala Asp Gln Pro
        50                  55                  60
```

His Ala His Ser Phe His Gly Phe Pro Ala Asn Gly Gly Val Glu Lys
 65                  70                  75                  80

Lys Glu Lys Gln Arg Gln Arg Leu Ser Glu Lys Phe Thr Ala Leu
                 85                  90                  95

Met Leu Leu Ile Pro Asn Arg Thr Lys Glu Asp Arg Ala Thr Val Ile
            100                 105                 110

Tyr Asp Ala Ile Glu Tyr Ile Gln Glu Leu Gly Arg Thr Val Glu Glu
            115                 120                 125

Leu Thr Leu Leu Val Glu Lys Arg Gly Arg Glu His Gln Gly
130                 135                 140

Asp Val Val Asp Pro Ala Pro Leu Val Val Ala Gly Glu Gly Glu Cys
145                 150                 155                 160

Ser Ala Gly Glu Leu Arg Ala Pro Pro Pro Pro Gln Pro Ile
                165                 170                 175

Arg Ser Thr Tyr Ile Gln Arg Arg Ser Lys Glu Thr Phe Val Asp Val
                180                 185                 190

Arg Ile Val Glu Asp Glu Val Asn Ile Lys Leu Thr Lys Arg Arg Arg
            195                 200                 205

Asp Gly Cys Leu Ala Ala Ala Ser Arg Ala Leu Asp Asp Leu His Leu
            210                 215                 220

Asp Leu Val His Leu Ser Gly Gly Lys Ile Gly Asp Cys His Ile Tyr
225                 230                 235                 240

Met Phe Asn Thr Lys Ile His Pro Gly Ser Pro Val Phe Ala Ser Ala
                245                 250                 255

Val Ala Ser Lys Leu Ile Glu Val Val Asp Glu Tyr
                260                 265

<210> SEQ ID NO 83
<211> LENGTH: 170
<212> TYPE: PRT
<213> ORGANISM: Zea mays

<400> SEQUENCE: 83

Met Val Phe Ser Lys Ile Gln Tyr Lys Val Val Ser Ser Lys Ile Gln
1               5                   10                  15

Thr Pro Thr Leu Val Arg Val Glu Thr Thr His Glu Thr Asn Met Glu
                20                  25                  30

Lys Lys Arg Arg Arg Arg Glu Leu Gln Gly Asp Val Asp Ala Ala
            35                  40                  45

Pro Ala Ala Val Val Ala Ala Ala Gly Glu Ala Glu Ser Ser Glu Gly
 50                  55                  60

Glu Val Ala Pro Pro Pro Ala Val Pro Arg Gln Pro Ile Arg Ser
65                  70                  75                  80

Thr Tyr Ile Gln Arg Arg Ser Lys Asp Thr Ser Val Asp Val Arg Ile
                85                  90                  95

Val Glu Glu Asp Val Asn Ile Lys Leu Thr Lys Arg Arg Arg Asp Gly
            100                 105                 110

Cys Leu Ala Ala Ala Ser Arg Ala Leu Asp Asp Leu Arg Leu Asp Leu
            115                 120                 125

Val His Leu Ser Gly Gly Lys Ile Gly Asp Cys Gln Ile Tyr Met Phe
            130                 135                 140

Asn Thr Lys Ile His Lys Gly Ser Ser Val Phe Ala Ser Ala Val Ala
145                 150                 155                 160

Gly Arg Leu Met Glu Val Val Asp Glu Tyr

<210> SEQ ID NO 84
<211> LENGTH: 433
<212> TYPE: PRT
<213> ORGANISM: Vitis vinifera

<400> SEQUENCE: 84

Met Cys Arg Lys Ile Thr Arg Pro Arg Met Tyr Val Tyr Glu Glu
1               5                   10                  15

Asn Ala Cys Phe Asp Gly Thr Lys Ser Val Ala Glu Gly Asp Asp Glu
            20                  25                  30

Gly Phe Ser Gln Ser Val Ala Pro Pro Thr Asn Asn Ser Phe Glu
        35                  40                  45

Asp Ser Thr Asn Met Arg Val Ser Met Glu Asp Ala Ser Ala Thr Met
    50                  55                  60

Glu Ile Glu Leu His Gln Gln Leu Ala Phe Asp Met Asp Gln Cys
65                  70                  75                  80

Tyr Asn Ser Asn Asn Asp Gly Asn Asp Ser Asn Gln Val Phe Ser Tyr
                85                  90                  95

Glu Met Gln Glu Met Gly Phe Asn His His Gln Gln Gln Glu Asp
            100                 105                 110

Pro Leu Leu Leu Gln Gln His Gln Ala Glu Met Gln Asn Ala His Gln
        115                 120                 125

Asn Phe Ser Ala Ala Tyr Pro Pro Thr Pro Asp Leu Leu Asn Leu Phe
    130                 135                 140

His Leu Pro Arg Cys Thr Pro Ser Ser Leu Leu Pro Asn Ser Ser Ile
145                 150                 155                 160

Ser Phe Thr Asn Pro Asp Ser Ser Ala Thr Ala Ala Ser Gly Ile Leu
                165                 170                 175

Tyr Asp Pro Leu Phe His Leu Asn Leu Pro Pro Gln Pro Val Gly
            180                 185                 190

Gly Gly Tyr Gly Asp Gly Asp Asp His Arg Gln Phe Asp Asn Gly Val
        195                 200                 205

Leu Lys Phe Thr Arg Asp Met Ala Cys Ile Gly Lys Gly Arg Glu Gly
210                 215                 220

Lys Gly Thr Lys Ser Phe Ala Thr Glu Lys Gln Arg Arg Glu His Leu
225                 230                 235                 240

Asn Asp Lys Tyr Asn Ala Leu Arg Ser Leu Val Pro Asn Pro Thr Lys
                245                 250                 255

Ser Asp Arg Ala Ser Val Val Gly Asp Ala Ile Glu Tyr Ile Arg Glu
            260                 265                 270

Leu Leu Arg Thr Val Asn Glu Leu Lys Leu Leu Val Glu Lys Lys Arg
        275                 280                 285

Cys Gly Arg Glu Arg Ser Lys Arg His Lys Thr Glu Asp Glu Ser Thr
    290                 295                 300

Gly Asp Val Lys Ser Ser Ser Ser Ile Lys Pro Glu Pro Asp Gln Ser
305                 310                 315                 320

Tyr Asn Glu Ser Leu Arg Ser Ser Trp Leu Gln Arg Lys Ser Lys Asp
                325                 330                 335

Thr Glu Val Asp Val Arg Ile Ile Asp Asp Glu Val Thr Ile Lys Leu
            340                 345                 350

Val Gln Arg Lys Lys Ile Asn Cys Leu Leu Phe Val Ser Lys Ile Leu
        355                 360                 365

```
Asp Glu Leu Gln Leu Asp Leu His His Val Ala Gly Gly His Val Gly
    370                 375                 380
Asp Tyr Tyr Ser Phe Leu Phe Asn Thr Lys Ile Tyr Glu Gly Ser Ser
385                 390                 395                 400
Val Tyr Ala Ser Ala Ile Ala Asn Lys Leu Ile Glu Val Val Asp Arg
                405                 410                 415
Gln Tyr Ala Ala Ile Pro Ile Pro Ile Pro Ile Pro Pro Thr Ser Ser
                420                 425                 430

Phe

<210> SEQ ID NO 85
<211> LENGTH: 456
<212> TYPE: PRT
<213> ORGANISM: Vitis vinifera

<400> SEQUENCE: 85

Met Tyr Met Tyr Glu Glu Asn Ala Cys Phe Asp Gly Thr Lys Ser Val
1               5                   10                  15
Ala Glu Gly Asp Asp Glu Gly Phe Ser Gln Ser Val Ala Pro Pro Pro
            20                  25                  30
Thr Asn Asn Ser Phe Glu Asp Ser Thr Asn Met Arg Val Ser Met Glu
        35                  40                  45
Asp Ala Ser Ala Thr Met Glu Ile Glu Leu His Gln Gln Leu Ala Phe
    50                  55                  60
Asp Met Asp Gln Gln Cys Tyr Asn Ser Asn Asn Asp Gly Asn Asp Ser
65                  70                  75                  80
Asn Gln Val Phe Ser Tyr Glu Met Gln Glu Met Gly Phe Asn His His
                85                  90                  95
His Gln Gln Gln Asp Asp Pro Leu Leu Leu Gln Gln His Gln Ala Glu
            100                 105                 110
Met Gln Asn Ala Gln Gln Asn Phe Ser Ala Ala Tyr Pro Pro Thr Pro
        115                 120                 125
Asp Leu Leu Asn Leu Phe His Leu Pro Arg Cys Thr Pro Ser Ser Leu
    130                 135                 140
Leu Pro Asn Ser Ser Ile Ser Phe Thr Asn Pro Asp Ser Ser Ala Thr
145                 150                 155                 160
Ala Ala Ser Gly Ile Leu Tyr Asp Pro Leu Phe His Leu Asn Leu Pro
                165                 170                 175
Pro Gln Pro Pro Val Phe Arg Glu Leu Phe Gln Ser Leu Pro His Gly
            180                 185                 190
Tyr Asn Leu Pro Ala Ser Arg Val Gly Ser Leu Phe Gly Gly Gly Met
        195                 200                 205
Asp Glu Arg Glu Ala Ser Gly Gly Tyr Gly Asp Gly Asp His
    210                 215                 220
Arg Gln Phe Asp Asn Gly Val Leu Lys Phe Thr Arg Asp Met Ala Cys
225                 230                 235                 240
Ile Gly Arg Gly Arg Glu Gly Lys Gly Thr Lys Ser Phe Ala Thr Glu
                245                 250                 255
Lys Gln Arg Arg Glu His Leu Asn Asp Lys Tyr Asn Ala Leu Arg Ser
            260                 265                 270
Leu Val Pro Asn Pro Thr Lys Ser Asp Arg Ala Ser Val Val Gly Asp
        275                 280                 285
Ala Ile Glu Tyr Ile Arg Glu Leu Leu Arg Thr Val Asn Glu Leu Lys
    290                 295                 300
```

```
Leu Leu Val Glu Lys Lys Arg Cys Gly Arg Glu Arg Ser Lys Arg His
305                 310                 315                 320

Lys Thr Glu Asp Glu Ser Thr Gly Asp Val Lys Ser Ser Ser Ser Ile
                325                 330                 335

Lys Pro Glu Pro Asp Gln Ser Tyr Asn Glu Ser Leu Arg Ser Ser Trp
                340                 345                 350

Leu Gln Arg Lys Ser Lys Asp Thr Glu Val Asp Val Arg Ile Ile Asp
                355                 360                 365

Asp Glu Val Thr Ile Lys Leu Val Gln Arg Lys Lys Ile Asn Cys Leu
370                 375                 380

Leu Phe Val Ser Lys Ile Leu Asp Glu Leu Gln Leu Asp Leu His His
385                 390                 395                 400

Val Ala Gly Gly His Val Gly Asp Tyr Tyr Ser Phe Leu Phe Asn Thr
                405                 410                 415

Lys Ile Tyr Glu Gly Ser Ser Val Tyr Ala Ser Ala Ile Ala Asn Lys
                420                 425                 430

Leu Ile Glu Val Val Asp Arg Gln Tyr Ala Ala Ile Pro Ile Pro Ile
                435                 440                 445

Pro Ile Pro Pro Thr Ser Ser Phe
    450                 455

<210> SEQ ID NO 86
<211> LENGTH: 568
<212> TYPE: PRT
<213> ORGANISM: Vitis vinifera

<400> SEQUENCE: 86

Met Gly Arg Gly Phe Ser His Leu Leu Gly Phe Cys Lys Ser Glu Asn
1               5                   10                  15

Pro Leu Asn Asp Leu Ser Arg Leu Lys Ser Arg Tyr Ser Gly Pro Asn
                20                  25                  30

Leu Arg Leu Val His Ser Glu Ser Asn Arg Asn Asn Ile Glu Asn Met
            35                  40                  45

Val Asp Ala Phe Pro Val Gln Ile Asp Leu Asn Phe Ser Asp Ser Arg
        50                  55                  60

Asn Asp Lys Ala Thr Gln Thr Ile Ser His Pro Arg Val Lys His Ser
65                  70                  75                  80

His Gln Gly Ala Arg Arg Ile Met Arg Ser Thr Asn His Ala Glu
                85                  90                  95

Gln Cys Gln Asn Lys Arg Gly Tyr Arg Lys Ile Thr Arg Pro Arg Arg
            100                 105                 110

Met Tyr Val Tyr Glu Glu Asn Ala Cys Phe Asp Gly Thr Lys Ser Val
            115                 120                 125

Ala Glu Gly Asp Asp Glu Gly Phe Ser Gln Ser Val Ala Pro Pro
        130                 135                 140

Thr Asn Asn Ser Phe Glu Asp Ser Thr Asn Met Arg Val Ser Met Glu
145                 150                 155                 160

Asp Ala Ser Ala Thr Met Glu Ile Glu Leu His Gln Gln Leu Ala Phe
                165                 170                 175

Asp Met Asp Gln Gln Cys Tyr Asn Ser Asn Asn Asp Gly Asn Asp Ser
            180                 185                 190

Asn Gln Val Phe Ser Tyr Glu Met Gln Glu Met Gly Phe Asn His His
        195                 200                 205

Gln Gln Gln Gln Glu Asp Pro Leu Leu Leu Gln Gln His Gln Ala Glu
    210                 215                 220
```

Met Gln Asn Ala His Gln Asn Phe Ser Ala Ala Tyr Pro Pro Thr Pro
225                 230                 235                 240

Asp Leu Leu Asn Leu Phe His Leu Pro Arg Cys Thr Pro Ser Ser Leu
            245                 250                 255

Leu Pro Asn Ser Ser Ile Ser Phe Thr Asn Pro Asp Ser Ser Ala Thr
        260                 265                 270

Ala Ala Ser Gly Ile Leu Tyr Asp Pro Leu Phe His Leu Asn Leu Pro
    275                 280                 285

Pro Gln Pro Pro Val Phe Arg Glu Leu Phe Gln Ser Leu Pro His Gly
290                 295                 300

Tyr Asn Leu Pro Ala Ser Arg Val Gly Ser Leu Phe Gly Gly Gly Met
305                 310                 315                 320

Asp Glu Arg Glu Ala Ser Gly Gly Tyr Gly Asp Gly Asp Asp His
                325                 330                 335

Arg Gln Phe Asp Asn Gly Val Leu Lys Phe Thr Arg Asp Met Ala Cys
            340                 345                 350

Ile Gly Lys Gly Arg Glu Gly Lys Gly Thr Lys Ser Phe Ala Thr Glu
        355                 360                 365

Lys Gln Arg Arg Glu His Leu Asn Asp Lys Tyr Asn Ala Leu Arg Ser
    370                 375                 380

Leu Val Pro Asn Pro Thr Lys Ser Asp Arg Ala Ser Val Val Gly Asp
385                 390                 395                 400

Ala Ile Glu Tyr Ile Arg Glu Leu Leu Arg Thr Val Asn Glu Leu Lys
                405                 410                 415

Leu Leu Val Glu Lys Lys Arg Cys Gly Arg Glu Arg Ser Lys Arg His
            420                 425                 430

Lys Thr Glu Asp Glu Ser Thr Gly Asp Val Lys Ser Ser Ser Ser Ile
        435                 440                 445

Lys Pro Glu Pro Asp Gln Ser Tyr Asn Glu Ser Leu Arg Ser Ser Trp
    450                 455                 460

Leu Gln Arg Lys Ser Lys Asp Thr Glu Val Asp Val Arg Ile Ile Asp
465                 470                 475                 480

Asp Glu Val Thr Ile Lys Leu Val Gln Arg Lys Ile Asn Cys Leu
                485                 490                 495

Leu Phe Val Ser Lys Ile Leu Asp Glu Leu Gln Leu Asp Leu His His
            500                 505                 510

Val Ala Gly Gly His Val Gly Asp Tyr Tyr Ser Phe Leu Phe Asn Thr
        515                 520                 525

Lys Ile Tyr Glu Gly Ser Ser Val Tyr Ala Ser Ala Ile Ala Asn Lys
    530                 535                 540

Leu Ile Glu Val Val Asp Arg Gln Tyr Ala Ala Ile Pro Ile Pro Ile
545                 550                 555                 560

Pro Ile Pro Pro Thr Ser Ser Phe
                565

<210> SEQ ID NO 87
<211> LENGTH: 469
<212> TYPE: PRT
<213> ORGANISM: Ricinus communis

<400> SEQUENCE: 87

Met Tyr Glu Glu Thr Gly Cys Phe Asp Pro Asn Ser Met Val Glu Gly
1               5                   10                  15

Ala Asp Asp Gly Leu Cys Gln Val Leu Gln Ile Pro Pro Gln Pro Gln

-continued

```
                    20                  25                  30
Pro Leu Met Ala Gly Ser Thr Thr Asn Ser His Asn Ser Tyr Glu Glu
            35                  40                  45
Asn Leu Lys Leu Ser Ala Asp Gln Glu Leu Ser Tyr His His Ser Asn
 50                  55                  60
Asn Pro His His His His Gln Glu Asp Asp Ala Ser Ala Ser Ala Ala
 65                  70                  75                  80
Ala Ala Met Glu Thr Gln Leu Gln Asn His Gln Met Gly Phe Asp Thr
                85                  90                  95
His Leu Met Gln Asp Ser Ser Asn Gln Val Met Ala Phe Asn Ser Ser
            100                 105                 110
Thr Ser Leu Gln Asp Ala Thr Phe Ala Gln Thr Pro Asp Leu Leu Asn
        115                 120                 125
Leu Phe His Leu Pro Arg Gly Ser Thr Ser Ser Leu Leu Pro Asn Ser
    130                 135                 140
Ser Ile Ser Phe Thr Asn Pro Ser His Thr Ala Pro Leu Gly Phe Val
145                 150                 155                 160
Gly Asp Leu Pro Met Ala Asp Thr Ala Ser Ala Ser Ser Ile Leu Tyr
                165                 170                 175
Asp Pro Leu Phe His Leu Asn Leu Pro Pro Gln Pro Pro Leu Phe Arg
            180                 185                 190
Asp Leu Phe Gln Ser Leu Pro Pro His Gly Tyr Ser Leu Pro Gly Ser
        195                 200                 205
Met Val Asn Ser Leu Phe Gly Ala Gly Val Gly Gly Asp Asp His Val
    210                 215                 220
Glu Gly Ser Gly Asp Gly Gly Ile Tyr Gln Asp Gly Asp Gly Glu
225                 230                 235                 240
Gln Gln Phe Asp Asn Gly Val Leu Asp Phe Thr Trp Asp Met Pro Cys
                245                 250                 255
Met Gly Lys Gly Arg Asp Ala Gly Lys Lys Thr Lys Pro Phe Ala Thr
            260                 265                 270
Glu Arg Gln Arg Gln His Leu Asn Asp Lys Tyr Lys Ala Leu Gln
        275                 280                 285
Asn Leu Val Pro Asn Pro Thr Lys Ala Asp Arg Thr Ser Val Val Gly
    290                 295                 300
Asp Ala Ile Asp Tyr Ile Lys Glu Leu Leu Arg Thr Val Asn Glu Leu
305                 310                 315                 320
Lys Leu Leu Val Glu Lys Lys Arg Cys Ala Arg Glu Arg Ser Lys Arg
                325                 330                 335
Gln Lys Thr Glu Glu Asp Ser Ile Gly Asn Gly His Asp Ser Ser Cys
            340                 345                 350
Ile Thr Lys Pro Leu Gly Asp Pro Asp Gln Ser Phe Asn Asn Gly Ser
        355                 360                 365
Leu Arg Ser Ser Trp Ile Glu Arg Lys Ser Lys Asp Thr Glu Val Asp
    370                 375                 380
Val Arg Ile Ile Asp Asp Glu Val Thr Ile Lys Leu Val Gln Arg Lys
385                 390                 395                 400
Lys Ile Asn Cys Leu Leu Phe Val Ser Lys Val Leu Asp Glu Leu Gln
                405                 410                 415
Leu Asp Leu His His Val Ala Gly Gly His Ile Gly Asp Tyr Tyr Ser
            420                 425                 430
Phe Leu Phe Asn Thr Lys Ile Phe Glu Gly Ser Ser Val Tyr Ala Ser
        435                 440                 445
```

```
Ala Ile Ala Asn Lys Leu Ile Glu Val Val Asp Arg His Tyr Ala Ser
        450                 455                 460
Thr Pro Ser Thr Asn
465

<210> SEQ ID NO 88
<211> LENGTH: 467
<212> TYPE: PRT
<213> ORGANISM: Populus trichocarpa

<400> SEQUENCE: 88

Met Tyr Val Glu Thr Ala Cys Phe Pro Asn Asn Ser Met Val Glu
1               5                   10                  15

Asp Val Thr Asp Asp Gly Phe Cys His Ala Ile Pro Leu Met Ala Gly
                20                  25                  30

Asn Ser Thr Asn Ser Phe Glu Glu His Leu Lys Leu Ser Met Glu
                35                  40                  45

Glu Phe Ser Ser His Tyr Pro Gln Glu Ser Ala Ala Ala Ala Ser
        50                  55                  60

Met Glu Glu Ile Gln Leu Gln His His Met Ala Phe Ser Asn Asn Asn
65                  70                  75                  80

Thr Asn His His Leu Met Gln Gln Tyr Pro Thr Gln Leu Leu Ser Tyr
                85                  90                  95

Asp His Ser Ser Asn Trp Asp Pro Asn Ile Ile Gln Phe Gln Glu Met
                100                 105                 110

His Gln Val Leu Asp Gln Asn Ser Ser Phe Asp Ala Thr Ala Asn Thr
            115                 120                 125

Gln Ser Ser Leu Pro Pro Asp Leu Leu Asn Leu Phe Asn Leu Pro Arg
        130                 135                 140

Cys Thr Ser Thr Ser Thr Leu Leu Pro Asn Ser Ser Ile Ser Phe Thr
145                 150                 155                 160

Asn Pro Ala His Lys Ala Pro Leu Gly Phe Met Gly Val Asp Asn Thr
                165                 170                 175

Ser Ala Arg Phe Asp Pro Tyr Thr Leu Ala Pro Gln Pro His Leu Phe
            180                 185                 190

Arg Glu Leu Val Gln Ser Leu Pro Pro His Gly Tyr Thr Leu Pro Thr
        195                 200                 205

Pro Leu Phe Gly Gly Gly Gln Gly Asp Asp His Val Asp Gly Gln Ser
    210                 215                 220

Gly Gly Gly Leu Ser Tyr Gln Asp Gly Asp His Gly Asp Gly Val Phe
225                 230                 235                 240

Glu Phe Thr Asp Glu Met Ala Cys Ile Gly Lys Gly Ile Lys Lys Thr
                245                 250                 255

Gly Lys Val Thr Lys His Phe Ala Thr Glu Arg Gln Arg Arg Glu His
                260                 265                 270

Leu Asn Gly Lys Tyr Thr Ala Leu Arg Asn Leu Val Pro Asn Pro Ser
        275                 280                 285

Lys Asn Asp Arg Ala Ser Val Val Gly Glu Ala Ile Asp Tyr Ile Lys
    290                 295                 300

Glu Leu Leu Arg Thr Val Gln Glu Leu Lys Leu Leu Val Glu Lys Lys
305                 310                 315                 320

Arg Cys Gly Arg Glu Arg Ser Lys Trp Arg Lys Thr Glu Asp Asp Gly
                325                 330                 335

Gly Val Glu Val Leu Asp Asn Ser Asp Ile Lys Val Glu Pro Asp Gln
```

```
                    340                 345                 350
Ser Ala Tyr Ser Asn Gly Ser Leu Arg Ser Ser Trp Leu Gln Arg Lys
            355                 360                 365

Ser Lys Asp Thr Glu Val Asp Val Arg Leu Ile Glu Asp Glu Val Thr
370                 375                 380

Ile Lys Leu Val Gln Arg Lys Arg Val Asn Cys Leu Leu Tyr Val Ser
385                 390                 395                 400

Lys Val Leu Asp Glu Leu Gln Leu Asp Leu His His Ala Ala Gly Gly
                405                 410                 415

Leu Ile Gly Asp Tyr Tyr Ser Phe Leu Phe Asn Thr Lys Ile Asn Glu
            420                 425                 430

Gly Ser Cys Val Tyr Ala Ser Ala Ile Ala Asn Arg Leu Ile Glu Val
            435                 440                 445

Val Asp Arg Gln Tyr Ala Ser Ser Thr Thr Thr Val Pro Ala Ala Gly
            450                 455                 460

Ser Cys Tyr
465

<210> SEQ ID NO 89
<211> LENGTH: 473
<212> TYPE: PRT
<213> ORGANISM: Zea mays
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid

<400> SEQUENCE: 89

Met Ile Ala Gly Gly Tyr Phe Asp Gly Ser His Asp His Ile Leu
1               5                   10                  15

Met Glu Gly Ser Met Ile His Asp Ser Ser Gln Ser Ser Ile Tyr Asp
                20                  25                  30

Asn Thr Asp Val Glu Gln Gln Asn Phe Arg Phe Ala Pro Phe Ile Ile
            35                  40                  45

Glu Asp His Ser Asn Pro Ala Asn Leu Thr Ser Glu Ala Ala Arg Val
        50                  55                  60

Ile Asp Gln Ile Gln His Gly Leu Gly Ile Asp Ile Glu Gln Asp His
65                  70                  75                  80

Ser Asp His Met Met Gln Glu Val Pro Pro Ala Glu Thr Glu Asn Leu
                85                  90                  95

Val Pro Ala Val Tyr Gly Val Gln Asp His Ile Leu Ser His Gln Ile
            100                 105                 110

Glu Gly Pro His Asn Ile Thr Val Glu Gln Gln Val Leu Gly Tyr Asp
        115                 120                 125

Pro Ala Ser Tyr Arg Asn Gly Thr Tyr Ala Ala His Asp Leu Leu
130                 135                 140

Asn Ser Leu His Ile Gln Arg Cys Ser Leu Ile Pro Glu Phe Pro Ser
145                 150                 155                 160

Thr Glu His Ile Phe Ser Asp Pro Ala Gln Asn Met Val Asn Arg Leu
                165                 170                 175

Asp Ile Thr Asn Asp Leu Pro Gly Val Ala Asn His Glu Ser Gly Met
            180                 185                 190

Met Phe Ser Asp Ser Thr Val Pro Leu Gly Tyr His Ala Thr Gln Ser
```

```
            195                 200                 205
His Met Leu Lys Asp Leu Tyr His Ser Leu Pro Gln Asn Tyr Gly Leu
210                 215                 220

Phe Thr Ser Asp Asp Glu Arg Asp Gly Met Val Gly Val Pro Gly Val
225                 230                 235                 240

Ser Gly Asn Ile Phe Gln Glu Ile Asp Gly Arg Gln Phe Asp Ser Pro
                245                 250                 255

Ile Leu Gly Ser Arg Lys Gln Lys Gly Gly Phe Gly Lys Gly Lys Gly
                260                 265                 270

Lys Ala Asn Phe Ala Thr Glu Arg Glu Arg Xaa Gln Phe Asn Val
            275                 280                 285

Lys Tyr Gly Ala Leu Arg Ser Leu Phe Pro Asn Pro Thr Lys Asn Asp
            290                 295                 300

Arg Ala Ser Ile Val Gly Asp Ala Ile Glu Tyr Ile Asn Glu Leu Asn
305                 310                 315                 320

Arg Thr Val Lys Glu Leu Lys Ile Leu Leu Glu Lys Lys Arg Asn Ser
                325                 330                 335

Ala Asp Arg Arg Lys Ile Leu Lys Leu Asp Glu Glu Ala Ala Asp Asp
                340                 345                 350

Gly Glu Ser Ser Ser Met Gln Pro Val Ser Asp Asp Gln Xaa Asn Gln
            355                 360                 365

Met Asn Gly Thr Ile Arg Ser Ser Trp Val Gln Arg Ser Lys Glu
370                 375                 380

Cys Asp Val Asp Val Arg Ile Val Asp Asp Glu Ile Asn Ile Lys Phe
385                 390                 395                 400

Thr Glu Lys Lys Arg Ala Asn Ser Leu Leu Cys Ala Ala Lys Val Leu
                405                 410                 415

Glu Glu Phe His Leu Glu Leu Ile His Val Val Gly Gly Ile Ile Gly
            420                 425                 430

Asp His His Ile Phe Met Phe Asn Thr Lys Ile Pro Lys Gly Ser Ser
            435                 440                 445

Val Tyr Ala Cys Ala Val Ala Lys Lys Leu Leu Glu Ala Val Glu Ile
450                 455                 460

Lys Lys Gln Ala Tyr Asn Ile Phe Asn
465                 470
```

<210> SEQ ID NO 90
<211> LENGTH: 463
<212> TYPE: PRT
<213> ORGANISM: Populus trichocarpa

<400> SEQUENCE: 90

```
Met Tyr Glu Glu Thr Ala Cys Phe Glu Thr Asn Asn Ser Ile Val Glu
1               5                   10                  15

Gly Gly Asn Asp Asp Gly Phe Cys Gln Val Ser Pro Phe Met Thr Gly
                20                  25                  30

Ser Ser Thr Thr Ser Ser Phe Glu Gly Ser Phe Lys Leu Ser Met Glu
            35                  40                  45

Glu Leu Ser Asn His Tyr His Gln Glu Glu Ser Ala Ala Ala Ala Ser
        50                  55                  60

Met Glu Glu Ile Gln Leu Gln His His Met Ala Phe Asn Asn Asn Cys
65                  70                  75                  80

His His Leu Met Glu Gln Tyr Pro Thr Asn His Gln Val Leu Ser
                85                  90                  95
```

```
Tyr Asp His Pro Ser Asn Trp Asp Pro Asn Thr Ile Gln Phe Gln Glu
            100                 105                 110

Met His Gln Val Leu Asp Gln Asn Gly Asn Phe Asn Ala Thr Ala Asn
            115                 120                 125

Thr Pro Ser Ser Leu Leu Pro Asp Leu Leu Asn Leu Phe Asn Leu Pro
            130                 135                 140

Arg Cys Thr Ser Thr Ser Thr Leu Leu Pro Asn Ser Ser Ile Ser Phe
145                 150                 155                 160

Thr Asn Pro Ala His Lys Thr Pro Ser Gly Phe Met Gly Val Asp Ser
                    165                 170                 175

Thr Ser Val Leu Phe Asp Ser Asn Pro Leu Ala Pro Gln Phe Arg Glu
            180                 185                 190

Leu Val His Ser Leu Pro Pro His Gly Tyr Gly Leu Pro Ala Pro Leu
            195                 200                 205

Phe Gly Gly Gly Gln Gly Gly Asp His Val Asp Gly Leu Ser Gly Gly
            210                 215                 220

Gly Leu Ser Tyr Gln Asp Gly His Gly Asp Gly Val Phe Glu Phe
225                 230                 235                 240

Thr Ala Glu Met Ala Cys Ile Gly Lys Gly Ile Arg Lys Ser Gly Lys
                    245                 250                 255

Val Ile Thr Lys His Phe Ala Thr Glu Arg Gln Arg Glu His Leu
            260                 265                 270

Asn Gly Lys Tyr Thr Ala Leu Arg Asn Leu Val Pro Asn Pro Ser Lys
            275                 280                 285

Asn Asp Arg Ala Ser Val Val Gly Asp Ala Ile Asn Tyr Ile Lys Glu
290                 295                 300

Leu Leu Arg Thr Val Glu Glu Leu Lys Leu Leu Val Glu Lys Lys Arg
305                 310                 315                 320

Asn Gly Arg Glu Arg Ile Lys Arg Arg Lys Pro Glu Glu Asp Gly Gly
                    325                 330                 335

Val Asp Val Leu Glu Asn Ser Asn Thr Lys Val Glu Gln Asp Gln Ser
            340                 345                 350

Thr Tyr Asn Asn Gly Ser Leu Arg Ser Ser Trp Leu Gln Arg Lys Ser
            355                 360                 365

Lys His Thr Glu Val Asp Val Arg Leu Ile Glu Asp Glu Val Thr Ile
            370                 375                 380

Lys Leu Val Gln Arg Lys Lys Val Asn Cys Leu Leu Ser Val Ser Lys
385                 390                 395                 400

Val Leu Asp Glu Leu Gln Leu Asp Leu His His Ala Ala Gly Gly Leu
            405                 410                 415

Ile Gly Asp Tyr Tyr Ser Phe Leu Phe Asn Thr Lys Ile Asn Glu Gly
            420                 425                 430

Ser Cys Val Tyr Ala Ser Gly Ile Ala Asn Lys Leu Leu Glu Val Val
            435                 440                 445

Asp Arg Gln Tyr Ala Ser Ser Thr Ser Val Pro Ala Ala Ser Cys
450                 455                 460

<210> SEQ ID NO 91
<211> LENGTH: 473
<212> TYPE: PRT
<213> ORGANISM: Sorghum bicolor

<400> SEQUENCE: 91

Met Ile Ala Gly Gly Gly Tyr Phe Asp Gly Ser His Asp His Ile Leu
1               5                   10                  15
```

```
Met Glu Gly Ser Met Ile His Asp Ser Ser Gln Ser Ser Ile Tyr Asp
                20                  25                  30

Asn Thr Asp Val Glu Gln Gln Asn Phe Arg Leu Ala Pro Phe Ile Ile
            35                  40                  45

Glu Asp His Ser Asn Pro Ala Asn Leu Thr Ser Glu Pro Ala Arg Val
 50                  55                  60

Ile Asp Gln Ile His His Gln Leu Gly Ile Asp Met Glu Gln Asp His
 65                  70                  75                  80

Ser Asp His Met Ile Gln Gly Val Pro Pro Ala Glu Thr Ala Asn Leu
                 85                  90                  95

Val Pro Val Val Tyr Gly Val Gln Asp Arg Ile Leu Ser His Gln Ile
            100                 105                 110

Glu Gly Pro His Asn Ile Thr Val Glu Gln Gln Val Leu Asp Tyr Asp
            115                 120                 125

Pro Ala Ser Tyr Gly Asn Gly Thr Tyr Ala Ala Ala His Asp Leu Leu
130                 135                 140

Asn Ser Leu Gln Ile Gln Arg Cys Ser Leu Ile Pro Glu Phe Pro Ser
145                 150                 155                 160

Thr Glu His Ile Phe Gly Asp Pro Ala Gln Asn Met Val Asn Pro Leu
                165                 170                 175

Asp Ile Thr Asn Asp Leu Gln Gly Val Ala Thr His Glu Ser Gly Met
                180                 185                 190

Met Phe Ser Asp Ser Thr Leu Pro Leu Gly Tyr His Ala Thr Gln Ser
            195                 200                 205

His Met Leu Lys Asp Leu Tyr His Ser Leu Pro Gln Asn Tyr Gly Ile
            210                 215                 220

Phe Thr Ser Asp Asp Glu Arg Asp Gly Met Val Gly Val Ala Gly Val
225                 230                 235                 240

Ser Gly Asn Ile Phe Gln Glu Ile Asp Gly Arg Gln Phe Asp Ser Pro
                245                 250                 255

Val Leu Gly Thr Arg Arg Gln Lys Gly Gly Phe Gly Lys Gly Lys Gly
            260                 265                 270

Lys Ala Asn Phe Ala Thr Glu Arg Glu Arg Glu Gln Leu Asn Val
            275                 280                 285

Lys Tyr Gly Ala Leu Arg Ser Leu Phe Pro Asn Pro Thr Lys Asn Asp
            290                 295                 300

Arg Ala Ser Ile Val Gly Asp Ala Ile Asp Tyr Ile Asn Glu Leu Asn
305                 310                 315                 320

Arg Thr Val Lys Glu Leu Lys Ile Leu Leu Glu Lys Lys Arg Asn Ser
                325                 330                 335

Thr Asp Arg Arg Lys Ile Leu Lys Leu Asp Asp Glu Ala Ala Asp Asp
            340                 345                 350

Gly Glu Ser Ser Ser Met Gln Pro Val Ser Asp Gln Asn Asn Gln
            355                 360                 365

Met Asn Gly Ala Ile Arg Ser Ser Trp Val Gln Arg Ser Lys Glu
            370                 375                 380

Cys Asp Val Asp Val Arg Ile Val Asp Asp Glu Ile Asn Ile Lys Phe
385                 390                 395                 400

Thr Glu Lys Lys Arg Ala Asn Ser Leu Leu Cys Ala Ala Lys Val Leu
                405                 410                 415

Glu Glu Phe Arg Leu Glu Leu Ile His Val Val Gly Gly Ile Ile Gly
            420                 425                 430
```

Asp His His Ile Phe Met Phe Asn Thr Lys Ile Pro Lys Gly Ser Ser
            435                 440                 445

Val Tyr Ala Cys Ala Val Ala Lys Lys Leu Leu Glu Ala Val Glu Ile
    450                 455                 460

Lys Lys Gln Ala Leu Asn Ile Phe Asn
465                 470

<210> SEQ ID NO 92
<211> LENGTH: 486
<212> TYPE: PRT
<213> ORGANISM: Medicago truncatula

<400> SEQUENCE: 92

Met Ser Ser Gly Ser Gly Asp Lys Gln Asn Met His Glu Gln Asn Gly
1               5                   10                  15

Cys Phe Asp Pro Asn Thr Lys Asp Glu Gly Val Glu Asn Ser Pro Asn
            20                  25                  30

Asp Asn Asn Thr Asn Asn Asn Ser Leu Glu Glu Asn Phe Lys Pro
        35                  40                  45

Ser Val Glu Glu Leu Pro Tyr His Asn His Gln Asn Ser Gln His Leu
    50                  55                  60

Asp Asp Val Ser Thr Tyr Thr Asn Gly Phe Thr Pro Ser Ser Val Asp
65                  70                  75                  80

Ile Glu Gln Leu Gln Asn Leu Gly Leu Asn Ile Gly Asn Thr Tyr Asn
                85                  90                  95

Asn Met Asp Asn His Leu Val Gln Glu Val Tyr Gln Asn Ser Thr Trp
            100                 105                 110

Asp Pro Ser Val Gln Asp Met Asp Tyr Val Asn His Gln Glu His Arg
        115                 120                 125

Gln Leu Ser Glu Gln Gln Tyr Gln Gln Phe Ile Glu Ala Gln Asn His
    130                 135                 140

Asn Gln Ser Tyr Asn Pro Ser Thr Ile Leu Asp Pro His Tyr Pro Ser
145                 150                 155                 160

Pro Asp Val Leu Asn Leu Leu Asn Leu Pro Arg Cys Ser Ser Ser Leu
                165                 170                 175

Leu Thr Asn Ser Ser Thr Ile Cys Met Thr Asn Pro Thr Gln Asn Pro
            180                 185                 190

Pro Asn Phe His Asn Ser Met Thr Phe Leu Gly Asp Leu Pro Ile Gly
        195                 200                 205

Ser Ser Asp Asn Thr Ser Gly Ser Ser Val Leu Tyr Asp Pro Leu Tyr
    210                 215                 220

Pro Leu Asn Leu Pro Pro Gln Pro Pro Ala Leu Arg Glu Leu Phe Gln
225                 230                 235                 240

Ser Leu Pro Arg Gly Tyr Ser Met Pro Thr Asn Ser Arg Asn Gly Ser
                245                 250                 255

Leu Phe Gly Gly Gly Asp Glu Met Glu Gly Asp Gly Asp Met Gly Val
            260                 265                 270

Leu Glu Phe Asn Arg Val Thr Ala Ser Val Gly Lys Gly Arg Gly Gly
        275                 280                 285

Lys Ala Thr Lys His Phe Ala Thr Glu Lys Gln Arg Arg Glu Gln Leu
    290                 295                 300

Asn Gly Lys Tyr Lys Ile Leu Arg Asp Leu Ile Pro Ser Pro Thr Lys
305                 310                 315                 320

Thr Asp Arg Ala Ser Val Val Gly Asp Ala Ile Glu Tyr Ile Arg Glu
                325                 330                 335

```
Leu Ile Arg Thr Val Asn Glu Leu Lys Leu Val Glu Lys Lys Arg
            340                 345                 350

His Gly Arg Glu Met Cys Lys Arg Leu Lys Thr Glu Asp Ala Ala
            355                 360                 365

Glu Ser Cys Asn Ile Lys Pro Phe Gly Asp Pro Asp Gly Ser Ile Arg
    370                 375                 380

Thr Ser Trp Leu Gln Arg Lys Ser Lys Asp Ser Glu Val Asp Val Arg
385                 390                 395                 400

Ile Ile Asp Asp Val Thr Ile Lys Leu Phe Gln Arg Lys Lys Val
                405                 410                 415

Asn Cys Leu Leu Phe Val Ser Lys Val Leu Asp Glu Leu Gln Leu Glu
                420                 425                 430

Leu His His Val Ala Gly Gly His Val Gly Glu Tyr Cys Ser Phe Leu
            435                 440                 445

Phe Asn Ser Lys Val Asn Glu Gly Ser Ser Val Tyr Ala Ser Ala Ile
            450                 455                 460

Ala Asn Arg Val Ile Asp Val Met Asp Thr Gln Tyr Ala Ala Gly Leu
465                 470                 475                 480

Pro His Ile Ser Arg Leu
                485

<210> SEQ ID NO 93
<211> LENGTH: 483
<212> TYPE: PRT
<213> ORGANISM: Medicago truncatula

<400> SEQUENCE: 93

Met Ser Ser Gly Ser Gly Asp Asn Gln Asn Met His Glu Gln Thr Gly
1               5                   10                  15

Cys Phe Asp Pro Asp Thr Met Ala Glu Gly Val Glu Asn Ser Pro Glu
            20                  25                  30

Asp Asn Asn Ser Pro Gln Thr Met Pro Asn Gln Val Val Ala Gly Asn
        35                  40                  45

Ser Asn Asn Ser Ile Glu Glu Asn Phe Arg Pro Ser Val Glu Glu Phe
50                  55                  60

Ser Tyr His Asn His His Ser Pro Gln His Leu Glu Asp Val Ser Thr
65                  70                  75                  80

Tyr Thr Asn Gly Phe Thr Pro Ser Ser Glu Asn Ile Ala Gln Gln Asn
                85                  90                  95

Leu Gly Leu Asn Ile Gly Asn Tyr Tyr Tyr Asn Asn Met Asp Asn Leu
            100                 105                 110

Leu Glu Gln Glu Val Tyr Gln Asn Ser Ser Trp Asp Pro Ser Ala Gln
        115                 120                 125

Asp Met Asp Tyr Ala Asn His Gln Glu Tyr His Gln Leu His Asn His
130                 135                 140

Lys Gln Ser Tyr Asn Pro Ser Thr Thr Gln Ala Pro His Tyr Pro Ser
145                 150                 155                 160

Pro Asp Val Leu Asn Leu His Phe Pro Arg Ser Ser Ala Ser Ser Leu
                165                 170                 175

Leu Thr Asn Pro Ser Thr Ile Cys Ile Thr Asn Pro Thr Gln Lys Pro
            180                 185                 190

Pro Asn Phe His Tyr Ser Met Ser Phe Leu Gly Asp Leu Pro Ile Gly
        195                 200                 205

Ser Asp Asn Ser Ser Gly Ser Ser Val Leu Tyr Asp Pro Leu Phe Pro
```

```
             210                 215                 220
Leu Asn Leu Pro Ala Gln Ser Pro Ala Leu Arg Glu Leu Pro Gln Ser
225                 230                 235                 240

Leu Pro Arg Val Tyr Ser Met Pro Thr Asn Ser Arg Asn Gly Ser Pro
                245                 250                 255

Phe Gly Gly Gly Asp Glu Met Glu Asp Gly Gly Met Gly Val Ser
                260                 265                 270

Gln Phe Asn Lys Val Thr Ala Phe Val Gly Lys Gly Lys Gly Lys Ala
                275                 280                 285

Thr Glu His Leu Thr Thr Glu Lys Gln Arg Arg Glu Gln Leu Lys Gly
    290                 295                 300

Arg Tyr Lys Ile Leu Arg Ser Leu Ile Pro Asn Ser Thr Lys Asp Asp
305                 310                 315                 320

Arg Ala Ser Val Val Gly Asp Ala Ile Glu Tyr Leu Arg Glu Leu Ile
                325                 330                 335

Arg Thr Val Asn Glu Leu Lys Leu Leu Val Glu Lys Lys Arg His Glu
                340                 345                 350

Ile Glu Ile Cys Lys Arg His Lys Thr Glu Asp Tyr Ala Ala Glu Ser
                355                 360                 365

Cys His Met Lys Pro Phe Gly Asp Pro Asp Gly Ser Ile Arg Thr Ser
    370                 375                 380

Trp Leu Gln Arg Lys Ser Lys Asp Ser Glu Val Asp Val Arg Ile Ile
385                 390                 395                 400

Asp Asp Asp Val Thr Ile Lys Leu Phe Gln Arg Lys Lys Val Asn Cys
                405                 410                 415

Leu Leu Phe Val Ser Lys Val Leu Asp Glu Leu Gln Leu Glu Leu Asn
                420                 425                 430

His Val Ala Gly Gly His Val Gly Glu Tyr Cys Ser Phe Leu Phe Asn
                435                 440                 445

Ser Lys Val Ile Glu Gly Ser Ser Val His Ala Ser Ala Ile Ala Asn
                450                 455                 460

Arg Val Ile Asp Val Leu Asp Thr Gln Tyr Ala Ala Val Val Pro His
465                 470                 475                 480

Asn Arg Met

<210> SEQ ID NO 94
<211> LENGTH: 412
<212> TYPE: PRT
<213> ORGANISM: Cucumis sativus

<400> SEQUENCE: 94

Met Glu Leu Asp Phe Gln Gln Ala Ala Ala Pro Thr Pro Gly Phe
1               5                   10                  15

Asp Gln Glu Leu Thr Ser Asp Ser Asn Pro Met Leu Cys Leu Asp Gln
                20                  25                  30

Ser Asn Trp Val Gly Thr Gln Ile Gln Glu Met Gly Phe Asn His Asn
                35                  40                  45

His Val Gln Ser Gln Phe Ser Asp Ser Ala Ile Pro Pro Thr Pro Tyr
    50                  55                  60

Thr Gln Pro Pro Asp Leu Leu Asn Phe Leu Asn Met Pro Pro Thr Ala
65                  70                  75                  80

Arg Cys Ser Asn Asn Ser Ser Ile Ser Phe Ser Asn Leu His Thr Pro
                85                  90                  95

Ala Met Gly Ala Phe Leu Gly Asp Leu Pro Pro Gly Asp Ala Pro Asn
```

100                 105                 110
Ser Ser Ser Thr Ser Leu Ser Ile Leu Tyr Asp Pro Leu Phe His Leu
            115                 120                 125

Asn Leu Pro Pro Gln Pro Pro Leu Phe Arg Glu Leu Phe His Ser Leu
130                 135                 140

Pro His Gly Tyr Gly Met Pro Ala Ala Ser Ser Arg Gly Arg Gly Gly
145                 150                 155                 160

Ser Leu Phe Pro Glu Gly Ser Glu Ile Val Glu Arg Glu Gly Thr Ala
                165                 170                 175

Gly Val Tyr Glu Asp Gly Asp Gly Ser Gly Val Leu Glu Phe Ser Arg
            180                 185                 190

Asp Met Ala Asp Cys Ile Gly Lys Arg Arg Asp Gly Lys Met Thr Lys
            195                 200                 205

His Phe Ala Thr Glu Arg Gln Arg Arg Val Gln Leu Asn Asp Lys Tyr
        210                 215                 220

Lys Ala Leu Arg Ser Leu Val Pro Ile Pro Thr Lys Asn Asp Arg Ala
225                 230                 235                 240

Ser Ile Val Gly Asp Ala Ile Asn Tyr Ile Gln Glu Leu Leu Arg Glu
                245                 250                 255

Val Lys Glu Leu Lys Leu Leu Val Glu Lys Lys Arg Ser Ser Arg Glu
            260                 265                 270

Arg Ser Lys Arg Val Arg Thr Ala Glu Glu Ile Glu Gln Gly Gly Gly
        275                 280                 285

Ser Glu Ser Ser Asn Ala Lys Gly Gly Glu Gly Val Val Glu Asp Gln
        290                 295                 300

Arg Tyr Asn Leu Arg Ser Ser Trp Leu Gln Arg Lys Thr Lys Asp Thr
305                 310                 315                 320

Glu Val Asp Val Arg Ile Val Asp Glu Val Thr Val Lys Leu Val
                325                 330                 335

Gln Arg Lys Leu Asn Cys Leu Leu Leu Val Ser Lys Leu Leu Glu Asp
            340                 345                 350

Leu Gln Leu Asp Leu His His Val Ala Gly Gly His Ile Gly Asp Tyr
        355                 360                 365

Tyr Ser Phe Leu Phe Asn Thr Lys Ile Tyr Glu Gly Ser Ser Val Tyr
        370                 375                 380

Ala Ser Ala Ile Ala Asn Lys Val Met Glu Ala Val Asp Arg Gln Tyr
385                 390                 395                 400

Asn Asn Thr Ser Ile Ser Pro Leu Thr Asn Thr Tyr
                405                 410

<210> SEQ ID NO 95
<211> LENGTH: 465
<212> TYPE: PRT
<213> ORGANISM: Brachypodium distachyon

<400> SEQUENCE: 95

Met Ile Ile Gly Gly Asp Tyr Phe Glu Gly Ser His Asp His Ser Leu
1               5                   10                  15

Met Ala Gly Ser Leu Ile His Asp Ser Ser Gln Ala Pro Lys Cys Asn
            20                  25                  30

Gly Asn Thr Asp Ile Glu Leu Gln Lys Phe Lys Val Pro Ser Phe Ser
        35                  40                  45

Ser Glu Ile Leu Thr Asn Ser Thr Asn Leu Ser Ser Glu Ala Ala Arg
50                  55                  60

```
Ala Ile Asn His Leu Gln His Gln Leu Gly Ile Asp Leu Glu Gln Asp
 65                  70                  75                  80

Met Gln Pro Val Glu Thr Ala Thr Trp Asp Ala Ser Ile Cys Ser Ile
                 85                  90                  95

Gln Asp His Ile Ile Asn Asn Gln Ile Ser Glu Asp Pro Gln Asn Ile
            100                 105                 110

Leu Val Glu Gln Gln Ile Gln Gln Tyr Asp Ala Ala Ile Tyr Pro Asn
        115                 120                 125

Ser Ser Tyr Thr Pro Ala Pro Asp Leu Leu Asn Leu Leu His Cys Thr
    130                 135                 140

Val Ala Pro Ala Phe Pro Thr Thr Thr Ser Val Phe Gly Asp Thr Ser
145                 150                 155                 160

Leu Ser Ser Thr Asn Tyr Leu Asp Leu Asn Gly Glu Phe Thr Gly Val
                165                 170                 175

Ala Ala Thr Pro Glu Ser Gly Leu Met Phe Thr Ser Asp Ser Ala Leu
            180                 185                 190

Gln Leu Gly Tyr His Ala Thr Gln Ser His Pro Leu Lys Asp Ile Cys
        195                 200                 205

His Ser Leu Pro Gln Asn Tyr Gly Leu Phe Pro Gly Glu Asp Glu Arg
    210                 215                 220

Glu Val Met Ile Gly Val Gly Ser Val Gly Gly Asp Ile Phe Gln Asp
225                 230                 235                 240

Ile Asp Asp Arg Gln Phe Asp Thr Val Leu Glu Cys Arg Arg Gly Lys
                245                 250                 255

Gly Glu Phe Gly Lys Gly Lys Gly Lys Ala Asn Phe Ala Thr Glu Arg
            260                 265                 270

Glu Arg Arg Glu Gln Leu Asn Val Lys Tyr Lys Thr Leu Lys Asp Leu
        275                 280                 285

Phe Pro Asn Pro Thr Lys Ser Asp Arg Ala Ser Val Val Gly Asp Ala
    290                 295                 300

Ile Glu Tyr Ile Asp Glu Leu Asn Arg Thr Val Lys Glu Leu Lys Ile
305                 310                 315                 320

Leu Val Glu Gln Lys Trp His Gly Asn Lys Arg Thr Lys Ile Ile Lys
                325                 330                 335

Leu Asp Glu Glu Val Ala Ala Asp Gly Glu Ser Ser Ser Met Lys Pro
            340                 345                 350

Met Arg Asp Asp Gln Asp Asn Gln Phe Asp Gly Thr Ile Arg Ser Ser
        355                 360                 365

Trp Val Gln Arg Arg Ser Lys Glu Cys His Ile Asp Val Arg Ile Val
    370                 375                 380

Glu Asn Glu Val Asn Ile Lys Leu Thr Glu Lys Lys Val Asn Ser
385                 390                 395                 400

Leu Leu His Ala Ala Arg Val Leu Asp Glu Phe Gln Leu Glu Leu Ile
                405                 410                 415

His Ala Val Gly Gly Ile Ile Gly Asp His His Ile Phe Met Phe Asn
            420                 425                 430

Thr Lys Val Ser Glu Gly Ser Ser Val Tyr Ala Cys Ala Val Ala Lys
        435                 440                 445

Arg Leu Leu Gln Ala Val Asp Ala Gln His Gln Ala Ile Asn Ile Phe
    450                 455                 460

His
465
```

```
<210> SEQ ID NO 96
<211> LENGTH: 480
<212> TYPE: PRT
<213> ORGANISM: Cucumis sativus

<400> SEQUENCE: 96

Met Tyr Glu Glu Thr Glu Cys Ser Asp Pro Asn Ser Ile Ser Pro Glu
1               5                   10                  15

Thr Met Pro His Ile Ser Ala Phe Pro Asn Ser Phe Pro Pro Pro Leu
            20                  25                  30

Ile Ala Gln Gln Thr His Pro Asn Phe His His Asn Asn Asn Leu Asn
        35                  40                  45

Leu Ser Ile Asp His Ile Ser Tyr His His Ser Thr Ala Leu Gln
    50                  55                  60

Pro Ala Asp Ala Met Glu Leu Asp Phe Gln Gln Ala Ala Ala Pro
65                  70                  75                  80

Thr Pro Gly Phe Asp Gln Glu Leu Thr Ser Asp Ser Asn Pro Met Leu
                85                  90                  95

Cys Leu Asp Gln Ser Asn Trp Val Gly Thr Gln Ile Gln Glu Met Gly
            100                 105                 110

Phe Asn His Asn His Val Gln Ser Gln Phe Ser Asp Ser Ala Ile Pro
        115                 120                 125

Pro Thr Pro Tyr Thr Gln Pro Pro Asp Leu Leu Asn Phe Leu Asn Met
    130                 135                 140

Pro Pro Thr Ala Arg Cys Ser Asn Asn Ser Ser Ile Ser Phe Ser Asn
145                 150                 155                 160

Leu His Thr Pro Ala Met Gly Ala Phe Leu Gly Asp Leu Pro Pro Gly
                165                 170                 175

Asp Ala Pro Asn Ser Ser Ser Thr Ser Leu Ser Ile Leu Tyr Asp Pro
            180                 185                 190

Leu Phe His Leu Asn Leu Pro Pro Gln Pro Pro Leu Phe Arg Glu Leu
        195                 200                 205

Phe His Ser Leu Pro His Gly Tyr Gly Met Pro Ala Ala Ser Ser Arg
    210                 215                 220

Gly Arg Gly Gly Ser Leu Phe Pro Glu Gly Ser Glu Ile Val Glu Arg
225                 230                 235                 240

Glu Gly Thr Ala Gly Val Tyr Glu Asp Gly Asp Gly Ser Gly Val Leu
                245                 250                 255

Glu Phe Ser Arg Asp Met Ala Asp Cys Ile Gly Lys Arg Arg Asp Gly
            260                 265                 270

Lys Met Thr Lys His Phe Ala Thr Glu Arg Gln Arg Arg Val Gln Leu
    275                 280                 285

Asn Asp Lys Tyr Lys Ala Leu Arg Ser Leu Val Pro Ile Pro Thr Lys
290                 295                 300

Asn Asp Arg Ala Ser Ile Val Gly Asp Ala Ile Asn Tyr Ile Gln Glu
305                 310                 315                 320

Leu Leu Arg Glu Val Lys Glu Leu Lys Leu Leu Val Glu Lys Lys Arg
                325                 330                 335

Ser Ser Arg Glu Arg Ser Lys Arg Val Arg Thr Ala Glu Glu Ile Glu
            340                 345                 350

Gln Gly Gly Gly Ser Glu Ser Ser Asn Ala Lys Gly Gly Glu Gly Val
        355                 360                 365

Val Glu Asp Gln Arg Tyr Asn Leu Arg Ser Ser Trp Leu Gln Arg Lys
    370                 375                 380
```

Thr Lys Asp Thr Glu Val Asp Val Arg Ile Val Asp Glu Val Thr
385                 390                 395                 400

Val Lys Leu Val Gln Arg Lys Leu Asn Cys Leu Leu Val Ser Lys
            405                 410                 415

Leu Leu Glu Asp Leu Gln Leu Asp Leu His His Val Ala Gly Gly His
        420                 425                 430

Ile Gly Asp Tyr Tyr Ser Phe Leu Phe Asn Thr Lys Ile Tyr Glu Gly
        435                 440                 445

Ser Ser Val Tyr Ala Ser Ala Ile Ala Asn Lys Val Met Glu Ala Val
    450                 455                 460

Asp Arg Gln Tyr Asn Asn Thr Ser Ile Ser Pro Leu Thr Asn Thr Tyr
465                 470                 475                 480

<210> SEQ ID NO 97
<211> LENGTH: 459
<212> TYPE: PRT
<213> ORGANISM: Aegilops tauschii

<400> SEQUENCE: 97

Met Ile Ala Glu Gly Gly Tyr Phe Asp Gly Ser Arg Asp Ala Ile Leu
1               5                   10                  15

Met Ala Gly Ser Leu Ile His Asp Ser Leu Asp Ser Ile Cys Asp Asn
            20                  25                  30

Thr Glu Ile Glu Gln Gly Asn Phe His Gly Pro Ser Phe Phe Ile Glu
        35                  40                  45

Asp Ile Cys Asn Pro Thr Asn Leu Thr Ser Glu Ser Ala Arg Thr Ile
    50                  55                  60

Asn His Ile Gln His Arg Ala Glu Phe Asp Met Asp Gln Asp Leu His
65                  70                  75                  80

Gly His Met Ile Gln Glu Thr Gln Val Glu Thr Ser Asn Trp Val Pro
                85                  90                  95

Ala Met Phe Gly Thr Gln Asn His Ile Ile Ser Gln Gln Ser Ile Glu
            100                 105                 110

Gln Gln Met Asp Asp Tyr Asp Ala Ala Ser Tyr Pro Asp Gly Ala His
        115                 120                 125

Thr Ala Ala Pro Asp Leu Leu Asn Leu Leu Gln Ile Pro Arg Tyr Ser
    130                 135                 140

Met Thr Thr Ala Phe Pro Ser Thr Glu His Ile Phe Gly Asp Pro Gly
145                 150                 155                 160

Gln Asn Ala Gly Asn Gln Leu Asp Ile Asn Asn Asp Val Leu Gly Arg
                165                 170                 175

Ala Ile His Asp Ser Gly Met Met Leu Gly Asp Ser Thr Leu Pro Leu
            180                 185                 190

Gln Tyr Asn Asp Asn Gln Ser His Leu Phe Lys Asp Leu Tyr His Ser
        195                 200                 205

Leu Pro Gln Ser Phe Gly Leu Phe Ser Ser Asp Asp Glu Arg Asp Arg
    210                 215                 220

Ala Met Gly Val Val Gly Ala Ala Gly Asn Ile Leu Gln Glu Ile Asp
225                 230                 235                 240

Gly Arg Gln Phe Gly Ser Pro Lys Leu Gly Arg Ser Lys Lys Gly Gly
                245                 250                 255

Phe Gly Lys Ala Lys Ala Asn Phe Ala Thr Glu Lys Glu Arg Arg Glu
            260                 265                 270

Gln Ile Asn Val Lys Tyr Gly Ala Leu Arg Ser Leu Leu Pro Ser Pro
        275                 280                 285

-continued

```
Thr Lys Asn Asp Arg Ala Ser Ile Val Gly Asp Ala Ile Glu Tyr Ile
    290                 295                 300
Asn Glu Leu Asn Arg Thr Leu Lys Glu Leu Thr Ser Leu Val Glu Gly
305                 310                 315                 320
Asp Thr Lys His Arg Met Lys Arg Leu Lys Leu Asp Asp Ala Ala Cys
                325                 330                 335
Asp Asn Gly Glu Ser Ser Leu Gln Gln Val Lys Asp Asp Gln Asp
                340                 345                 350
Ser Gln Leu Asn Gly Ala Ile Arg Ser Ser Trp Ile Gln Arg Arg Ser
                355                 360                 365
Lys Glu Cys His Val Asp Val Arg Ile Val Gly Asn Glu Ile Asn Ile
    370                 375                 380
Lys Phe Thr Glu Lys Lys Lys Thr Asn Ser Leu Leu Cys Ala Ala Lys
385                 390                 395                 400
Val Ile Asp Glu Phe Arg Leu Glu Leu Ile His Val Val Gly Gly Val
                405                 410                 415
Ile Gly Asp Gln Arg Ile Phe Met Phe Asn Thr Lys Ile Ser Glu Gly
                420                 425                 430
Ser Ser Val Tyr Ala Ser Ala Leu Ala Ser Lys Leu Leu Arg Ala Met
                435                 440                 445
Glu Met Glu His Leu Ala Val Asp Ile Phe Ser
    450                 455

<210> SEQ ID NO 98
<211> LENGTH: 465
<212> TYPE: PRT
<213> ORGANISM: Fragaria vesca

<400> SEQUENCE: 98

Met Tyr Val Asp Ser Ser Thr Ala Ala Gly Ala Cys Asn Phe Asp
1               5                   10                  15
Pro Asn Thr Asp Thr Asn Pro Met Ser Glu Ser Ala Pro Glu Val Val
                20                  25                  30
Leu His His Gln Asn Asn Pro Thr Thr Phe Ala Ser Thr His Asp Glu
            35                  40                  45
Asn Leu Arg Ser Leu Ser Met Glu Glu Glu Leu Ser Asn Tyr His His
    50                  55                  60
Asn His Asn Ala Ala Met Glu Ile Glu Gln Gln Leu Gln Thr Glu Met
65                  70                  75                  80
Gly Phe Gly Thr Met Asp Gln Asn Thr Asn Thr Asn Pro His Leu
                85                  90                  95
Ile Asn Pro Phe Asp Thr His Gln Ala Thr Asn Trp Asp Asn Asn Asp
                100                 105                 110
Glu Met Gln Gln Gln Gln Leu Pro Pro Val Ala Pro Thr Pro Asp
            115                 120                 125
Leu Leu Ser Leu Phe His Leu Pro Asn Ser Ser Val Leu Pro His Ser
    130                 135                 140
Ser Ile Thr Phe Thr Asn Pro Lys Thr Pro Gly Gly Cys Phe Pro Gly
145                 150                 155                 160
Ser Phe Gly Tyr Glu Thr Leu Pro Glu Thr Pro Ser Gly Ala Val Ala
                165                 170                 175
Ser Asn Ser Val Met Tyr Asp Pro Met Phe His Leu Asn Gln Leu Pro
                180                 185                 190
Pro Gln Pro Gln Pro Pro Leu Phe Arg Glu Leu Leu Gln Ser Leu Pro
```

```
                195                 200                 205
His Gly Tyr Lys Arg Asn Gly Ser Ser Leu Phe Ser Asn Gly Gly Asp
    210                 215                 220

Glu Val Asp Asp Gly Ser Arg Gln Leu Phe Glu Asn Gly Val Leu Glu
225                 230                 235                 240

Phe Ser Lys Glu Met Lys Pro Phe Gly Arg Gly Arg Gly Gly Asn Lys
                245                 250                 255

Gly Thr Lys His Phe Ala Thr Glu Arg Gln Arg Arg Val Gln Leu Asn
                260                 265                 270

Asp Lys Phe Ser Ala Leu Arg Glu Leu Val Pro Asn Pro Thr Lys Pro
            275                 280                 285

Asp Arg Ala Ser Val Val Gly Asp Ala Ile Asp Tyr Ile Gln Glu Leu
        290                 295                 300

Lys Arg Thr Val Ser Glu Leu Lys Leu Leu Val Glu Lys Lys Arg Cys
305                 310                 315                 320

Gly Arg Glu Arg Ser Lys Arg His Lys Thr Glu Gln Asp Ile Gly Ala
                325                 330                 335

Arg Asp Asp Asp Glu Ser Cys Asn Met Lys Pro Leu Gly Asp Pro Asp
            340                 345                 350

His Asp His Ser Tyr Asn Asn Gly Ser Leu Arg Ser Ser Trp Leu Gln
        355                 360                 365

Arg Lys Ser Lys Asp Thr Glu Val Asp Val Arg Ile Ile Asp Asp Glu
    370                 375                 380

Val Thr Ile Lys Leu Val Gln Arg Lys Lys Ile Asn Leu Leu Leu Ser
385                 390                 395                 400

Val Ser Lys Leu Leu Asp Glu Leu Gln Leu Glu Leu His His Ala Ala
                405                 410                 415

Gly Gly His Ile Gly Asn Ser Tyr Ser Phe Leu Phe Asn Thr Lys Met
                420                 425                 430

Tyr Glu Gly Ser Ser Leu Tyr Ala Ser Ala Ile Ala Asn Lys Leu Ile
            435                 440                 445

Asp Thr Val Asp Arg Gln Tyr Ala Ala Ala Ile Pro Pro Thr Asn Ser
        450                 455                 460

Tyr
465

<210> SEQ ID NO 99
<211> LENGTH: 480
<212> TYPE: PRT
<213> ORGANISM: Aegilops tauschii

<400> SEQUENCE: 99

Met Ile Trp Ile Glu Gly Ala Arg His Cys Phe Val Lys Met Ile Val
1               5                   10                  15

Gly Gly Asp Tyr Phe Glu Gly Ser His Asp His Asn Leu Met Thr Gly
                20                  25                  30

Ser Leu Thr His Asp Ser Ser Leu Ala Pro Lys Cys Asn Asp Asn Thr
            35                  40                  45

Asn Ile Glu Leu Gln Arg Phe Lys Val Gln Ser Phe Ser Ala Asp Ile
    50                  55                  60

Leu Ser Asp Ser Thr Asn Leu Ser Ser Glu Ala Ala Arg Ala Ile Asn
65                  70                  75                  80

His Leu Gln His Gln Leu Gly Ile Gly Leu Glu Gln Asp Met Pro Pro
                85                  90                  95
```

```
Val Glu Thr Ala Thr Trp Asp Thr Ser Ile Cys Thr Ile Gln Asp Gln
            100                 105                 110

Ile Ile Asn His Gln Leu Ser Glu Asp Pro Gln Asn Ile Leu Val Gln
        115                 120                 125

Gln Gln Ile Gln Gln Tyr Asp Ala Ala Leu Tyr Pro Asn Ser Gly Tyr
    130                 135                 140

Thr Pro Ala Pro Asp Leu Leu Asn Leu Leu His Cys Thr Val Ala Pro
145                 150                 155                 160

Val Phe Pro Ala Thr Ala Ser Val Phe Gly Asp Thr Ala Leu Ser Gly
                165                 170                 175

Gly Thr Asn Tyr Leu Asp Leu Asn Gly Glu Phe Thr Gly Val Ala Ala
            180                 185                 190

Ile Pro Asp Ser Gly Leu Met Tyr Thr Ser Asp Pro Ala Leu Gln Leu
        195                 200                 205

Gly Tyr His Ala Ala Pro Ser His Ala Leu Lys Asp Ile Cys His Ser
    210                 215                 220

Leu Pro Gln Asn Tyr Gly Leu Phe Pro Ser Glu Asp Glu Arg Asp Val
225                 230                 235                 240

Met Leu Gly Val Gly Ser Val Gly Gly Asp Leu Phe Gln Asp Met Asp
                245                 250                 255

Asp Arg Gln Phe Glu Thr Val Leu Glu Gly Arg Gly Lys Gly Glu
            260                 265                 270

Phe Gly Lys Gly Lys Gly Lys Ala Asn Phe Ala Thr Glu Arg Glu Arg
        275                 280                 285

Arg Glu Gln Leu Asn Val Lys Tyr Lys Thr Leu Arg Met Leu Phe Pro
    290                 295                 300

Asn Pro Thr Lys Asn Asp Arg Ala Ser Val Val Gly Asp Ala Ile Glu
305                 310                 315                 320

Tyr Ile Asp Glu Leu Asn Arg Thr Val Lys Glu Leu Lys Ile Leu Val
                325                 330                 335

Glu Gln Lys Trp His Gly Thr Asn Arg Arg Ile Arg Lys Leu Asp
            340                 345                 350

Glu Glu Ala Ala Ala Asp Gly Glu Ser Ser Ser Met Arg Pro Met Arg
        355                 360                 365

Asp Glu Gln Asp Asn Gln Leu Asp Gly Ala Ile Arg Ser Ser Trp Val
370                 375                 380

Gln Arg Arg Ser Arg Glu Cys His Val Asp Val Arg Ile Val Glu Asn
385                 390                 395                 400

Glu Ile Asn Ile Lys Leu Thr Glu Lys Lys Ala Asn Ser Ser Leu
        405                 410                 415

Leu His Val Ala Lys Val Leu Asp Glu Phe His Leu Glu Ile His
    420                 425                 430

Val Val Gly Gly Ile Ile Gly Asp His Tyr Ile Phe Met Phe Asn Thr
                435                 440                 445

Lys Val Thr Glu Gly Ser Ser Val Tyr Ala Cys Ala Val Ala Lys Arg
        450                 455                 460

Ile Leu Gln Ala Val Asp Ala Gln His Gln Ala Leu Asp Ile Phe Asn
465                 470                 475                 480

<210> SEQ ID NO 100
<211> LENGTH: 430
<212> TYPE: PRT
<213> ORGANISM: Arabidopsis lyrata

<400> SEQUENCE: 100
```

```
Met Tyr Glu Glu Ser Ser Cys Phe Asp Pro Asn Pro Met Val Asp Asn
1               5                   10                  15

Asn Gly Ser Phe Cys Ala Ala Glu Thr Thr Phe Pro Val Ser His Gln
            20                  25                  30

Phe Gln Pro Pro Val Gly Ser Thr Thr Asn Ser Phe Asn Asp Asp Leu
        35                  40                  45

Lys Leu Pro Thr Met Glu Glu Phe Ser Ala Phe Pro Ser Val Ile Ser
50                  55                  60

Leu Pro Asn Ser Glu Thr Gln Asn Gln Asn Ile Ser Asn Asn Asn His
65                  70                  75                  80

Leu Ile Asn Gln Met Ile Gln Glu Pro Asn Trp Gly Val Ser Glu Asp
                85                  90                  95

Asn Thr Gly Phe Phe Met Asn Thr Ser His Pro Asn Thr Thr Thr Thr
            100                 105                 110

Pro Ile Pro Asp Leu Leu Ser Leu Leu His Leu Pro Arg Cys Ser Met
        115                 120                 125

Ala Leu Pro Ser Ser Asn Leu Ser Asp Ile Met Ala Gly Ser Cys Phe
130                 135                 140

Thr Tyr Asp Pro Leu Cys His Leu Asn Leu Pro Pro Gln Pro Pro Leu
145                 150                 155                 160

Ile Pro Ser Asn Asp Tyr Ser Gly Tyr Leu Leu Gly Ile Asp Thr Asn
                165                 170                 175

Thr Thr Thr Gln Gly Asp Glu Ser Asn Val Gly Asp Glu Asn Asn Asn
            180                 185                 190

Ala Gln Phe Asp Ser Gly Ile Ile Glu Phe Ser Lys Glu Ile Arg Arg
        195                 200                 205

Lys Gly Arg Gly Lys Arg Lys Asn Lys Pro Phe Thr Thr Glu Arg Glu
210                 215                 220

Arg Arg Cys His Leu Asn Glu Arg Tyr Glu Ala Leu Lys Leu Leu Ile
225                 230                 235                 240

Pro Asn Pro Ser Lys Gly Asp Arg Ala Ser Ile Leu Gln Asp Gly Ile
                245                 250                 255

Asp Tyr Ile Asn Glu Leu Arg Arg Arg Val Ser Glu Leu Lys Tyr Leu
            260                 265                 270

Val Glu Arg Lys Arg Cys Gly Gly Arg His Lys Asn Asn Glu Leu Asp
        275                 280                 285

Asn Asn Ile Asn Asn Asn Ser Asn Asp His Asp Asn Asp Glu Asp
290                 295                 300

Asp Ile Asp Asp Glu Asn Met Glu Lys Lys Pro Glu Ser Asp Val Val
305                 310                 315                 320

Asp Gln Cys Ser Ser Asn Asn Ser Leu Arg Cys Ser Trp Leu Gln Arg
                325                 330                 335

Lys Ser Lys Val Thr Glu Val Asp Val Arg Ile Val Asp Asp Glu Val
            340                 345                 350

Thr Ile Lys Val Val Gln Lys Lys Ile Asn Cys Leu Leu Val
        355                 360                 365

Ser Lys Val Leu Asp Gln Leu Gln Leu Asp Leu Tyr His Val Ala Gly
370                 375                 380

Gly Gln Ile Gly Glu His Tyr Ser Phe Leu Phe Asn Thr Lys Ile Tyr
385                 390                 395                 400

Glu Gly Ser Thr Ile Tyr Ala Ser Ala Ile Ala Asn Arg Val Ile Glu
                405                 410                 415
```

```
Val Val Asp Lys His Tyr Met Ala Ala Leu Pro Ile Asn Tyr
            420                 425                 430
```

<210> SEQ ID NO 101
<211> LENGTH: 421
<212> TYPE: PRT
<213> ORGANISM: Arabidopsis lyrata

<400> SEQUENCE: 101

```
Met Glu Gly Gly Gly Met Phe Glu Glu Ile Gly Cys Phe Asp Pro Asn
  1               5                  10                  15

Ala Pro Ala Glu Met Thr Ala Glu Ser Ser Phe Ser Pro Ala Glu Pro
             20                  25                  30

Pro Pro Thr Ile Thr Val Ile Gly Ser Asn Ser Asn Ser Asn Cys Ser
         35                  40                  45

Leu Glu Asp Leu Ser Glu Phe His Leu Ser Pro Gln Asp Ser Ser Leu
     50                  55                  60

Pro Ala Ser Ala Ser Ala Tyr Val His Gln Leu His Val Asn Ala Thr
 65                  70                  75                  80

Pro Asn Cys Asp His Gln Phe Gln Ser Ser Met His Gln Thr Leu Gln
                 85                  90                  95

Gly Pro Ser Tyr Pro Gln Gln Ser Asn Asn Trp Asn Gly Tyr Gln
            100                 105                 110

Asp Phe Val Asn Leu Val Pro Asn His Thr Thr Pro Asp Leu Leu Ser
            115                 120                 125

Leu Leu Gln Leu Pro Arg Ser Ser Leu Pro Pro Phe Ala Asn Pro Ser
        130                 135                 140

Leu Gln Asp Ile Ile Met Thr Thr Ser Ser Ser Val Ala Ala Tyr Asp
145                 150                 155                 160

Pro Leu Phe His Leu Asn Phe Pro Leu Gln Pro Pro Asn Gly Thr Phe
                165                 170                 175

Ile Gly Val Asp Gln Asp Gln Thr Glu Ile Glu Asn Gln Gly Val Asn
            180                 185                 190

Leu Met Tyr Asp Glu Glu Asn Asn Asn Leu Asp Asn Gly Leu Asn Arg
        195                 200                 205

Lys Gly Arg Gly Ser Arg Lys Arg Lys Val Phe Pro Thr Glu Arg Glu
    210                 215                 220

Arg Arg Val His Phe Lys Asp Arg Phe Gly Asp Leu Lys Asn Leu Ile
225                 230                 235                 240

Pro Asn Pro Thr Lys Asn Asp Arg Ala Ser Ile Val Gly Glu Ala Ile
                245                 250                 255

Asp Tyr Ile Lys Glu Leu Leu Arg Thr Ile Asp Glu Phe Lys Leu Leu
            260                 265                 270

Val Glu Lys Lys Arg Thr Lys Gln Arg Asn Arg Glu Gly Asp Asp Val
        275                 280                 285

Ile Asp Glu Asn Phe Lys Ala Gln Ser Glu Val Val Glu Gln Cys Leu
    290                 295                 300

Ile Asn Lys Lys Asn Asn Ala Leu Arg Cys Ser Trp Leu Lys Arg Lys
305                 310                 315                 320

Ser Lys Phe Thr Glu Val Asp Val Arg Ile Ile Asp Asp Val Thr
                325                 330                 335

Ile Lys Ile Val Gln Lys Lys Ile Asn Cys Leu Val Phe Val Ser
            340                 345                 350

Lys Val Val Asp Gln Leu Gln Leu Asp Leu His His Val Ala Gly Ala
        355                 360                 365
```

```
Gln Ile Gly Glu His His Ser Phe Leu Phe Asn Ala Lys Ile Cys Glu
        370                 375                 380

Gly Ser Ser Val Tyr Ala Ser Ala Ile Ala Asp Arg Val Met Glu Val
385                 390                 395                 400

Leu Glu Lys Gln Tyr Met Glu Ala Leu Ser Thr Asn Asn Gly Tyr His
                405                 410                 415

Cys Tyr Ser Ser Asp
                420

<210> SEQ ID NO 102
<211> LENGTH: 428
<212> TYPE: PRT
<213> ORGANISM: Arabidopsis thaliana

<400> SEQUENCE: 102

Met Tyr Glu Glu Ser Ser Cys Phe Asp Pro Asn Ser Met Val Asp Asn
1               5                   10                  15

Asn Gly Gly Phe Cys Ala Ala Glu Thr Thr Phe Thr Val Ser His Gln
                20                  25                  30

Phe Gln Pro Pro Leu Gly Ser Thr Thr Asn Ser Phe Asp Asp Asp Leu
            35                  40                  45

Lys Leu Pro Thr Met Asp Glu Phe Ser Val Phe Pro Ser Val Ile Ser
50                  55                  60

Leu Pro Asn Ser Glu Thr Gln Asn Gln Asn Ile Ser Asn Asn Asn His
65                  70                  75                  80

Leu Ile Asn Gln Met Ile Gln Glu Ser Asn Trp Gly Val Ser Glu Asp
                85                  90                  95

Asn Ser Asn Phe Phe Met Asn Thr Ser His Pro Asn Thr Thr Thr Thr
                100                 105                 110

Pro Ile Pro Asp Leu Leu Ser Leu Leu His Leu Pro Arg Cys Ser Met
            115                 120                 125

Ser Leu Pro Ser Ser Asp Ile Met Ala Gly Ser Cys Phe Thr Tyr Asp
        130                 135                 140

Pro Leu Phe His Leu Asn Leu Pro Pro Gln Pro Pro Leu Ile Pro Ser
145                 150                 155                 160

Asn Asp Tyr Ser Gly Tyr Leu Leu Gly Ile Asp Thr Asn Thr Thr Thr
                165                 170                 175

Gln Arg Asp Glu Ser Asn Val Gly Asp Glu Asn Asn Asn Ala Gln Phe
            180                 185                 190

Asp Ser Gly Ile Ile Glu Phe Ser Lys Glu Ile Arg Arg Lys Gly Arg
        195                 200                 205

Gly Lys Arg Lys Asn Lys Pro Phe Thr Thr Glu Arg Glu Arg Arg Cys
210                 215                 220

His Leu Asn Glu Arg Tyr Glu Ala Leu Lys Leu Leu Ile Pro Ser Pro
225                 230                 235                 240

Ser Lys Gly Asp Arg Ala Ser Ile Leu Gln Asp Gly Ile Asp Tyr Ile
                245                 250                 255

Asn Glu Leu Arg Arg Arg Val Ser Glu Leu Lys Tyr Leu Val Glu Arg
            260                 265                 270

Lys Arg Cys Gly Gly Arg His Lys Asn Asn Glu Val Asp Asp Asn Asn
        275                 280                 285

Asn Asn Lys Asn Leu Asp Asp His Gly Asn Glu Asp Asp Asp Asp Asp
290                 295                 300

Asp Glu Asn Met Glu Lys Lys Pro Glu Ser Asp Val Ile Asp Gln Cys
```

```
305                 310                 315                 320
Ser Ser Asn Asn Ser Leu Arg Cys Ser Trp Leu Gln Arg Lys Ser Lys
            325                 330                 335

Val Thr Glu Val Asp Val Arg Ile Val Asp Glu Val Thr Ile Lys
            340                 345                 350

Val Val Gln Lys Lys Ile Asn Cys Leu Leu Val Ser Lys Val
            355                 360                 365

Leu Asp Gln Leu Gln Leu Asp Leu His His Val Ala Gly Gly Gln Ile
            370                 375                 380

Gly Glu His Tyr Ser Phe Leu Phe Asn Thr Lys Ile Tyr Glu Gly Ser
385                 390                 395                 400

Thr Ile Tyr Ala Ser Ala Ile Ala Asn Arg Val Ile Glu Val Val Asp
            405                 410                 415

Lys His Tyr Met Ala Ser Leu Pro Asn Ser Asn Tyr
            420                 425

<210> SEQ ID NO 103
<211> LENGTH: 428
<212> TYPE: PRT
<213> ORGANISM: Arabidopsis thaliana

<400> SEQUENCE: 103

Met Tyr Glu Glu Ser Ser Cys Phe Asp Pro Asn Ser Met Val Asp Asn
1               5                  10                  15

Asn Gly Gly Phe Cys Ala Ala Glu Thr Thr Phe Thr Val Ser His Gln
            20                  25                  30

Phe Gln Pro Pro Leu Gly Ser Thr Thr Asn Ser Phe Asp Asp Asp Leu
        35                  40                  45

Lys Leu Pro Thr Met Asp Glu Phe Ser Val Phe Pro Ser Val Ile Ser
    50                  55                  60

Leu Pro Asn Ser Glu Thr Gln Asn Gln Asn Ile Ser Asn Asn Asn His
65                  70                  75                  80

Leu Ile Asn Gln Met Ile Gln Glu Ser Asn Trp Gly Val Ser Glu Asp
                85                  90                  95

Asn Ser Asn Phe Phe Met Asn Thr Ser His Pro Asn Thr Thr Thr Thr
            100                 105                 110

Pro Ile Pro Asp Leu Leu Ser Leu Leu His Leu Pro Arg Cys Ser Met
        115                 120                 125

Ser Leu Pro Ser Ser Asp Ile Met Ala Gly Ser Cys Phe Thr Tyr Asp
    130                 135                 140

Pro Leu Phe His Leu Asn Leu Pro Pro Gln Pro Leu Ile Pro Ser
145                 150                 155                 160

Asn Asp Tyr Ser Gly Tyr Leu Leu Gly Ile Asp Thr Asn Thr Thr Thr
                165                 170                 175

Gln Arg Asp Glu Ser Asn Val Gly Asp Glu Asn Asn Asn Ala Gln Phe
            180                 185                 190

Asp Ser Gly Ile Ile Glu Phe Ser Lys Glu Ile Arg Arg Lys Gly Arg
        195                 200                 205

Gly Lys Arg Lys Asn Lys Pro Phe Thr Thr Glu Arg Glu Arg Cys
    210                 215                 220

His Leu Asn Glu Arg Tyr Glu Ala Leu Lys Leu Leu Ile Pro Ser Pro
225                 230                 235                 240

Ser Lys Gly Asp Arg Ala Ser Ile Leu Gln Asp Gly Ile Asp Tyr Ile
                245                 250                 255
```

```
Asn Glu Leu Arg Arg Val Ser Glu Leu Lys Tyr Leu Val Glu Arg
            260                 265                 270
Lys Arg Cys Gly Gly Arg His Lys Asn Glu Val Asp Asp Asn Asn
        275                 280                 285
Asn Asn Lys Asn Leu Asp Asp His Gly Asn Glu Asp Asp Asp Asp
    290                 295                 300
Asp Glu Asn Met Glu Lys Lys Pro Glu Ser Asp Val Ile Asp Gln Cys
305                 310                 315                 320
Ser Ser Asn Asn Ser Leu Arg Cys Ser Trp Leu Gln Arg Lys Ser Lys
                325                 330                 335
Val Thr Glu Val Asp Val Arg Ile Val Asp Asp Glu Val Thr Ile Lys
            340                 345                 350
Val Val Gln Lys Lys Ile Asn Cys Leu Leu Val Ser Lys Val
        355                 360                 365
Leu Asp Gln Leu Gln Leu Asp Leu His His Val Ala Gly Gly Gln Ile
    370                 375                 380
Gly Glu His Tyr Ser Phe Leu Phe Asn Thr Lys Ile Tyr Glu Gly Ser
385                 390                 395                 400
Thr Ile Tyr Ala Ser Ala Ile Ala Asn Arg Val Ile Glu Val Val Asp
                405                 410                 415
Lys His Tyr Thr Ala Ser Leu Pro Asn Ser Asn Tyr
            420                 425

<210> SEQ ID NO 104
<211> LENGTH: 420
<212> TYPE: PRT
<213> ORGANISM: Arabidopsis thaliana

<400> SEQUENCE: 104

Met Gly Gly Gly Gly Met Phe Glu Glu Ile Gly Cys Phe Asp Pro Asn
1               5                   10                  15
Ala Pro Ala Glu Met Thr Ala Glu Ser Ser Phe Ser Pro Ser Glu Pro
            20                  25                  30
Pro Pro Thr Ile Thr Val Ile Gly Ser Asn Ser Asn Ser Asn Cys Ser
        35                  40                  45
Leu Glu Asp Leu Ser Ala Phe His Leu Ser Pro Gln Asp Ser Ser Leu
    50                  55                  60
Pro Ala Ser Ala Ser Ala Tyr Ala His Gln Leu His Ile Asn Ala Thr
65                  70                  75                  80
Pro Asn Cys Asp His Gln Phe Gln Ser Ser Met His Gln Thr Leu Gln
                85                  90                  95
Asp Pro Ser Tyr Ala Gln Gln Ser Asn His Trp Asp Asn Gly Tyr Gln
            100                 105                 110
Asp Phe Val Asn Leu Gly Pro Asn His Thr Thr Pro Asp Leu Leu Ser
        115                 120                 125
Leu Leu Gln Leu Pro Arg Ser Ser Leu Pro Pro Phe Ala Asn Pro Ser
    130                 135                 140
Ile Gln Asp Ile Ile Met Thr Thr Ser Ser Ser Val Ala Ala Tyr Asp
145                 150                 155                 160
Pro Leu Phe His Leu Asn Phe Pro Leu Gln Pro Pro Asn Gly Ser Phe
                165                 170                 175
Met Gly Val Asp Gln Asp Gln Thr Glu Thr Asn Gln Gly Val Asn Leu
            180                 185                 190
Met Tyr Asp Glu Glu Asn Asn Asn Leu Asp Asp Gly Leu Asn Arg Lys
        195                 200                 205
```

```
Gly Arg Gly Ser Lys Lys Arg Lys Ile Phe Pro Thr Glu Arg Glu Arg
            210                 215                 220

Arg Val His Phe Lys Asp Arg Phe Gly Asp Leu Lys Asn Leu Ile Pro
225                 230                 235                 240

Asn Pro Thr Lys Asn Asp Arg Ala Ser Ile Val Gly Glu Ala Ile Asp
                245                 250                 255

Tyr Ile Lys Glu Leu Leu Arg Thr Ile Asp Glu Phe Lys Leu Leu Val
            260                 265                 270

Glu Lys Lys Arg Val Lys Gln Arg Asn Arg Glu Gly Asp Asp Val Val
            275                 280                 285

Asp Glu Asn Phe Lys Ala Gln Ser Glu Val Val Glu Gln Cys Leu Ile
290                 295                 300

Asn Lys Lys Asn Asn Ala Leu Arg Cys Ser Trp Leu Lys Arg Lys Ser
305                 310                 315                 320

Lys Phe Thr Asp Val Asp Val Arg Ile Ile Asp Asp Glu Val Thr Ile
                325                 330                 335

Lys Ile Val Gln Lys Lys Ile Asn Cys Leu Leu Phe Val Ser Lys
            340                 345                 350

Val Val Asp Gln Leu Glu Leu Asp Leu His His Val Ala Gly Ala Gln
            355                 360                 365

Ile Gly Glu His His Ser Phe Leu Phe Asn Ala Lys Ile Ser Glu Gly
            370                 375                 380

Ser Ser Val Tyr Ala Ser Ala Ile Ala Asp Arg Val Met Glu Val Leu
385                 390                 395                 400

Lys Lys Gln Tyr Met Glu Ala Leu Ser Ala Asn Asn Gly Tyr His Cys
                405                 410                 415

Tyr Ser Ser Asp
            420

<210> SEQ ID NO 105
<211> LENGTH: 380
<212> TYPE: PRT
<213> ORGANISM: Glycine max

<400> SEQUENCE: 105

Met Tyr Glu Glu Ser Ser Cys Tyr Asp Pro Asp Ala Met Met Ala Glu
1               5                   10                  15

Gly Ala Glu Asp Cys Phe Pro Gln Met Val Ser Glu Ser Glu Ala Val
            20                  25                  30

Met Ser Ala Thr Pro Thr Gln Thr His Thr His Asn Thr Phe Ala Tyr
        35                  40                  45

Ser Tyr Ser Cys Gly Glu Asp Ala Ala Asn Ala Asn Gly Pro Ile Ala
    50                  55                  60

Met Glu His Pro Gln Gln Asn Pro Tyr Asn Tyr Ser Asn Thr Gln Phe
65              70                  75                  80

Val Glu Glu Leu Tyr Ser Asn Gln Gln Phe Thr Tyr His Thr Pro Thr
                85                  90                  95

Pro Asp Leu Leu Asp Leu Leu His Leu Pro Asn Pro Ile Pro Gly Asp
            100                 105                 110

Asn Arg Thr Asn Val Ser Ser Val Ser Tyr Asp Pro Tyr Leu His Leu
            115                 120                 125

Asn Leu Gln Gln Gln Gln Gln Pro Thr Leu Arg Glu Leu Leu Pro His
        130                 135                 140

Met Pro Ala Leu Arg Asn Asp Phe Pro Phe Gly Gly Ala Ala Gly Gly
```

```
            145                 150                 155                 160
Asp Asp Ile Gln Asp Phe Gly Asn Gly Leu Val Asp Phe Thr Gln Gln
                165                 170                 175

Glu Val Gly Lys Arg Gly Gly Lys Arg Thr Lys Gln Phe Thr Ser
                180                 185                 190

Thr Thr Thr Glu Arg Gln Arg Arg Val Asp Leu Ser Ser Lys Phe Asp
                195                 200                 205

Ala Leu Lys Glu Leu Ile Pro Asn Pro Ser Lys Ser Asp Arg Ala Ser
            210                 215                 220

Val Val Gly Asp Ala Ile Asn Tyr Ile Arg Glu Leu Lys Arg Thr Val
225                 230                 235                 240

Glu Glu Leu Lys Leu Leu Val Glu Lys Lys Arg Leu Glu Lys Gln Arg
                245                 250                 255

Val Met Met Arg His Lys Val Glu Thr Glu Gly Glu Ser Ser Asn Leu
                260                 265                 270

Asp Pro Ala Glu Tyr Ser Glu Ser Leu Arg Ser Ser Trp Ile Gln Arg
                275                 280                 285

Lys Thr Lys Asp Thr Glu Val Asp Val Arg Ile Val Asp Asn Glu Val
            290                 295                 300

Thr Ile Lys Leu Val Gln Arg Lys Lys Ile Asp Cys Leu Val His Val
305                 310                 315                 320

Ser His Leu Leu Asp Gln Leu Asn Leu Asp Leu Gln His Val Ala Gly
                325                 330                 335

Gly His Ile Gly Asp Phe Cys Ser Tyr Leu Phe Asn Thr Lys Ile Cys
                340                 345                 350

Glu Gly Ser Ser Ile Tyr Ala Ser Ala Ile Ala Asn Lys Leu Ile Gln
            355                 360                 365

Val Met Asp Thr Ser Leu Ala Ala Ala Ser Leu Ala
            370                 375                 380

<210> SEQ ID NO 106
<211> LENGTH: 463
<212> TYPE: PRT
<213> ORGANISM: Glycine max
<220> FEATURE:
<221> NAME/KEY: misc_feature
<222> LOCATION: (429)..(429)
<223> OTHER INFORMATION: Xaa can be any naturally occurring amino acid

<400> SEQUENCE: 106

Met His Glu Gln Thr Gly Cys Phe Asp Pro Asn Thr Met Gly Glu Ser
1               5                   10                  15

Val Pro Phe Leu Lys Asp Asn Phe Pro Gln Thr Leu Pro Pro Ser Pro
            20                  25                  30

Ile Val Val Gly Asn Thr Thr Asn Ser Asn Asn Asn Met Asp Asn His
        35                  40                  45

Leu Val Gln Glu Val Ile Asp Ala Tyr Pro Tyr Gln Leu Ser Thr Trp
    50                  55                  60

Asp Pro Ala Thr Val Gln Glu Leu Gln Asp Ile Ala Tyr Ala Asn His
65                  70                  75                  80

Thr Glu Gln Gln Gln Gln Gln Gln Asn Glu Gln Gln Phe Gln Gln
                85                  90                  95

Ile Glu Thr Gln Asn Cys Ser Gln Ser Tyr Asn Asn Pro Ser Ser Ile
            100                 105                 110

Leu Asp Pro Pro Tyr Pro Ser Pro Asp Leu Leu Asn Leu Leu His Met
        115                 120                 125
```

Pro Arg Cys Ser Ala Ser Ser Leu Leu Thr Asn Pro Ser Ile Cys Leu
            130                 135                 140

Thr Asn Pro Thr Gln Asn Thr Pro Asn Phe Gln Asn Pro Met Ala Phe
145                 150                 155                 160

Leu Gly Asp Leu Thr Ile Gly Ser Glu Asn Thr Ser Ala Ser Ser Val
                165                 170                 175

Leu Tyr Asp Pro Leu Phe His Leu Asn Leu Pro Pro Gln Pro Pro Ala
            180                 185                 190

Leu Arg Glu Leu Phe Gln Ser Leu Pro Arg Gly Tyr Ser Leu Pro Thr
        195                 200                 205

Asn Ser Arg Asn Gly Ser Leu Phe Ala Gly Gly Asp Glu Met Glu Gly
    210                 215                 220

Asp Gly Ser Gln Leu Asp Met Gly Val Leu Glu Phe Asn Arg Val Thr
225                 230                 235                 240

Pro Ser Val Gly Lys Gly Arg Gly Gly Lys Ala Thr Lys His Phe Ala
                245                 250                 255

Thr Glu Lys Gln Arg Arg Glu Gln Leu Asn Gly Lys Tyr Lys Ile Leu
            260                 265                 270

Arg Asn Leu Ile Pro Ser Pro Thr Lys Leu Ile Gly Trp Val Trp Phe
        275                 280                 285

Asn Thr Asp Asp Arg Ala Ser Val Val Gly Asp Ala Ile Asp Tyr Ile
    290                 295                 300

Arg Glu Leu Ile Arg Thr Val Asn Glu Leu Lys Leu Leu Val Glu Lys
305                 310                 315                 320

Lys Arg Tyr Ala Lys Glu Arg Tyr Lys Arg Pro Lys Thr Glu Glu Asp
                325                 330                 335

Ala Ala Glu Ser Cys Asn Ile Lys Pro Phe Gly Asp Pro Asp Gly Gly
            340                 345                 350

Ile Arg Thr Ser Trp Leu Gln Arg Lys Ser Lys Asp Ser Glu Val Asp
        355                 360                 365

Val Arg Ile Ile Asp Asp Val Thr Ile Lys Leu Phe Gln Arg Lys
    370                 375                 380

Lys Ile Asn Cys Leu Leu Phe Val Ser Lys Val Leu Asp Glu Leu Gln
385                 390                 395                 400

Leu Glu Leu His His Val Ala Gly Gly His Val Gly Glu Tyr Cys Ser
                405                 410                 415

Phe Leu Phe Asn Ser Lys Gly Leu Val Ser Leu Arg Xaa Ile Met Glu
            420                 425                 430

Gly Ser Ser Val Tyr Ala Ser Ala Ile Ala Asn Arg Val Ile Asp Val
        435                 440                 445

Leu Asp Ser Gln Tyr Thr Ala Ala Val Pro His Thr Asn Ser Tyr
    450                 455                 460

<210> SEQ ID NO 107
<211> LENGTH: 475
<212> TYPE: PRT
<213> ORGANISM: Glycine max
<220> FEATURE:
<221> NAME/KEY: misc_feature
<222> LOCATION: (441)..(441)
<223> OTHER INFORMATION: Xaa can be any naturally occurring amino acid

<400> SEQUENCE: 107

Met Ser Thr Gly Asp Arg Pro Lys Met His Asp Gln Thr Gly Cys Phe
1               5                   10                  15

-continued

Asp Pro Asn Thr Thr Gly Glu Ser Val Pro Ser Leu Lys Asp Asn Phe
            20                  25                  30

Pro Gln Thr Leu Pro Pro Ser Ser Pro Met Val Val Gly Asn Thr
        35                  40                  45

Thr Thr Asn Ser Asn Asn Asn Met Asp Asn His Leu Val Gln Glu Val
    50                  55                  60

Ile Asp Ala Phe Pro Tyr Gln Gln Ser Thr Trp Asp Pro Thr Ile Val
65                  70                  75                  80

Gln Glu Leu Gln Asp Met Ala Tyr Ala Asn His Thr Glu Gln Thr Gln
                85                  90                  95

Gln Gln Gln Gln Asn Glu Gln Gln Phe Gln Gln Phe Glu Thr Gln Asn
            100                 105                 110

Cys Ser Gln Ser Tyr Asn Asn Pro Ser Ser Ile Leu Asp Pro Pro Tyr
        115                 120                 125

Pro Ser Pro Asp Leu Leu Asn Leu Leu His Met Pro Arg Cys Ser Ala
    130                 135                 140

Ser Ser Leu Leu Thr Asn Pro Ser Ile Cys Leu Thr Asn Pro Thr Gln
145                 150                 155                 160

Asn Thr Pro Asn Phe Gln Asn Pro Met Ala Phe Leu Gly Asp Leu Pro
                165                 170                 175

Ile Gly Ser Glu Asn Thr Ser Ala Ser Ser Val Leu Tyr Asp Pro Leu
            180                 185                 190

Phe His Leu Asn Leu Pro Pro Gln Pro Pro Ala Leu Arg Glu Leu Phe
        195                 200                 205

Gln Ser Leu Pro Arg Gly Tyr Ser Leu Pro Thr Asn Ser Arg Asn Gly
    210                 215                 220

Ser Leu Phe Gly Gly Asp Glu Met Glu Gly Asp Gly Ser Gln Leu
225                 230                 235                 240

Asp Met Gly Val Leu Glu Phe Asn Arg Val Thr Leu Thr Pro Ser Val
                245                 250                 255

Gly Lys Gly Arg Arg Gly Lys Ala Thr Lys His Phe Ala Thr Glu Lys
            260                 265                 270

Gln Arg Arg Glu Gln Leu Asn Gly Lys Tyr Lys Ile Leu Arg Asn Leu
        275                 280                 285

Ile Pro Ser Pro Thr Lys Leu Val Gly Phe Val Leu Thr Gln Thr Asp
    290                 295                 300

Arg Ala Ser Val Val Gly Asp Ala Ile Asp Tyr Ile Arg Glu Leu Ile
305                 310                 315                 320

Arg Thr Val Asn Glu Leu Lys Leu Leu Val Glu Lys Lys Arg Tyr Ala
                325                 330                 335

Lys Asp Arg Cys Lys Arg Pro Lys Thr Glu Glu Asp Ala Ala Glu Ser
            340                 345                 350

Cys Asn Ile Lys Pro Phe Gly Asp Pro Asp Gly Gly Ile Arg Thr Ser
        355                 360                 365

Trp Leu Gln Arg Lys Ser Lys Asp Ser Glu Val Asp Val Arg Ile Ile
    370                 375                 380

Asp Asp Asp Val Thr Ile Lys Leu Phe Gln Arg Lys Lys Ile Asn Cys
385                 390                 395                 400

Leu Leu Phe Val Ser Lys Val Leu Asp Glu Leu Gln Leu Glu Leu His
                405                 410                 415

His Val Ala Gly Gly His Val Gly Glu Tyr Cys Ser Phe Leu Phe Asn
            420                 425                 430

```
Ser Lys Gly Leu Val Ser Leu Arg Xaa Ile Met Glu Gly Ser Ser Val
            435                 440                 445

Tyr Ala Ser Ala Ile Ala Asn Arg Val Ile Asp Val Leu Asp Ser Gln
450                 455                 460

Tyr Ala Ala Ala Val Pro His Thr Asn Ser Tyr
465                 470                 475

<210> SEQ ID NO 108
<211> LENGTH: 443
<212> TYPE: PRT
<213> ORGANISM: Lotus japonicus

<400> SEQUENCE: 108

Met Ala Glu Gly Val Ser Ser Gln Lys Asp Ser Phe Pro Gln Thr Leu
1               5                   10                  15

Leu Asp Pro Gln Pro Gln Ser Leu Met Val Thr Glu Asn Thr Thr Asn
                20                  25                  30

Ser Asn Asn Ile Met Asp Asn His Leu Val Gln Glu Val Ile Asp Ala
            35                  40                  45

Pro Leu Tyr Gln Gln Ser Thr Trp Asp Pro Asn Val Gln Glu Val Gln
50                  55                  60

Asp Met Ser Tyr Ala Asn His Pro Glu Gln Gln Phe Gln His Ile Asp
65                  70                  75                  80

Ala Gln Asn Tyr Cys Gln Ser Tyr Thr Pro Ser Ile Leu Asp Pro Ser
                85                  90                  95

Tyr Pro Ser Pro Asp Leu Leu Asn Phe Leu His Leu Pro Thr Cys Ser
            100                 105                 110

Ala Ser Ser Leu Leu Thr Asn Pro Pro Asn Ile Cys Ile Ser Asn Pro
        115                 120                 125

Thr Gln Arg Thr Pro Asn Phe Gln Asn Ser Met Thr Phe Leu Gly Asp
    130                 135                 140

Leu Pro Met Gly Pro Asp Asn Thr Ser Ala Ser Ser Val Leu Tyr Asp
145                 150                 155                 160

Pro Leu Phe His Leu Asn Leu Pro Pro Gln Pro Ala Leu Arg Glu
                165                 170                 175

Leu Phe Gln Ser Leu Pro Arg Gly Tyr Arg Leu Pro Thr Ser Ser Arg
                180                 185                 190

Asp Asp Ser Leu Phe Gly Gly Gly Asp Glu Met Glu Gly Asp Gly Ser
            195                 200                 205

Gln Leu Asp Met Gly Val Leu Asp Phe Asn Arg Asp Thr Ala Ser Val
    210                 215                 220

Gly Lys Gly Arg Glu Gly Lys Gly Ala Lys Pro Phe Ala Thr Glu Lys
225                 230                 235                 240

Asp Arg Arg Glu Gln Leu Asn Gly Lys Tyr Lys Ile Leu Arg Ser Leu
                245                 250                 255

Ile Pro Asn Pro Thr Lys Leu Ile Gly Trp Val Leu Phe Lys Pro Asp
                260                 265                 270

Arg Ala Ser Val Val Gly Asp Ala Ile Glu Tyr Ile Arg Glu Leu Ile
            275                 280                 285

Arg Thr Val Asn Glu Leu Lys Leu Leu Val Glu Lys Lys Arg His Glu
    290                 295                 300

Arg Glu Arg Cys Lys Arg Pro Lys Asn Glu Glu Asp Ala Glu Glu Ser
305                 310                 315                 320

Cys Asn Ile Lys Pro Phe Gly Asp Pro Asp Gly Tyr Ile Arg Thr Ser
                325                 330                 335
```

```
Trp Leu Gln Arg Lys Ser Lys Asp Ser Glu Val Asp Val Arg Ile Ile
            340                 345                 350

Asp Asp Asp Val Thr Ile Lys Phe Phe Gln Arg Lys Lys Ile Asn Cys
        355                 360                 365

Leu Leu Phe Val Ser Lys Val Leu Asp Glu Leu Gln Leu Glu Leu His
    370                 375                 380

His Leu Ala Gly Gly His Val Gly Glu Tyr Trp Ser Phe Leu Phe Asn
385                 390                 395                 400

Ser Lys Arg Pro Val Ser Leu Thr Gln Val Ile Glu Gly Ser Ser Val
                405                 410                 415

Tyr Ala Ser Ala Ile Ala Asn Arg Val Ile Asp Val Leu Asp Ser Gln
            420                 425                 430

Tyr Ala Ala Val Pro Gln Thr Ser Ser Tyr
        435                 440

<210> SEQ ID NO 109
<211> LENGTH: 447
<212> TYPE: PRT
<213> ORGANISM: Arabidopsis thaliana

<400> SEQUENCE: 109

Met Gly Cys Phe Asp Pro Asn Thr Pro Ala Glu Val Thr Val Glu Ser
1               5                   10                  15

Ser Phe Ser Gln Ala Glu Pro Pro Pro Pro Gln Val Leu Val
            20                  25                  30

Ala Gly Ser Thr Ser Asn Ser Asn Cys Ser Val Glu Val Glu Glu Leu
        35                  40                  45

Ser Glu Phe His Leu Ser Pro Gln Asp Cys Pro Gln Ala Ser Ser Thr
    50                  55                  60

Pro Leu Gln Phe His Ile Asn Pro Pro Pro Pro Pro Pro Pro Cys
65                  70                  75                  80

Asp Gln Leu His Asn Asn Leu Ile His Gln Met Ala Ser His Gln Gln
                85                  90                  95

Gln His Ser Asn Trp Asp Asn Gly Tyr Gln Asp Phe Val Asn Leu Gly
            100                 105                 110

Pro Asn Ser Ala Thr Thr Pro Asp Leu Leu Ser Leu Leu His Leu Pro
        115                 120                 125

Arg Cys Ser Leu Pro Pro Asn His His Pro Ser Met Leu Pro Thr
    130                 135                 140

Ser Phe Ser Asp Ile Met Ser Ser Ser Ala Ala Ala Val Met Tyr
145                 150                 155                 160

Asp Pro Leu Phe His Leu Asn Phe Pro Met Gln Pro Arg Asp Gln Asn
                165                 170                 175

Gln Leu Arg Asn Gly Ser Cys Leu Leu Gly Val Glu Asp Gln Ile Gln
            180                 185                 190

Met Asp Ala Asn Gly Gly Met Asn Val Leu Tyr Phe Glu Gly Ala Asn
        195                 200                 205

Asn Asn Asn Gly Gly Phe Glu Asn Glu Ile Leu Glu Phe Asn Asn Gly
    210                 215                 220

Val Thr Arg Lys Gly Arg Gly Ser Arg Lys Ser Arg Thr Ser Pro Thr
225                 230                 235                 240

Glu Arg Glu Arg Arg Val His Phe Asn Asp Arg Phe Phe Asp Leu Lys
                245                 250                 255

Asn Leu Ile Pro Asn Pro Thr Lys Ile Asp Arg Ala Ser Ile Val Gly
            260                 265                 270
```

Glu Ala Ile Asp Tyr Ile Lys Glu Leu Leu Arg Thr Ile Glu Glu Phe
            275                 280                 285

Lys Met Leu Val Glu Lys Lys Arg Cys Gly Arg Phe Arg Ser Lys Lys
        290                 295                 300

Arg Ala Arg Val Gly Glu Gly Gly Gly Glu Asp Gln Glu Glu
305                 310                 315                 320

Glu Asp Thr Val Asn Tyr Lys Pro Gln Ser Glu Val Asp Gln Ser Cys
                    325                 330                 335

Phe Asn Lys Asn Asn Asn Ser Leu Arg Cys Ser Trp Leu Lys Arg
            340                 345                 350

Lys Ser Lys Val Thr Glu Val Asp Val Arg Ile Ile Asp Asp Glu Val
        355                 360                 365

Thr Ile Lys Leu Val Gln Lys Lys Ile Asn Cys Leu Leu Phe Thr
    370                 375                 380

Thr Lys Val Leu Asp Gln Leu Gln Leu Asp Leu His His Val Ala Gly
385                 390                 395                 400

Gly Gln Ile Gly Glu His Tyr Ser Phe Leu Phe Asn Thr Lys Ile Cys
                    405                 410                 415

Glu Gly Ser Cys Val Tyr Ala Ser Gly Ile Ala Asp Thr Leu Met Glu
            420                 425                 430

Val Val Glu Lys Gln Tyr Met Glu Ala Val Pro Ser Asn Gly Tyr
        435                 440                 445

<210> SEQ ID NO 110
<211> LENGTH: 458
<212> TYPE: PRT
<213> ORGANISM: Arabidopsis thaliana

<400> SEQUENCE: 110

Met Glu Glu Glu Arg Glu Ser Leu Tyr Glu Met Gly Cys Phe Asp
1               5                   10                  15

Pro Asn Thr Pro Ala Glu Val Thr Val Glu Ser Ser Phe Ser Gln Ala
            20                  25                  30

Glu Pro Pro Pro Pro Pro Gln Val Leu Val Ala Gly Ser Thr Ser
        35                  40                  45

Asn Ser Asn Cys Ser Val Glu Val Glu Glu Leu Ser Glu Phe His Leu
50                  55                  60

Ser Pro Gln Asp Cys Pro Gln Ala Ser Ser Thr Pro Leu Gln Phe His
65                  70                  75                  80

Ile Asn Pro Pro Pro Pro Pro Pro Cys Asp Gln Leu His Asn
            85                  90                  95

Asn Leu Ile His Gln Met Ala Ser His Gln Gln His Ser Asn Trp
        100                 105                 110

Asp Asn Gly Tyr Gln Asp Phe Val Asn Leu Gly Pro Asn Ser Ala Thr
            115                 120                 125

Thr Pro Asp Leu Leu Ser Leu Leu His Leu Pro Arg Cys Ser Leu Pro
    130                 135                 140

Pro Asn His His Pro Ser Ser Met Leu Pro Thr Ser Phe Ser Asp Ile
145                 150                 155                 160

Met Ser Ser Ser Ala Ala Ala Val Met Tyr Asp Pro Leu Phe His
                    165                 170                 175

Leu Asn Phe Pro Met Gln Pro Arg Asp Gln Asn Gln Leu Arg Asn Gly
            180                 185                 190

Ser Cys Leu Leu Gly Val Glu Asp Gln Ile Gln Met Asp Ala Asn Gly
        195                 200                 205

Gly Met Asn Val Leu Tyr Phe Glu Gly Ala Asn Asn Asn Gly Gly
    210                 215                 220

Phe Glu Asn Glu Ile Leu Glu Phe Asn Gly Val Thr Arg Lys Gly
225                 230                 235                 240

Arg Gly Ser Arg Lys Ser Arg Thr Ser Pro Thr Glu Arg Glu Arg Arg
                245                 250                 255

Val His Phe Asn Asp Arg Phe Phe Asp Leu Lys Asn Leu Ile Pro Asn
                260                 265                 270

Pro Thr Lys Ile Asp Arg Ala Ser Ile Val Gly Glu Ala Ile Asp Tyr
                275                 280                 285

Ile Lys Glu Leu Leu Arg Thr Ile Glu Glu Phe Lys Met Leu Val Glu
    290                 295                 300

Lys Lys Arg Cys Gly Arg Phe Arg Ser Lys Lys Arg Ala Arg Val Gly
305                 310                 315                 320

Glu Gly Gly Gly Gly Glu Asp Gln Glu Glu Glu Asp Thr Val Asn
                325                 330                 335

Tyr Lys Pro Gln Ser Glu Val Asp Gln Ser Cys Phe Asn Lys Asn Asn
                340                 345                 350

Asn Asn Ser Leu Arg Cys Ser Trp Leu Lys Arg Lys Ser Lys Val Thr
    355                 360                 365

Glu Val Asp Val Arg Ile Ile Asp Asp Glu Val Thr Ile Lys Leu Val
    370                 375                 380

Gln Lys Lys Lys Ile Asn Cys Leu Leu Phe Thr Thr Lys Val Leu Asp
385                 390                 395                 400

Gln Leu Gln Leu Asp Leu His His Val Ala Gly Gly Gln Ile Gly Glu
                405                 410                 415

His Tyr Ser Phe Leu Phe Asn Thr Lys Ile Cys Glu Gly Ser Cys Val
                420                 425                 430

Tyr Ala Ser Gly Ile Ala Asp Thr Leu Met Glu Val Val Glu Lys Gln
                435                 440                 445

Tyr Met Glu Ala Val Pro Ser Asn Gly Tyr
    450                 455

<210> SEQ ID NO 111
<211> LENGTH: 315
<212> TYPE: PRT
<213> ORGANISM: Oryza sativa

<400> SEQUENCE: 111

Met Asp Glu Gln Arg Gly Arg Gly Gly Phe Asp Glu Leu Val Leu Leu
1               5                   10                  15

His Gln Gln Gln Glu Gln Arg Arg Arg Glu Gln Gln Gln Glu Glu
                20                  25                  30

Glu Glu Glu Glu Glu Val Arg Arg Gln Met Phe Gly Ala Val Val Gly
            35                  40                  45

Gly Leu Ala Ala Phe Pro Ala Ala Ala Ala Leu Gly Gln Gln Gln
    50                  55                  60

Val Asp Cys Gly Gly Glu Leu Gly Gly Phe Cys Asp Ser Glu Ala Gly
65                  70                  75                  80

Gly Ser Ser Glu Pro Glu Ala Ala Gly Ala Arg Pro Arg Gly Gly
                85                  90                  95

Ser Gly Ser Lys Arg Ser Arg Ala Ala Glu Val His Asn Leu Ser Glu
                100                 105                 110

Lys Arg Arg Arg Ser Lys Ile Asn Glu Lys Met Lys Ala Leu Gln Ser
            115                 120                 125

```
Leu Ile Pro Asn Ser Asn Lys Thr Asp Lys Ala Ser Met Leu Asp Glu
        130                 135                 140

Ala Ile Glu Tyr Leu Lys Gln Leu Gln Leu Gln Val Gln Met Leu Ser
145                 150                 155                 160

Met Arg Asn Gly Val Tyr Leu Asn Pro Ser Tyr Leu Ser Gly Ala Leu
                165                 170                 175

Glu Pro Ala Gln Ala Ser Gln Met Phe Ala Ala Leu Gly Gly Asn Asn
            180                 185                 190

Val Thr Val Val His Pro Gly Thr Val Met Pro Val Asn Gln Ser
        195                 200                 205

Ser Gly Ala His His Leu Phe Asp Pro Leu Asn Ser Pro Gln Asn
210                 215                 220

Gln Pro Gln Ser Leu Ile Leu Pro Ser Val Pro Ser Thr Ala Ile Pro
225                 230                 235                 240

Glu Pro Pro Phe His Leu Glu Ser Ser Gln Ser His Leu Arg Gln Phe
                245                 250                 255

Gln Leu Pro Gly Ser Ser Glu Phe His Lys Ile Leu Phe Leu His Val
            260                 265                 270

Leu Leu Ser Val Lys Asp Gly Val Ser Trp Arg Asp Asn Ala Lys Ala
            275                 280                 285

Pro Pro Ile Ile Thr Ser Arg Lys Ser Ala Arg Lys Arg Asp Glu Leu
290                 295                 300

His Gln Glu Arg Ile Ile His Val Glu His Gln
305                 310                 315

<210> SEQ ID NO 112
<211> LENGTH: 464
<212> TYPE: PRT
<213> ORGANISM: Oryza sativa

<400> SEQUENCE: 112

Met Ile Val Gly Ala Gly Tyr Phe Glu Asp Ser His Asp Gln Ser Leu
1               5                   10                  15

Met Ala Gly Ser Leu Ile His Asp Ser Asn Gln Ala Pro Ala Ser Ser
                20                  25                  30

Glu Asn Thr Ser Ile Asp Leu Gln Lys Phe Lys Val His Pro Tyr Ser
            35                  40                  45

Thr Glu Ala Leu Ser Asn Thr Ala Asn Leu Ala Glu Ala Ala Arg Ala
        50                  55                  60

Ile Asn His Leu Gln His Gln Leu Glu Ile Asp Leu Glu Gln Glu Val
65                  70                  75                  80

Pro Pro Val Glu Thr Ala Asn Trp Asp Pro Ala Ile Cys Thr Ile Pro
                85                  90                  95

Asp His Ile Ile Asn His Gln Phe Ser Glu Asp Pro Gln Asn Ile Leu
                100                 105                 110

Val Glu Gln Gln Ile Gln Gln Tyr Asp Ser Ala Leu Tyr Pro Asn Gly
            115                 120                 125

Val Tyr Thr Pro Ala Pro Asp Leu Leu Asn Leu Met Gln Cys Thr Met
        130                 135                 140

Ala Pro Ala Phe Pro Ala Thr Thr Ser Val Phe Gly Asp Thr Thr Leu
145                 150                 155                 160

Asn Gly Thr Asn Tyr Leu Asp Leu Asn Gly Glu Leu Thr Gly Val Ala
                165                 170                 175

Ala Val Pro Asp Ser Gly Ser Gly Leu Met Phe Ala Ser Asp Ser Ala
            180                 185                 190
```

```
Leu Gln Leu Gly Tyr His Gly Thr Gln Ser His Leu Ile Lys Asp Ile
            195                 200                 205

Cys His Ser Leu Pro Gln Asn Tyr Gly Leu Phe Pro Ser Glu Asp Glu
    210                 215                 220

Arg Asp Val Ile Ile Gly Val Gly Ser Gly Asp Leu Phe Gln Glu Ile
225                 230                 235                 240

Asp Asp Arg Gln Phe Asp Ser Val Leu Glu Cys Arg Arg Gly Lys Gly
                245                 250                 255

Glu Phe Gly Lys Gly Lys Gly Lys Ala Asn Phe Ala Thr Glu Arg Glu
            260                 265                 270

Arg Arg Glu Gln Leu Asn Val Lys Phe Arg Thr Leu Arg Met Leu Phe
        275                 280                 285

Pro Asn Pro Thr Lys Asn Asp Arg Ala Ser Ile Val Gly Asp Ala Ile
    290                 295                 300

Glu Tyr Ile Asp Glu Leu Asn Arg Thr Val Lys Glu Leu Lys Ile Leu
305                 310                 315                 320

Val Glu Gln Lys Arg His Gly Asn Asn Arg Arg Lys Val Leu Lys Leu
                325                 330                 335

Asp Gln Glu Ala Ala Ala Asp Gly Glu Ser Ser Ser Met Arg Pro Val
            340                 345                 350

Arg Asp Asp Gln Asp Asn Gln Leu His Gly Ala Ile Arg Ser Ser Trp
        355                 360                 365

Val Gln Arg Arg Ser Lys Glu Cys His Val Asp Val Arg Ile Val Asp
    370                 375                 380

Asp Glu Val Asn Ile Lys Leu Thr Glu Lys Lys Lys Ala Asn Ser Leu
385                 390                 395                 400

Leu His Ala Ala Lys Val Leu Asp Glu Phe Gln Leu Glu Leu Ile His
                405                 410                 415

Val Val Gly Gly Ile Ile Gly Asp His His Ile Phe Met Phe Asn Thr
            420                 425                 430

Lys Val Ser Glu Gly Ser Ala Val Tyr Ala Cys Ala Val Ala Lys Lys
        435                 440                 445

Leu Leu Gln Ala Val Asp Val Gln His Gln Ala Leu Asp Ile Phe Asn
    450                 455                 460

<210> SEQ ID NO 113
<211> LENGTH: 379
<212> TYPE: PRT
<213> ORGANISM: Oryza sativa

<400> SEQUENCE: 113

Met Tyr His Pro Gln Cys Glu Leu Leu Met Pro Leu Glu Ser Leu Glu
1               5                   10                  15

Met Asp Val Gly Gln Ser His Leu Ala Ala Val Ala Ala Ala Ala Met
            20                  25                  30

Pro Gly Glu Leu Asn Phe His Leu Leu His Ser Leu Asp Ala Ala Ala
        35                  40                  45

Ala Ala Ala Ser Ser Thr Ala Ala Ser Ala Ser Ser Gln Pro Thr Val
    50                  55                  60

Asp Tyr Phe Phe Gly Gly Ala Asp Gln Gln Pro Pro Pro Ala Ala
65                  70                  75                  80

Met Gln Tyr Asp Gln Leu Ala Ala Pro His His Gln Thr Val Ala
                85                  90                  95

Met Leu Arg Asp Tyr Tyr Gly Gly His Tyr Pro Pro Ala Ala Ala Ala
            100                 105                 110
```

-continued

```
Ala Ala Ala Thr Glu Ala Tyr Phe Arg Gly Gly Pro Arg Thr Ala Gly
            115                 120                 125

Ser Ser Ser Leu Val Phe Gly Pro Ala Asp Asp Glu Ser Ala Phe Met
        130                 135                 140

Val Gly Pro Phe Glu Ser Ser Pro Thr Pro Arg Ser Gly Gly Gly Arg
145                 150                 155                 160

Lys Arg Ser Arg Ala Thr Ala Gly Phe His Gly Gly Gly Pro Ala Asn
                165                 170                 175

Gly Val Glu Lys Lys Glu Lys Gln Arg Arg Leu Arg Leu Thr Glu Lys
            180                 185                 190

Tyr Asn Ala Leu Met Leu Leu Ile Pro Asn Arg Thr Lys Glu Asp Arg
        195                 200                 205

Ala Thr Val Ile Ser Asp Ala Ile Glu Tyr Ile Gln Glu Leu Gly Arg
    210                 215                 220

Thr Val Glu Glu Leu Thr Leu Leu Val Glu Lys Lys Arg Arg Arg Arg
225                 230                 235                 240

Glu Met Gln Gly Asp Val Val Asp Ala Ala Thr Ser Ser Val Val Ala
                245                 250                 255

Gly Met Asp Gln Ala Ala Glu Ser Ser Glu Gly Glu Val Met Ala Ala
            260                 265                 270

Ala Ala Met Gly Ala Val Ala Pro Pro Arg Gln Ala Pro Ile Arg
        275                 280                 285

Ser Thr Tyr Ile Gln Arg Arg Ser Lys Glu Thr Phe Val Asp Val Arg
    290                 295                 300

Ile Val Glu Asp Asp Val Asn Ile Lys Leu Thr Lys Arg Arg Arg Asp
305                 310                 315                 320

Gly Cys Leu Ala Ala Ala Ser Arg Ala Leu Asp Asp Leu Arg Leu Asp
                325                 330                 335

Leu Val His Leu Ser Gly Gly Lys Ile Gly Asp Cys His Ile Tyr Met
            340                 345                 350

Phe Asn Thr Lys Ile His Ser Gly Ser Pro Val Phe Ala Ser Ala Val
        355                 360                 365

Ala Ser Arg Leu Ile Glu Val Val Asp Glu Tyr
    370                 375
```

<210> SEQ ID NO 114
<211> LENGTH: 234
<212> TYPE: PRT
<213> ORGANISM: Oryza sativa

<400> SEQUENCE: 114

```
Met Pro Arg Arg Ala Arg Ala Arg Gly Gly Gly Gly Gly Gly Gly Glu
1               5                   10                  15

Glu Val Lys Val Glu Asp Asp Phe Ile Asp Ser Val Leu Asn Phe Gly
            20                  25                  30

Gly Gly Gly Gly Gly Glu Glu Asp Gly Asp Asp Gly Glu Glu Glu Gln
        35                  40                  45

Gln Gln Gln Gln Ala Ala Ala Ala Met Gly Lys Glu Phe Lys Ser
    50                  55                  60

Lys Asn Leu Glu Ala Glu Arg Arg Arg Gly Arg Leu Asn Gly Asn
65                  70                  75                  80

Ile Phe Ala Leu Arg Ala Val Val Pro Lys Ile Thr Lys Met Ser Lys
                85                  90                  95

Glu Ala Thr Leu Ser Asp Ala Ile Glu His Ile Lys Asn Leu Gln Asn
            100                 105                 110
```

```
Glu Val Leu Glu Leu Gln Arg Gln Leu Gly Asp Ser Pro Gly Glu Ala
            115                 120                 125

Trp Glu Lys Gln Cys Ser Ala Ser Cys Ser Glu Ser Phe Val Pro Thr
130                 135                 140

Glu Asn Ala His Tyr Gln Gly Gln Val Glu Leu Ile Ser Leu Gly Ser
145                 150                 155                 160

Cys Lys Tyr Asn Leu Lys Ile Phe Trp Thr Lys Arg Ala Gly Leu Phe
                165                 170                 175

Thr Lys Val Leu Glu Ala Leu Cys Ser Tyr Lys Val Gln Val Leu Ser
            180                 185                 190

Leu Asn Thr Ile Ser Phe Tyr Gly Tyr Ala Glu Ser Phe Phe Thr Ile
            195                 200                 205

Glu Val Lys Gly Glu Gln Asp Val Val Met Val Glu Leu Arg Ser Leu
    210                 215                 220

Leu Ser Ser Ile Val Glu Val Pro Ser Ile
225                 230
```

<210> SEQ ID NO 115
<211> LENGTH: 552
<212> TYPE: PRT
<213> ORGANISM: Oryza sativa

<400> SEQUENCE: 115

```
Met Gly Arg Gly Asp His Leu Leu Met Lys Asn Ser Asn Ala Ala Ala
1               5                   10                  15

Ala Ala Ala Val Asn Gly Gly Thr Ser Leu Asp Ala Ala Leu
            20                  25                  30

Arg Pro Leu Val Gly Ser Asp Gly Trp Asp Tyr Cys Ile Tyr Trp Arg
            35                  40                  45

Leu Ser Pro Asp Gln Arg Phe Leu Glu Met Thr Gly Phe Cys Cys Ser
    50                  55                  60

Ser Glu Leu Glu Ala Gln Val Ser Ala Leu Leu Asp Leu Pro Ser Ser
65                  70                  75                  80

Ile Pro Leu Asp Ser Ser Ser Ile Gly Met His Ala Gln Ala Leu Leu
                85                  90                  95

Ser Asn Gln Pro Ile Trp Gln Ser Ser Ser Glu Glu Glu Glu Ala Asp
            100                 105                 110

Gly Gly Gly Gly Ala Lys Thr Arg Leu Leu Val Pro Val Ala Gly Gly
            115                 120                 125

Leu Val Glu Leu Phe Ala Ser Arg Tyr Met Ala Glu Glu Gln Gln Met
            130                 135                 140

Ala Glu Leu Val Met Ala Gln Cys Gly Gly Gly Ala Gly Asp Asp
145                 150                 155                 160

Gly Gly Gly Gln Ala Trp Pro Pro Glu Thr Pro Ser Phe Gln Trp
                165                 170                 175

Asp Gly Gly Ala Asp Ala Gln Arg Leu Met Tyr Gly Gly Ser Ser Leu
            180                 185                 190

Asn Leu Phe Asp Ala Ala Ala Asp Asp Pro Phe Leu Gly Gly
            195                 200                 205

Gly Gly Gly Asp Ala Val Gly Asp Glu Ala Ala Ala Gly Ala Trp
    210                 215                 220

Pro Tyr Ala Gly Met Ala Val Ser Glu Pro Ser Val Ala Val Ala Gln
225                 230                 235                 240

Glu Gln Met Gln His Ala Ala Gly Gly Val Ala Glu Ser Gly Ser
                245                 250                 255
```

Glu Gly Arg Lys Leu His Gly Asp Pro Glu Asp Gly Asp Gly
            260                 265                 270

Glu Gly Arg Ser Gly Gly Ala Lys Arg Gln Gln Cys Lys Asn Leu Glu
            275                 280                 285

Ala Glu Arg Lys Arg Arg Lys Lys Leu Asn Gly His Leu Tyr Lys Leu
            290                 295                 300

Arg Ser Leu Val Pro Asn Ile Thr Lys Met Asp Arg Ala Ser Ile Leu
305                 310                 315                 320

Gly Asp Ala Ile Asp Tyr Ile Val Gly Leu Gln Lys Gln Val Lys Glu
                325                 330                 335

Leu Gln Asp Glu Leu Glu Asp Asn His Val His His Lys Pro Pro Asp
            340                 345                 350

Val Leu Ile Asp His Pro Pro Ala Ser Leu Val Gly Leu Asp Asn
            355                 360                 365

Asp Asp Ala Ser Pro Pro Asn Ser His Gln Gln Gln Pro Pro Leu Ala
            370                 375                 380

Val Ser Gly Ser Ser Ser Arg Arg Ser Asn Lys Asp Pro Ala Met Thr
385                 390                 395                 400

Asp Asp Lys Val Gly Gly Gly Gly Gly Gly His Arg Met Glu Pro
            405                 410                 415

Gln Leu Glu Val Arg Gln Val Gln Gly Asn Glu Leu Phe Val Gln Val
            420                 425                 430

Leu Trp Glu His Lys Pro Gly Gly Phe Val Arg Leu Met Asp Ala Met
            435                 440                 445

Asn Ala Leu Gly Leu Glu Val Ile Asn Val Asn Val Thr Thr Tyr Lys
            450                 455                 460

Thr Leu Val Leu Asn Val Phe Arg Val Met Val Arg Asp Ser Glu Val
465                 470                 475                 480

Ala Val Gln Ala Asp Arg Val Arg Asp Ser Leu Leu Glu Val Thr Arg
            485                 490                 495

Glu Thr Tyr Pro Gly Val Trp Pro Ser Pro Gln Glu Glu Asp Asp Ala
            500                 505                 510

Lys Phe Asp Gly Gly Asp Gly Gly Gln Ala Ala Ala Ala Ala Ala
            515                 520                 525

Ala Gly Gly Glu His Tyr His Asp Glu Val Gly Gly Tyr His Gln
            530                 535                 540

His Leu His Tyr Leu Ala Phe Asp
545                 550

<210> SEQ ID NO 116
<211> LENGTH: 15
<212> TYPE: PRT
<213> ORGANISM: Artificial Sequence
<220> FEATURE:
<223> OTHER INFORMATION: antigen

<400> SEQUENCE: 116

Cys Ser Pro Thr Pro Arg Ser Gly Gly Arg Lys Arg Ser Arg
1               5                   10                  15

<210> SEQ ID NO 117
<211> LENGTH: 20
<212> TYPE: DNA
<213> ORGANISM: Artificial Sequence
<220> FEATURE:
<223> OTHER INFORMATION: primer

```
<400> SEQUENCE: 117
tgacctcgtc cacctctccg                                                20

<210> SEQ ID NO 118
<211> LENGTH: 22
<212> TYPE: DNA
<213> ORGANISM: Artificial Sequence
<220> FEATURE:
<223> OTHER INFORMATION: primer

<400> SEQUENCE: 118
cagtctgtaa cgagcaagcg ga                                             22

<210> SEQ ID NO 119
<211> LENGTH: 286
<212> TYPE: DNA
<213> ORGANISM: Oryza sativa

<400> SEQUENCE: 119
catgttcaac accaagattc attcgggatc tccagtgttt gcaagtgcag tggccagcag    60
gctgattgaa gtggtggatg agtactaact agctcgagct agctaattag ccgaccgacc   120
gatcgatatg atgaaagttt ctatgttgct agctagctag ggttcttgga tgcatgagta   180
ctgagtagct ctttaattaa tttccttttta attttagact gtttaatttg gattggtaaa  240
gactcgtgtt agcttttggg agatctttgg tatgtcatgg tttgca                  286

<210> SEQ ID NO 120
<211> LENGTH: 149
<212> TYPE: DNA
<213> ORGANISM: Oryza sativa

<400> SEQUENCE: 120
caacaaacct agttaattta gctctagttg gttcatccct gctgcactgc gagctcaagt    60
aatcgatctg agctctgaag aaaaaggtgg tagagtgcga ggaagatgta tcacccgcag   120
tgcgagctcc tgatgccgct tgagagcct                                     149
```